United States Patent
Richardson et al.

(10) Patent No.: US 11,515,136 B2
(45) Date of Patent: Nov. 29, 2022

(54) SPECTROMETRIC ANALYSIS

(71) Applicant: Micromass UK Limited, Wilmslow (GB)

(72) Inventors: Keith Richardson, High Peak (GB);
Steven Derek Pringle, Darwen (GB);
Julia Balog, Solymar (HU); Zoltan Takats, Cambridge (GB)

(73) Assignee: Micromass UK Limited, Wilmslow (GB)

( * ) Notice: Subject to any disclaimer, the term of this patent is extended or adjusted under 35 U.S.C. 154(b) by 54 days.

(21) Appl. No.: 17/012,865

(22) Filed: Sep. 4, 2020

(65) Prior Publication Data

US 2020/0402785 A1 Dec. 24, 2020

Related U.S. Application Data

(63) Continuation of application No. 15/555,860, filed as application No. PCT/GB2016/050622 on Mar. 7, 2016, now Pat. No. 10,777,398.

(30) Foreign Application Priority Data

Mar. 6, 2015 (GB) ..................... 1503863
Mar. 6, 2015 (GB) ..................... 1503864

(Continued)

(51) Int. Cl.
*H01J 49/00* (2006.01)
*H01J 49/04* (2006.01)
(Continued)

(52) U.S. Cl.
CPC ............ *H01J 49/049* (2013.01); *A61B 1/041* (2013.01); *A61B 1/2736* (2013.01);
(Continued)

(58) Field of Classification Search
CPC .. H01J 49/049; H01J 49/0004; H01J 49/0027; H01J 49/0031; H01J 49/0036;
(Continued)

(56) References Cited

U.S. PATENT DOCUMENTS 4,408,125 A   10/1983   Meuzelaar
5,210,412 A   5/1993    Levis et al.
(Continued)

FOREIGN PATENT DOCUMENTS

CA    2339552 A1   2/2000
CA    2527886 A1   12/2004
(Continued)

OTHER PUBLICATIONS

Arena, K., et al., "Exploration of Rapid Evaporative-Ionization Mass Spectrometry as a Shotgun Approach for the Comprehensive Characcgerization of Kigelia Africana (Lam) Beth. Fruit", Molecules 25(4) 19 pages (2020).
(Continued)

*Primary Examiner* — Michael Maskell
(74) *Attorney, Agent, or Firm* — Goodwin Procter LLP

(57) ABSTRACT

A method of spectrometric analysis comprises obtaining one or more sample spectra for an aerosol, smoke or vapour sample. The one or more sample spectra are subjected to pre-processing and then multivariate and/or library based analysis so as to classify the aerosol, smoke or vapour sample. The results of the analysis are used for various surgical or non-surgical applications.

19 Claims, 100 Drawing Sheets

(30) Foreign Application Priority Data

| | | |
|---|---|---|
| Mar. 6, 2015 | (GB) | 1503867 |
| Mar. 6, 2015 | (GB) | 1503876 |
| Mar. 6, 2015 | (GB) | 1503877 |
| Mar. 6, 2015 | (GB) | 1503878 |
| Mar. 6, 2015 | (GB) | 1503879 |
| Sep. 9, 2015 | (GB) | 1516003 |
| Oct. 16, 2015 | (GB) | 1518369 |

(51) Int. Cl.

| | |
|---|---|
| A61B 10/02 | (2006.01) |
| A61B 17/32 | (2006.01) |
| A61B 18/00 | (2006.01) |
| A61B 18/14 | (2006.01) |
| A61B 18/20 | (2006.01) |
| G01N 3/00 | (2006.01) |
| G01N 9/00 | (2006.01) |
| G01N 33/68 | (2006.01) |
| H01J 49/06 | (2006.01) |
| H01J 49/16 | (2006.01) |
| A61B 90/13 | (2016.01) |
| A61B 1/04 | (2006.01) |
| A61B 1/273 | (2006.01) |
| A61B 5/00 | (2006.01) |
| A61B 5/01 | (2006.01) |
| A61B 5/0507 | (2021.01) |
| A61B 5/055 | (2006.01) |
| A61B 6/03 | (2006.01) |
| A61B 8/13 | (2006.01) |
| A61B 10/00 | (2006.01) |
| A61B 17/00 | (2006.01) |
| A61B 18/04 | (2006.01) |
| A61B 18/18 | (2006.01) |
| A61F 13/38 | (2006.01) |
| C12Q 1/02 | (2006.01) |
| C12Q 1/04 | (2006.01) |
| C12Q 1/18 | (2006.01) |
| C12Q 1/24 | (2006.01) |
| G01N 1/22 | (2006.01) |
| G01N 27/622 | (2021.01) |
| G01N 27/624 | (2021.01) |
| G01N 30/72 | (2006.01) |
| G01N 33/487 | (2006.01) |
| G01N 33/92 | (2006.01) |
| H01J 49/02 | (2006.01) |
| H01J 49/10 | (2006.01) |
| H01J 49/14 | (2006.01) |
| H01J 49/24 | (2006.01) |
| H01J 49/26 | (2006.01) |
| G16B 20/00 | (2019.01) |
| G16H 10/40 | (2018.01) |
| G16H 15/00 | (2018.01) |
| G16H 50/20 | (2018.01) |
| A61B 1/00 | (2006.01) |
| A61B 1/31 | (2006.01) |
| A61B 5/145 | (2006.01) |

(52) U.S. Cl.
CPC .......... *A61B 5/0066* (2013.01); *A61B 5/0075* (2013.01); *A61B 5/015* (2013.01); *A61B 5/055* (2013.01); *A61B 5/0507* (2013.01); *A61B 6/032* (2013.01); *A61B 6/037* (2013.01); *A61B 8/13* (2013.01); *A61B 10/00* (2013.01); *A61B 10/0041* (2013.01); *A61B 10/0233* (2013.01); *A61B 10/0283* (2013.01); *A61B 17/00* (2013.01); *A61B 17/320068* (2013.01); *A61B 18/00* (2013.01); *A61B 18/04* (2013.01); *A61B 18/042* (2013.01); *A61B 18/14* (2013.01); *A61B 18/1445* (2013.01); *A61B 18/1815* (2013.01); *A61B 18/20* (2013.01); *A61B 90/13* (2016.02); *A61F 13/38* (2013.01); *C12Q 1/025* (2013.01); *C12Q 1/04* (2013.01); *C12Q 1/18* (2013.01); *C12Q 1/24* (2013.01); *G01N 1/2202* (2013.01); *G01N 3/00* (2013.01); *G01N 9/00* (2013.01); *G01N 27/622* (2013.01); *G01N 27/624* (2013.01); *G01N 30/724* (2013.01); *G01N 33/487* (2013.01); *G01N 33/6848* (2013.01); *G01N 33/6851* (2013.01); *G01N 33/92* (2013.01); *H01J 49/0004* (2013.01); *H01J 49/0027* (2013.01); *H01J 49/0031* (2013.01); *H01J 49/0036* (2013.01); *H01J 49/025* (2013.01); *H01J 49/044* (2013.01); *H01J 49/0404* (2013.01); *H01J 49/0409* (2013.01); *H01J 49/0422* (2013.01); *H01J 49/0445* (2013.01); *H01J 49/0459* (2013.01); *H01J 49/0463* (2013.01); *H01J 49/0468* (2013.01); *H01J 49/061* (2013.01); *H01J 49/068* (2013.01); *H01J 49/10* (2013.01); *H01J 49/14* (2013.01); *H01J 49/16* (2013.01); *H01J 49/164* (2013.01); *H01J 49/24* (2013.01); *H01J 49/26* (2013.01); *A61B 1/00013* (2013.01); *A61B 1/31* (2013.01); *A61B 5/14542* (2013.01); *A61B 2010/0083* (2013.01); *A61B 2017/320069* (2017.08); *A61B 2018/00577* (2013.01); *A61B 2018/00589* (2013.01); *A61B 2018/00994* (2013.01); *A61B 2218/002* (2013.01); *A61B 2218/008* (2013.01); *G01N 33/48735* (2013.01); *G01N 2001/2223* (2013.01); *G01N 2333/195* (2013.01); *G01N 2405/00* (2013.01); *G01N 2405/04* (2013.01); *G01N 2405/08* (2013.01); *G01N 2570/00* (2013.01); *G01N 2800/26* (2013.01); *G16B 20/00* (2019.02); *G16H 10/40* (2018.01); *G16H 15/00* (2018.01); *G16H 50/20* (2018.01)

(58) Field of Classification Search
CPC .. H01J 49/025; H01J 49/0404; H01J 49/0409; H01J 49/0422; H01J 49/044; H01J 49/0445; H01J 49/0459; H01J 49/0463; H01J 49/0468; H01J 49/061; H01J 49/068; H01J 49/10; H01J 49/14; H01J 49/16; H01J 49/164; H01J 49/24; H01J 49/26; A61B 1/041; A61B 1/2736; A61B 5/0066; A61B 5/0075; A61B 5/015; A61B 5/0507; A61B 5/055; A61B 6/032; A61B 6/037; A61B 8/13; A61B 10/00; A61B 10/0041; A61B 10/0233; A61B 10/0283; A61B 17/00; A61B 17/320068; A61B 18/00; A61B 18/04; A61B 18/042; A61B 18/14; A61B 18/1445; A61B 18/1815; A61B 18/20; A61B 90/13; A61B 1/00013; A61B 1/31; A61B 5/14542; A61B 2010/0083; A61B 2017/320069; A61B 2018/00577; A61B 2018/00589; A61B 2018/00994; A61B 2218/002; A61B 2218/008; A61F 13/38; C12Q 1/025; C12Q 1/04; C12Q 1/18; C12Q 1/24; G01N 1/2202; G01N 3/00; G01N 9/00; G01N 27/622; G01N 27/624; G01N 30/724; G01N 33/487; G01N 33/6848;

G01N 33/6851; G01N 33/92; G01N 33/48735; G01N 2001/2223; G01N 2333/195; G01N 2405/00; G01N 2405/04; G01N 2405/08; G01N 2570/00; G01N 2800/26; G16B 20/00; G16H 10/40; G16H 15/00; G16H 50/20; Y02A 90/10

USPC .................. 250/281, 282, 288; 702/27, 28

See application file for complete search history.

(56) References Cited

U.S. PATENT DOCUMENTS

| | | | |
|---|---|---|---|
| 5,663,561 | A | 9/1997 | Franzen et al. |
| 5,696,352 | A | 12/1997 | Kourimsky |
| 7,057,168 | B2 | 6/2006 | Miller et al. |
| 7,247,845 | B1 | 7/2007 | Gebhardt et al. |
| 8,980,577 | B2 | 3/2015 | Maier et al. |
| 10,077,461 | B2 | 9/2018 | Beaulieu et al. |
| 10,867,779 | B2 * | 12/2020 | Richardson ......... H01J 49/0036 |
| 2005/0179366 | A1 | 8/2005 | Rose et al. |
| 2005/0230611 | A1 | 10/2005 | Denny et al. |
| 2005/0255606 | A1 | 11/2005 | Ahmed et al. |
| 2006/0027744 | A1 | 2/2006 | Stults et al. |
| 2006/0038120 | A1 | 2/2006 | Lean et al. |
| 2007/0114388 | A1 | 5/2007 | Ogawa et al. |
| 2007/0176092 | A1 | 8/2007 | Miller et al. |
| 2008/0132890 | A1 | 6/2008 | Woloszko et al. |
| 2009/0088772 | A1 | 4/2009 | Blumenkranz |
| 2009/0272893 | A1 | 11/2009 | Hieftje et al. |
| 2009/0294660 | A1 | 12/2009 | Whitehouse et al. |
| 2010/0273666 | A1 | 10/2010 | Bernatchez et al. |
| 2011/0012016 | A1 | 1/2011 | Maier et al. |
| 2011/0049352 | A1 | 3/2011 | Ding et al. |
| 2011/0066147 | A1 | 3/2011 | He et al. |
| 2012/0043460 | A1 | 2/2012 | Wouters et al. |
| 2012/0048264 | A1 | 3/2012 | Finlay et al. |
| 2012/0141789 | A1 | 6/2012 | Wyndham et al. |
| 2012/0190055 | A1 * | 7/2012 | Cezar ..................... G01N 33/94 250/282 |
| 2012/0201846 | A1 | 8/2012 | Rehm et al. |
| 2012/0308555 | A1 | 12/2012 | Polakiewicz et al. |
| 2013/0123919 | A1 | 5/2013 | Goldstein et al. |
| 2013/0303846 | A1 | 11/2013 | Cybulski et al. |
| 2013/0306856 | A1 | 11/2013 | Trimpin et al. |
| 2014/0039480 | A1 | 2/2014 | Van Wyk |
| 2014/0127734 | A1 | 5/2014 | Charretier et al. |
| 2014/0268134 | A1 | 9/2014 | O'Connor |
| 2014/0303449 | A1 | 10/2014 | Balog |
| 2014/0336456 | A1 | 11/2014 | Demers et al. |
| 2014/0350534 | A1 | 11/2014 | Kircher et al. |
| 2015/0087003 | A1 | 3/2015 | Charles et al. |
| 2015/0144782 | A1 | 5/2015 | Fogwill et al. |
| 2015/0340215 | A1 | 11/2015 | Pringle et al. |
| 2016/0341712 | A1 | 11/2016 | Agar |
| 2018/0047551 | A1 | 2/2018 | Jones et al. |
| 2018/0053644 | A1 | 2/2018 | Jones et al. |
| 2018/0254177 | A1 | 9/2018 | Gao et al. |
| 2018/0256239 | A1 | 9/2018 | Johnson et al. |
| 2020/0144044 | A1 | 5/2020 | Zarrine-Afsar et al. |

FOREIGN PATENT DOCUMENTS

| | | |
|---|---|---|
| CA | 2876731 A1 | 12/2013 |
| CN | 1672238 A | 9/2005 |
| CN | 1774627 A | 5/2006 |
| CN | 101073137 A | 11/2007 |
| CN | 101178381 A | 5/2008 |
| CN | 101372502 A | 2/2009 |
| CN | 102169791 A | 8/2011 |
| CN | 102768236 A | 11/2012 |
| CN | 103426712 A | 12/2013 |
| CN | 103456595 A | 12/2013 |
| CN | 103748233 A | 4/2014 |
| CN | 103764812 A | 4/2014 |
| CN | 104062348 A | 9/2014 |
| CN | 104284984 A | 1/2015 |
| EP | 1225616 A2 | 7/2002 |
| EP | 1530721 A2 | 5/2005 |
| EP | 1650549 A2 | 4/2006 |
| EP | 2592420 A1 | 5/2013 |
| EP | 3266035 A1 | 1/2018 |
| GB | 2420008 B | 5/2006 |
| GB | 2462190 A | 2/2010 |
| GB | 2491484 A | 12/2012 |
| GB | 2507298 A | 4/2014 |
| JP | 2000097913 A | 4/2000 |
| JP | 2008249563 A | 10/2008 |
| WO | 2008148557 A2 | 12/2008 |
| WO | 2009070555 A1 | 6/2009 |
| WO | 2014139018 A1 | 9/2014 |
| WO | 2014167828 A1 | 10/2014 |
| WO | 2018142091 A2 | 8/2018 |

OTHER PUBLICATIONS

Combined Search and Examination Report under Sections 17 and 18(3), for Application No. GB2110454.2, dated Aug. 19, 2021, 9 pages.

Dixit, et al., "Development of a High Sensitivity Rapid Sandwich ELISA Procedure and Its Comparison with the Conventional Approach", Anal Chem 82(16):7049-7052 (2010).

Gholami, A.M., et al., "Global Proteome Analysis of the NCI-60 Cell Line Panel", Cell Reports 4(3):609-620 (2013).

Hanson, et al., "Polymer-coated reversed-phase packings in high-performance liquid chromatography", J Chromat. A656:369-380 (1993). Abstract.

Herog, R., et al., "LipidXplorer: A Software for Consensual Cross-Platform Lipidomics" Plos ONE 7(1): e29851.

Kind, T., et al., "LipidBlast-in-silico tandem mass spectrometry database for lipid identification", Nat Methods 10(8):755-758 (2013).

Kochenmuss, R., "Ion Formation Mechanisms in UV-MALDI" Analyst 131:966-986 (2006).

Krishtalik, Lev I., "The mechanism of the proton transfer: an outline", Biochimica et Biophysica Acta (BBA)—Bioenergetics 1458(1):6-27 (2000).

Lipid Maps® [online] [retrieved on Jul. 2, 2021], Retrieved from URL: http://www.lipidmaps.org , 3 pages.

Shamir, E.R., Ewald, A.J., "Three-dimensional organotypic culture: experimental models of mammalian biology and disease", Nature Rev Mol Cell Biol 15(10):647-664 (2014).

Shoemaker, Robert H., "The NCI60 Human Tumour Cell Line Anticancer Drug Screen", Nature Reviews Cancer 6:813-823 (2006).

Weinstein, "Integromic analysis of the NCI-60 cancer cell lines", Breast Dis 19:11-22 (2004). Abstract.

White, D.C., et al., "Fatty Acid Composition of the Complex Lipids of Staphylococcus aureus During the Formation of Membrane-bound Electron Transport System", Journal of Bacteriology 95:2198-2209 (1968).

CNOA_20191104563.7, dated Oct. 11, 2021, original document 14 pages.

Examination Report under Section 18(3) for Application No. GB1715750.4, dated Oct. 11, 2021, 5 pages.

Chen Liru, Master student of Nanchang University, Thesis defense date Jun. 7, 2014 "Atmospheric pressure true mass spectrometry technology for rapid identification of lung cancer tissues and experimental study on tissues adjacent to lung cancer—Ambient Mass Spectrometry for Fast Identification of Lung Cancer", original and translated documents.

Partial European Search Report for EP20181905.9, dated Aug. 27, 2020, 14 pages.

Roddy, T., et al., "Imaging of Freeze-Fractured Cells with in Situ Fluorescence and Time-of-Flight Secondary Ion Mass Spectrometry", Analytical Chemistry 74(16):4011-4019(2002).

Petrotchenko, E.V., et al., "Combining Fluorescence Detection and Mass Spectrometric Analysis for Comprehensive and Quantitative Analysis of Redox-Sensitive Cysteines in Native Membrane Proteins", Analytical Chemistry 78 (23):7959-7966 (2006).

(56) References Cited

OTHER PUBLICATIONS

Ablonczy, Z., et al., "The utilization of fluorescence to identify the components of lipofuscin by imaging mass spectrometry", Proteomics 14(7-8):936-944.
Enthaler, B., et al., "Improved sample preparation for MALDI-MSI of endogenous compounds in skin tissue sections and mapping of exogenous active compounds subsequent to ex-vivo skin penetration" Anal Bioanal Chem 402:1159-1167 (2012).
Extended EP search report for EP Application No. 20172634.6, dated Sep. 14, 2020, 8 pages.
CNOA for application No. CN201680025801.0 dated Oct. 12, 2020 original document and translation.
Adams, F., et al., "Inorganic Mass Spectrometry", (1993) Abstract.
Dong, Y.M.B.A., "Polymer Analysis Handbook", China Petromchemical Press (2004) 8 pages.
Examination Report under Section 18(3) for Application No. GB1713964.3, dated Oct. 26, 2020, 3 pages.
Examination report for Application No. GB1715787.6, dated Oct. 26, 2020, 3 pages.
Shin, Y-S., et al., "Desorption Electrospray Ionization-Mass Spectrometry of Proteins" Analytical Chemistry 79:3514-3518 (2007).
Search and Examination Report under Sections 17 and 18(3) for GB1715767.8, dated Nov. 26, 2020, 6 pages.
Waters DESI System Operators Guide 715004701/Revision A, Waters Corporation, [online] Jan. 2015 [retrieved or Dec. 3, 2020]. Retrieved from Internet URL: https://www.waters.com/webassets/cms/support/docs/715004701ra.pdf. 141 pages.
Chen, X., ed., "Liquid Chromatography-Mass Spectrometry—Chapter 8", in Principle and Application of Chromatographic Analysis Technology, Chinese People's Public Security University Press, (Jan. 2014) 6 pages.
Song, Y., et al., "Rapid ambient mass spetrometric profiling of intact, untreated bacteria using desoprtion electrospray ionization" ChemComm pp. 61-63 (2007).
Wiseman, J.M. and Li, J.B., "Eluction, Partial Separation, and Identification of Lipids Directly from Tissue Slices on Planar Chromatogrpahy Media by Desoprtion Electrospray Ionization Mass Spectrometry", Anal Chem 82:8866-8874 (2010).
Examination Report under Section 18(3) for Application No. GB2015580.0, dated Jan. 21, 2021, 4 pages.
Krouskop, T., et al., "Elastic moduli of breast and prostate tissues under compression" Ultrasonic Imaging 20:260-274 (1998).
Aberg, P., et al., "Skin Cancer Identification Using Multifrequency Electrical Impedance—A Potential Screening Tool", IEEE Transactions on Biomedical Engineering, 51(12): 2097-2102 (2004).
Extended European Search Report for Application No. 20210062.4, dated Mar. 9, 2021, 13 pages.
Rath, C.M., et al., "Molecular Analysis of Model Gut Microbiotas by Imaging Mass Spectrometry and Nanodesorption Electrospray Ionization Reveals Dietary Metabolite Tranformations" Analytical Chemistry 84(21):9259-9267 (2012).
Fenselau, C.C., "Rapid Characterization of Microorganisms by Mass Spectrometr—What Can Be Learned and How" Journal of the American Society for Mass Spectrometry 24(8):1161-1166 (2013).
Jetrecht, C. et al., "Modern Biomolecular Mass Spectrometry and its Role in Studying Virus Structure, Dynamics and Assembly" Angewandte Chemie International Edition 50(36):8248-8262 (2011).
Forbes, T.P. et al., "Chemical imaging of ailincial Fingerprints by desorption electro-flow focusing ionization mass spectrometry" Analyst 139(12):2982-2985 (2014).
Examination Report for GB Patent Application No. GB2015580.0, dated Mar. 12, 2021.
Cornett, D. S., et al., "A Novel Histology-directed Strategy for MALDI-MS Tissue Profiling That Improves Throughput and Cellular Specificity in Human Breast Cancer", American Society for Biochemistry and Molecular Biology, p. 1975-1983, Jul. 18, 2006.
EP Search Report for application No. 20154538.1 dated May 12, 2020, 14 pages.
CNOA for Application No. 201680026939.2, dated Apr. 27, 2021, original 10 pp.
CNOA for Application No. 201910350273.1 dated May 8, 2021, 15 pages.
Examination Report under Section 18(3) for Application No. GB1714165.6, dated Mar. 22, 2021, 6 pages.
Examination Report under Section 18(3) for Application No. GB1715750.4 dated Mar. 22, 2021, 5 pages.
Extended European Search Report for Application No. 21156646.8, dated May 10, 2021,10 pages.
Hillenkamp, F., et al., "Matrix-Assisted Laser Desorption/Ionization Mass Spectrometry of Biopolymers", Anal Chem 63 (24): 1193A-1203A (1991). Abstract.
Hrabak, J., et al., "Matrix-Assisted Laser Desorption lonizataion-Time of Flight (MALDITOF) Mass Spectrometry for Detection of Antibiotic Resistance Mechanisms: from Research to Routine Diagnosis", CMR Journal 26(1): 103-114 (2013).
Gonzalez-Dominguez, R., et al. "Development of a metabolomic approach based on urine samples and direct infusion mass spectrometry", Analytical Biochemistry, 465:20-27, Jul. 23, 2014.
Djidja, M-C., et al., "Novel molecular tumour classification using MALDI-mass spectrometry imaging of tissue micro-array", Analytical and Bioanalytical Chemistry, 397(2): 587-601, Mar. 4, 2010.

\* cited by examiner

Fig. 31
Awake craniotomy for left frontal low grade glioma. With Raman analysis
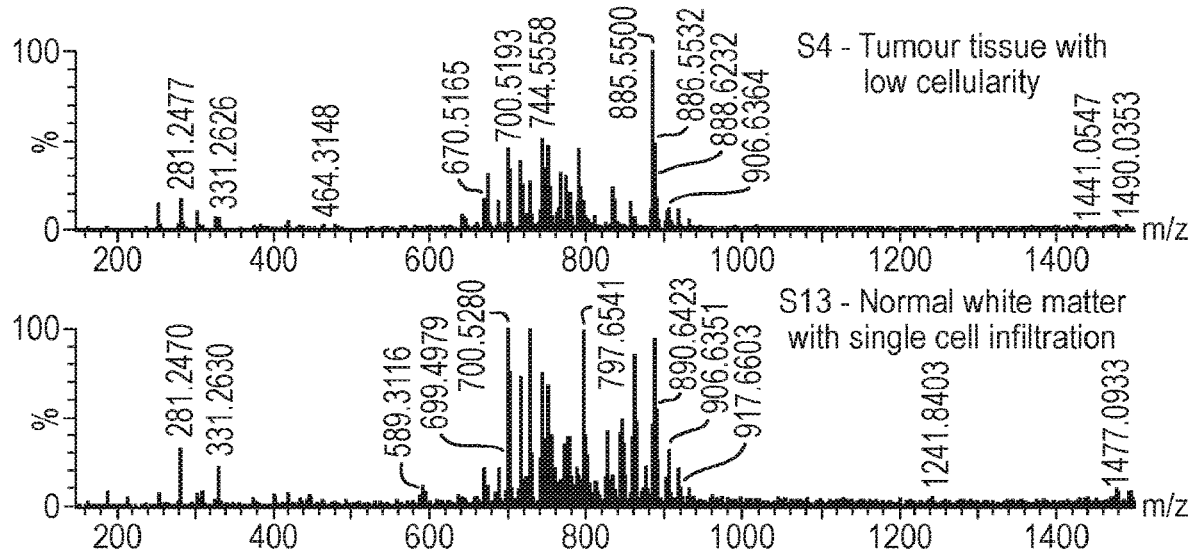
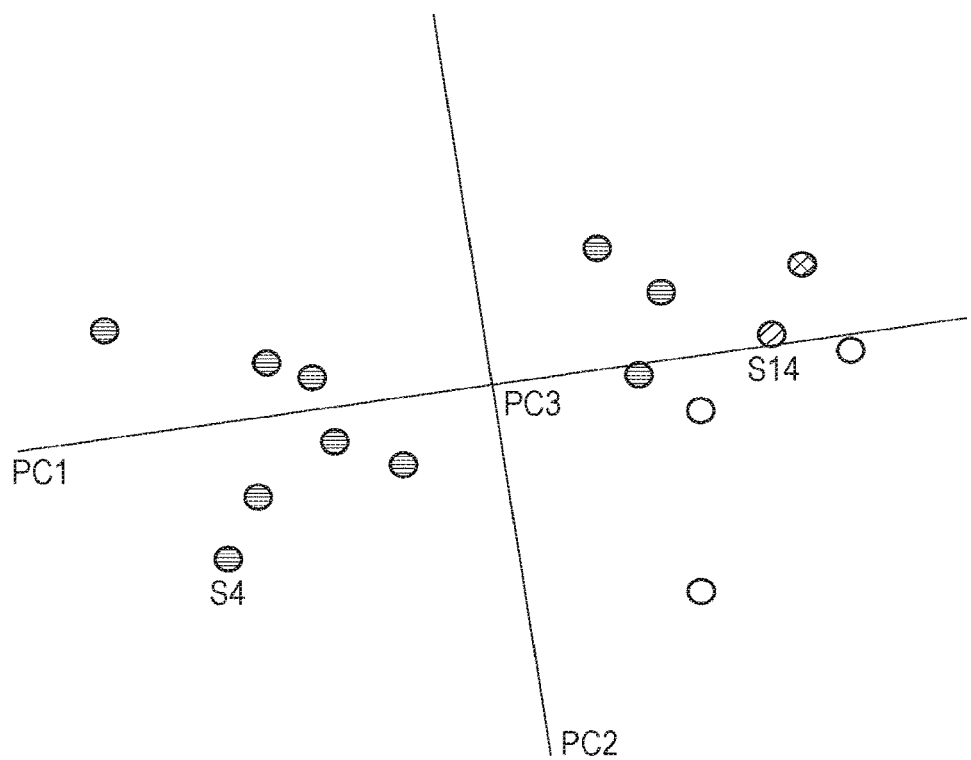
- Low grade astrocytoma
- Normal white matter infiltrated by tumour cells
- Normal white matter with single cell infiltration
- Mixed samples containing both normal cortex and tumour

- ⊗ Malignant tissue
- ⊘ Tumor section fibrous section
- ⊕ Tumor section adipose tissue
- ⊜ Tumor section glandular tissue
- ○ Necrotic

- ⊗ Malignant tissue
- ⊘ Tumor section fibrous section
- ⊕ Tumor section adipose tissue
- ⊜ Tumor section glandular tissue

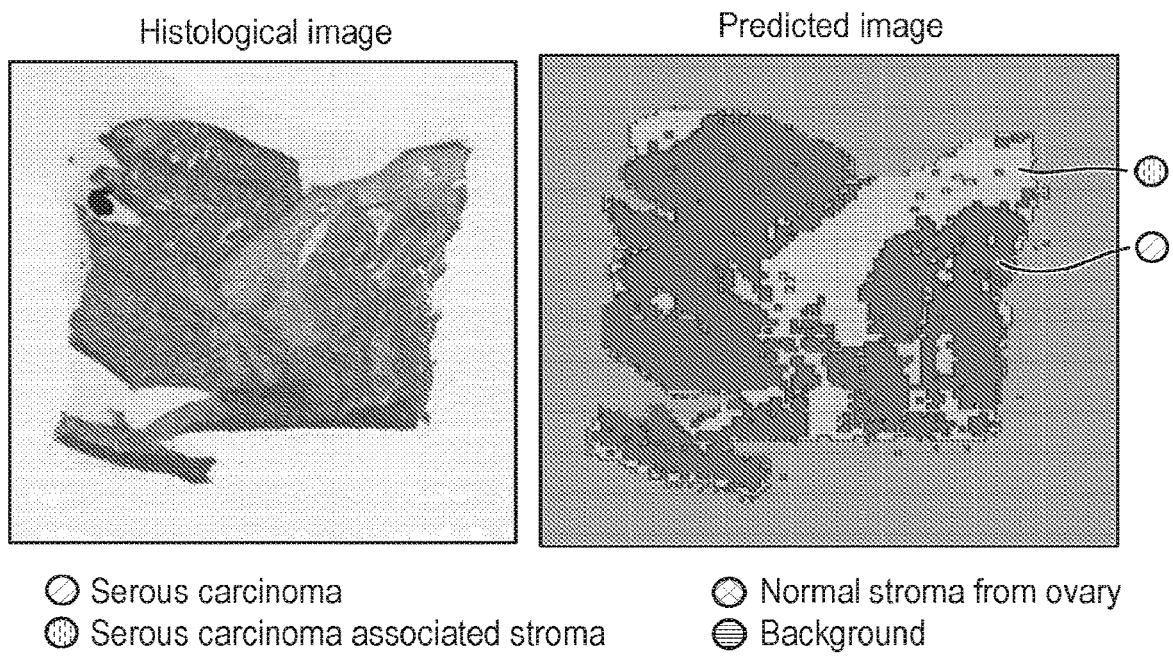

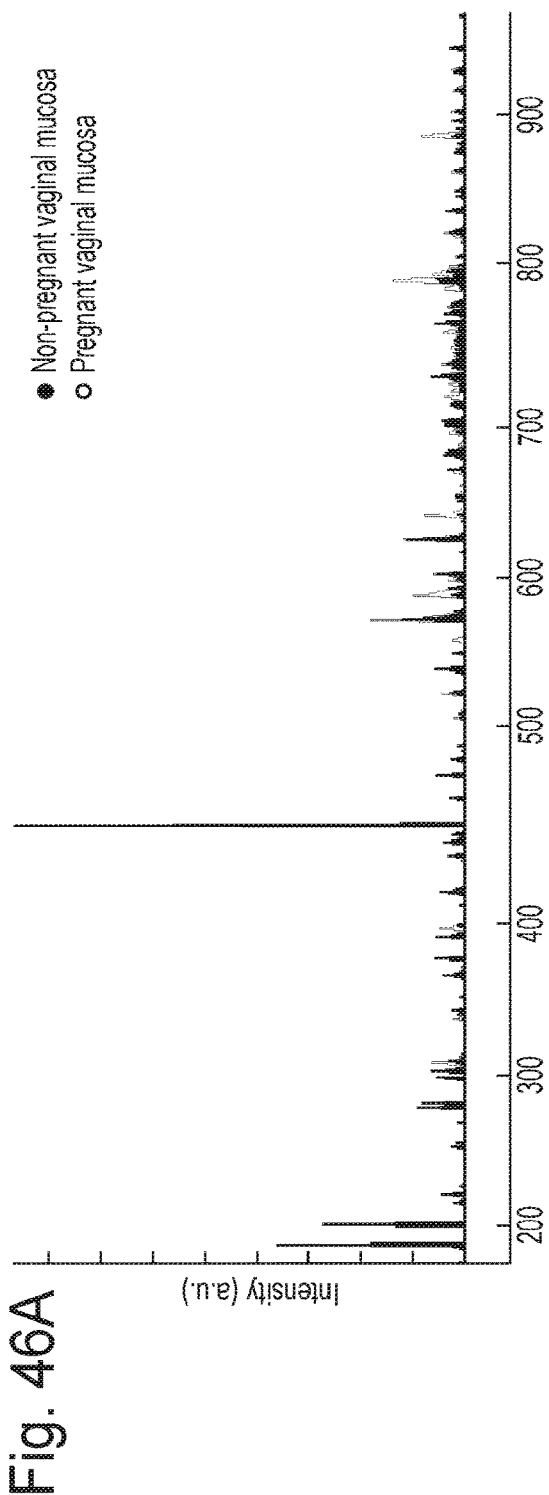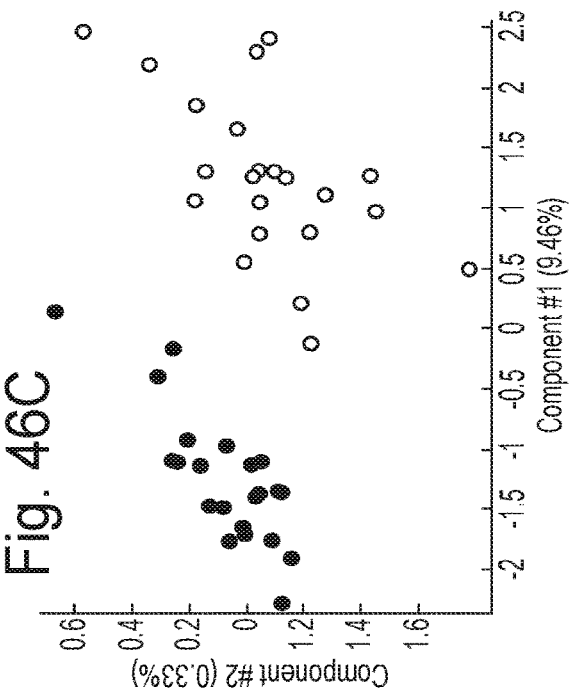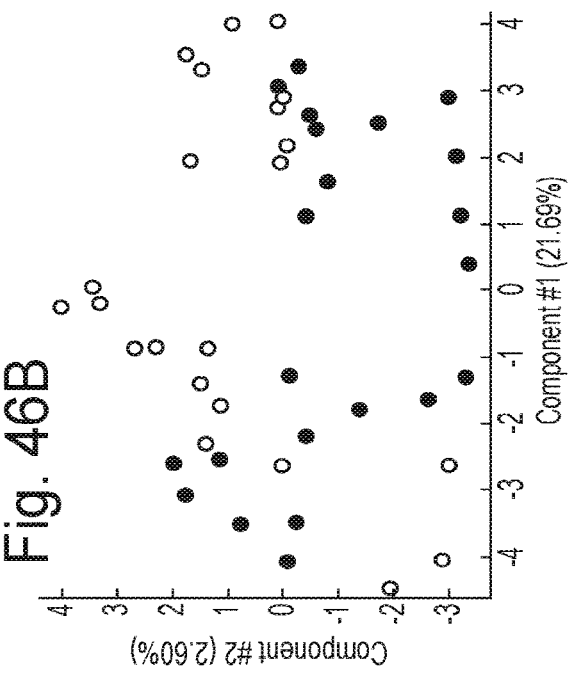
Fig. 46A
Fig. 46B
Fig. 46C

Fig. 47A
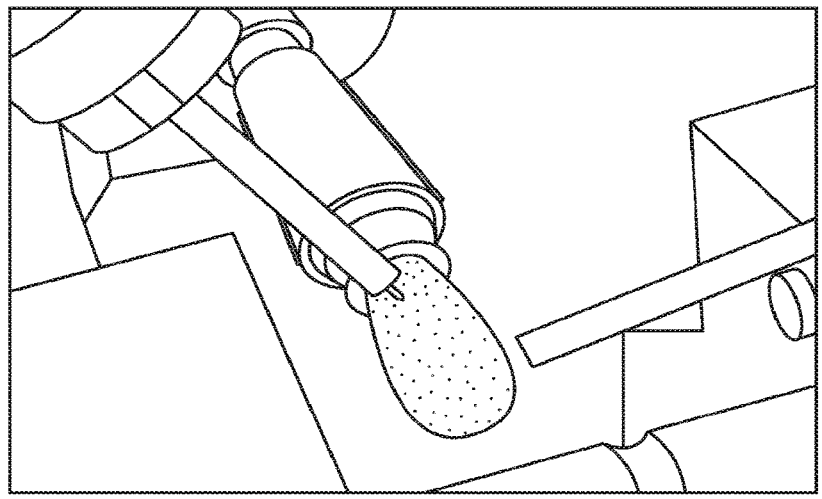
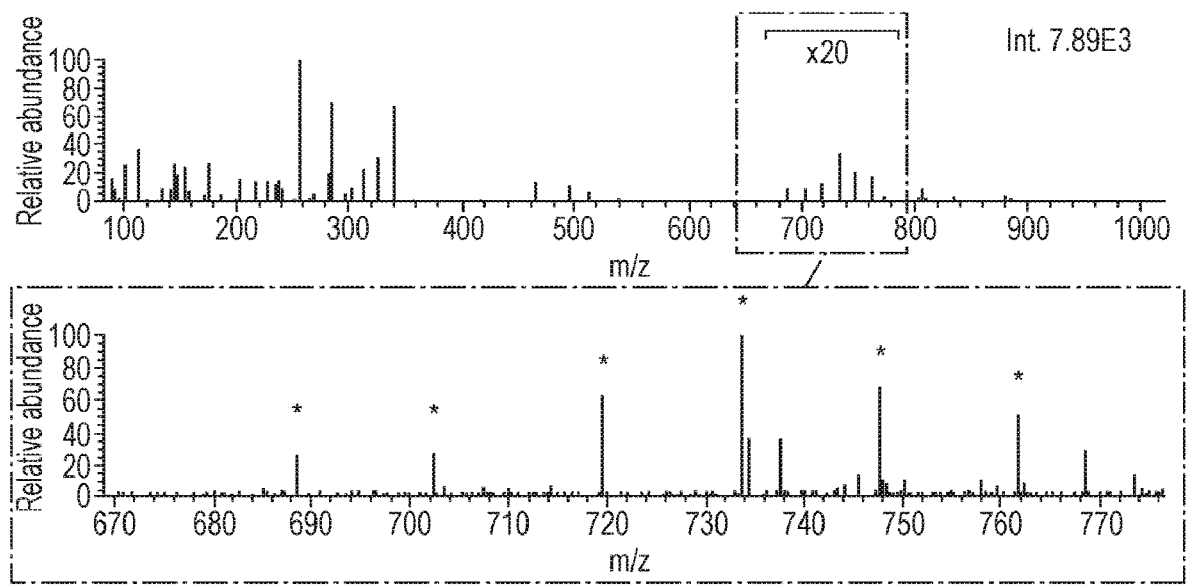

Fig. 47B
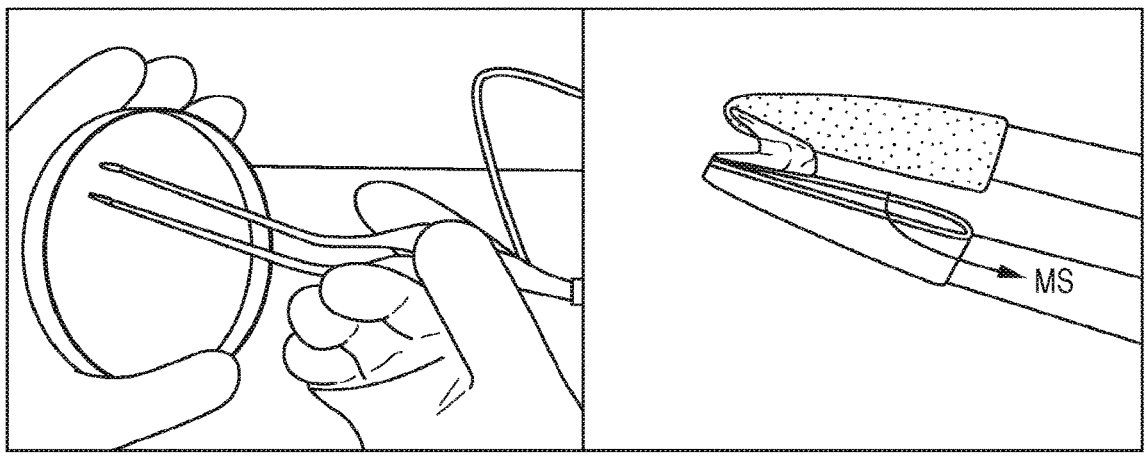
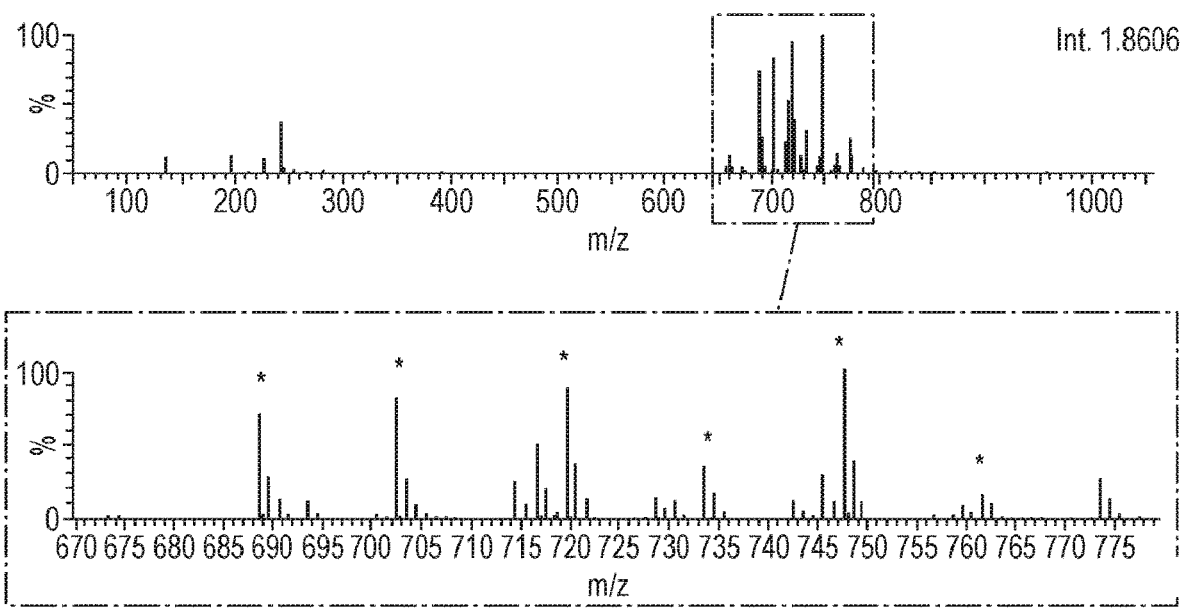

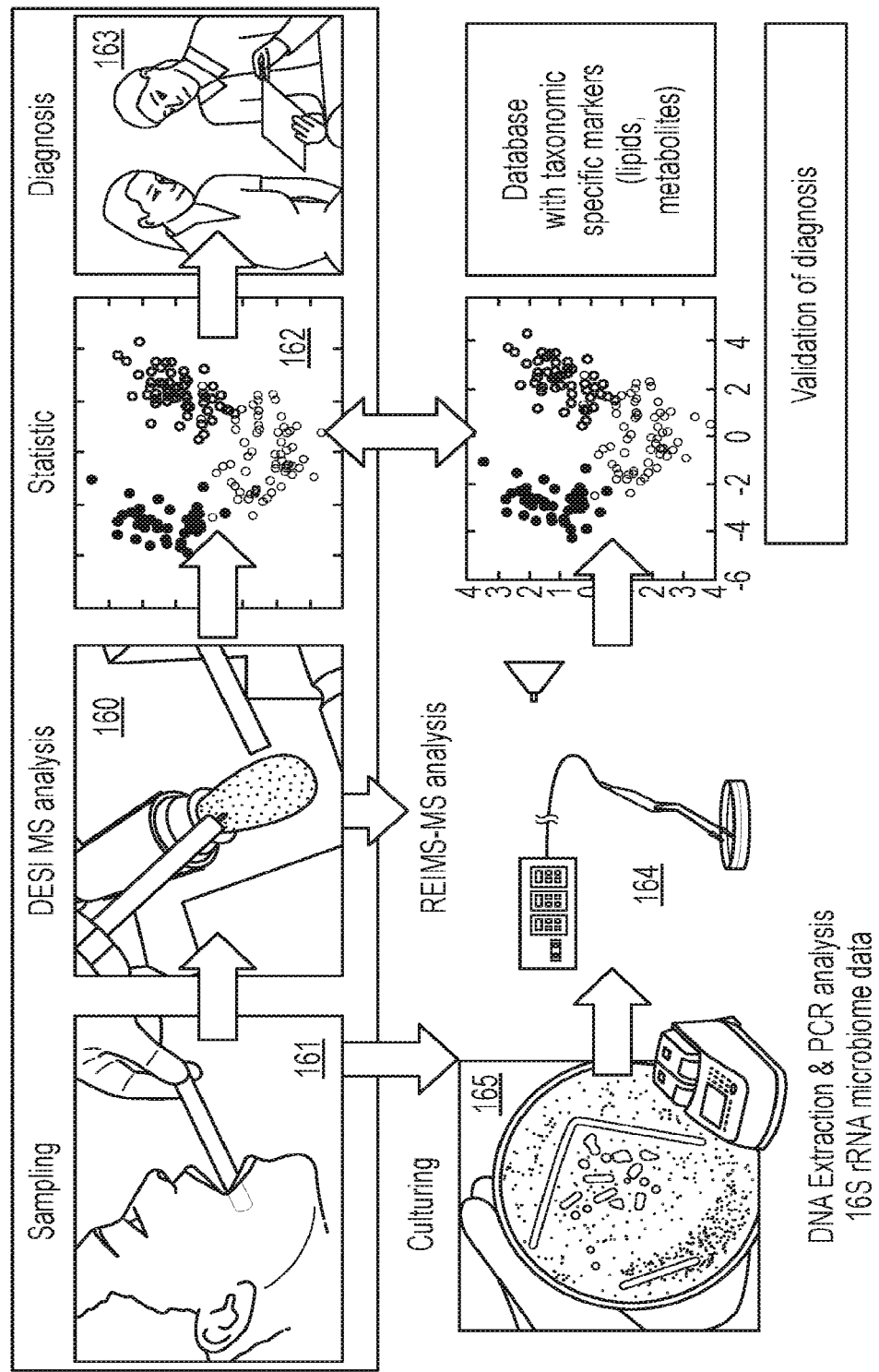

○ Porcine brain-day1
+ Porcine brain-day2
* Porcine brain-day3
● Porcine brain-day4

* Porcine kidney cortex
○ Porcine liver
● Porcine brain
○ Porcine heart muscle
* Porcine muscle □ Colonic adenocarcinoma
○ Healthy colon mucosa
△ Adenomatous polyp □ Stomach adenocarcinoma
○ Healthy stomach mucosa
△ Healthy stomach submucosa

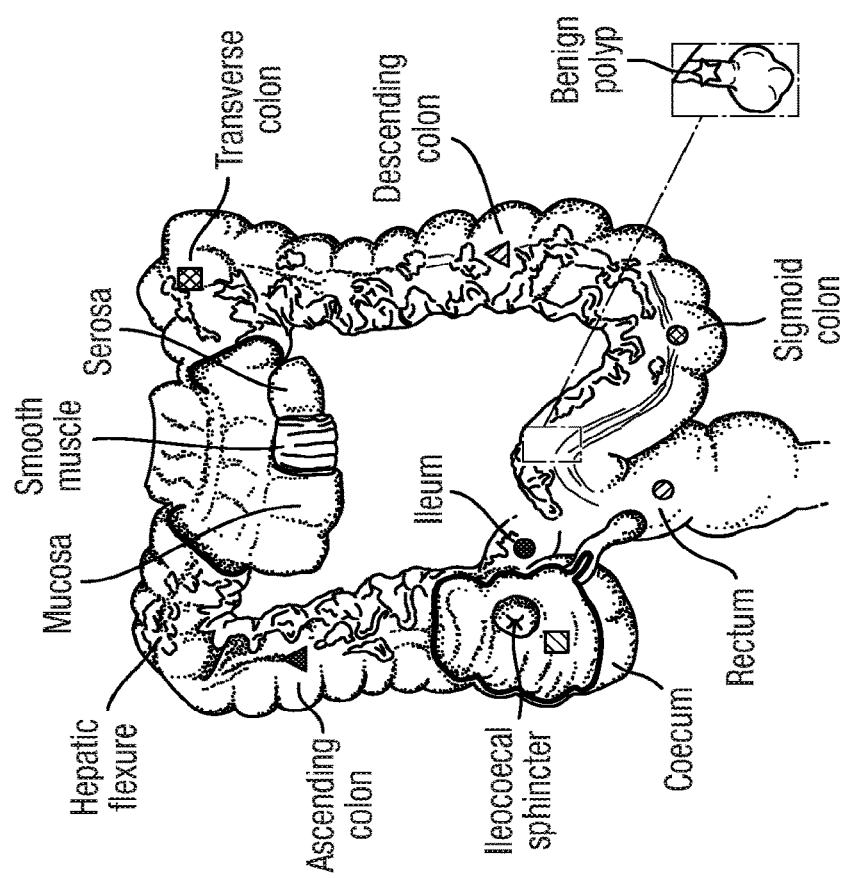
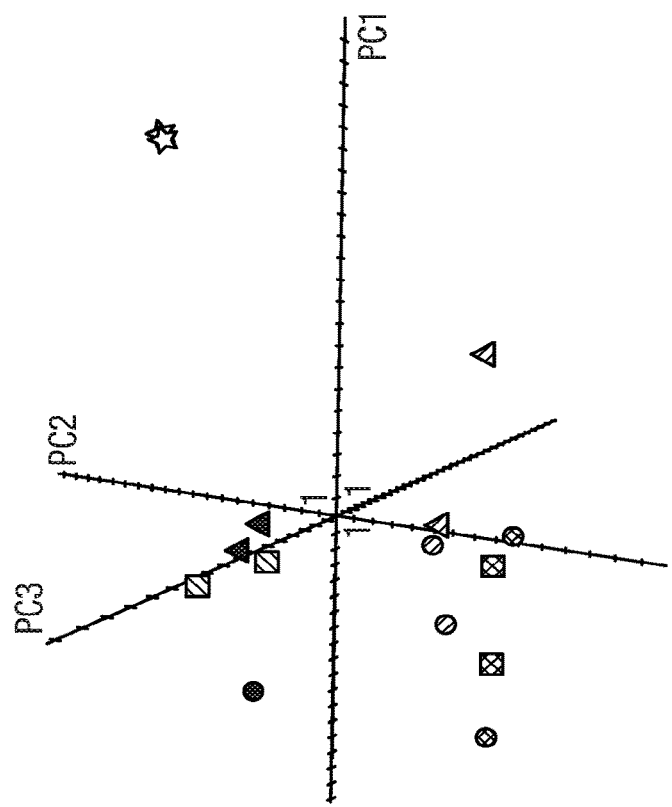
Fig. 54A
Fig. 54B

Fig. 58 (Cont.)
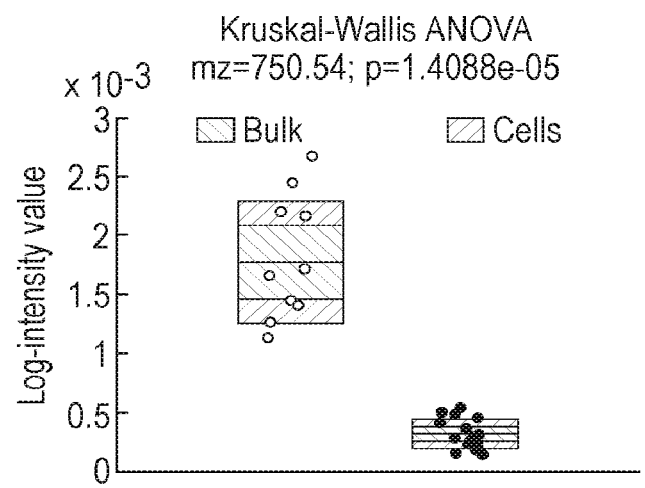
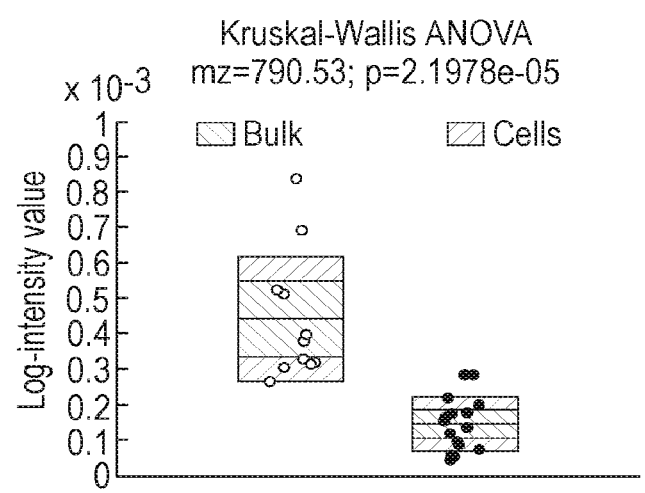
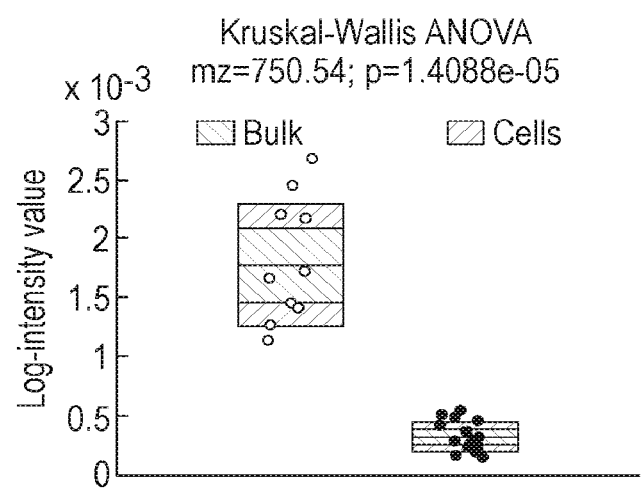

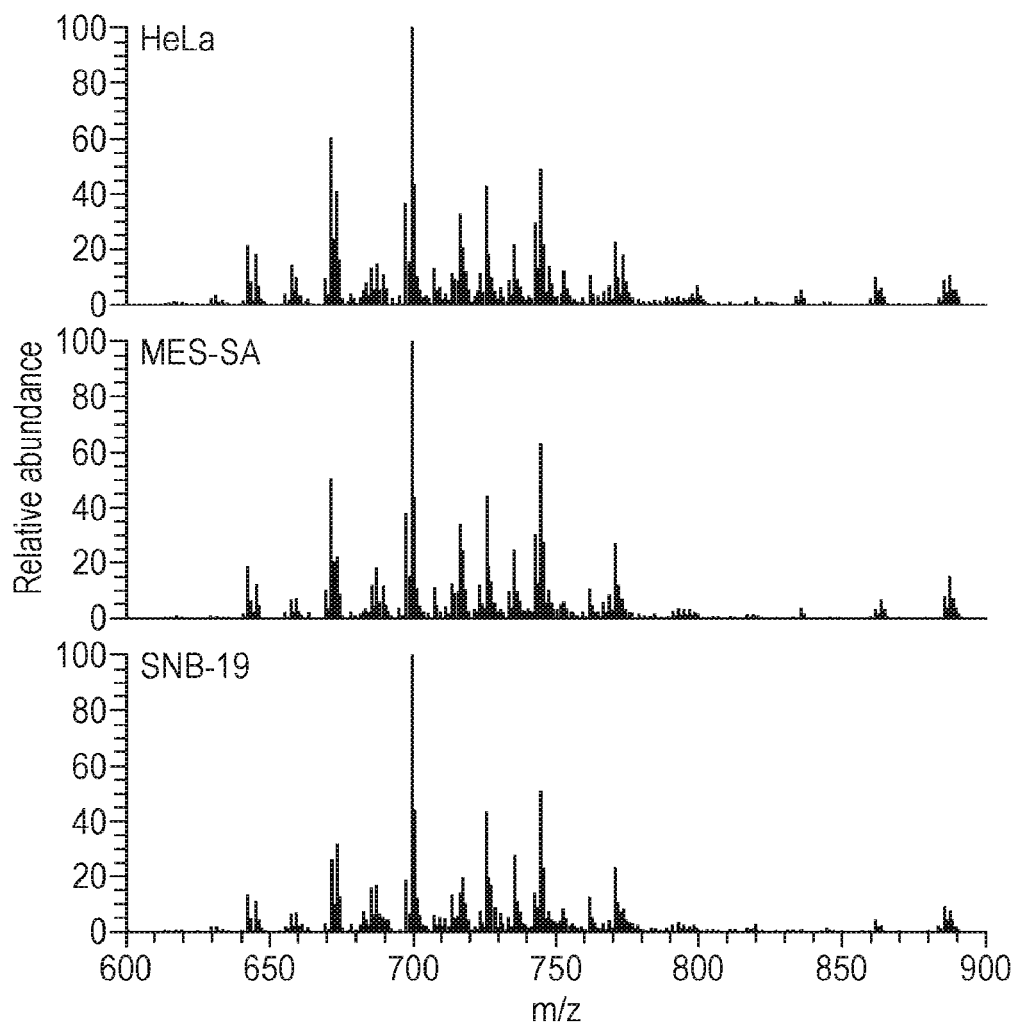

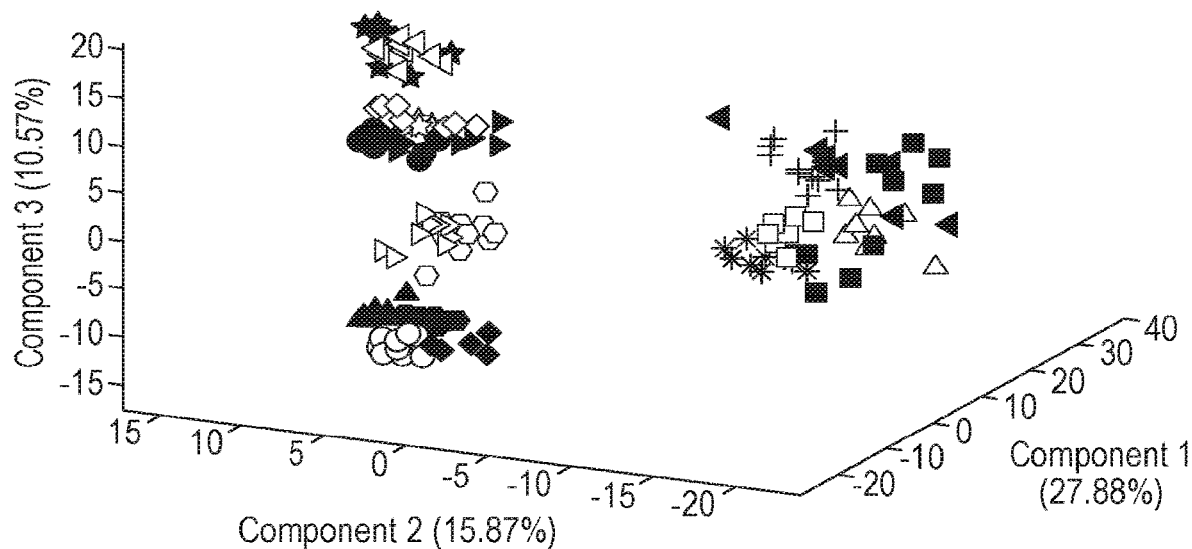

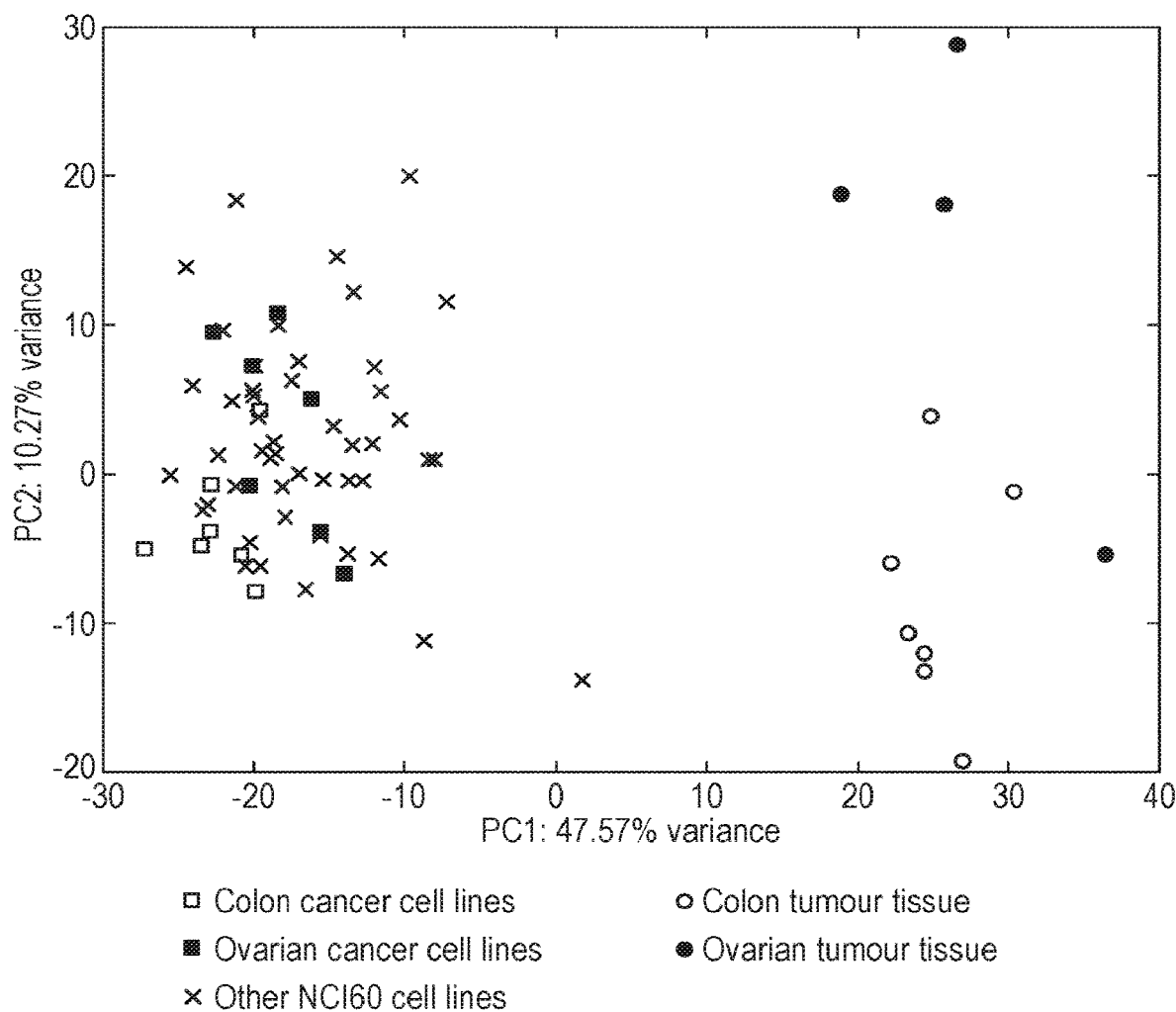

Fig. 66
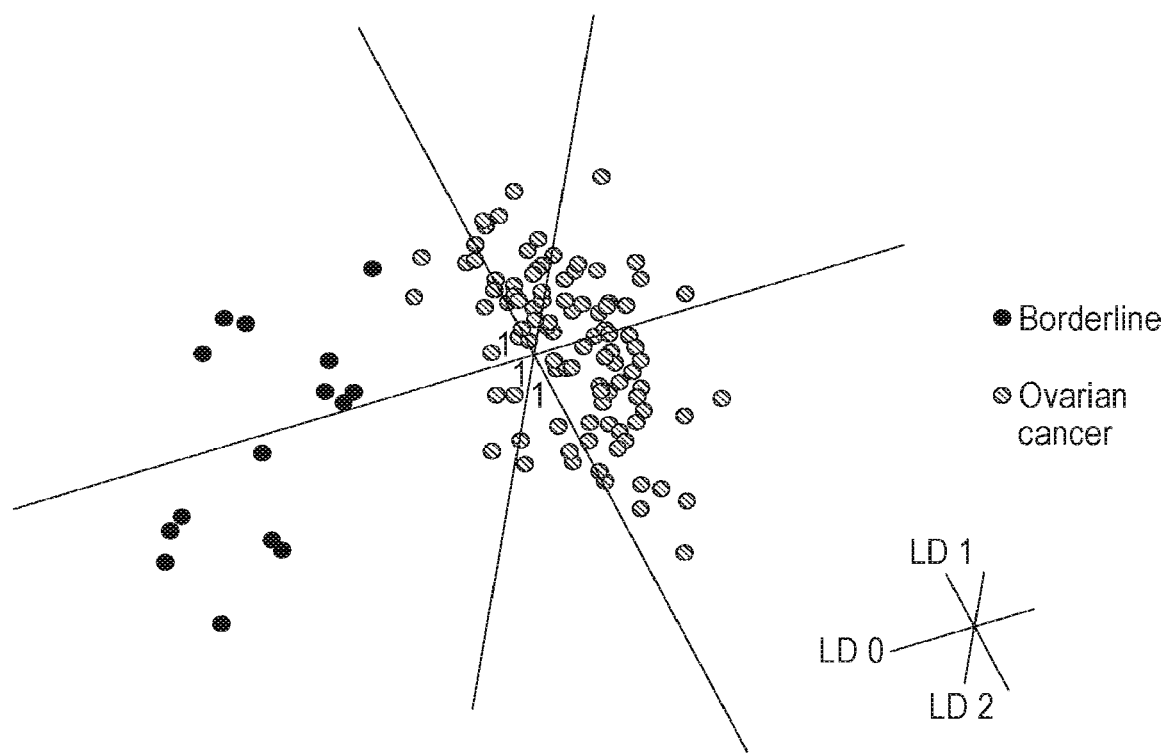
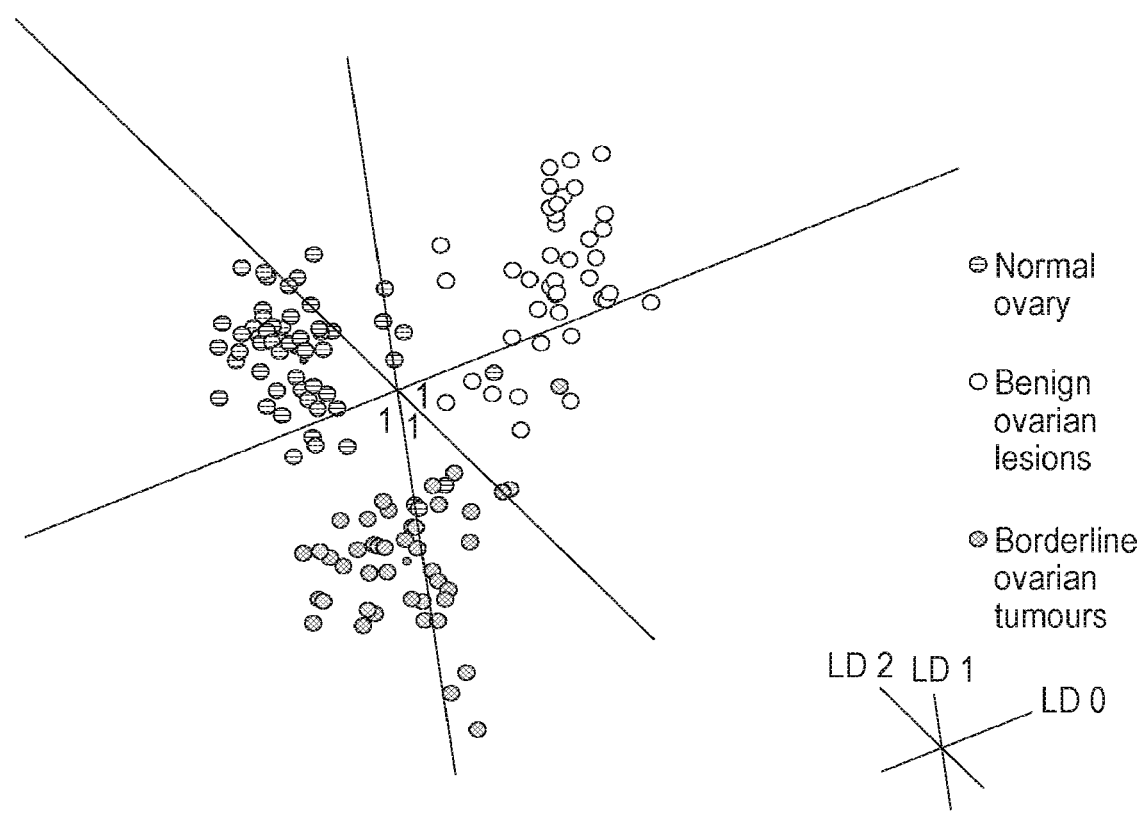

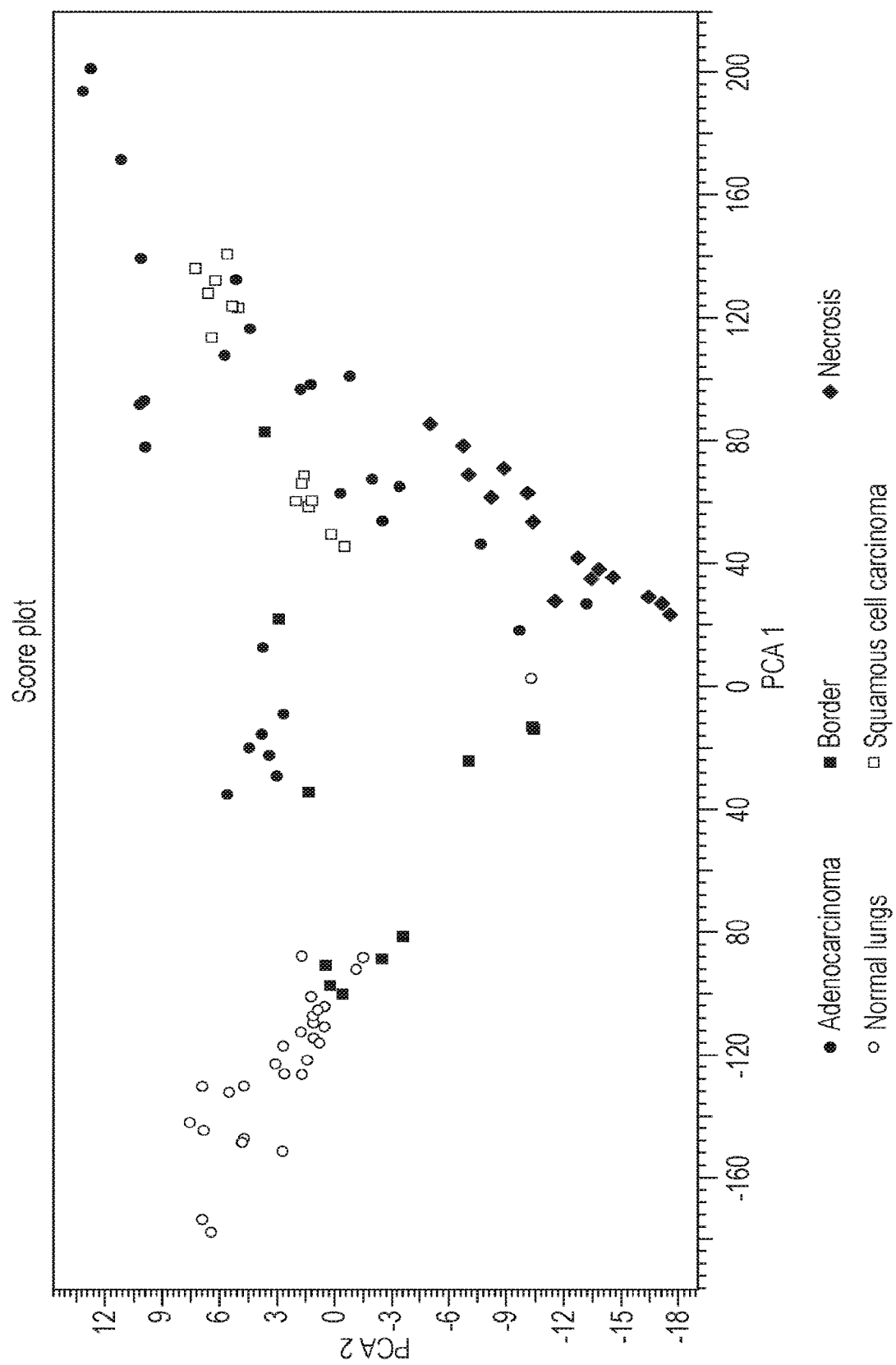

Fig. 68

○ Normal ovary
● Normal peritoneum
■ Normal fallopian tube

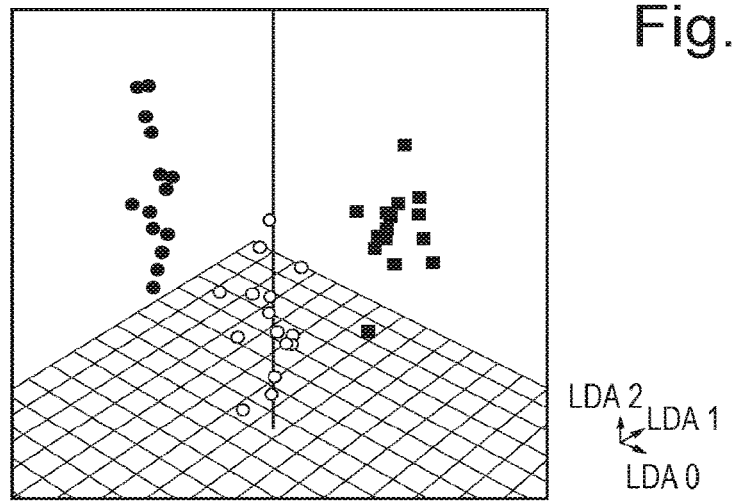

| Overall correct classification 97.7% | Predicted class | | |
|---|---|---|---|
| | Normal fallopian | Normal ovary | Normal peritoneum |
| Actual class | Normal fallopian | 100% (15) | 0% (0) | 0% (0) |
| | Normal ovary | 6.7% (1) | 93.3% (14) | 0% (0) |
| | Normal peritoneum | 0% (0) | 0% (0) | 100% (14) |

○ Ovarian cancer
● Normal ovary
■ Normal fallopian tube
□ Normal peritoneum

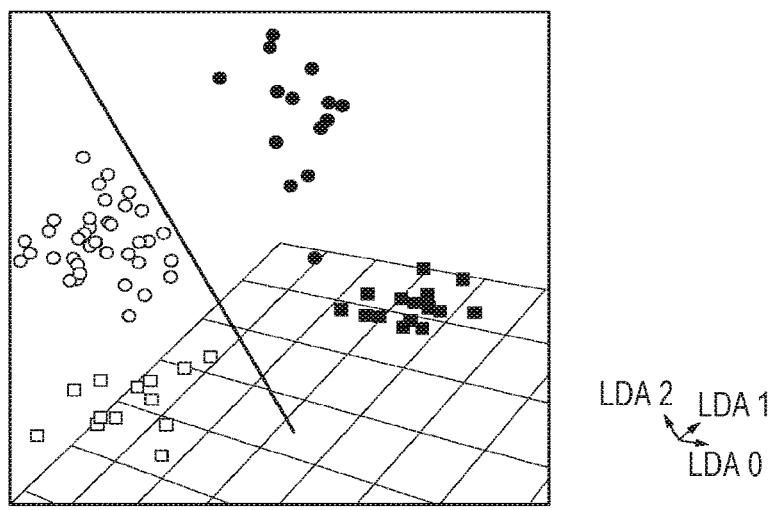

| Overall correct classification 97.6% | Predicted class | | | |
|---|---|---|---|---|
| | Normal fallopian | Normal ovary | Normal peritoneum | Ovarian cancer |
| Actual class | Normal fallopian | 93.3% (14) | 6.7% (1) | 0% (0) | 0% (0) |
| | Normal ovary | 0% (0) | 100% (15) | 0% (0) | 0% (0) |
| | Normal peritoneum | 0% (0) | 0% (0) | 100% (14) | 0% (0) |
| | Ovarian cancer | 0% (0) | 0% (0) | 2.6% (1) | 97.4% (38) |

○ Ovarian cancer
● Benign
■ Borderline

| Overall correct classification 94.7% | | Predicted class | | |
|---|---|---|---|---|
| | | Benign | Borderline | Ovarian cancer |
| Actual class | Benign | 100% (32) | 0% (0) | 0% (0) |
| | Borderline | 0% (0) | 100% (33) | 0% (0) |
| | Ovarian cancer | 0% (0) | 11.3% (6) | 88.7% (43) |

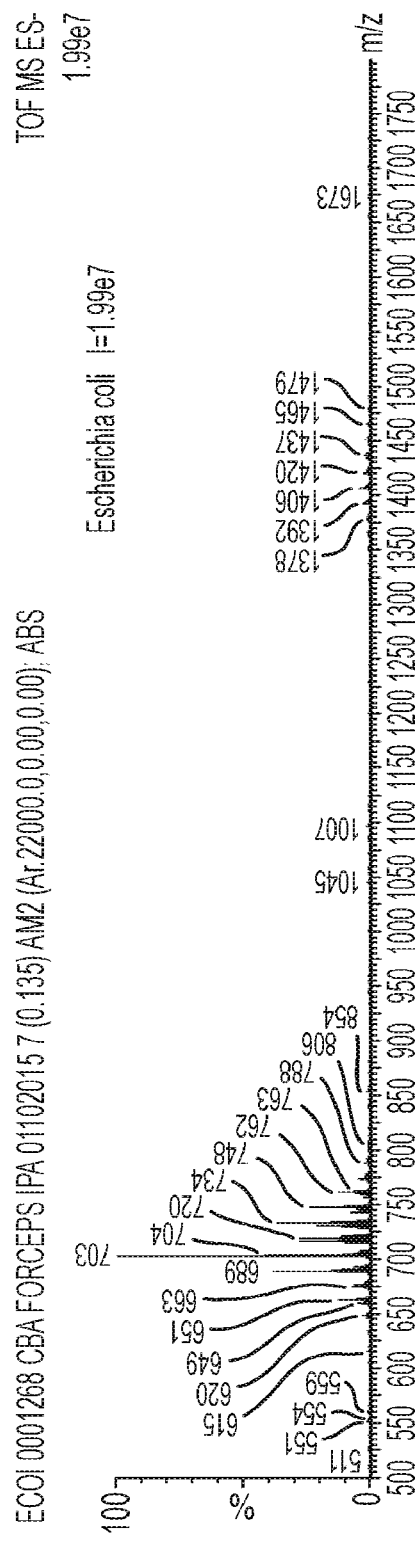
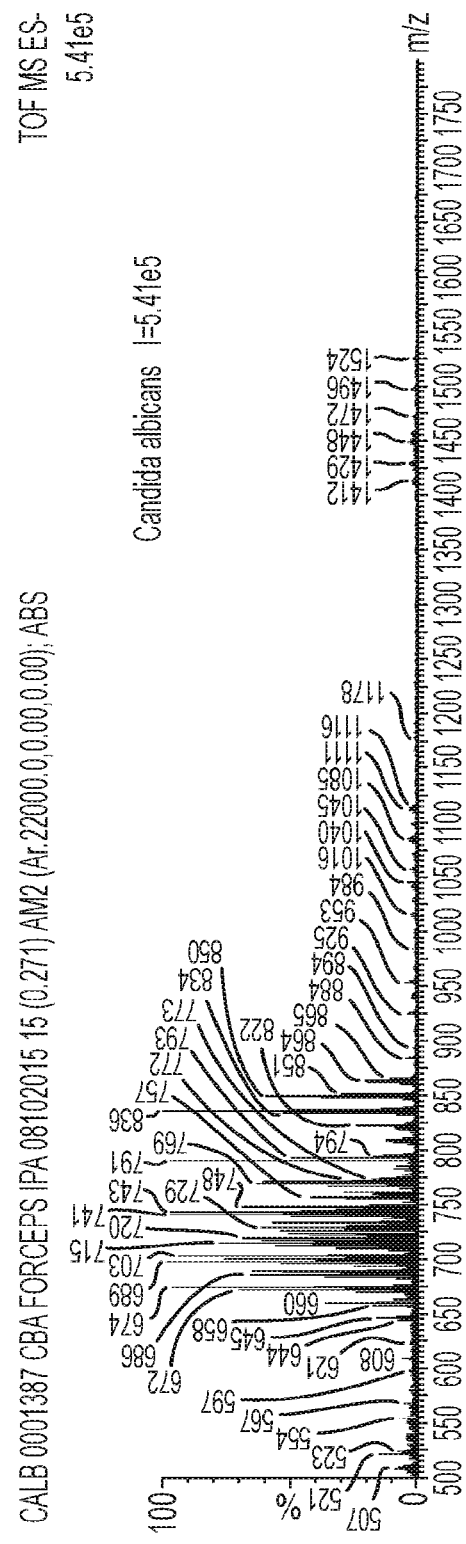

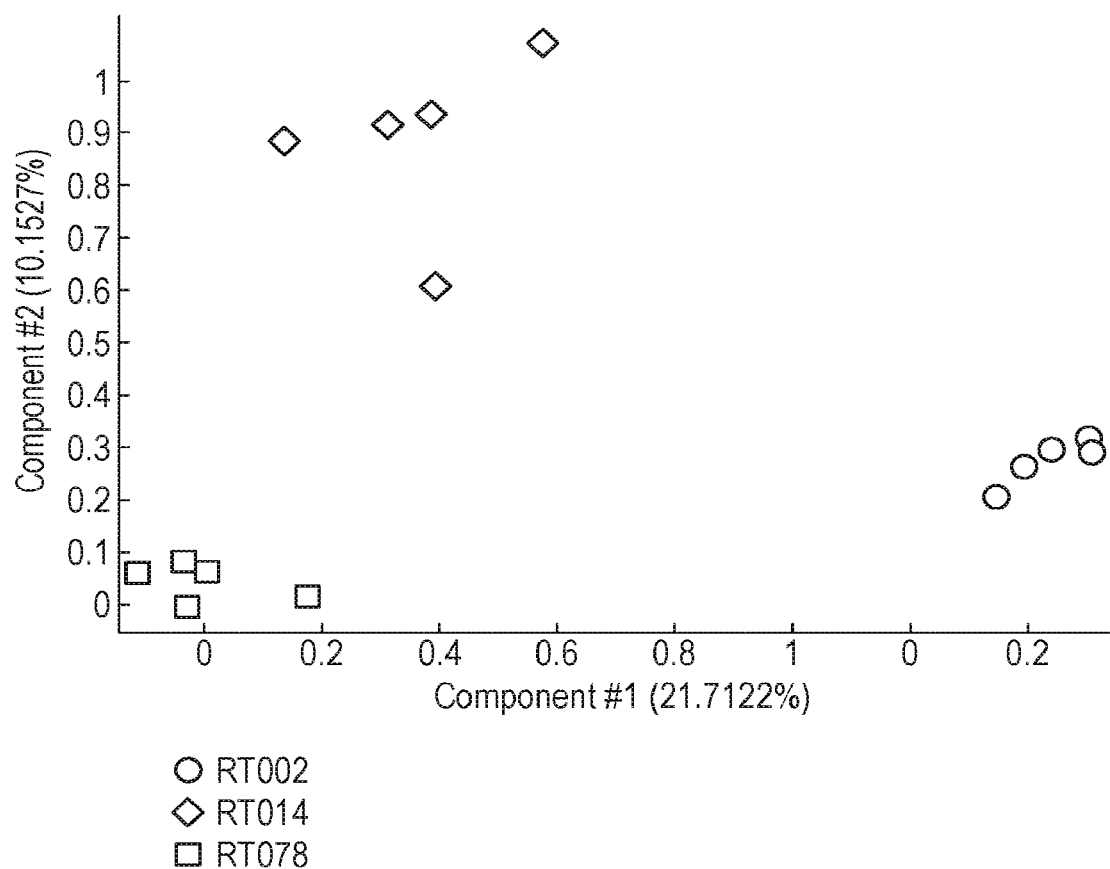

Fig. 81
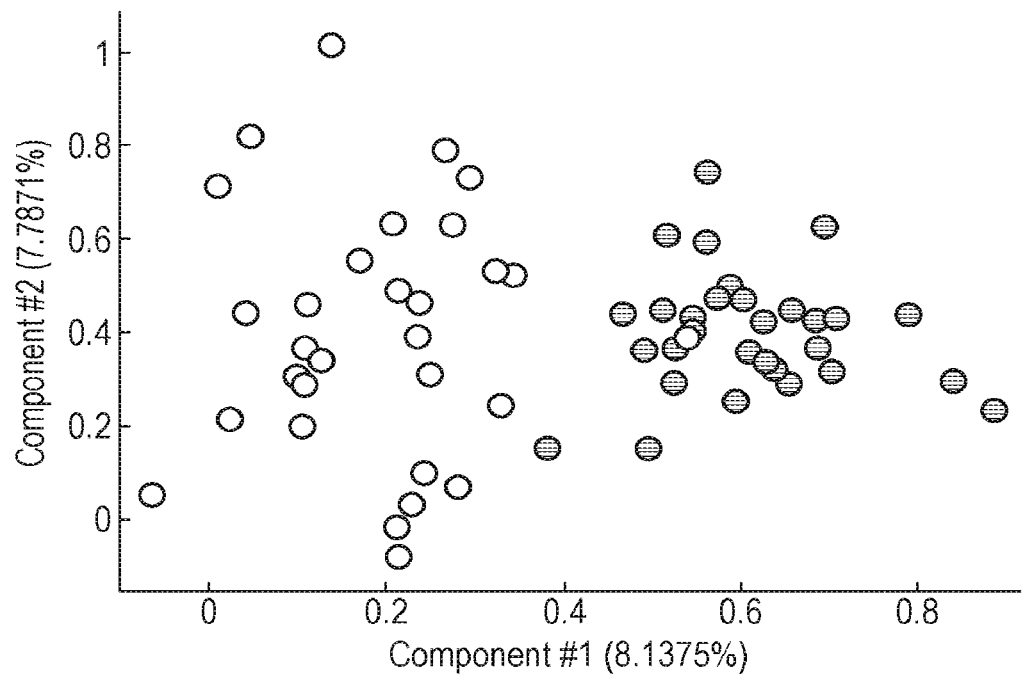
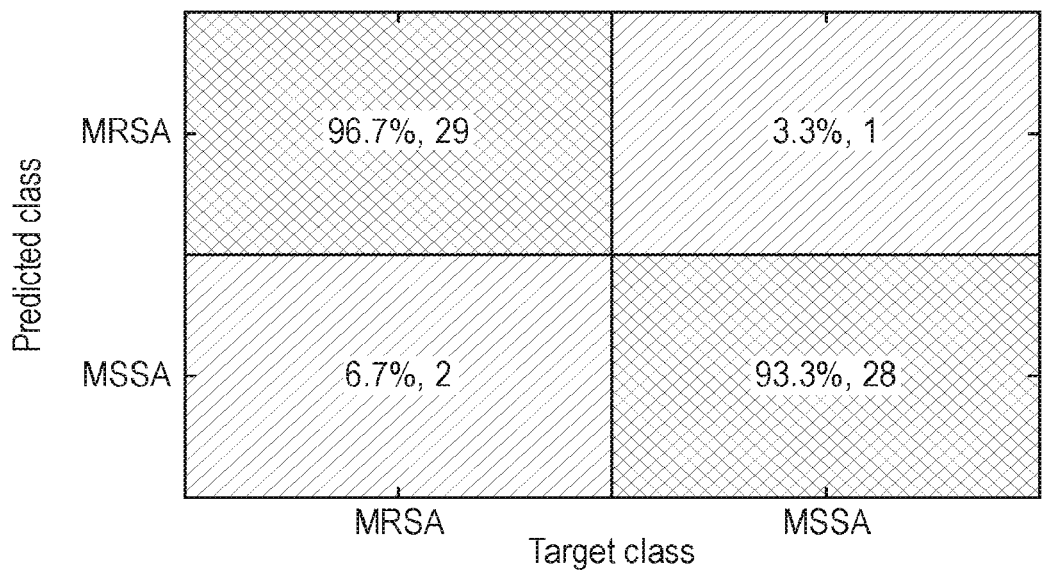

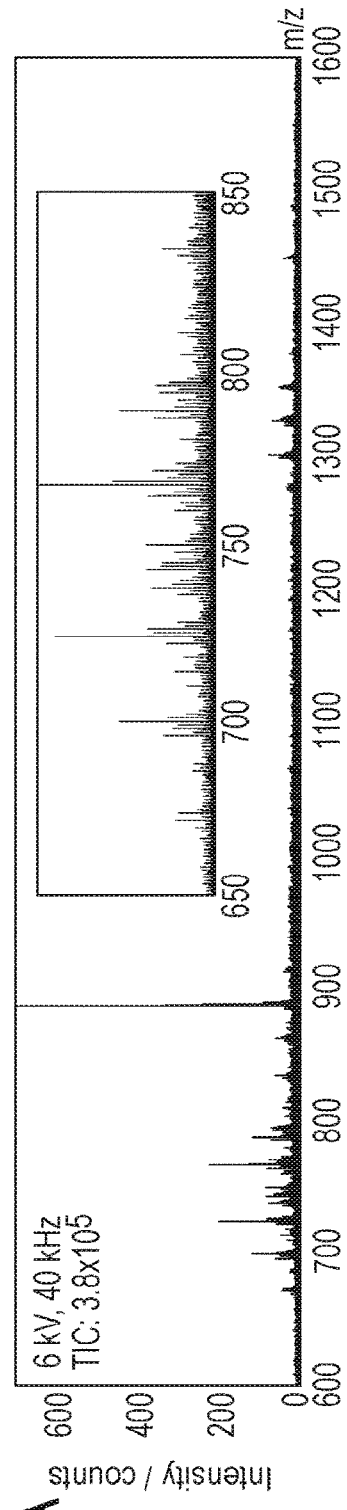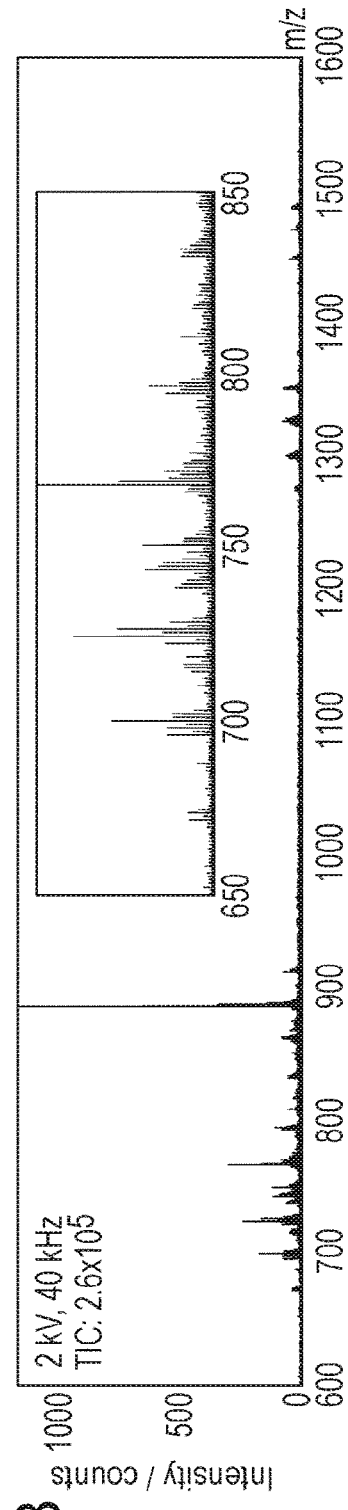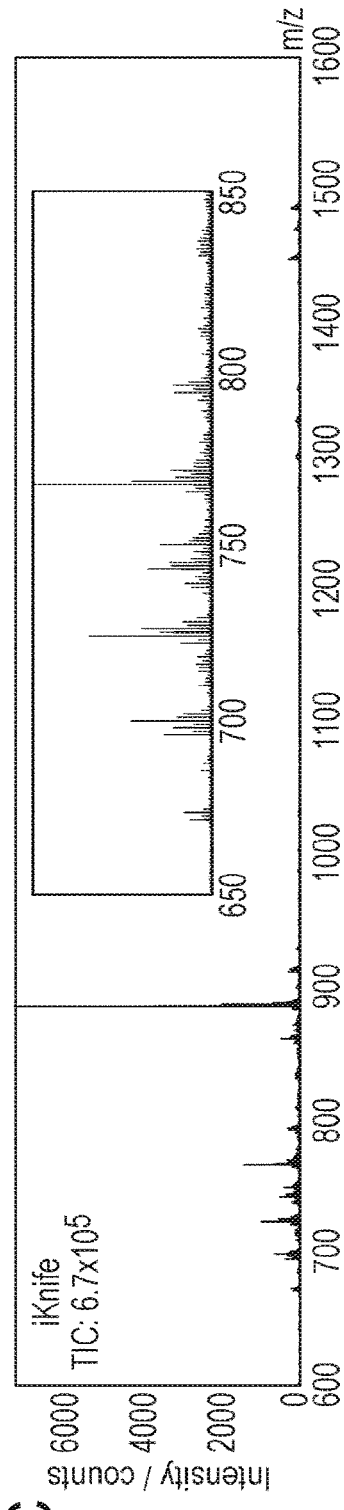

SPECTROMETRIC ANALYSIS

CROSS-REFERENCE TO RELATED APPLICATIONS

This application is a continuation application of U.S. patent application Ser. No. 15/555,860, filed Sep. 5, 2017, which represents the U.S. National Phase of International Application number PCT/GB2016/050622 entitled "Spectrometric Analysis" filed 7 Mar. 2016, which claims priority from and the benefit of United Kingdom patent application No. 1503876.3 filed on 6 Mar. 2015, United Kingdom patent application No. 1503864.9 filed on 6 Mar. 2015, United Kingdom patent application No. 1518369.2 filed on 16 Oct. 2015, United Kingdom patent application No. 1503877.1 filed on 6 Mar. 2015, United Kingdom patent application No. 1503867.2 filed on 6 Mar. 2015, United Kingdom patent application No. 1503863.1 filed on 6 Mar. 2015, United Kingdom patent application No. 1503878.9 filed on 6 Mar. 2015, United Kingdom patent application No. 1503879.7 filed on 6 Mar. 2015 and United Kingdom patent application No. 1516003.9 filed on 9 Sep. 2015. The entire contents of these applications are incorporated herein by reference.

FIELD OF THE INVENTION

The present invention relates generally to spectrometry and in particular to methods of spectrometric analysis in order to classify aerosol, smoke or vapour samples.

BACKGROUND

Rapid evaporative ionization mass spectrometry ("REIMS") is a technology which has recently been developed for the real-time identification of target substances, for example for the identification of biological tissues during surgical interventions. REIMS analysis of biological tissues has been shown to yield phospholipid profiles having high histological and histopathological specificity.

Coupling of REIMS technology with handheld sampling devices has resulted in iKnife sampling technology, which can provide intra-operative tissue identification. This technology allows surgeons to resect target tissues, such as tumours, more efficiently by providing intra-operative information that can assist a surgeon in minimizing the amount of healthy tissue removed whilst helping to resect the target tissue.

In a known iKnife sampling system, a target substance is subjected to alternating electric current at radiofrequency which causes localized Joule-heating and the disruption of the target substance along with desorption of charged and neutral particles. The resulting aerosol is then transported to a mass spectrometer for on-line mass spectrometric analysis. The mass spectrometric analysis generates one or more mass spectra for the aerosol, which are then analysed so as to classify the target substance.

Correct classification of target substances can be extremely important for determining courses of action. For example, when it is desired to resect unhealthy tissue in a human subject, it is important that sufficient unhealthy tissue is correctly identified and removed and that sufficient healthy tissue is correctly identified and left behind.

REIMS technology can also be used by non-surgical operators in non-surgical procedures to identify target substances ex vivo or in vitro. Correct classification of target substances is also highly desirable in these non-surgical procedures.

Reference is made to N. Strittmatter et al., Anal. Chem. 2014, 86, 6555-6562 which discloses an investigation into the suitability of using rapid evaporative ionisation mass spectrometry as a general identification system for bacteria and fungi.

The known approach for analysing bacterial colonies by rapid evaporative ionisation mass spectrometry involves using bipolar electrosurgical forceps and an electrosurgical RF generator. A bacterial colony is scraped from the surface of an agar layer using the bipolar electrosurgical forceps and a short burst of RF voltage from the electrosurgical RF generator is applied between the bipolar electrosurgical forceps. For example, it is known to apply 60 W of power in a bipolar mode at a frequency of 470 kHz sinusoid. The RF voltage which is applied to the electrosurgical forceps has the result of rapidly heating the particular portion of the bacterial colony which is being analysed due to its nonzero impedance. The rapid heating of the microbial mass results in an aerosol being generated. The aerosol is transferred directly into a mass spectrometer and the aerosol sample may then be analysed. It is known to utilise multivariate statistical analysis of spectrometric data in order to help distinguish and identify different samples.

It is desired to provide improved methods of spectrometric analysis in order to classify aerosol, smoke or vapour samples.

SUMMARY

According to various aspects and embodiments there is provided a method of spectrometric analysis comprising:

obtaining one or more sample spectra for an aerosol, smoke or vapour sample; and analysing the one or more sample spectra so as to classify the aerosol, smoke or vapour sample.

Similarly, according to various aspects and embodiments there is provided a spectrometric analysis system comprising:

control circuitry arranged and adapted to:

obtain one or more sample spectra for an aerosol, smoke or vapour sample; and analyse the one or more sample spectra so as to classify the aerosol, smoke or vapour sample.

The various aspects and embodiments described herein provide improved methods of spectrometric analysis in order to classify aerosol, smoke or vapour samples.

Obtaining the one or more sample spectra may comprise generating the aerosol, smoke or vapour sample using a sampling device.

The sampling device may comprise or form part of an ambient ion ionisation or source.

The sampling device may comprise one or more ion sources selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source;

(xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; NO a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

The sampling device may comprise or form part of a point of care ("POC") diagnostic or surgical device.

The sampling device may comprise an electrosurgical device, a diathermy device, an ultrasonic device, a hybrid ultrasonic electrosurgical device, a surgical water jet device, a hybrid electrosurgery device, an argon plasma coagulation device, a hybrid argon plasma coagulation device and water jet device and/or a laser device. The term "water" used here may include a solution such as a saline solution.

The sampling device may comprise or form part of a rapid evaporation ionization mass spectrometry ("REIMS") device.

Generating the aerosol, smoke or vapour sample may comprise contacting a target with one or more electrodes.

The one or more electrodes may comprise or form part of: (i) a monopolar device, wherein said monopolar device optionally further comprises a separate return electrode or electrodes; (ii) a bipolar device, wherein said bipolar device optionally further comprises a separate return electrode or electrodes; or (iii) a multi phase RF device, wherein said RF device optionally further comprises a separate return electrode or electrodes. Bipolar sampling devices can provide particularly useful sample spectra for classifying aerosol, smoke or vapour samples.

Generating the aerosol, smoke or vapour sample may comprise applying an AC or RF voltage to the one or more electrodes in order to generate the aerosol, smoke or vapour sample.

Applying the AC or RF voltage to the one or more electrodes may comprise applying one or more pulses of the AC or RF voltage to the one or more electrodes.

Applying the AC or RF voltage to the one or more electrodes may cause heat to be dissipated into a target.

Generating the aerosol, smoke or vapour sample may comprise irradiating a target with a laser.

Generating the aerosol, smoke or vapour sample may comprise direct evaporation or vaporisation of target material from a target by Joule heating or diathermy.

Generating the aerosol, smoke or vapour sample may comprise directing ultrasonic energy into a target.

The aerosol, smoke or vapour sample may comprise uncharged aqueous droplets optionally comprising cellular material.

At least 50%, 55%, 60%, 65%, 70%, 75%, 80%, 85%, 90% or 95% of the mass or matter generated which forms the aerosol, smoke or vapour sample may be in the form of droplets.

The Sauter mean diameter ("SMD", d32) of the aerosol, smoke or vapour sample may be in a range selected from the group consisting of: (i) $\leq$ or $\geq 5$ μm; (ii) 5-10 μm; (iii) 10-15 μm; (iv) 15-20 μm; (v) 20-25 μm; and (vi) $\leq$ or $\geq 25$ μm.

The aerosol, smoke or vapour sample may traverse a flow region with a Reynolds number (Re) in a range selected from the group consisting of: (i) $\leq$ or $\geq 2000$; (ii) 2000-2500; (iii) 2500-3000; (iv) 3000-3500; (v) 3500-4000; and (vi) $\leq$ or $\geq 4000$.

Substantially at the point of generating the aerosol, smoke or vapour sample, the aerosol, smoke or vapour sample may comprise droplets having a Weber number (We) in a range selected from the group consisting of: (i) $\leq$ or $\geq 50$; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) $\leq$ or $\geq 1000$.

Substantially at the point of generating the aerosol, smoke or vapour sample, the aerosol, smoke or vapour sample may comprise droplets having a Stokes number ($S_k$) in a range selected from the group consisting of: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) $\leq$ or $\geq 50$.

Substantially at the point of generating the aerosol, smoke or vapour sample, the aerosol, smoke or vapour sample may comprise droplets having a mean axial velocity in a range selected from the group consisting of: (i) $\leq$ or $\geq 20$ m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) $\leq$ or $\geq 150$ m/s.

The aerosol, smoke or vapour sample may be obtained from a target.

The aerosol, smoke or vapour sample may be obtained from one or more regions of a target.

The target may comprise target material.

The target may comprise native and/or unmodified target material.

The native and/or unmodified target material may be unmodified by the addition of a matrix and/or reagent.

The aerosol, smoke or vapour sample may be obtained from the target without the target requiring prior preparation.

The target may be from or form part of a human or non-human animal subject (e.g., a patient).

The target may comprise biological tissue, biological matter, a bacterial colony or a fungal colony.

The biological tissue may comprise human tissue or non-human animal tissue.

The biological tissue may comprise in vivo biological tissue.

The biological tissue may comprise ex vivo biological tissue.

The biological tissue may comprise in vitro biological tissue.

The biological tissue may comprise one or more of: (i) adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue; (ii) grade I, grade II, grade III or grade IV cancerous tissue; (iii) metastatic cancerous tissue; (iv) mixed grade cancerous tissue; (v) a sub-grade cancerous tissue; (vi) healthy or normal tissue; and/or (vii) cancerous or abnormal tissue.

Obtaining the one or more sample spectra may comprise obtaining the aerosol, smoke or vapour sample over a period of time in seconds that is within a range selected from the group consisting of: (i) $\leq$ or $\geq 0.1$; (ii) 0.1-0.2; (iii) 0.2-0.5; (iv) 0.5-1.0; (v) 1.0-2.0; (vi) 2.0-5.0; (vii) 5.0-10.0; and (viii)

≤ or ≥10.0. Longer periods of time can increase signal to noise ratio and improve ion statistics whilst shorter periods of time can speed up the spectrometric analysis process. In some embodiments, one or more reference and/or known aerosol, smoke or vapour samples may be obtained over a longer period of time to improve signal to noise ratio. In some embodiments, one or more unknown aerosol, smoke or vapour samples may be obtained over a shorter period of time to speed up the classification process.

The one or more sample spectra may comprise one or more sample mass and/or mass to charge ratio and/or ion mobility (drift time) spectra. Plural sample ion mobility spectra may be obtained using different ion mobility drift gases, or dopants may be added to the drift gas to induce a change in drift time, for example of one or more species. The plural sample spectra may then be combined. Combining the plural sample spectra may comprise a concatenation, (e.g., weighted) summation, average, quantile or other statistical property for the plural spectra or parts thereof, such as one or more selected peaks. Obtaining the one or more sample spectra may comprise generating a plurality of analyte ions from the aerosol, smoke or vapour sample.

Obtaining the one or more sample spectra may comprise ionising at least some of the aerosol, smoke or vapour sample so as to generate a plurality of analyte ions.

Obtaining the one or more sample spectra may comprise generating a plurality of analyte ions upon generating the aerosol, smoke or vapour sample.

Obtaining the one or more sample spectra may comprise directing at least some of the aerosol, smoke or vapour sample into a vacuum chamber of a mass and/or ion mobility spectrometer.

Obtaining the one or more sample spectra may comprise ionising at least some the aerosol, smoke or vapour sample within a vacuum chamber of a mass and/or ion mobility spectrometer so as to generate a plurality of analyte ions.

Obtaining the one or more sample spectra may comprise causing the aerosol, smoke or vapour sample to impact upon a collision surface located within a vacuum chamber of a mass and/or ion mobility spectrometer so as to generate a plurality of analyte ions.

Obtaining the one or more sample spectra may comprise generating a plurality of analyte ions using ambient ionisation.

Obtaining the one or more sample spectra may comprise generating a plurality of analyte ions in positive ion mode and/or negative ion mode. The mass and/or ion mobility spectrometer may obtain data in negative ion mode only, positive ion mode only, or in both positive and negative ion modes. Positive ion mode spectrometric data may be combined with negative ion mode spectrometric data. Combining the spectrometric data may comprise a concatenation, (e.g., weighted) summation, average, quantile or other statistical property for plural spectra or parts thereof, such as one or more selected peaks. Negative ion mode can provide particularly useful sample spectra for classifying some aerosol, smoke or vapour samples, such as aerosol, smoke or vapour samples from targets comprising lipids.

Obtaining the one or more sample spectra may comprise mass, mass to charge ratio and/or ion mobility analysing a plurality of analyte ions.

Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

Obtaining the one or more sample spectra may comprise mass, mass to charge ratio and/or ion mobility analysing the aerosol, smoke or vapour sample, or a plurality of analyte ions derived from the aerosol, smoke or vapour sample.

Obtaining the one or more sample spectra may comprise generating a plurality of precursor ions.

Obtaining the one or more sample spectra may comprise generating a plurality of fragment ions and/or reaction ions from precursor ions.

Obtaining the one or more sample spectra may comprise scanning, separating and/or filtering a plurality of analyte ions.

The plurality of analyte ions may be scanned, separated and/or filtered according to one or more of: mass; mass to charge ratio; ion mobility; and charge state.

Scanning, separating and/or filtering the plurality of analyte ions may comprise onwardly transmitting a plurality of ions having mass or mass to charge ratios in Da or Th (Da/e) within one or more ranges selected from the group consisting of: (i) ≤ or ≥200; (ii) 200-400; (iii) 400-600; (iv) 600-800; (v) 800-1000; (vi) 1000-1200; (vii) 1200-1400; (viii) 1400-1600; (ix) 1600-1800; (x) 1800-2000; and (xi) ≤ or ≥2000.

Scanning, separating and/or filtering the plurality of analyte ions may comprise at least partially or fully attenuating a plurality of ions having mass or mass to charge ratios in Da or Th (Da/e) within one or more ranges selected from the group consisting of: (i) ≤ or ≥200; (ii) 200-400; (iii) 400-600; (iv) 600-800; (v) 800-1000; (vi) 1000-1200; (vii) 1200-1400; (viii) 1400-1600; (ix) 1600-1800; (x) 1800-2000; and (xi) ≤ or ≥2000.

Ions having a mass or mass to charge ratio within a range of 600-2000 Da or Th (Da/e) can provide particularly useful sample spectra for classifying some aerosol, smoke or vapour samples, such as samples obtained from bacteria. Ions having a mass or mass to charge ratio within a range of 600-900 Da or Th (Da/e) can provide particularly useful sample spectra for classifying some aerosol, smoke or vapour samples, such as samples obtained from tissues.

Obtaining the one or more sample spectra may comprise partially attenuating a plurality of analyte ions.

The partial attenuation may be applied so as to avoid ion detector saturation.

The partial attenuation may be applied automatically upon detecting that ion detector saturation has occurred or upon predicting that ion detector saturation will occur.

The partial attenuation may be switched (e.g., on or off, higher or lower, etc.) so as to provide sample spectra having different degrees of attenuation.

The partial attenuation may be switched periodically.

Obtaining the one or more sample spectra may comprise detecting a plurality of analyte ions using an ion detector device.

The ion detector device may comprise or form part of a mass and/or ion mobility spectrometer. The mass and/or ion mobility spectrometer may comprise one or more: ion traps; ion mobility separation (IMS) devices (e.g., drift tube and/or IMS travelling wave devices, etc.); and/or mass analysers or filters. The one or more mass analysers or filters may comprise a quadrupole mass analyser or filter and/or Time-of-Flight (TOF) mass analyser.

Obtaining the one or more sample spectra may comprise generating a set of analytical value-intensity groupings or "tuplets" (e.g., time-intensity pairs, time-drifttime-intensity tuplets) for the one or more sample spectra, with each grouping comprising: (i) one or more analytical values, such as times, time-based values, or operational parameters; and (ii) one or more corresponding intensities. The operational parameters used for various modes of operation are discussed in more detail below. For example, the operational parameters may include one or more of: collision energy; resolution; lens setting; ion mobility parameter (e.g. gas pressure, dopant status, gas type, etc.).

A set of analytical value-intensity groupings may be obtained for each of one or more modes of operation.

The one or more modes of operation may comprise substantially the same or repeated modes of operation. The one or more modes of operation may comprise different modes of operation. Possible differences between modes of operation are discussed in more detail below.

The one or more modes of operation may comprise substantially the same or repeated modes of operation that use the substantially the same operational parameters. The one or more modes of operation may comprise different modes of operation that use different operational parameters. The operational parameters that may be varied are discussed in more detail below The set of analytical value-intensity groupings may be, or may be used to derive, a set of sample intensity values for the one or more sample spectra.

Obtaining the one or more sample spectra may comprise a binning process to derive a set of analytical value-intensity groupings and/or a set of sample intensity values for the one or more sample spectra. The set of time-intensity groupings may comprise a vector of intensities, with each point in the one or more analytical dimension(s) (e.g., mass to charge, ion mobility, operational parameter, etc.) being represented by an element of the vector.

The binning process may comprise accumulating or histogramming ion detections and/or intensity values in a set of plural bins.

Each bin in the binning process may correspond to one or more particular ranges of times or time-based values, such as masses, mass to charge ratios, and/or ion mobilities. When plural analytical dimensions are used (e.g., mass to charge, ion mobility, operational parameter, etc.), the bins may be regions in the analytical space. The shape of the region may be regular or irregular.

The bins in the binning process may each have a width equivalent to:

a width in Da or Th (Da/e) in a range selected from a group consisting of: (i) ≤ or ≥0.01; (ii) 0.01-0.05; (iii) 0.05-0.25; (iv) 0.25-0.5; (v) 0.5-1.0; (vi) 1.0-2.5; (vii) 2.5-5.0; and (viii) ≤ or ≥5.0; and/or a width in milliseconds in a range selected from a group consisting of: (i) ≤ or ≥0.01; (ii) 0.01-0.05; (iii) 0.05-0.25; (iv) 0.25-0.5; (v) 0.5-1.0; (vi) 1.0-2.5; (vii) 2.5-5.0; (viii) 5.0-10; (ix) 10-25; (x) 25-50; (xi) 50-100; (xii) 100-250; (xiii) 250-500; (xiv) 500-1000; and (xv) ≤ or ≥1000.

It has been identified that bins having widths equivalent to widths in the range 0.01-1 Da or Th (Da/e) can provide particularly useful sample spectra for classifying some aerosol, smoke or vapour samples, such as samples obtained from tissues.

The bins may or may not all have the same width.

The widths of the bin in the binning process may vary according to a bin width function.

The bin width function may vary with a time or time-based value, such as mass, mass to charge ratio and/or ion mobility.

The bin width function may be non-linear (e.g., logarithmic-based or power-based, such as square or square-root based). The bin width function may take into account the fact that the time of flight of an ion may not be directly proportional to its mass, mass to charge ratio, and/or ion mobility. For example, the time of flight of an ion may be directly proportional to the square-root of its mass to charge ratio.

The bin width function may be derived from the known variation of instrumental peak width with time or time-based value, such as mass, mass to charge ratio and/or ion mobility.

The bin width function may be related to known or expected variations in spectral complexity or peak density. For example, the bin width may be chosen to be smaller in regions of the one or more spectra which are expected to contain a higher density of peaks.

Obtaining the one or more sample spectra may comprise receiving the one or more sample spectra from a first location at a second location.

The method may comprise transmitting the one or more sample spectra from the first location to the second location.

The first location may be a remote or distal sampling location and/or the second location may be a local or proximal analysis location. This can allow, for example, the one or more sample spectra to be obtained at a disaster location (e.g., earthquake zone, war zone, etc.) but analysed at a relatively safer or more convenient location.

One or more sample spectra or parts thereof may be periodically transmitted and/or received at a frequency in Hz in a range selected from a group consisting of: (i) ≤ or ≥0.1; (ii) 0.1-0.2; (iii) 0.2-0.5; (iv) 0.5-1.0; (v) 1.0-2.0; (vi) 2.0-5.0; (vii) 5.0-10.0; and (viii) ≤ or ≥10.0.

One or more sample spectra or parts thereof may be transmitted and/or received when the sample spectra or parts thereof are above an intensity threshold.

The intensity threshold may be based on a statistical property of the one or more sample spectra or parts thereof, such as one or more selected peaks.

The statistical property may be based on a total ion current (TIC), a base peak intensity, an average intensity value, or quantile for the one or more sample spectra or parts thereof, such as one or more selected peaks.

The average intensity may be a mean average or a median average for the one or more sample spectra or parts thereof, such as one or more selected peaks.

Other measures, e.g., of spectral quality, may be used to select one or more spectra or parts thereof for transmission such as signal to noise ratio, the presence or absence of one or more spectral peaks (for example contaminants), the presence of data flags indicating potential issues with data quality, etc.

Obtaining the one or more sample spectra for the aerosol, smoke or vapour sample may comprise retrieving the one or more sample spectra from electronic storage of the spectrometric analysis system.

The method may comprise storing the one or more sample spectra in electronic storage of the spectrometric analysis system.

The electronic storage may form part of or may be coupled to a spectrometer, such as a mass and/or ion mobility spectrometer, of the spectrometric analysis system.

Obtaining the one or more sample spectra may comprise decompressing a compressed version of the one or more sample spectra, for example subsequent to receiving or retrieving the compressed version of the one or more sample spectra.

The method may comprise compressing the one or more sample spectra, for example prior to transmitting or storing the compressed version of the one or more sample spectra.

Obtaining the one or more sample spectra may comprise obtaining one or more sample spectra from one or more unknown aerosol, smoke or vapour samples.

Obtaining the one or more sample spectra may comprise obtaining one or more sample spectra to be identified using one or more classification models and/or libraries.

Obtaining the one or more sample spectra may comprise obtaining one or more sample spectra from one or more known aerosol, smoke or vapour samples.

Obtaining the one or more sample spectra may comprise obtaining one or more reference sample spectra to be used to develop and/or modify one or more classification models and/or libraries.

The method may comprise pre-processing the one or more sample spectra prior to analysing the one or more sample spectra.

Pre-processing the one or more sample spectra may be performed by pre-processing circuitry of the spectrometric analysis system.

The pre-processing circuitry may form part of or may be coupled to a spectrometer, such as a mass and/or ion mobility spectrometer, of the spectrometric analysis system.

Any one or more of the following pre-processing steps may be performed in any desired and suitable order.

Pre-processing the one or more sample spectra may comprise combining plural obtained sample spectra or parts thereof, such as one or more selected peaks.

Combining the plural obtained sample spectra may comprise a concatenation, (e.g., weighted) summation, average, quantile or other statistical property for the plural spectra or parts thereof, such as one or more selected peaks.

The average may be a mean average or a median average for the plural spectra or parts thereof, such as one or more selected peaks.

Pre-processing the one or more sample spectra may comprise a background subtraction process.

The background subtraction process may comprise obtaining one or more background noise profiles and subtracting the one or more background noise profiles from the one or more sample spectra to produce one or more background-subtracted sample spectra.

The one or more background noise profiles may be derived from the one or more sample spectra themselves. However, adequate background noise profiles for a sample spectrum can often be difficult to derive from the sample spectrum itself, particularly where relatively little sample or poor quality sample is available such that the sample spectrum comprises relatively weak peaks and/or comprises poorly defined noise.

Accordingly, in some embodiments, the one or more background noise profiles may be derived from one or more background reference sample spectra other than the sample spectra themselves.

The one or more background noise profiles may comprise one or more background noise profiles for each class of one or more classes of sample.

The one or more background noise profiles may be stored in electronic storage of the spectrometric analysis system.

The electronic storage may form part of or may be coupled to a spectrometer, such as a mass and/or ion mobility spectrometer, of the spectrometric analysis system.

Thus, according to various aspects and embodiments there is provided a method of spectrometric analysis comprising:

obtaining one or more background reference sample spectra for one or more aerosol, smoke or vapour samples;

deriving one or more background noise profiles for the one or more background reference sample spectra, wherein the one or more background noise profiles comprise one or more background noise profiles for each class of one or more classes of aerosol, smoke or vapour sample; and storing the one or more background noise profiles in electronic storage for use when pre-processing and analysing one or more sample spectra obtained from a different aerosol, smoke or vapour sample to the one or more aerosol, smoke or vapour samples.

Similarly, according to various aspects and embodiments there is provided a spectrometric analysis system comprising:

control circuitry arranged and adapted to:

obtain one or more background reference sample spectra for one or more aerosol, smoke or vapour samples;

derive one or more background noise profiles for the one or more background reference sample spectra, wherein the one or more background noise profiles comprise one or more background noise profiles for each class of one or more classes of aerosol, smoke or vapour sample; and store the one or more background noise profiles in electronic storage for use when pre-processing and analysing one or more sample spectra obtained from a different aerosol, smoke or vapour sample to the one or more aerosol, smoke or vapour samples.

The method may comprise performing a background subtraction process on the one or more background reference spectra using the one or more background noise profiles so as to provide one or more background-subtracted reference spectra.

The method may comprise developing a classification model and/or library using the one or more background-subtracted reference spectra.

According to various aspects and embodiments there is provided a method of spectrometric analysis comprising:

obtaining one or more sample spectra for an aerosol, smoke or vapour sample;

pre-processing the one or more sample spectra, wherein pre-processing the one or more sample spectra comprises a background subtraction process, wherein the background subtraction process comprises retrieving one or more background noise profiles from electronic storage and subtracting the one or more background noise profiles from the one or more sample spectra to produce one or more background-subtracted sample spectra, wherein the one or more background noise profiles are derived from one or more background reference sample spectra obtained for one or more aerosol, smoke or vapour samples that are different to the aerosol, smoke or vapour sample, and wherein the one or more background noise profiles comprise one or more background noise profiles for each class of one or more classes of aerosol, smoke or vapour sample; and analysing the one or more background-subtracted sample spectra so as to classify the aerosol, smoke or vapour sample.

Similarly, according to various aspects and embodiments there is provided a spectrometric analysis system comprising:

control circuitry arranged and adapted to:

obtain one or more sample spectra for an aerosol, smoke or vapour sample;

pre-process the one or more sample spectra, wherein pre-processing the one or more sample spectra comprises a background subtraction process, wherein the background subtraction process comprises retrieving one or more background noise profiles from electronic storage and subtracting the one or more background noise profiles from the one or more sample spectra to produce one or more background-subtracted sample spectra, wherein the one or more background noise profiles are derived from one or more background reference sample spectra obtained for one or more aerosol, smoke or vapour samples that are different to the aerosol, smoke or vapour sample, and wherein the one or more background noise profiles comprise one or more background noise profiles for each class of one or more classes of aerosol, smoke or vapour sample; and analyse the one or more background-subtracted sample spectra so as to classify the aerosol, smoke or vapour sample.

N. Strittmatter et al., Anal. Chem. 2014, 86, 6555-6562 does not teach or suggest inter alia deriving or using a background noise profile from one or more background reference sample spectra obtained for a different aerosol, smoke or vapour sample. Reference sample spectra for classes of aerosol, smoke or vapour sample often have a characteristic (e.g., periodic) background noise profile due to particular ions that tend to be generated when ionising samples of that class. Thus, a well-defined background noise profile can be derived in advance for a particular class of aerosol, smoke or vapour sample using one or more background reference sample spectra obtained for aerosol, smoke or vapour samples of that class. The one or more background reference sample spectra may, for example, be obtained from a relatively higher quality or larger amount of aerosol, smoke or vapour sample. These aspects and embodiments can, therefore, allow a well-defined background noise profile to be used during a background subtraction process for one or more different sample spectra, particularly in the case where those different sample spectra comprise weak peaks and/or poorly defined noise.

The aerosol, smoke or vapour sample and one or more different aerosol, smoke or vapour samples may or may not be from the same target and/or subject.

The one or more background noise profiles may comprise one or more normalised (e.g., scaled and/or offset) background noise profiles.

The one or more background noise profiles may be normalised based on a statistical property of the one or more background reference sample spectra or parts thereof, such as one or more selected peaks.

The statistical property may be based on a total ion current (TIC), a base peak intensity, an average intensity value, or quantile for the one or more background reference sample spectra or parts thereof, such as one or more selected peaks.

The average intensity may be a mean average or a median average for the one or more background reference sample spectra or parts thereof, such as one or more selected peaks.

The one or more background noise profiles may be normalised and/or offset such that they have a selected combined intensity, such as a selected summed intensity or a selected average intensity (e.g., 0 or 1).

The one or more normalised background noise profiles may be appropriately scaled and/or offset so as to correspond to the one or more sample spectra before performing the background subtraction process on the one or more sample spectra.

The one or more normalised background noise profiles may be scaled and/or offset based on statistical property of the one or more sample spectra or parts thereof, such as one or more selected peaks.

The statistical property may be based on a total ion current (TIC), a base peak intensity, an average intensity value, or quantile for the one or more sample spectra or parts thereof, such as one or more selected peaks.

The average intensity may be a mean average or a median average for the one or more sample spectra or parts thereof, such as one or more selected peaks.

Alternatively, the one or more sample spectra may be appropriately normalised (e.g., scaled and/or offset) so as to correspond to the normalised background noise profiles before performing the background subtraction process on the one or more sample spectra.

The one or more sample spectra may be normalised based on statistical property of the one or more sample spectra or parts thereof, such as one or more selected peaks.

The statistical property may be based on a total ion current (TIC), a base peak intensity, an average intensity value, or quantile for the one or more sample spectra or parts thereof, such as one or more selected peaks.

The average intensity may be a mean average or a median average for the one or more sample spectra or parts thereof, such as one or more selected peaks.

The one or more sample spectra may be normalised and/or offset such that they have a selected combined intensity, such as a selected summed intensity or a selected average intensity (e.g., 0 or 1).

The normalisation to use may be determined by fitting the one or more background profiles to the one or more sample spectra. The normalisation may be optimal or close to optimal. Fitting the one or more background profiles to the one or more sample spectra may use one or more parts of the spectra that do not, or are not likely to contain, non-background data.

The background subtraction process may be performed on the one or more sample spectra using each of the one or more background noise profiles to produce one or more background-subtracted sample spectra for each class of one or more classes of aerosol, smoke or vapour sample.

Analysing the one or more sample spectra may comprise analysing each of the one or more background-subtracted sample spectra so as to provide a distance, classification score or probability for each class of the one or more classes of aerosol, smoke or vapour sample.

Each distance, classification score or probability may indicate the likelihood that the aerosol, smoke or vapour sample belongs to the class of aerosol, smoke or vapour sample that pertains to the one or more background noise profiles that were used to produce the background-subtracted sample spectra.

The aerosol, smoke or vapour sample may be classified into one or more classes of aerosol, smoke or vapour sample having less than a threshold distance or at least a threshold classification score or probability and/or a lowest distance or a highest classification score or probability.

The distance, classification score or probability may be provided using a classification model and/or library that was developed using the one or more background reference spectra that were used to derive the one or more background noise profiles.

The one or more background reference spectra may have been subjected to a background subtraction process using the one or more background noise profiles so as to provide one or more background subtracted reference spectra prior to building the classification model and/or library using the one or more background subtracted reference spectra.

Regardless of whether the one or more background noise profiles are derived from the one or more sample spectra themselves or from one or more background reference sample spectra, the one or more background noise profiles may each be derived from one or more sample spectra as follows.

Each background noise profile may be derived using a technique as described in US 2005/0230611. However, as will be appreciated, in US 2005/0230611 a background noise profile is not derived from a spectrum for a sample and stored for use with a spectrum for a different sample as in embodiments.

Each background noise profile may be derived by translating a window over the one or more sample spectra or by dividing each of the one or more sample spectra into plural, e.g., overlapping, windows.

The window may or the windows may each correspond to a particular range of times or time-based values, such as masses, mass to charge ratios and/or ion mobilities.

The window may or the windows may each have a width equivalent to a width in Da or Th (Da/e) in a range selected from a group consisting of: (i) $\leq$ or $\geq 5$; (ii) 5-10; (iii) 10-25; (iv) 25-50; (v) 50-100; (vi) 100-250; (vii) 250-500; and (viii) $\leq$ or $\geq 500$.

The size of the window or windows may be selected to be sufficiently wide that an adequate statistical picture of the background can be formed and/or the size of the window or windows may be selected to be narrow enough that the (e.g., periodic) profile of the background does not change significantly within the window.

Each background noise profile may be derived by dividing each of the one or more sample spectra, e.g., the window or each of the windows of the one or more sample spectra, into plural segments. There may be M segments in a window, where M may be in a range selected from a group consisting of: (i) $\geq 2$; (ii) 2-5 (iii) 5-10; (iv) 10-20; (v) 20-50; (vi) 50-100; (vii) 100-200; and (viii) $\leq$ or $\geq 200$.

The segments may each correspond to a particular range of times or time-based values, such as masses, mass to charge ratios and/or ion mobilities.

The segments may each have a width equivalent to a width in Da or Th (Da/e) in a range selected from a group consisting of: (i) $\leq$ or $\geq 0.5$; (ii) 0.5-1; (iii) 1-2.5; (iv) 2.5-5; (v) 5-10; (vi) 10-25; (vii) 25-50; and (viii) $\leq$ or $\geq 50$.

The size of the segments may be selected to correspond to an integer number of repeat units of a periodic profile that may be, or may be expected to be, in the background and/or the size of the segments may be selected such that the window or each window contains sufficiently many segments for adequate statistical analysis of the background. In some embodiments, the size of a window is an odd number of segments. This allows there to be a single central segment in the plural segments, giving the process symmetry.

Each background noise profile may be derived by dividing each of the one or more sample spectra, e.g., the window or each window and/or each segment of the one or more sample spectra, into plural sub-segments. There may be N sub-segments in a segment, where N may be in a range selected from a group consisting of: (i) $\geq 2$; (ii) 2-5 (iii) 5-10; (iv) 10-20; (v) 20-50; (vi) 50-100; (vii) 100-200; and (viii) $\leq$ or $\geq 200$.

The sub-segments may each correspond to a particular range of times or time-based values, such as masses, mass to charge ratios and/or ion mobilities.

The sub-segments may each have a width equivalent to a width in Da or Th (Da/e) in a range selected from a group consisting of: (i) $\leq$ or $\geq 0.05$; (ii) 0.05-0.1; (iii) 0.1-0.25; (iv) 0.25-0.5; (v) 0.5-1; (vi) 1-2.5; (vii) 2.5-5; and (viii) $\leq$ or $\geq 5$.

The background noise profile value for each nth sub-segment (where $1 \leq n \leq N$), e.g., of a given (e.g., central) segment and/or in a window at a given position, may comprise a combination of the intensity values for the nth sub-segment and the nth sub-segments, e.g., of other segments and/or in the window at the given position, that correspond to the nth sub-segment.

The combination may comprise a (e.g., weighted) summation, average, quantile or other statistical property of the intensity values for the sub-segments.

The average may be a mean average or a median average for intensity values for the sub-segments.

The background noise profile may be derived by fitting a piecewise polynomial to the spectrum. The piecewise polynomial describing the background noise profile may be fitted such that a selected proportion of the spectrum lies below the polynomial in each segment of the piecewise polynomial.

The background noise profile may be derived by filtering in the frequency domain, for example using (e.g., fast) Fourier transforms. The filtering may remove components of the one or more sample spectra that vary relatively slowly with time or time-based value, such as mass, mass to charge ratio and/or ion mobility, The filtering may remove components of the one or more sample spectra that are periodic in time or a time derived time or time-based value, such as mass, mass to charge ratio and/or ion mobility.

The background noise profile values and corresponding time or time-based values for the sub-segments, segments and/or windows may together form the background noise profile for the sample spectrum.

The one or more background noise profiles may each be derived from plural sample spectra.

The plural sample spectra may be combined and then a background noise profile may be derived for the combined sample spectra.

Alternatively, a background noise profile may be derived for each of the plural sample spectra and then the background noise profiles may be combined.

The combination may comprise a (e.g., weighted) summation, average, quantile or other statistical property of the sample spectra or background noise profiles. The average may be a mean average or a median average of the sample spectra or background noise profiles.

Pre-processing the one or more sample spectra may comprise a time value to time-based value conversion process, e.g., a time value to mass, mass to charge ratio and/or ion mobility value conversion process.

The conversion process may comprise converting time-intensity groupings (e.g., flight time-intensity pairs or drift time-intensity pairs) to time-based value-intensity groupings (e.g., mass-intensity pairs, mass to charge ratio-intensity pairs, mobility-intensity pairs, collisional cross-section-intensity pairs, etc.).

The conversion process may be non-linear (e.g., logarithmic-based or power-based, such as square or square-root based). This non-linear conversion may account for the fact that the time of flight of an ion may not be directly proportional to its mass, mass to charge ratio, and/or ion mobility, for example the time of flight of an ion may be directly proportional to the square-root of its mass to charge ratio.

Pre-processing the one or more sample spectra may comprise performing a time or time-based correction, such as a mass, mass to charge ratio and/or ion mobility correction. The time or time-based correction process may comprise a (full or partial) calibration process.

The time or time-based correction may comprise a peak alignment process.

The time or time-based correction process may comprise a lockmass and/or lockmobility (e.g., lock collision cross-section (CCS)) process.

The lockmass and/or lockmobility process may comprise providing lockmass and/or lockmobility ions having one or more known spectral peaks (e.g., at known times or time-based values, such as masses, mass to charge ratios or ion mobilities) together with a plurality of analyte ions.

The lockmass and/or lockmobility process may comprise correcting the one or more sample spectra using the one or more known spectral peaks.

The lockmass and/or lockmobility process may comprise one point lockmass and/or lockmobility correction (e.g., scale or offset) or two point lockmass and/or lockmobility correction (e.g., scale and offset).

The lockmass and/or lockmobility process may comprise measuring the position of each of the one or more known spectral peaks (e.g., during the current experiment) and using the position as a reference position for correction (e.g., rather than using a theoretical or calculated position, or a position derived from a separate experiment). Alternatively, the position may be a theoretical or calculated position, or a position derived from a separate experiment.

The one or more known spectral peaks may be present in the one or more sample spectra either as endogenous or spiked species.

The lockmass and/or lockmobility ions may be provided by a matrix solution, for example IPA.

Pre-processing the one or more sample spectra may comprise normalising and/or offsetting and/or scaling the intensity values of the one or more sample spectra.

The intensity values of the one or more sample spectra may be normalised and/or offset and/or scaled based on a statistical property of the one or more sample spectra or parts thereof, such as one or more selected peaks.

The statistical property may be based on a total ion current (TIC), a base peak intensity, an average intensity value, or quantile for the one or more sample spectra or parts thereof, such as one or more selected peaks.

The average intensity may be a mean average or a median average for the one or more sample spectra or parts thereof, such as one or more selected peaks.

The normalising and/or offsetting and/or scaling process may be different for different parts of the one or more sample spectra.

The normalising and/or offsetting and/or scaling process may vary according to a normalising and/or offsetting and/or scaling function, e.g., that varies with a time or time-based value, such as mass, mass to charge ratio and/or ion mobility.

Different parts of the one or more sample spectra may be separately subjected to a different normalising and/or offsetting and/or scaling process and then recombined.

Pre-processing the one or more sample spectra may comprise applying a function to the intensity values in the one or more sample spectra.

The function may be non-linear (e.g., logarithmic-based or power-based, for example square or square-root-based).

The function may comprise a variance stabilising function that substantially removes a correlation between intensity variance and intensity in the one or more sample spectra.

The function may enhance one or more particular regions in the one or more sample spectra, such as low, medium and/or high masses, mass to charge ratios, and/or ion mobilities.

The one or more particular regions may be regions identified as having relatively lower intensity variance, for example as identified from one or more reference sample spectra.

The particular regions may be regions identified as having relatively lower intensity, for example as identified from one or more reference sample spectra.

The function may diminish one or more particular other regions in the one or more sample spectra, such as low, medium and/or high masses, mass to charge ratios, and/or ion mobilities.

The one or more particular other regions may be regions identified as having relatively higher intensity variance, for example as identified from one or more reference sample spectra.

The particular other regions may be regions identified as having relatively higher intensity, for example as identified from one or more reference sample spectra.

The function may apply a normalising and/or offsetting and/or scaling, for example described above.

Pre-processing the one or more sample spectra may comprise retaining and/or selecting one or more parts of the one or more sample spectra for further pre-processing and/or analysis based on a time or time-based value, such as a mass, mass to charge ratio and/or ion mobility value. This selection may be performed either prior to or following peak detection. When peak detection is performed prior to selection, the uncertainty in the measured peak position (resulting from ion statistics and calibration uncertainty) may be used as part of the selection criteria.

Pre-processing the one or more sample spectra may comprise retaining and/or selecting one or more parts of the one or more sample spectra that are equivalent to a mass or mass to charge ratio range in Da or Th (Da/e) within one or more ranges selected from the group consisting of: (i) $\leq$ or $\geq 200$; (ii) 200-400; (iii) 400-600; (iv) 600-800; (v) 800-1000; (vi) 1000-1200; (vii) 1200-1400; (viii) 1400-1600; (ix) 1600-1800; (x) 1800-2000; and (xi) $\leq$ or $\geq 2000$.

Pre-processing the one or more sample spectra may comprise discarding and/or disregarding one or more parts of the one or more sample spectra from further pre-processing and/or analysis based on a time or time-based value, such as a mass, mass to charge ratio and/or ion mobility value.

Pre-processing the one or more sample spectra may comprise discarding and/or disregarding one or more parts of the one or more sample spectra that are equivalent to a mass or mass to charge ratio range in Da or Th (Da/e) within one or more ranges selected from the group consisting of: (i) $\leq$ or $\geq 200$; (ii) 200-400; (iii) 400-600; (iv) 600-800; (v) 800-1000; (vi) 1000-1200; (vii) 1200-1400; (viii) 1400-1600; (ix) 1600-1800; (x) 1800-2000; and (xi) $\leq$ or $\geq 2000$.

This process of retaining and/or selecting and/or discarding and/or disregarding one or more parts of the one or more sample spectra from further pre-processing and/or analysis based on a time or time-based value, such as a mass, mass to charge ratio and/or ion mobility value may be referred to herein as "windowing".

The windowing process may comprise discarding and/or disregarding one or more parts of the one or more sample spectra known to comprise: one or more lockmass and/or lockmobility peaks; and/or one or more peaks for background ions. These parts of the one or more sample spectra typically are not useful for classification and indeed may interfere with classification.

The one or more predetermined parts of the one or more sample spectra that are retained and/or selected and/or discarded and/or disregarded may be one or more regions in multidimensional analytical space (e.g., mass or mass to charge ratio and ion mobility (drift time) space).

One or more analytical dimensions (e.g. relating to a time or time-based value, such as a mass, mass to charge ratio and/or ion mobility value) used for windowing may not be used for further processing and/or analysis once windowing has been performed. For example, where ion mobility is used for windowing and ion mobility is then not used for further processing and/or analysis, the one or more sample spectra may be treated as one or more non-mobility sample spectra.

As discussed above, ions having a mass and/or mass to charge ratios within a range of 600-2000 Da or Th (Da/e) can provide particularly useful sample spectra for classifying some aerosol, smoke or vapour samples, such as samples obtained from bacteria. Also, ions having a mass and/or mass to charge ratio within a range of 600-900 Da or Th (Da/e) can provide particularly useful sample spectra for classifying some aerosol, smoke or vapour samples, such as samples obtained from tissues.

Pre-processing the one or more sample spectra may comprise disregarding, suppressing or flagging regions of the one or more sample spectra that are affected by space charge effects and/or detector saturation and/or ADC saturation and/or data rate limitations.

Pre-processing the one or more sample spectra may comprise a filtering and/or smoothing process. This filtering and/or smoothing process may remove unwanted, e.g., higher frequency, fluctuations in the one or more sample spectra.

The filtering and/or smoothing process may comprise a Savitzky-Golay process.

Pre-processing the one or more sample spectra may comprise a data reduction process, such as a thresholding, peak detection/selection, deisotoping and/or binning process.

The data reduction process may reduce the number of intensity values to be subjected to analysis. The data reduction process may increase the accuracy and/or efficiency and/or reduce the burden of the analysis.

Pre-processing the one or more sample spectra may comprise a thresholding process.

The thresholding process may comprise retaining one or more parts of the one or more sample spectra that are above an intensity threshold or intensity threshold function, e.g., that varies with a time or time-based value, such as mass, mass to charge ratio and/or ion mobility.

The thresholding process may comprise discarding and/or disregarding one or more parts of the one or more sample spectra that are below an intensity threshold or intensity threshold function, e.g., that varies with a time or time-based value, such as mass, mass to charge ratio and/or ion mobility.

The intensity threshold or intensity threshold function may be based on a statistical property of the one or more sample spectra or parts thereof, such as one or more selected peaks.

The statistical property may be based on a total ion current (TIC), a base peak intensity, an average intensity value, or quantile for the one or more sample spectra or parts thereof, such as one or more selected peaks.

The average intensity may be a mean average or a median average for the one or more sample spectra or parts thereof, such as one or more selected peaks.

The thresholding process may comprise discarding and/or disregarding one or more parts of the one or more sample spectra known to comprise: one or more lockmass and/or lockmobility peaks; and/or one or more peaks for background ions. These parts of the one or more sample spectra typically are not useful for classification and indeed may interfere with classification.

The one or more predetermined parts of the one or more sample spectra that are retained and/or selected and/or discarded and/or disregarded may be one or more regions in multidimensional analytical space (e.g., mass or mass to charge ratio and ion mobility (drift time) space).

One or more analytical dimensions (e.g. relating to a time or time-based value, such as a mass, mass to charge ratio and/or ion mobility value) used for thresholding may not be used for further processing and/or analysis once thresholding has been performed. For example, where ion mobility is used for thresholding and ion mobility is then not used for further processing and/or analysis, the one or more sample spectra may be treated as one or more non-mobility sample spectra.

Pre-processing the one or more sample spectra may comprise a peak detection/selection process.

The peak detection/selection process may comprise finding the gradient or second derivate of the one or more sample spectra and using a gradient threshold or second derivate threshold and/or zero crossing in order to identify rising edges and/or falling edges of peaks and/or peak turning points or maxima.

The peak detection/selection process may comprise a probabilistic peak detection/selection process.

The peak detection process may comprise a USDA (US Department of Agriculture) peak detection process.

The peak detection/selection process may comprise generating one or more peak matching scores. Each of the one or more peak matching scores may be based on a ratio of detected peak intensity to theoretical peak intensity for species suspected to be present in the sample.

One or more peaks may be selected based on the one or more peak matching scores. For example, one or more peaks may be selected that have at least a threshold peak matching score or the highest peak matching score.

The peak detection/selection process may comprise comparing plural sample spectra and identifying common peaks (e.g., using a peak clustering method).

The peak detection/selection process may comprise performing a multidimensional peak detection. The peak detection/selection process may comprise performing a two dimensional or three dimensional peak detection where the two or three dimensions are time or time-based values, such as mass, mass to charge ratio, and/or ion mobility.

Pre-processing the one or more sample spectra may comprise a deisotoping process.

It has been identified that deisotoping is particularly useful prior to classification using multivariate and/or library based analysis.

Thus, according to various aspects and embodiments there is provided a method of spectrometric analysis comprising:

obtaining one or more sample spectra for an aerosol, smoke or vapour sample;

pre-processing the one or more sample spectra, wherein pre-processing the one or more sample spectra comprises a deisotoping process; and analysing the one or more pre-processed sample spectra so as to classify the aerosol, smoke or vapour sample, wherein analysing the one or more sample spectra comprises multivariate and/or library-based analysis.

Similarly, according to various aspects and embodiments there is provided a spectrometric analysis system comprising:

control circuitry arranged and adapted to:

obtain one or more sample spectra for an aerosol, smoke or vapour sample;

pre-process the one or more sample spectra, wherein pre-processing the one or more sample spectra comprises a deisotoping process; and analyse the one or more pre-processed sample spectra so as to classify the aerosol, smoke or vapour sample, wherein analysing the one or more sample spectra comprises multivariate and/or library-based analysis.

N. Strittmatter et al., Anal. Chem. 2014, 86, 6555-6562 describes multivariate analysis but does not teach or suggest inter alia using a deisotoping process prior to multivariate and/or library-based analysis in order to classify one or more sample spectra. Deisotoping can significantly reduce dimensionality in the one or more sample spectra. This is particularly useful when carrying out multivariate and/or library-based analysis of sample spectra so as to classify a sample since simpler and/or less resource intensive analysis may be carried out. Furthermore, deisotoping can help to distinguish between spectra by removing commonality due to isotopic distributions. Again, this is particularly useful when carrying out multivariate and/or library-based analysis of sample spectra so as to classify a sample. In particular, a more accurate or confident classification may be provided, for example due to greater separation between classes in multivariate space and/or greater differences between classification scores or probabilities in library based analysis. These aspects and embodiments can, therefore, facilitate classification of an aerosol, smoke or vapour sample.

The deisotoping process may comprise identifying one or more additional isotopic peaks in the one or more sample spectra and/or reducing or removing the one or more additional isotopic peaks in or from the one or more sample spectra.

The deisotoping process may comprise generating a deisotoped version of the one or more sample spectra in which one or more additional isotopic peaks are reduced or removed.

The deisotoping process may comprise isotopic deconvolution.

The deisotoping process may comprise an iterative process, optionally comprising iterative forward modelling.

The deisotoping process may comprise a probabilistic process, optionally a Bayesian inference process.

The deisotoping process may comprise a Monte Carlo method.

The deisotoping process may comprise one or more of: nested sampling; massive inference; and maximum entropy.

The deisotoping process may comprise generating a set of trial hypothetical monoisotopic sample spectra.

Each trial hypothetical monoisotopic sample spectra may be generated using probability density functions for one or more of: mass, intensity, charge state, and number of peaks, for a class of sample.

The deisotoping process may comprise deriving a likelihood of the one or more sample spectra given each trial hypothetical monoisotopic sample spectrum.

The deisotoping process may comprise generating a set of modelled sample spectra having isotopic peaks from the set of trial hypothetical monoisotopic sample spectra.

Each modelled sample spectra may be generated using known average isotopic distributions for a class of sample.

The deisotoping process may comprise deriving a likelihood of the one or more sample spectra given each trial hypothetical monoisotopic sample spectrum by comparing a modelled sample spectrum to the one or more sample spectra.

The deisotoping process may comprise regenerating a trial hypothetical monoisotopic sample spectrum that gives a lowest likelihood $L_n$ until the regenerated trial hypothetical monoisotopic sample spectrum gives a likelihood $L_{n+1} > L_n$.

The deisotoping process may comprise regenerating the trial hypothetical monoisotopic sample spectra until a maximum likelihood $L_m$ is or appears to have been reached for the trial hypothetical monoisotopic sample spectra or until another termination criterion is met.

The deisotoping process may comprise generating a representative set of one or more deisotoped sample spectra from the trial monoisotopic sample spectra.

The deisotoping process may comprise combining the representative set of one or more deisotoped sample spectra into a combined deisotoped sample spectrum. The combined deisotoped sample spectrum may be the deisotoped version of the one or more sample spectra referred to above.

One or more peaks in the combined deisotoped sample spectrum may correspond to one or more peaks in the representative set of one or more deisotoped sample spectra that have: at least a threshold probability of presence in the representative set of one or more deisotoped sample spectra; less than a threshold mass uncertainty in the representative set of one or more deisotoped sample spectra; and/or less than a threshold intensity uncertainty in the representative set of one or more deisotoped sample spectra.

The combination may comprise identifying clusters of peaks across the representative set of sample spectra.

One or more peaks in the combined deisotoped sample spectrum may each comprise a summation, average, quantile or other statistical property of a cluster of peaks identified across the representative set of one or more deisotoped sample spectra.

The average may be a mean average or a median average of the peaks in a cluster of peaks identified across the representative set of one or more deisotoped sample spectra.

The deisotoping process may comprise one or more of: a least squares process, a non-negative least squares process; and a Fourier transform process.

The deisotoping process may comprise deconvolving the one or more sample spectra with respect to theoretical mass and/or isotope and/or charge distributions.

The theoretical mass and/or isotope and/or charge distributions may be derived from known and/or typical and/or average properties of one or more classes of sample. The theoretical mass and/or isotope and/or charge distributions may be derived from known and/or typical and/or average properties of a spectrometer, for example that was used to obtain the one or more sample spectra.

The theoretical distributions may vary within each of the one or more classes of sample. For example, spectral peak width may vary with mass to charge ratio and/or the isotopic distribution may with molecular mass.

The theoretical mass and/or isotope and/or charge distributions may be modelled using one or more probability density functions.

Pre-processing the one or more sample spectra may comprise a re-binning process.

The re-binning process may comprise accumulating or histogramming ion detections and/or intensity values in a set of plural bins.

Each bin in the re-binning process may correspond to one or more particular ranges of times or time-based values, such as mass, mass to charge ratio and/or ion mobility. When plural analytical dimensions are used (e.g., mass to charge, ion mobility, operational parameter, etc.), the bins may be regions in the analytical space. The shape of the region may be regular or irregular.

The bins in the re-binning process may each have a width equivalent to:

a width in Da or Th (Da/e) in a range selected from a group consisting of: (i) ≤ or ≥0.01; (ii) 0.01-0.05; (iii) 0.05-0.25; (iv) 0.25-0.5; (v) 0.5-1.0; (vi) 1.0-2.5; (vii) 2.5-5.0; and (viii) ≤ or ≥5.0; and/or a width in milliseconds in a range selected from a group consisting of: (i) ≤ or ≥0.01; (ii) 0.01-0.05; (iii) 0.05-0.25; (iv) 0.25-0.5; (v) 0.5-1.0; (vi) 1.0-2.5; (vii) 2.5-5.0; (viii) 5.0-10; (ix) 10-25; (x) 25-50; (xi) 50-100; (xii) 100-250; (xiii) 250-500; (xiv) 500-1000; and (xv) ≤ or ≥1000.

This re-binning process may reduce the dimensionality (i.e., number of intensity values) for the one or more sample spectra and therefore increase the speed of the analysis.

As discussed above, bins having widths equivalent to widths in the range 0.01-1 Da or Th (Da/e) may provide particularly useful sample spectra for classifying some aerosol, smoke or vapour samples, such as sample obtained from tissues.

The bins may or may not all have the same width.

The bin widths in the re-binning process may vary according to a bin width function, e.g., that varies with a time or time-based value, such as mass, mass to charge ratio and/or ion mobility.

The bin width function may be non-linear (e.g., logarithmic-based or power-based, such as square or square-root-based. The function may take into account the fact that the time of flight of an ion may not be directly proportional to its mass, mass to charge ratio, and/or ion mobility, for example the time of flight of an ion may be directly proportional to the square-root of its mass to charge ratio.

The bin width function may be derived from the known variation of instrumental peak width with time or time-based value, such as mass, mass to charge ratio and/or ion mobility.

The bin width function may be related to known or expected variations in spectral complexity or peak density. For example, the bin width may be chosen to be smaller in regions of the one or more spectra which are expected to contain a higher density of peaks.

Pre-processing the one or more sample spectra may comprise performing a (e.g., further) time or time-based correction, such as a mass, mass to charge ratio or ion mobility correction.

The (e.g., further) time or time-based correction process may comprise a (full or partial) calibration process.

The (e.g., further) time or time-based correction may comprise a (e.g., detected/selected) peak alignment process.

The (e.g., further) time or time-based correction process may comprise a lockmass and/or lockmobility (e.g., lock collision cross-section (CCS)) process.

The lockmass and/or lockmobility process may comprise providing lockmass and/or lockmobility ions having one or more known spectral peaks (e.g., at known times or time-based values, such as masses, mass to charge ratios or ion mobilities) together with a plurality of analyte ions.

The lockmass and/or lockmobility process may comprise aligning the one or more sample spectra using the one or more known spectral peaks.

The lockmass and/or lockmobility process may comprise one point lockmass and/or lockmobility correction (e.g., scale or offset) or two point lockmass and/or lockmobility correction (e.g., scale and offset).

The lockmass and/or lockmobility process may comprise measuring the position of each of the one or more known spectral peaks (e.g., during the current experiment) and using the position as a reference position for correction (e.g., rather than using a theoretical or calculated position, or a position derived from a separate experiment). Alternatively, the position may be a theoretical or calculated position, or a position derived from a separate experiment.

The one or more known spectral peaks may be present in the one or more sample spectra either as endogenous or spiked species.

The lockmass and/or lockmobility ions may be provided by a matrix solution, for example IPA.

Pre-processing the one or more sample spectra may comprise (e.g., further) normalising and/or offsetting and/or scaling the intensity values of the one or more sample spectra.

The intensity values of the one or more sample spectra may be normalised and/or offset and/or scaled based on a statistical property of the one or more sample spectra or parts thereof, such as one or more selected peaks.

The statistical property may be based on a total ion current (TIC), a base peak intensity, an average intensity value, or quantile for the one or more sample spectra or parts thereof, such as one or more selected peaks.

The average intensity may be a mean average or a median average for the one or more sample spectra or parts thereof, such as one or more selected peaks.

The (e.g., further) normalising and/or offsetting and/or scaling may prepare the intensity values for analysis, e.g., multivariate, univariate and/or library-based analysis.

The intensity values may be normalised and/or offset and/or scaled so as to have a particular average (e.g., mean or median) value, such as 0 or 1.

The intensity values may be normalised and/or offset and/or scaled so as to have a particular minimum value, such as −1, and/or so as to have a particular maximum value, such as 1.

Pre-processing the one or more sample spectra may comprise pre-processing plural sample spectra, for example in a manner as described above.

Pre-processing the one or more sample spectra may comprise combining the plural pre-processed sample spectra or parts thereof, such as one or more selected peaks.

Combining the plural pre-processed sample spectra may comprise a concatenation, (weighted) summation, average, quantile or other statistical property for the plural spectra or parts thereof, such as one or more selected peaks.

The average may be a mean average or a median average for the plural spectra or parts thereof, such as one or more selected peaks.

Analysing the one or more sample spectra may comprise analysing the one or more sample spectra in order: (i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances may be present in the target; (vi) to confirm the identity or authenticity of the target; (vii) to determine whether or not one or more impurities, illegal substances or undesired substances may be present in the target; (viii) to determine whether a human or animal patient may be at an increased risk of suffering an adverse outcome; (ix) to make or assist in the making a diagnosis or prognosis; and/or (x) to inform a surgeon, nurse, medic or robot of a medical, surgical or diagnostic outcome.

Analysing the one or more sample spectra may comprise classifying the sample into one or more classes.

Analysing the one or more sample spectra may comprise classifying the sample as belonging to one or more classes within a classification model and/or library.

The one of more classes may relate to the type, identity, state and/or composition of sample, target and/or subject.

The one of more classes may relate to one or more of: (i) a type and/or subtype of disease (e.g., cancer, cancer type, etc.); (ii) a type and/or subtype of infection (e.g., genus, species, sub-species, gram group, antibiotic or antimicrobial resistance, etc.); (iii) an identity of target and/or subject (e.g., cell, biomass, tissue, organ, subject and/or organism identity); (iv) healthy/unhealthy state or quality (e.g., cancerous, tumorous, malignant, diseased, septic, infected, contaminated, necrotic, stressed, hypoxic, medicated and/or abnormal); (v) degree of healthy/unhealthy state or quality (e.g., advanced, aggressive, cancer grade, low quality, etc.); (vi) chemical, biological or physical composition; (vii) a type of target and/or subject (e.g., genotype, phenotype, sex etc.); (viii) target and/or subject phenotype and/or genotype; and (ix) an actual or expected target and/or subject outcome (e.g., life expectancy, life quality, recovery time, remission rate, surgery success rate, complication rate, complication type, need for further treatment rate, and treatment type typically needed (e.g., surgery, chemotherapy, radiotherapy, medication; hormone treatment, level of dose, etc.), etc.).

The one of more classes can be used to inform decisions, such as whether and how to carry out surgery, therapy and/or diagnosis for a subject. For example, whether and how much target tissue should be removed from a subject and/or whether and how much adjacent non-target tissue should be removed from a subject.

It has been recognised that there can be strong correlation between target and/or subject genotype and/or phenotype on the one hand and expected target and/or subject outcome (e.g., treatment success) on the other. It has further been recognised that knowledge of actual or expected subject outcome relating to aerosol, smoke or vapour samples can be extremely useful for informing decisions, such as treatment decisions.

Thus, according to various aspects and embodiments there is provided a method of spectrometric analysis comprising:

obtaining one or more sample spectra for an aerosol, smoke or vapour sample obtained from one or more targets and/or subjects; and analysing the one or more sample spectra so as to classify the aerosol, smoke or vapour sample, wherein analysing the one or more sample spectra comprises classifying the aerosol, smoke or vapour sample based on one or more classes of genotype and/or phenotype for the one or more targets and/or subjects.

Similarly, according to various aspects and embodiments there is provided a spectrometric analysis system comprising:

control circuitry arranged and adapted to:

obtain one or more sample spectra for an aerosol, smoke or vapour sample obtained from one or more targets and/or subjects; and analyse the one or more sample spectra so as to classify the aerosol, smoke or vapour sample, wherein analysing the one or more sample spectra comprises classifying the aerosol, smoke or vapour sample based on one or more classes of genotype and/or phenotype for the one or more targets and/or subjects.

N. Strittmatter et al., Anal. Chem. 2014, 86, 6555-6562 does not teach or suggest inter alia classifying an aerosol, smoke or vapour sample based on one or more classes of genotype and/or phenotype for one or more targets and/or subjects. A genotype and/or phenotype class can be extremely useful for informing decisions, such as whether and how to carry out surgery, therapy and/or diagnosis for a subject. These aspects and embodiments can, therefore, provide particularly useful classifications for aerosol, smoke or vapour samples.

The term "phenotype" may be used to refer to the physical and/or biochemical characteristics of a cell whereas the term "genotype" may be used to refer to the genetic constitution of a cell.

The term "phenotype" may be used to refer to a collection of a cell's physical and/or biochemical characteristics, which may optionally be the collection of all of the cell's physical and/or biochemical characteristics; and/or to refer to one or more of a cell's physical and/or biochemical characteristics. For example, a cell may be referred to as having the phenotype of a specific cell type, e.g., a breast cell, and/or as having the phenotype of expressing a specific protein, e.g., a receptor, e.g., HER2 (human epidermal growth factor receptor 2).

The term "genotype" may be used to refer to genetic information, which may include genes, regulatory elements, and/or junk DNA. The term "genotype" may be used to refer to a collection of a cell's genetic information, which may optionally be the collection of all of the cell's genetic information; and/or to refer to one or more of a cell's genetic information. For example, a cell may be referred to as having the genotype of a specific cell type, e.g., a breast cell, and/or as having the genotype of encoding a specific protein, e.g., a receptor, e.g., HER2 (human epidermal growth factor).

The genotype of a cell may or may not affect its phenotype, as explained below.

The relationship between a genotype and a phenotype may be straightforward. For example, if a cell includes a functional gene encoding a particular protein, such as HER2, then it will typically be phenotypically HER2-positive, i.e. have the HER2 protein on its surface, whereas if a cell lacks a functional HER2 gene, then it will have a HER2-negative phenotype.

A mutant genotype may result in a mutant phenotype. For example, if a mutation destroys the function of a gene, then the loss of the function of that gene may result in a mutant phenotype. However, factors such as genetic redundancy may prevent a genotypic trait to result in a corresponding phenotypic trait. For example, human cells typically have two copies of each gene, one from each parent. Talking the example of a genetic disease, a cell may comprise one mutant (diseased) copy of a gene and one non-mutant (healthy) copy of the gene, which may or may not result in a mutant (diseased) phenotype, depending on whether the mutant gene is recessive or dominant. Recessive genes do not, or not significantly, affect a cell's phenotype, whereas dominant genes do affect a cell's phenotype.

It must also be borne in mind that many genotypic changes may have no phenotypic effect, e.g., because they are in junk DNA, i.e. DNA which seems to serve no sequence-dependent purpose, or because they are silent mutations, i.e. mutations which do not change the coding information of the DNA because of the redundancy of the genetic code.

The phenotype of a cell may be determined by its genotype in that a cell requires genetic information to carry out cellular processes and any particular protein may only be generated within a cell if the cell contains the relevant genetic information. However, the phenotype of a cell may also be affected by environmental factors and/or stresses, such as, temperature, nutrient and/or mineral availability, toxins and the like. Such factors may influence how the genetic information is used, e.g., which genes are expressed and/or at which level. Environmental factors and/or stresses may also influence other characteristics of a cell, e.g., heat may make membranes more fluid.

If a functional transgene is inserted into a cell at the correct genomic position, then this may result in a corresponding phenotype The insertion of a transgene may affect a cell's phenotype, but an altered phenotype may optionally only be observed under the appropriate environmental conditions. For example, the insertion of a transgene encoding a protein involved in a synthesis of a particular substance will only result in cells that produce that substance if and when the cells are provided with the required starting materials.

Optionally, the method may involve the analysis of the phenotype and/or genotype of a cell population.

The genotype and/or phenotype of cell population may be manipulated, e.g., to analyse a cellular process, to analyse a disease, such as cancer, to make a cell population more suitable for drug screening and/or production, and the like. Optionally, the method may involve the analysis of the effect of such a genotype and/or phenotype manipulation on the cell population, e.g., on the genotype and/or phenotype of the cell population.

As discussed above, it has been recognised that knowledge of actual or expected subject outcome relating to aerosol, smoke or vapour samples can be extremely useful for informing decisions, such as treatment decisions.

Thus, according to various aspects and embodiments there is provided a method of spectrometric analysis comprising:

obtaining one or more sample spectra for an aerosol, smoke or vapour sample obtained from one or more targets and/or subjects; and analysing the one or more sample spectra so as to classify the aerosol, smoke or vapour sample, wherein analysing the one or more sample spectra comprises classifying the aerosol, smoke or vapour sample based on one or more classes of expected outcome for the one or more targets and/or subjects.

Similarly, according to various aspects and embodiments there is provided a spectrometric analysis system comprising:

control circuitry arranged and adapted to:

obtain one or more sample spectra for an aerosol, smoke or vapour sample obtained from one or more targets and/or subjects; and analyse the one or more sample spectra so as to classify the aerosol, smoke or vapour sample, wherein analysing the one or more sample spectra comprises classifying the aerosol, smoke or vapour sample based on one or more classes of expected outcome for the one or more targets and/or subjects.

N. Strittmatter et al., Anal. Chem. 2014, 86, 6555-6562 does not teach or suggest inter alia classifying an aerosol, smoke or vapour sample based on one or more classes of expected outcome for one or more targets and/or subjects. An expected outcome class can be extremely useful for informing decisions, such as whether and how to carry out surgery, therapy and/or diagnosis for a subject. These aspects and embodiments can, therefore, provide particularly useful classifications for aerosol, smoke or vapour samples.

The one or more classes of genotype and/or phenotype and/or expected outcome for the one or more targets and/or subjects may be indicative of one or more of: (i) life expectancy; (ii) life quality; (iii) recovery time; (iv) remission rate; (v) surgery success rate; (vi) complication rate; (vii) complication type; (viii) need for further treatment rate; and (ix) treatment type typically needed (e.g., surgery, chemotherapy, radiotherapy, medication; hormone treatment, level of dose, etc.).

The one or more classes of genotype and/or phenotype and/or expected outcome for the one or more targets and/or subjects may be indicative of an outcome of following a particular course of action (e.g., treatment).

The method may comprise following the particular course of action when the outcome of following the particular course of action is indicated as being relatively good, e.g., longer life expectancy; better life quality; shorter recovery time; higher remission rate; higher surgery success rate; lower complication rate; less severe complication type; lower need for further treatment rate; and/or less severe further treatment type typically needed.

The method may comprise not following the particular course of action when the outcome of following the particular course of action is indicated as being relatively poor, e.g., shorter life expectancy; worse life quality; longer recovery time; lower remission rate; lower surgery success rate; higher complication rate; more severe complication type; higher need for further treatment rate; and/or more severe further treatment type typically needed.

The particular course of action may be: (i) an amputation; (ii) a debulking; (iii) a resection; (iv) a transplant; or (v) a (e.g., bone or skin) graft.

The method may comprise monitoring and/or separately testing one or more targets and/or subjects in order to determine and/or confirm the genotype and/or phenotype and/or outcome.

Analysing the one or more sample spectra may be performed by analysis circuitry of the spectrometric analysis system.

The analysis circuitry may form part of or may be coupled to a spectrometer, such as a mass and/or ion mobility spectrometer, of the spectrometric analysis system.

Analysing the one or more sample spectra may comprise unsupervised analysis of the one or more sample spectra (e.g., for dimensionality reduction) and/or supervised analysis (e.g., for classification) of the one or more sample spectra. Analysing the one or more sample spectra may comprise unsupervised analysis (e.g., for dimensionality reduction) followed by supervised analysis (e.g., for classification).

Analysing the one or more sample spectra may comprise using one or more of: (i) univariate analysis; (ii) multivariate analysis; (iii) principal component analysis (PCA); (iv) linear discriminant analysis (LDA); (v) maximum margin criteria (MMC); (vi) library-based analysis; (vii) soft independent modelling of class analogy (SIMCA); (viii) factor analysis (FA); (ix) recursive partitioning (decision trees); (x) random forests; (xi) independent component analysis (ICA); (xii) partial least squares discriminant analysis (PLS-DA); (xiii) orthogonal (partial least squares) projections to latent structures (OPLS); (xiv) OPLS discriminant analysis (OPLS-DA); (xv) support vector machines (SVM); (xvi) (artificial) neural networks; (xvii) multilayer perceptron; (xviii) radial basis function (RBF) networks; (xix) Bayesian analysis; (xx) cluster analysis; (xxi) a kernelized method; (xxii) subspace discriminant analysis; (xxiii) k-nearest neighbours (KNN); (xxiv) quadratic discriminant analysis (QDA); (xxv) probabilistic principal component Analysis (PPCA); (xxvi) non negative matrix factorisation; (xxvii) k-means factorisation; (xxviii) fuzzy c-means factorisation; and (xxix) discriminant analysis (DA).

Analysing the one or more sample spectra may comprise a combination of the foregoing analysis techniques, such as PCA-LDA, PCA-MMC, PLS-LDA, etc.

Analysing the one or more sample spectra may comprise developing a classification model and/or library using one or more reference sample spectra.

The one or more reference sample spectra may each have been or may each be obtained and/or pre-processed, for example in a manner as described above.

A set of reference sample intensity values may be derived from each of the one or more reference sample spectra, for example in a manner as described above.

In multivariate analysis, each set of reference sample intensity values may correspond to a reference point in a multivariate space having plural dimensions and/or plural intensity axes.

Each dimension and/or intensity axis may correspond to a particular time or time-based value, such as a particular mass, mass to charge ratio and/or ion mobility.

Each dimension and/or intensity axis may also correspond to a particular mode of operation.

Each dimension and/or intensity axis may correspond to a range, region or bin (e.g., comprising (an identified cluster of) one or more peaks) in an analytical space having one or more analytical dimensions. Where plural analytical dimensions are used (e.g., mass to charge, ion mobility, operational parameter, etc.), each dimension and/or intensity axis in multivariate space may correspond to a region or bin (e.g., comprising one or more peaks) in the analytical space. The shape of the region or bin may be regular or irregular.

The multivariate space may be represented by a reference matrix having have rows associated with respective reference sample spectra and columns associated with respective time or time-based values and/or modes of operation, or vice versa, the elements of the reference matrix being the reference sample intensity values for the respective time or time-based values and/or modes of operation of the respective reference sample spectra.

The multivariate analysis may be carried out on the reference matrix in order to define a classification model having one or more (e.g., desired or principal) components and/or to define a classification model space having one or more (e.g., desired or principal) component dimensions or axes.

A first component and/or component dimension or axis may be in a direction of highest variance and each subsequent component and/or component dimension or axis may be in an orthogonal direction of next highest variance.

The classification model and/or classification model space may be represented by one or more classification model vectors or matrices (e.g., one or more score matrices, one or more loading matrices, etc.). The multivariate analysis may also define an error vector or matrix, which does not form part of, and is not "explained" by, the classification model.

The reference matrix and/or multivariate space may have a first number of dimensions and/or intensity axes, and the classification model and/or classification model space may have a second number of components and/or dimensions or axes.

The second number may be lower than the first number.

The second number may be selected based on a cumulative variance or "explained" variance of the classification model being above an explained variance threshold and/or based on an error variance or an "unexplained" variance of the classification model being below an unexplained variance threshold.

The second number may be lower than the number of reference sample spectra.

Analysing the one or more sample spectra may comprise principal component analysis (PCA). In these embodiments, a PCA model may be calculated by finding eigenvectors and eigenvalues. The one or more components of the PCA model may correspond to one or more eigenvectors having the highest eigenvalues.

The PCA may be performed using a non-linear iterative partial least squares (NIPALS) algorithm or singular value decomposition. The PCA model space may define a PCA space. The PCA may comprise probabilistic PCA, incremental PCA, non-negative PCA and/or kernel PCA.

Analysing the one or more sample spectra may comprise linear discriminant analysis (LDA).

Analysing the one or more sample spectra may comprise performing linear discriminant analysis (LDA) (e.g., for classification) after performing principal component analysis (PCA) (e.g., for dimensionality reduction). The LDA or PCA-LDA model may define an LDA or PCA-LDA space. The LDA may comprise incremental LDA.

As discussed above, analysing the one or more sample spectra may comprise a maximum margin criteria (MMC) process.

Analysing the one or more sample spectra may comprise performing a maximum margin criteria (MMC) process (e.g., for classification) after performing principal component analysis (PCA) (e.g., for dimensionality reduction). The MMC or PCA-MMC model may define an MMC or PCA-MMC space.

As discussed above, analysing the one or more sample spectra may comprise library-based analysis.

Thus, according to various aspects and embodiments there is provided a method of spectrometric analysis comprising:

obtaining one or more sample spectra for an aerosol, smoke or vapour sample; and analysing the one or more sample spectra so as to classify the aerosol, smoke or vapour sample, wherein analysing the one or more sample spectra comprises library-based analysis.

Similarly, according to various aspects and embodiments there is provided a spectrometric analysis system comprising:

control circuitry arranged and adapted to:

obtain one or more sample spectra for an aerosol, smoke or vapour sample; and analyse the one or more sample spectra so as to classify the aerosol, smoke or vapour sample, wherein analysing the one or more sample spectra comprises library-based analysis.

N. Strittmatter et al., Anal. Chem. 2014, 86, 6555-6562 describes multivariate analysis but does not teach or suggest inter alia using library-based analysis in order to classify one or more sample spectra. Library-based analysis is particularly suitable for classification of aerosol, smoke or vapour samples, for example in real-time. An advantage of library based analysis is that a classification score or probability may be calculated independently for each library entry. The addition of a new library entry or data representing a library entry may also be done independently for each library entry. In contrast, multivariate or neural network based analysis may involve rebuilding a model, which can be time and/or resource consuming. These aspects and embodiments can, therefore, facilitate classification of an aerosol, smoke or vapour sample.

In library-based analysis, analysing the one or more sample spectra may comprise deriving one or more sets of metadata for the one or more sample spectra.

Each set of metadata may be representative of a class of one or more classes of sample.

Each set of metadata may be stored in an electronic library.

Each set of metadata for a class of aerosol, smoke or vapour sample may be derived from a set of plural reference sample spectra for that class of aerosol, smoke or vapour sample.

Each set of plural reference sample spectra may comprise plural channels of corresponding (e.g., in terms of time or time-based value, e.g., mass, mass to charge ratio, and/or ion mobility) intensity values, and wherein each set of metadata comprises an average value, such as mean or median, and/or a deviation value for each channel.

Use of this metadata is described in more detail below.

Analysing the one or more sample spectra may comprise defining one or more classes within a classification model and/or library.

The one or more classes may be defined within a classification model and/or library in a supervised and/or unsupervised manner.

Analysing the one or more sample spectra may comprise defining one or more classes within a classification model and/or library manually or automatically according to one or more class criteria.

The one or more class criteria for each class may be based on one or more of: (i) a distance (e.g., squared or root-squared distance and/or Mahalanobis distance and/or (variance) scaled distance) between one or more pairs of reference points for reference sample spectra within a classification model space; (ii) a variance value between groups of reference points for reference sample spectra within a classification model space; and (iii) a variance value within a group of reference points for reference sample spectra within a classification model space.

The one or more classes may each be defined by one or more class definitions.

The one or more class definitions may comprise one or more of: (i) a set of one or more reference points for reference sample spectra, values, boundaries, lines, planes, hyperplanes, variances, volumes, Voronoi cells, and/or positions, within a classification model space; and (ii) one or more positions within a hierarchy of classes.

Analysing the one or more sample spectra may comprise identifying one or more outliers in a classification model and/or library.

Analysing the one or more sample spectra may comprise removing one or more outliers from a classification model and/or library.

Analysing the one or more sample spectra may comprise subjecting a classification model and/or library to cross-validation to determine whether or not the classification model and/or library is successfully developed.

The cross-validation may comprise leaving out one or more reference sample spectra from a set of plural reference sample spectra used to develop a classification model and/or library.

The one or more reference sample spectra that are left out may relate to one or more particular targets and/or subjects.

The one or more reference sample spectra that are left out may be a percentage of the set of plural reference sample spectra used to develop the classification model and/or library, the percentage being in a range selected from a group consisting of: (i) ≤ or ≥0.1%; (ii) 0.1-0.2%; (iii) 0.2-0.5%; (iv) 0.5-1.0%; (v) 1.0-2.0%; (vi) 2.0-5%; (vii) 5-10.0%; and (viii) or 10.0%.

The cross-validation may comprise using the classification model and/or library to classify one or more reference sample spectra that are left out of the classification model and/or library.

The cross-validation may comprise determining a cross-validation score based on the proportion of reference sample spectra that are correctly classified by the classification model and/or library.

The cross-validation score may be a rate or percentage of reference sample spectra that are correctly classified by the classification model and/or library.

The classification model and/or library may be considered successfully developed when the sensitivity (true-positive rate or percentage) of the classification model and/or library is greater than a sensitivity threshold and/or when the specificity (true-negative rate or percentage) of the classification model and/or library is greater than a specificity threshold.

Analysing the one or more sample spectra may comprise using a classification model and/or library, for example a classification model and/or library as described above, to classify one or more sample spectra as belonging to one or more classes of sample. The one or more sample spectra may each have been or may each be obtained and/or pre-processed, for example in a manner as described above.

A set of sample intensity values may be derived from each of the one or more sample spectra, for example in a manner as described above. For example, a different set of background-subtracted sample intensity values may be derived for each class of one or more classes of sample.

In multivariate analysis, each set of sample intensity values may correspond to a sample point in a multivariate space having plural dimensions and/or plural intensity axes.

Each dimension and/or intensity axis may correspond to a particular time or time-based value.

Each dimension and/or intensity axis may correspond to a particular mode of operation.

Each set of sample intensity values may be represented by a sample vector, the elements of the sample vector being the intensity values for the respective time or time-based values and/or modes of operation of the one or more sample spectra.

A sample point and/or vector for the one or more sample spectra may be projected into a classification model space so as to classify the one or more sample spectra.

Thus, according to various aspects and embodiments there is provided a method of spectrometric analysis comprising:

obtaining one or more sample spectra for an aerosol, smoke or vapour sample;

analysing the one or more sample spectra so as to classify the aerosol, smoke or vapour sample, wherein analysing the one or more sample spectra comprises projecting a sample point and/or vector for the one or more sample spectra into a classification model space.

Similarly, according to various aspects and embodiments there is provided a spectrometric analysis system comprising:

control circuitry arranged and adapted to:

obtain one or more sample spectra for an aerosol, smoke or vapour sample;

analyse the one or more sample spectra so as to classify the aerosol, smoke or vapour sample, wherein analysing the one or more sample spectra comprises projecting a sample point and/or vector for the one or more sample spectra into a classification model space.

N. Strittmatter et al., Anal. Chem. 2014, 86, 6555-6562 describes multivariate analysis but does not disclose or suggest inter alia later projecting a sample point and/or vector for one or more sample spectra into a classification model space in order to classify a sample. Previously developed multivariate modes spaces are particularly suitable for later classification of aerosol, smoke or vapour samples, for example in real-time. These aspects and embodiments can, therefore, facilitate classification of an aerosol, smoke or vapour sample.

The sample point and/or vector may be projected into the classification model space using one or more vectors or matrices of the classification model (e.g., one or more loading matrices, etc.).

The one or more sample spectra may be classified as belonging to a class based on the position of the projected sample point and/or vector in the classification model space.

In library-based analysis, analysing the one or more sample spectra may comprise calculating one or more probabilities or classification scores based on the degree to which the one or more sample spectra correspond to one or more classes of sample represented in an electronic library.

As discussed above, one or more sets of metadata that are each representative of a class of one or more classes of sample may be stored in the electronic library.

Analysing the one or more sample spectra may comprise, for each of the one or more classes, calculating a likelihood of each intensity value in a set of sample intensity values for the one or more sample spectra given the set of metadata stored in the electronic library that is representative of that class. As discussed above, a different set of background-subtracted sample intensity values may be derived for each class of one or more classes of sample.

Each likelihood may be calculated using a probability density function.

The probability density function may be based on a generalised Cauchy distribution function.

The probability density function may be a Cauchy distribution function, a Gaussian (normal) distribution function, or other probability density function based on a combination of a Cauchy distribution function and a Gaussian (normal) distribution function.

Plural likelihoods calculated for a class may be combined (e.g., multiplied) to give a probability that the one or more sample spectra belongs to that class.

Alternatively, analysing the one or more sample spectra may comprise, for each of the one or more classes, calculating a classification score (e.g., a distance score, such as a root-mean-square score) for a intensity values in the set of intensity values for the one or more sample spectra using the metadata stored in the electronic library that is representative of that class.

A probability or classification score may be calculated for each one of plural classes, for example in the manner described above.

The probabilities or classification scores for the plural classes may be normalised across the plural classes.

The one or more sample spectra may be classified as belonging to a class based on the one or more (e.g., normalised) probabilities or classification scores.

Analysing the one or more sample spectra may comprise classifying one or more sample spectra as belonging to one or more classes in a supervised and/or unsupervised manner.

Analysing the one or more sample spectra may comprise classifying one or more sample spectra manually or automatically according to one or more classification criteria.

The one or more classification criteria may be based on one or more class definitions.

The one or more class definitions may comprise one or more of: (i) a set of one or more reference points for reference sample spectra, values, boundaries, lines, planes, hyperplanes, variances, volumes, Voronoi cells, and/or positions, within a classification model space; and (ii) one or more positions within a hierarchy of classes.

The one or more classification criteria may comprise one or more of: (i) a distance (e.g., squared or root-squared distance and/or Mahalanobis distance and/or (variance) scaled distance) between a projected sample point for one or more sample spectra within a classification model space and a set of one or more reference points for one or more reference sample spectra, values, boundaries, lines, planes, hyperplanes, volumes, Voronoi cells, or positions, within the classification model space being below a distance threshold or being the lowest such distance; (ii) one or more projected sample points for one or more sample spectra within a classification model space being one side or other of one or more reference points for one or more reference sample spectra, values, boundaries, lines, planes, hyperplanes, or positions, within the classification model space; (iii) one or more projected sample points within a classification model space being within one or more volumes or Voronoi cells within the classification model space; (iv) a probability that one or more projected sample points for one or more sample spectra within a classification model space belong to a class being above a probability threshold or being the highest such probability; and (v) a probability or classification score being above a probability or classification score threshold or being the highest such probability or classification score.

The one or more classification criteria may be different for different types of class.

The one or more classification criteria for a first type of class may be relatively less stringent and the one or more classification criteria for a second type of class may be relatively more stringent. This may increase the likelihood that the aerosol, smoke or vapour sample is classified as being in a class belonging to the first type of class and/or may reduce the likelihood that the aerosol, smoke or vapour sample is classified as being in a class belonging to the second type of class. This may be useful when incorrect classification in a class belonging to the first type of class is more acceptable than incorrect classification in a class belonging to the second type of class.

The first type of class may comprise unhealthy and/or undesirable and/or lower quality target matter and the second type of class may comprise healthy and/or desirable and/or higher quality target matter, or vice versa.

Analysing the one or more sample spectra may comprise modifying a classification model and/or library.

Modifying the classification model and/or library may comprise adding one or more previously unclassified sample spectra to one or more reference sample spectra used to develop the classification model and/or library to provide an updated set of reference sample spectra.

Modifying the classification model and/or library may comprise deriving one or more background noise profiles for one or more previously unclassified sample spectra and storing the one or more background noise profiles in electronic storage for use when pre-processing and analysing one or more further sample spectra obtained from a further different aerosol, smoke or vapour sample.

Modifying the classification model and/or library may comprise re-developing the classification model and/or library using the updated set of reference sample spectra.

Modifying the classification model and/or library may comprise re-defining one or more classes of the classification model and/or library using the updated set of reference sample spectra. This can account for targets whose characteristics may change over time, such as developing cancers, evolving microorganisms, etc.

As discussed above, the one or more sample spectra may be obtained using a sampling device. In these embodiments, analysing the one or more sample spectra may take place while the sampling device remains in use.

Thus, according to various aspects and embodiments there is provided a method of spectrometric analysis comprising:

obtaining one or more sample spectra for an aerosol, smoke or vapour sample using a sampling device;

analysing the one or more sample spectra so as to classify the aerosol, smoke or vapour sample, wherein analysing the one or more sample spectra takes place while the sampling device remains in use.

Similarly, according to various aspects and embodiments there is provided a spectrometric analysis system comprising:

control circuitry arranged and adapted to:

obtain one or more sample spectra for an aerosol, smoke or vapour sample using a sampling device;

analyse the one or more sample spectra so as to classify the aerosol, smoke or vapour sample, wherein analysing the one or more sample spectra takes place while the sampling device remains in use.

N. Strittmatter et al., Anal. Chem. 2014, 86, 6555-6562 does not teach or suggest inter alia analysing one or more sample spectra while a sampling device remains in use. Analysing one or more sample spectra while a sampling device remains in use can allow a classification model and/or library to be developed and/or modified and/or used for classification substantially in real-time. The aspects and embodiments are, therefore, particularly advantageous for applications, for example where real-time analysis is desired.

Analysing the one or more sample spectra may comprise developing and/or modifying a classification model and/or library while the sampling device remains in use, for example while and/or subsequent to obtaining one or more reference sample spectra.

Analysing the one or more sample spectra may comprise using a classification model and/or library while the sampling device remains in use, for example while and/or subsequent to obtaining one or more sample spectra.

The method may comprise stopping a mode of operation, for example to avoid unwanted sampling and/or target or subject damage.

The method may comprise selecting a mode of operation so as to classify the aerosol, smoke or vapour sample.

The method may comprise changing from a first mode of operation to a second different mode of operation, or vice versa, so as to classify the aerosol, smoke or vapour sample.

Thus, according to various aspects and embodiments there is provided a method of spectrometric analysis comprising:

obtaining one or more sample spectra for an aerosol, smoke or vapour sample;

analysing the one or more sample spectra so as to classify the aerosol, smoke or vapour sample;

the method comprising:

selecting a mode of operation and/or changing from a first mode of operation to a second different mode of operation, or vice versa, so as to classify the aerosol, smoke or vapour sample.

Similarly, according to various aspects and embodiments there is provided a spectrometric analysis system comprising:

control circuitry arranged and adapted to:

obtain one or more sample spectra for an aerosol, smoke or vapour sample;

analyse the one or more sample spectra so as to classify the aerosol, smoke or vapour sample;

control circuitry being arranged and adapted to:

select a mode of operation and/or change from a first mode of operation to a second different mode of operation, or vice versa, so as to classify the aerosol, smoke or vapour sample.

N. Strittmatter et al., Anal. Chem. 2014, 86, 6555-6562 does not teach or suggest inter alia selecting a mode of operation and/or changing between first and second different modes of operations so as to classify an aerosol, smoke or vapour sample. Selecting a mode of operation and/or changing between first and second different modes of operations can reduce or resolve ambiguity in one or more sample spectra classifications, provide one or more sample spectra sub-classifications, and/or provide confirmation of one or more sample spectra classifications. Selecting a mode of operation and/or changing between first and second different modes of operations can also facilitate accurate classification of an aerosol, smoke or vapour sample, for example by improving the quality, e.g., peak strength, signal to noise, etc., in the sample spectra and/or improve the relevancy or accuracy of the classification. These aspects and embodiments are, therefore, particularly advantageous.

The mode of operation may be selected and/or changed based on a classification for a target and/or subject sample and/or a classification for one or more previous sample spectra.

The target and/or subject sample and/or one or more previous sample spectra may have been obtained from the same target and/or subject as the one or more sample spectra.

The one or more previous sample spectra may have been obtained and/or pre-processed and/or analysed in a manner as described above.

The mode of operation may be selected and/or changed manually or automatically.

The mode of operation may be selected and/or changed based on a likelihood of a previous classification being correct. For example, a relatively lower likelihood may cause a different mode of operation to be used whereas a relatively higher likelihood may not.

Selecting and/or changing the mode of operation may comprise selecting and/or changing a mode of operation for obtaining sample spectra.

The mode of operation for obtaining sample spectra may be selected and/or changed with respect to: (i) the condition of the target or subject that is sampled when obtaining an aerosol, smoke or vapour sample (e.g., stressed, hypoxic, medicated, etc.); (ii) the type of device used to obtain an aerosol, smoke or vapour sample (e.g., needle, probe, forceps, etc.); (iii) the device settings used when obtaining an aerosol, smoke or vapour sample (e.g., the potentials, frequencies, etc., used); (iv) the device mode of operation when obtaining an aerosol, smoke or vapour sample (e.g., probing mode, pointing mode, cutting mode, resecting mode, coagulating mode, desiccating mode, fulgurating mode, cauterising mode, etc.); (v) the type of ambient ion or ionisation source used; (vi) the sampling time over which an aerosol, smoke or vapour sample is obtained; (vii) the ion mode used to generate analyte ions for an aerosol, smoke or vapour sample (e.g., positive ion mode and/or negative ion mode); (viii) the spectrometer settings used when obtaining the one or more sample spectra (e.g., potentials, potential waveforms (e.g., waveform profiles and/or velocities), frequencies, gas types and/or pressures, dopants, etc., used); (ix) the use, number and/or type of fragmentation or reaction steps (e.g., MS/MS, $MS^n$, $MS^E$, higher energy or lower energy fragmentation or reaction steps, Electron-Transfer Dissociation (ETD), etc.); (x) the use, number and/or type of mass or mass to charge ratio separation or filtering steps (e.g., the range of masses or mass to charge ratios that are scanned, selected or filtered); (xi) the use, number and/or type of ion mobility separation or filtering steps (e.g., the range of drift times that are scanned, selected or filtered, the gas types and/or pressures, dopants, etc., used); (xii) the use, number and/or type of charge state separation or filtering steps (e.g., the charge states that are scanned, selected or filtered); (xiii) the type of ion detector used when obtaining one or more sample spectra; (xiv) the ion detector settings (e.g., the potentials, frequencies, gains, etc., used); and (xv) the binning process (e.g., bin widths) used.

Selecting and/or changing the mode of operation may comprise selecting and/or changing a mode of operation for pre-processing sample spectra.

The mode of operation for pre-processing sample spectra may be selected and/or changed with respect to one or more of: (i) the number and type of spectra that are combined; (ii) the background subtraction process; (iii) the conversion/correction process; (iv) the normalising, offsetting, scaling and/or function application process; the windowing process (e.g., range(s) of masses, mass to charge ratios, or ion mobilities that are retained or selected); (v) the filtering/smoothing process; (vi) the data reduction process; (vii) the thresholding process; (viii) the peak detection/selection process; (ix) the deisotoping process; the re-binning process; (x) the (further) correction process; and (xi) the (further) normalising, offsetting, scaling and/or function application process.

Selecting and/or changing the mode of operation may comprise selecting and/or changing a mode of operation for analysing sample spectra.

The mode of operation for analysing the one or more sample spectra may be selected and/or changed with respect to one or more of: (i) the one or more types of classification analysis (e.g., multivariate, univariate, library-based, supervised, unsupervised, etc.) used; (ii) the one or more particular classification models and/or libraries used; (iii) the one or more particular reference sample spectra used for the classification model and/or library; (iv) the one or more particular classes or class definitions used.

The method may comprise obtaining and/or pre-processing and/or analysing one or more sample spectra for an aerosol, smoke or vapour sample using a first mode of operation.

The method may comprise obtaining and/or pre-processing and/or analysing one or more sample spectra for an aerosol, smoke or vapour sample using a second mode of operation.

A mode of operation may comprise one or more of: (i) mass, mass to charge ratio and/or ion mobility spectrometry; (ii) spectroscopy, including Raman and/or Infra-Red (IR) spectroscopy; and (iii) Radio-Frequency (RF) impedance ultrasound.

As discussed above, the one or more sample spectra may be obtained using a sampling device. In these embodiments, the mode of operation may be selected and/or changed while the sampling device remains in use.

The method may comprise using a first mode of operation to provide a first classification for a particular target and/or subject, and using a second different mode of operation to provide a second classification for the same particular target and/or subject.

Thus, according to various aspects and embodiments there is provided a method of spectrometric analysis comprising:

obtaining one or more sample spectra for an aerosol, smoke or vapour sample for particular target and/or subject;

analysing the one or more sample spectra so as to classify the aerosol, smoke or vapour sample;

the method comprising:

using a first mode of operation to provide a first classification for the particular target and/or subject; and using a second different mode of operation to provide a second classification for the same particular target and/or subject.

Similarly, according to various aspects and embodiments there is provided a spectrometric analysis system comprising:

control circuitry arranged and adapted to:

obtain one or more sample spectra for an aerosol, smoke or vapour sample for particular target and/or subject;

analyse the one or more sample spectra so as to classify the aerosol, smoke or vapour sample;

the control circuitry being arranged and adapted to:

use a first mode of operation to provide a first classification for the particular target and/or subject; and use second different mode of operation to provide a second classification for the same particular target and/or subject.

N. Strittmatter et al., Anal. Chem. 2014, 86, 6555-6562 does not teach or suggest inter alia using first and second modes of operation to obtain first and second classifications for a particular target and/or subject. Using first and second modes of operation to obtain first and second classifications for a particular target and/or subject can reduce or resolve ambiguity in one or more sample spectra classifications, provide one or more sample spectra sub-classifications, and/or provide confirmation of one or more sample spectra classifications. Using first and second modes of operation to obtain first and second classifications for a particular target and/or subject can also facilitate accurate classification of an aerosol, smoke or vapour sample, for example by appropriately changing the mode of operation so as to improve the quality, e.g., peak strength, signal to noise, etc., in the sample spectra and/or improve the relevancy or accuracy of the classification. These aspects and embodiments are, therefore, particularly advantageous.

The first mode of operation may be used before or after or at substantially the same time as the second mode of operation.

The first mode of operation may provide a first classification score based on the likelihood of the first classification being correct. The second different mode of operation may provide a second classification score based on the likelihood of the second classification being correct.

The first classification score and second classification score may be combined so as to provide a combined classification score.

The combined classification score may be based on (e.g., weighted) summation, multiplication or average of the first classification score and second classification score.

The aerosol, smoke or vapour sample may be classified based on the combined classification score.

In some embodiments, the second classification may be the same as the first classification or may be a sub-classification within the first classification or may be a classification that contains the first classification. The second classification may confirm the first classification.

Alternatively, the second classification may not be the same as the first classification and/or may not be a sub-classification within the first classification and/or may not be a classification that contains the first classification. The second classification may contradict the first classification.

As discussed above, the one or more sample spectra may be obtained using a sampling device. In these embodiments, the mode of operation may be changed while the sampling device remains in use.

In some embodiments, obtaining the one or more sample spectra may comprise obtaining one or more (e.g., known) reference sample spectra and one or more (e.g., unknown) sample spectra for the same particular target and/or subject, and analysing the one or more sample spectra may comprise developing and/or modifying and/or using a classification model and/or library tailored for the particular target and/or subject.

Thus, according to various aspects and embodiments there is provided a method of spectrometric analysis comprising:

obtaining one or more reference sample spectra for an aerosol, smoke or vapour sample for a particular target and/or subject;

analysing the one or more reference sample spectra so as to classify the aerosol, smoke or vapour sample, wherein analysing the one or more reference sample spectra comprises developing and/or modifying a classification model and/or library for the particular target and/or subject;

obtaining one or more sample spectra for an aerosol, smoke or vapour sample for the same particular target and/or subject; and analysing the one or more sample spectra so as to classify the aerosol, smoke or vapour sample, wherein analysing the one or more sample spectra comprises using the classification model and/or library developed and/or modified for the particular target and/or subject.

Similarly, according to various aspects and embodiments there is provided a spectrometric analysis system comprising:

obtain one or more reference sample spectra for an aerosol, smoke or vapour sample for a particular target and/or subject;

analyse the one or more reference sample spectra so as to classify the aerosol, smoke or vapour sample, wherein analysing the one or more reference sample spectra comprises developing and/or modifying a classification model and/or library for the particular target and/or subject;

obtain one or more sample spectra for an aerosol, smoke or vapour sample for the same particular target and/or subject; and analyse the one or more sample spectra so as to classify the aerosol, smoke or vapour sample, wherein analysing the one or more sample spectra comprises using the classification model and/or library developed and/or modified for the particular target and/or subject.

N. Strittmatter et al., Anal. Chem. 2014, 86, 6555-6562 does not teach or suggest inter alia using a classification model and/or library developed and/or modified specifically for a particular target and/or subject. Using a classification model and/or library developed and/or modified specifically for a particular target and/or subject can improve the relevancy and/or accuracy of the classification for the particular target and/or subject. These aspects and embodiments are, therefore, particularly advantageous.

As discussed above, the one or more sample spectra may be obtained using a sampling device. In these embodiments, the classification model and/or library for the particular target and/or subject may be developed and/or modified and/or used while the sampling device remains in use.

Plural classification models and/or libraries, for example each having one or more classes, may be developed and/or modified and/or used as described above in any aspect or embodiment.

Analysing the one or more sample spectra may produce one or more results. The one or more results may comprise one or more classification models and/or libraries and/or class definitions and/or classification criteria and/or classifications for the aerosol, smoke or vapour sample. The one or more results may correspond to one or more regions of a target and/or subject.

The results may be used by control circuitry of the spectrometric analysis system. The control circuitry may form part of or may be coupled to a spectrometer, such as a mass and/or ion mobility spectrometer, of the spectrometric analysis system.

The method may comprise stopping a mode of operation, for example in a manner as discussed above, based on the one or more results.

The method may comprise selecting and/or changing a mode of operation, for example in a manner as discussed above, based on the one or more results.

The method may comprise developing and/or modifying a classification model and/or library, for example in a manner as discussed above, based on the one or more results.

The method may comprise outputting the one or more results to electronic storage of the spectrometric analysis system.

The electronic storage may form part of or may be coupled to a spectrometer, such as a mass and/or ion mobility spectrometer, of the spectrometric analysis system.

The method may comprise transmitting the one or more results to a first location from a second location.

The method may comprise receiving the one or more results at a first location from a second location.

As discussed above, the first location may be a remote or distal sampling location and/or the second location may be a local or proximal analysis location. This can allow, for example, the one or more sample spectra to be analysed at a safer or more convenient location but used at a disaster location (e.g., earthquake zone, war zone, etc.) at which the one or more sample spectra were obtained.

As discussed above, the one or more sample spectra may be obtained using a sampling device. In these embodiments, the method may comprise providing feedback based on the one or more results while the sampling device remains in use while the sampling device remains in use.

Thus, according to various aspects and embodiments there is provided a method of spectrometric analysis comprising:

obtaining one or more sample spectra for an aerosol, smoke or vapour sample using a sampling device;

analysing the one or more sample spectra so as to classify the aerosol, smoke or vapour sample, wherein analysing the one or more sample spectra produces one or more results; and providing feedback based on the one or more results while the sampling device remains in use.

Similarly, according to various aspects and embodiments there is provided a spectrometric analysis system comprising:

control circuitry arranged and adapted to:

obtain one or more sample spectra for an aerosol, smoke or vapour sample using a sampling device;

analyse the one or more sample spectra so as to classify the aerosol, smoke or vapour sample, wherein analysing the one or more sample spectra produces one or more results; and provide feedback based on the one or more results while the sampling device remains in use.

N. Strittmatter et al., Anal. Chem. 2014, 86, 6555-6562 does not teach or suggest inter alia providing feedback based on one or more results while a sampling device remains in use. Providing feedback based on one or more results while a sampling device remains in use can make timely (e.g., intra-operative) use of an aerosol, smoke or vapour sample classification. These aspects and embodiments are, therefore, particularly advantageous.

Providing feedback may comprise outputting the one or more results to one or more feedback devices of the spectrometric analysis system.

The one or more feedback devices may comprise one or more of: a haptic feedback device, a visual feedback device, and/or an audible feedback device.

Providing the one or more results may comprise displaying the one or more results, e.g., using a visual feedback device.

Displaying the one or more results may comprise displaying one or more of: (i) one or more classification model spaces comprising one or more reference points for one or more reference sample spectra; (ii) one or more classification model spaces comprising one or more sample points for one or more sample spectra; (iii) one or more library entries (e.g., metadata) for one or more classes of sample; (iv) one or more class definitions for one or more classes of sample; (v) one or more classification criteria for one or more classes of aerosol, smoke or vapour sample; (vi) one or more probabilities or classification scores for the aerosol, smoke or vapour sample; (vii) one or more classifications for the aerosol, smoke or vapour sample; and/or (viii) one or more scores or loadings for a classification model.

Displaying the one or more results may comprise displaying the one or more results graphically and/or alphanumerically.

Displaying the one or more results graphically may comprise displaying one or more graphical representations of the one or more results.

The one or more graphical representations may have a shape, size, pattern and/or colour based on the one or more results.

Displaying the one or more results may comprise displaying a guiding line or guiding area on a target and/or subject, and/or overlaying a guiding line or guiding area on an image that corresponds to a target and/or subject.

Displaying the one or more results may comprise displaying the one or more results on one or more regions of a target and/or subject, and/or overlaying the one or more results on one or more areas of an image that correspond to one or more regions of a target and/or subject.

The method may be used in the context of one or more of: (i) humans; (ii) animals; (iii) plants; (iv) microbes; (v) food; (vi) drink; (vii) e-cigarettes; (viii) cells; (ix) tissues; (x) faeces; (xi) chemicals; and (xii) bio-pharma (e.g., fermentation broths).

In some embodiments, the method may encompass treatment of a human or animal body by surgery or therapy and/or may encompass diagnosis practiced on a human or animal body. The method may be surgical and/or therapeutic and/or diagnostic.

According to various aspects and embodiments there is provided a method of pathology, surgery, therapy, treatment, diagnosis, biopsy and/or autopsy comprising a method of spectrometric analysis as described herein in any aspect or embodiment.

In other embodiments, the method does not encompass treatment of a human or animal body by surgery or therapy and/or does not include diagnosis practiced on a human or animal body. The method may be non-surgical and/or non-therapeutic and/or non-diagnostic.

According to various aspects and embodiments there is provided a method of quality control comprising a method of spectrometric analysis as described herein in any aspect or embodiment.

Various embodiments are contemplated which relate to generating smoke, aerosol or vapour from a target (details of which are provided elsewhere herein) using an ambient ionisation ion source. The aerosol, smoke or vapour may then be mixed with a matrix and aspirated into a vacuum chamber of a mass spectrometer and/or ion mobility spectrometer. The mixture may be caused to impact upon a collision surface causing the aerosol, smoke or vapour to be ionised by impact ionization which results in the generation of analyte ions. The resulting analyte ions (or fragment or product ions derived from the analyte ions) may then be mass analysed and/or ion mobility analysed and the resulting mass spectrometric data and/or ion mobility spectrometric data may be subjected to multivariate analysis or other mathematical treatment in order to determine one or more properties of the target in real time.

According to an embodiment the device for generating aerosol, smoke or vapour from the target may comprise a tool which utilises an RF voltage, such as a continuous RF waveform.

Other embodiments are contemplated wherein the device for generating aerosol, smoke or vapour from the target may comprise an argon plasma coagulation ("APC") device. An argon plasma coagulation device involves the use of a jet of ionised argon gas (plasma) that is directed through a probe. The probe may be passed through an endoscope. Argon plasma coagulation is essentially a non-contact process as the probe is placed at some distance from the target. Argon gas is emitted from the probe and is then ionized by a high voltage discharge (e.g., 6 kV). High-frequency electric current is then conducted through the jet of gas, resulting in coagulation of the target on the other end of the jet. The depth of coagulation is usually only a few millimetres.

The device for generating aerosol, smoke or vapour, e.g., surgical or electrosurgical tool, device or probe or other sampling device or probe, disclosed in any of the aspects or embodiments herein may comprise a non-contact surgical device, such as one or more of a hydrosurgical device, a surgical water jet device, an argon plasma coagulation device, a hybrid argon plasma coagulation device, a water jet device and a laser device.

A non-contact surgical device may be defined as a surgical device arranged and adapted to dissect, fragment, liquefy, aspirate, fulgurate or otherwise disrupt biologic tissue without physically contacting the tissue. Examples include laser devices, hydrosurgical devices, argon plasma coagulation devices and hybrid argon plasma coagulation devices.

As the non-contact device may not make physical contact with the tissue, the procedure may be seen as relatively safe and can be used to treat delicate tissue having low intracellular bonds, such as skin or fat.

According to various embodiments the mass spectrometer and/or ion mobility spectrometer may obtain data in negative ion mode only, positive ion mode only, or in both positive and negative ion modes. Positive ion mode spectrometric data may be combined or concatenated with negative ion mode spectrometric data. Negative ion mode can provide particularly useful spectra for classifying aerosol, smoke or vapour samples, such as aerosol, smoke or vapour samples from targets comprising lipids.

Ion mobility spectrometric data may be obtained using different ion mobility drift gases, or dopants may be added to the drift gas to induce a change in drift time of one or more species. This data may then be combined or concatenated.

It will be apparent that the requirement to add a matrix or a reagent directly to a sample may prevent the ability to perform in vivo analysis of tissue and also, more generally, prevents the ability to provide a rapid simple analysis of target material.

According to other embodiments the ambient ionisation ion source may comprise an ultrasonic ablation ion source or a hybrid electrosurgical-ultrasonic ablation source that generates a liquid sample which is then aspirated as an aerosol. The ultrasonic ablation ion source may comprise a focused or unfocussed ultrasound.

Optionally, the device for generating aerosol, smoke or vapour comprises or forms part of an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electroflow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

According to an aspect there is provided a method of mass and/or ion mobility spectrometry comprising a method of spectrometric analysis as described herein in any aspect or embodiment.

According to an aspect there is provided a mass and/or ion mobility spectrometric analysis system and/or a mass and/or ion mobility spectrometer comprising a spectrometric analysis system as described herein in any aspect or embodiment.

Even if not explicitly stated, the methods of spectrometric analysis described herein may comprise performing any step or steps performed by the spectrometric analysis system as described herein in any aspect or embodiment, as appropriate.

Similarly, even if not explicitly stated, the (e.g., circuitry and/or devices of the) spectrometric analysis systems described herein may be arranged and adapted to perform any functional step or steps of a method of spectrometric analysis as described herein in any aspect or embodiment, as appropriate.

The functional step or steps may be implemented using hardware and/or software as desired.

Thus, according to an aspect there is provided a computer program comprising computer software code for performing a method of spectrometric analysis as described herein in any aspect or embodiment when the program is run on control circuitry of a spectrometric analysis system.

The computer program may be provided on a tangible computer readable medium (e.g., diskette, CD, DVD, ROM, RAM, flash memory, hard disk, etc.) and/or via a tangible medium (e.g., using optical or analogue communications lines) or intangible medium (e.g. using wireless techniques).

BRIEF DESCRIPTION OF THE DRAWINGS

Various embodiments will now be described, by way of example only, and with reference to the accompanying drawings in which:

FIG. 31 shows (above) mass spectra obtained by rapid evaporative ionisation mass spectrometry ("REIMS") together with a 3D PCA plot (below) from two sampling points, one consisting mainly from tumour, the other mainly from normal white matter and wherein there is a visible difference in the phospholipid composition (a trend can be observed from right to left on the PCA plot showing the amount of infiltration within the normal brain cells)

FIG. 42A shows a sample with unknown histology used to predict different tissue types and FIG. 42B shows a cross validation of the prediction based on the histological annotation;

FIG. 46A shows averaged desorption electrospray ionisation ("DESI") mass spectra from a pregnant (highlighted in blue) and a non-pregnant group (highlighted in red) acquired in negative ion mode in the mass range m/z 150-1000, FIG. 46B shows principal component analysis and discriminatory analysis using recursive maximum margin criterion ("RMMC"), FIG. 46C shows analysis with leave-one-out cross-validation for enhanced separation of group classes with highly accurate identification (80%) based on chemical signatures in the vaginal mucosal membrane.

FIG. 47A shows desorption electrospray ionisation ("DESI") mass spectral analysis of a bacteria sample on a swab in accordance with various embodiments and shows that bacterial samples can be detected using DESI and FIG. 47B shows a comparison with rapid evaporative ionisation mass spectrometry ("REIMS") analysis in conjunction with a Time of Flight mass analysis of a bacterial sample directly from an agar plate;

FIG. 49 shows schematically desorption electrospray ionisation ("DESI") mass spectrometry analysis, rapid evaporative ionisation mass spectrometry ("REIMS") mass spectrometry analysis and culturing based analysis of a sample on a swab according to various embodiments;

FIG. 54A shows in vivo utilization of a rapid evaporative ionisation mass spectrometry compatible endoscope system according to an embodiment and sampling points taken from three patients undergoing colonoscopy and FIG. 54B shows the sampling points depicted on a 3-dimensional PCA plot wherein the spectra acquired in vivo when the polyps were removed localize in a different part of space whilst all other mucosal spectra are quasi uniformly independent from the sampling location;

FIG. 60A shows representative mass spectral profiles between m/z 600-900 as obtained for HeLa, MES-SA and SNB cell line pellets; and FIG. 60B shows 3-dimensional PCA plot of averaged REIMS data collected from several independent cultures of HeLa, MES-SA and SNB-19 cells over the spectral mass range of m/z 600-900, wherein circles, squares and triangles represent different measurement times and shades reflect passage numbers;

FIG. 62 shows a 2-dimensional PCA plot of averaged REIMS data collected from the NCI-60 cells (squares) and cancer tissue samples (circles) wherein the tissue of origin is indicated by red (colon) and blue (ovarian) colors;

FIG. 63A shows the mass spectral profile for bulk ovarian cancer tissue, FIG. 63B shows a corresponding mass spectral profile for ovarian cancer cell line OVCAR-3, FIG. 63C shows a mass spectral profile for bulk colorectal cancer tissue and FIG. 63D shows a mass spectral profile for colon cancer cell line HCT-15;

FIG. 66 shows data from ovarian cancer analysis using REIMS technology where linear discriminant analysis shows separation of tissue that is borderline margin between normal and cancer, and between normal, borderline and ovarian lesions;

FIG. 79A shows spectral profiles of a pure *Escherichia coli* isolate; FIG. 79B shows spectral profiles of a pure *Candida albicans* isolate.

FIG. 80 shows LDA analysis of spectrometric data obtained using REIMS technology with *C. difficile* ribotyped isolates;

FIG. 81 shows LDA and cross validation analysis of MRSA and MSSA isolates

FIG. 85A shows a mass spectral pattern of porcine liver obtained in a cutting mode of operation for high voltages, FIG. 85B shows a mass spectral pattern of porcine liver obtained in a cutting mode of operation for low voltages and FIG. 85C shows an iKnife technology reference spectrum;

DETAILED DESCRIPTION

Overview

Various embodiments will now be described in more detail below which in general relate to obtaining one or more sample spectra for an aerosol, surgical smoke or vapour sample, and then analyzing the one or more sample spectra so as to classify the aerosol, surgical smoke or vapour sample.

In these embodiments, the aerosol, surgical smoke or vapour sample is generated from a target (e.g., in vivo tissue) using an ambient ionisation ion source. The aerosol, surgical smoke or vapour is then aspirated into a vacuum chamber of a mass and/or ion mobility (drift time) spectrometer and may be caused to impact upon a collision surface causing the aerosol, smoke or vapour sample to be ionised by impact ionisation which results in the generation of analyte ions. The resulting analyte ions (or fragment or product ions derived from the analyte ions) are then mass and/or ion mobility analyzed and the resulting mass and/or ion mobility spectrometric data is then subjected to analysis in order to determine one or more properties of the target in real time.

For example, the analysis may enable a determination to be made as to whether or not a portion of tissue which is currently being resected is cancerous or not. The analysis techniques can enable tissue which is of potential concern to be identified either prior to and/or during a surgical procedure and can enable a surgeon to have a greater confidence that all undesired or potentially cancerous tissue is both located and completely removed whilst at the same time ensuring that the minimum amount of healthy tissue is removed.

Figure 1:
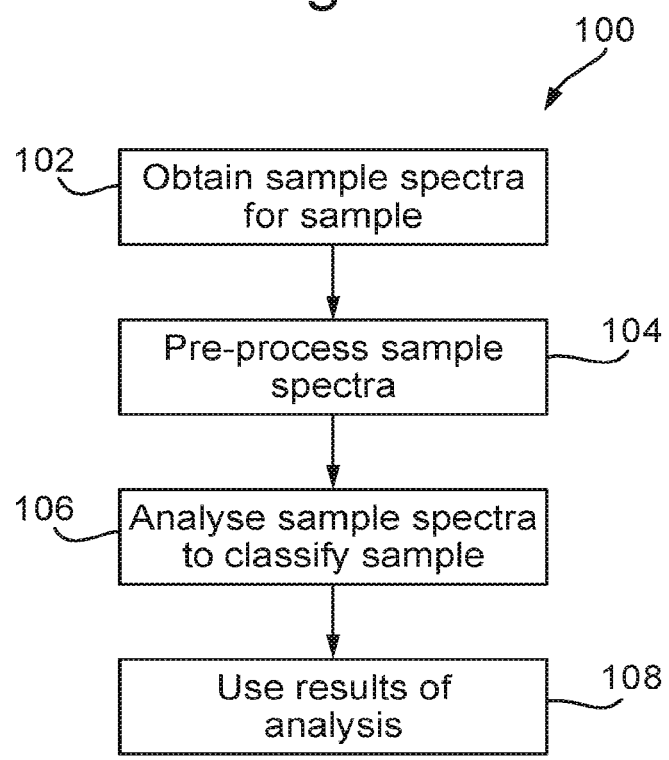
FIG. 1 shows an overview of a method of spectrometric analysis according to various embodiments.

FIG. 1 shows an overview of a method of spectrometric analysis 100 according to various embodiments.

The spectrometric analysis method 100 comprises a step 102 of obtaining one or more sample spectra for one or more aerosol, smoke or vapour samples. The spectrometric analysis method 100 then comprises a step 104 of pre-processing the one or more sample spectra. The spectrometric analysis method 100 then comprises a step 106 of analyzing the one or more sample spectra so as to classify the one or more aerosol, smoke or vapour samples. The spectrometric analysis method 100 then comprises a step 108 of using the results of the analysis. The steps in the spectrometric analysis method 100 will be discussed in more detail below.

Figure 2:
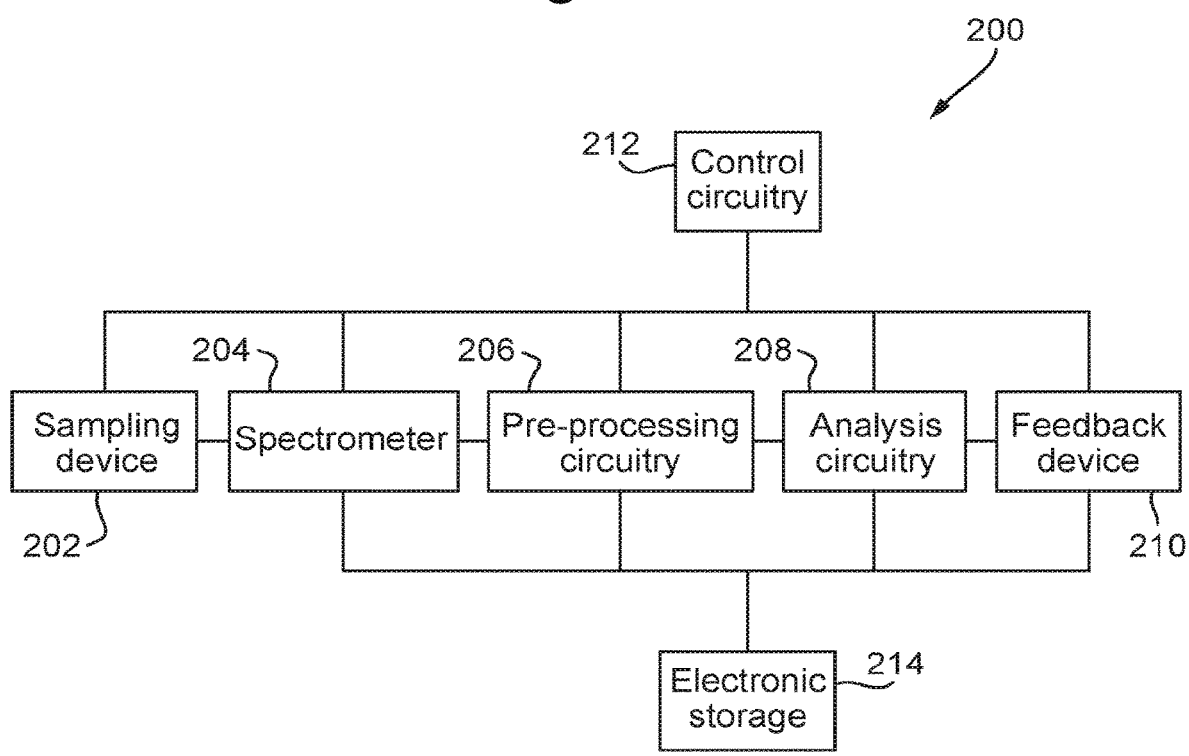
FIG. 2 shows an overview of a system arranged and adapted to perform spectrometric analysis according to various embodiments.

FIG. 2 shows an overview of a system 200 arranged and adapted to perform spectrometric analysis according to various embodiments.

The spectrometric analysis system 200 comprises a sampling device 202 and spectrometer 204 arranged and adapted to obtain one or more sample spectra for one or more aerosol, smoke or vapour samples.

The spectrometric analysis system 200 also comprises pre-processing circuitry 206 arranged and adapted to pre-process the one or more sample spectra obtained by the sampling device 202 and spectrometer 204. The pre-processing circuitry 206 may be directly connected or wirelessly connected to the spectrometer 204. A wireless connection can allow the one or more sample spectra to be obtained at a remote or distal disaster location, such as an earthquake or war zone, and then processed at a, for example more convenient or safer, local or proximal location. Furthermore, the spectrometer 204 may compress the data in the one or more sample spectra so that less data needs to be transmitted.

The spectrometric analysis system 200 also comprises analysis circuitry 208 arranged and adapted to analyze the one or more sample spectra so as to classify the one or more aerosol, smoke or vapour samples. The analysis circuitry 208 may be directly connected or wirelessly connected to the pre-processing circuitry 206. Again, a wireless connection can allow the one or more sample spectra to be obtained at a remote or distal disaster location and then processed at a, for example more convenient or safer, local or proximal location. Furthermore, the pre-processing circuitry 206 may reduce the amount of data in the one or more sample spectra so that less data needs to be transmitted.

The spectrometric analysis system 200 also comprises a feedback device 210 arranged and adapted to provide feedback based on the results of the analysis. The feedback device 210 may be directly connected or wirelessly connected to the analysis circuitry 208. A wireless connection can allow the one or more sample spectra to be pre-processed and analysed at a more convenient or safer local or proximal location and then feedback provided at a remote or distal disaster location. The feedback device may comprise a haptic, visual, and/or audible feedback device.

The system 200 also comprises control circuitry 212 arranged and adapted to control the operation of the elements of the system 200. The control circuitry 212 may be directly connected or wirelessly connected to each of the elements of the system 200. In some embodiments, one or more of the elements of the system 200 may also or instead have their own control circuitry.

The system 200 also comprises electronic storage 214 arranged and adapted to store the various data (e.g., sample spectra, background noise profiles, isotopic models, classification models and/or libraries, results, etc.) that are provided and/or used by the various elements of the system 200. The electronic storage 214 may be directly connected or wirelessly connected to the various elements of the system 200 to enable transfer of some or all of the data. Alternatively, some or all of the data may be transferred via a removable storage medium.

In some embodiments, the pre-processing circuitry 206, analysis circuitry 208, feedback device 210, control circuitry 212 and/or electronic storage 214 can form part of the spectrometer 204.

In some embodiments, the pre-processing circuitry 206 and analysis circuitry 208 can form part of the control circuitry 212.

The elements of the spectrometric analysis system 200 will be discussed in more detail below.

Obtaining Sample Spectra

As discussed above, the spectrometric analysis method 100 of FIG. 1 comprises a step 102 of obtaining the one or more sample spectra.

Also, as discussed above, the spectrometric analysis system 200 of FIG. 2 comprises a sampling device 202 and spectrometer 204 arranged and adapted to obtain one or more sample spectra for one or more aerosol, smoke or vapour samples.

By way of example, a number of different techniques for obtaining sample spectra will now be described.

Ambient Ionisation Ion Sources

According to various embodiments a sampling device is used to generate an aerosol, smoke or vapour sample from a target (e.g., in vivo tissue). The device may comprise an ambient ionisation ion source which is characterised by the ability to generate analyte aerosol, smoke or vapour samples from a native or unmodified target. For example, other types of ionisation ion sources such as Matrix Assisted Laser Desorption Ionisation ("MALDI") ion sources require a matrix or reagent to be added to the sample prior to ionisation.

It will be apparent that the requirement to add a matrix or a reagent to a sample prevents the ability to perform in vivo analysis of tissue and also, more generally, prevents the ability to provide a rapid simple analysis of target material.

In contrast, therefore, ambient ionisation techniques are particularly advantageous since firstly they do not require the addition of a matrix or a reagent (and hence are suitable for the analysis of in vivo tissue) and since secondly they enable a rapid simple analysis of target material to be performed.

A number of different ambient ionisation techniques are known and are intended to fall within the scope of the present invention. As a matter of historical record, Desorption Electrospray Ionisation ("DESI") was the first ambient ionisation technique to be developed and was disclosed in 2004. Since 2004, a number of other ambient ionisation techniques have been developed. These ambient ionisation techniques differ in their precise ionisation method but they share the same general capability of generating gas-phase ions directly from native (i.e. untreated or unmodified) samples. A particular advantage of the various ambient ionisation techniques which are intended to fall within the scope of the present invention is that the various ambient ionisation techniques do not require any prior sample preparation. As a result, the various ambient ionisation techniques enable both in vivo tissue and ex vivo tissue samples to be analysed without necessitating the time and expense of adding a matrix or reagent to the tissue sample or other target material.

A list of ambient ionisation techniques which are intended to fall within the scope of the present invention are given in the following table:

| Acronym | Ionisation technique |
| --- | --- |
| DESI | Desorption electrospray ionisation |
| DeSSI | Desorption sonic spray ionisation |
| DAPPI | Desorption atmospheric pressure photoionization |
| EASI | Easy ambient sonic-spray ionization |
| JeDI | Jet desorption electrospray ionization |
| TM-DESI | Transmission mode desorption electrospray ionization |
| LMJ-SSP | Liquid microjunction-surface sampling probe |
| DICE | Desorption ionization by charge exchange |
| Nano-DESI | Nanospray desorption electrospray ionization |
| EADESI | Electrode-assisted desorption electrospray ionization |
| APTDCI | Atmospheric pressure thermal desorption chemical ionization |
| V-EASI | Venturi easy ambient sonic-spray ionization |
| AFAI | Air flow-assisted ionization |
| LESA | Liquid extraction surface analysis |
| PTC-ESI | Pipette tip column electrospray ionization |
| AFADESI | Air flow-assisted desorption electrospray ionization |
| DEFFI | Desorption electro-flow focusing ionization |
| ESTASI | Electrostatic spray ionization |
| PASIT | Plasma-based ambient sampling ionization transmission |
| DAPCI | Desorption atmospheric pressure chemical ionization |
| DART | Direct analysis in real time |
| ASAP | Atmospheric pressure solid analysis probe |
| APTDI | Atmospheric pressure thermal desorption ionization |
| PADI | Plasma assisted desorption ionization |
| DBDI | Dielectric barrier discharge ionization |
| FAPA | Flowing atmospheric pressure afterglow |
| HAPGDI | Helium atmospheric pressure glow discharge ionization |
| APGDDI | Atmospheric pressure glow discharge desorption ionization |
| LTP | Low temperature plasma |
| LS-APGD | Liquid sampling-atmospheric pressure glow discharge |
| MIPDI | Microwave induced plasma desorption ionization |
| MFGDP | Microfabricated glow discharge plasma |
| RoPPI | Robotic plasma probe ionization |
| PLASI | Plasma spray ionization |
| MALDESI | Matrix assisted laser desorption electrospray ionization |
| ELDI | Electrospray laser desorption ionization |
| LDTD | Laser diode thermal desorption |
| LAESI | Laser ablation electrospray ionization |
| CALDI | Charge assisted laser desorption ionization |
| LA-FAPA | Laser ablation flowing atmospheric pressure afterglow |
| LADESI | Laser assisted desorption electrospray ionization |
| LDESI | Laser desorption electrospray ionization |
| LEMS | Laser electrospray mass spectrometry |
| LSI | Laser spray ionization |
| IR-LAMICI | Infrared laser ablation metastable induced chemical ionization |
| LDSPI | Laser desorption spray post-ionization |
| PAMLDI | Plasma assisted multiwavelength laser desorption ionization |
| HALDI | High voltage-assisted laser desorption ionization |
| PALDI | Plasma assisted laser desorption ionization |
| ESSI | Extractive electrospray ionization |
| PESI | Probe electrospray ionization |
| ND-ESSI | Neutral desorption extractive electrospray ionization |
| PS | Paper spray |
| DIP-APCI | Direct inlet probe-atmospheric pressure chemical ionization |
| TS | Touch spray |
| Wooden-tip | Wooden-tip electrospray |
| CBS-SPME | Coated blade spray solid phase microextraction |
| TSI | Tissue spray ionization |
| RADIO | Radiofrequency acoustic desorption ionization |
| LIAD-ESI | Laser induced acoustic desorption electrospray ionization |

| Acronym | Ionisation technique |
| --- | --- |
| SAWN | Surface acoustic wave nebulization |
| UASI | Ultrasonication-assisted spray ionization |
| SPA-nanoESI | Solid probe assisted nanoelectrospray ionization |
| PAUSI | Paper assisted ultrasonic spray ionization |
| DPESI | Direct probe electrospray ionization |
| ESA-Py | Electrospray assisted pyrolysis ionization |
| APPIS | Ambient pressure pyroelectric ion source |
| RASTIR | Remote analyte sampling transport and ionization relay |
| SACI | Surface activated chemical ionization |
| DEMI | Desorption electrospray metastable-induced ionization |
| REIMS | Rapid evaporative ionization mass spectrometry |
| SPAM | Single particle aerosol mass spectrometry |
| TDAMS | Thermal desorption-based ambient mass spectrometry |
| MAII | Matrix assisted inlet ionization |
| SAII | Solvent assisted inlet ionization |
| SwiFERR | Switched ferroelectric plasma ionizer |
| LPTD | Leidenfrost phenomenon assisted thermal desorption |

According to an embodiment the ambient ionisation ion source may comprise a rapid evaporative ionisation mass spectrometry ("REIMS") ion source wherein a RF voltage is applied to one or more electrodes in order to generate an aerosol or plume of surgical smoke by Joule heating.

However, it will be appreciated that other ambient ion sources including those referred to above may also be utilised. For example, according to another embodiment the ambient ionisation ion source may comprise a laser ionisation ion source. According to an embodiment the laser ionisation ion source may comprise a mid-IR laser ablation ion source. For example, there are several lasers which emit radiation close to or at 2.94 μm which corresponds with the peak in the water absorption spectrum. According to various embodiments the ambient ionisation ion source may comprise a laser ablation ion source having a wavelength close to 2.94 μm on the basis of the high absorption coefficient of water at 2.94 μm. According to an embodiment the laser ablation ion source may comprise a Er:YAG laser which emits radiation at 2.94 μm.

Other embodiments are contemplated wherein a mid-infrared optical parametric oscillator ("OPO") may be used to produce a laser ablation ion source having a longer wavelength than 2.94 μm. For example, an Er:YAG pumped ZGP-OPO may be used to produce laser radiation having a wavelength of e.g., 6.1 μm, 6.45 μm or 6.73 μm. In some situations it may be advantageous to use a laser ablation ion source having a shorter or longer wavelength than 2.94 μm since only the surface layers will be ablated and less thermal damage may result. According to an embodiment a $Co:MgF_2$ laser may be used as a laser ablation ion source wherein the laser may be tuned from 1.75-2.5 μm. According to another embodiment an optical parametric oscillator ("OPO") system pumped by a Nd:YAG laser may be used to produce a laser ablation ion source having a wavelength between 2.9-3.1 μm. According to another embodiment a $CO_2$ laser having a wavelength of 10.6 μm may be used to generate the aerosol, smoke or vapour sample.

According to other embodiments the ambient ionisation ion source may comprise an ultrasonic ablation ion source which generates a liquid sample which is then aspirated as an aerosol. The ultrasonic ablation ion source may comprise a focused or unfocussed source.

According to an embodiment the sampling device for generating aerosol, smoke or vapour samples from one or more regions of a target may comprise an electrosurgical tool which utilises a continuous RF waveform.

According to other embodiments a radiofrequency tissue dissection system may be used which is arranged to supply pulsed plasma RF energy to a tool. The tool may comprise, for example, a PlasmaBlade®. Pulsed plasma RF tools operate at lower temperatures than conventional electrosurgical tools (e.g., 40-170° C. c.f. 200-350° C.) thereby reducing thermal injury depth. Pulsed waveforms and duty cycles may be used for both cut and coagulation modes of operation by inducing electrical plasma along the cutting edge(s) of a thin insulated electrode.

Rapid Evaporative Ionisation Mass Spectrometry ("REIMS")

Figure 3:
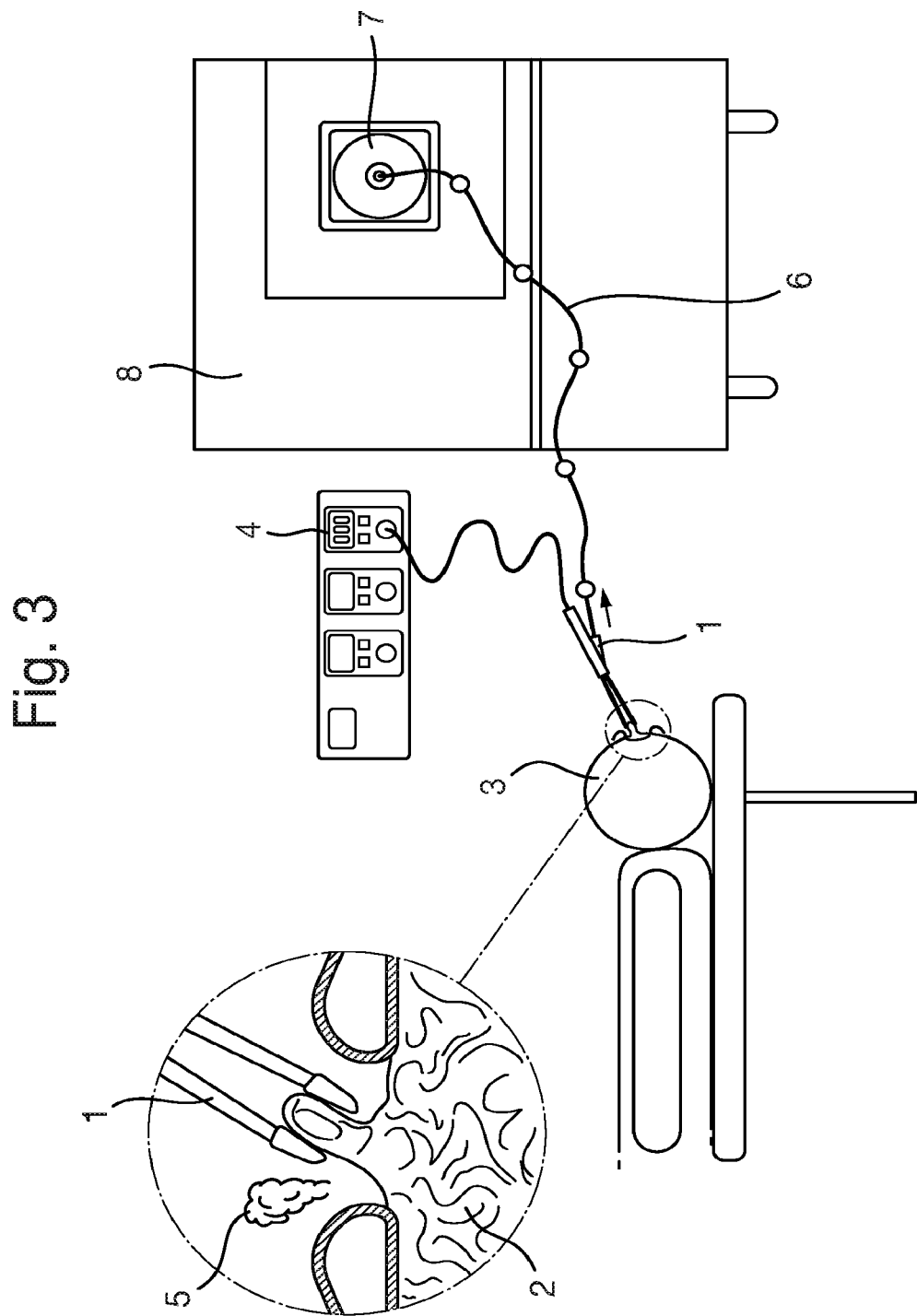
FIG. 3 shows a method of rapid evaporative ionisation mass spectrometry ("REIMS") wherein an RF voltage is applied to bipolar forceps resulting in the generation of an aerosol or surgical plume which is then captured through an irrigation port of the bipolar forceps and is then transferred to a mass spectrometer for mass and/or ion mobility analysis.

FIG. 3 illustrates a method of rapid evaporative ionisation mass spectrometry ("REIMS") wherein bipolar forceps 1 may be brought into contact with in vivo tissue 2 of a patient 3. In the example shown in FIG. 3, the bipolar forceps 1 may be brought into contact with brain tissue 2 of a patient 3 during the course of a surgical operation on the patient's brain. An RF voltage from an RF voltage generator 4 may be applied to the bipolar forceps 1 which causes localised Joule or diathermy heating of the tissue 2. As a result, an aerosol or surgical plume 5 is generated. The aerosol or surgical plume 5 may then be captured or otherwise aspirated through an irrigation port of the bipolar forceps 1. The irrigation port of the bipolar forceps 1 is therefore reutilised as an aspiration port. The aerosol or surgical plume 5 may then be passed from the irrigation (aspiration) port of the bipolar forceps 1 to tubing 6 (e.g., ⅛" or 3.2 mm diameter Teflon® tubing). The tubing 6 is arranged to transfer the aerosol or surgical plume 5 to an atmospheric pressure interface 7 of a mass and/or ion mobility spectrometer 8.

According to various embodiments a matrix comprising an organic solvent such as isopropanol may be added to the aerosol or surgical plume 5 at the atmospheric pressure interface 7. The mixture of aerosol 3 and organic solvent may then be arranged to impact upon a collision surface within a vacuum chamber of the mass and/or ion mobility spectrometer 8. According to one embodiment the collision surface may be heated. The aerosol is caused to ionise upon impacting the collision surface resulting in the generation of analyte ions. The ionisation efficiency of generating the analyte ions may be improved by the addition of the organic solvent. However, the addition of an organic solvent is not essential.

Analyte ions which are generated by causing the aerosol, smoke or vapour sample 5 to impact upon the collision surface are then passed through subsequent stages of the mass and/or ion mobility spectrometer and are subjected to mass and/or ion mobility analysis in a mass and/or ion mobility analyser. The mass and/or ion mobility analyser may, for example, comprise a quadrupole mass analyser or a Time of Flight mass analyser. The output of the mass analyser comprises plural sample spectra for the sample with each spectrum being represented by a set of time-intensity pairs. Each set of time-intensity pairs is obtained by binning ion detections into plural bins. In this embodiment, each bin has a mass or mass to charge ratio equivalent width of 0.1 Da or Th.

Pre-Processing Sample Spectra

As discussed above, the spectrometric analysis method 100 of FIG. 1 comprises a step 104 of pre-processing the one or more sample spectra.

Also, as discussed above, the spectrometric analysis system 200 of FIG. 2 comprises pre-processing circuitry 206 arranged and adapted to pre-process the one or more sample spectra.

By way of example, a number of different pre-processing steps will now be described. Any one or more of the steps may be performed so as to pre-process one or more sample spectra. The one or more steps may also be performed in any desired and suitable order.

Figure 4:
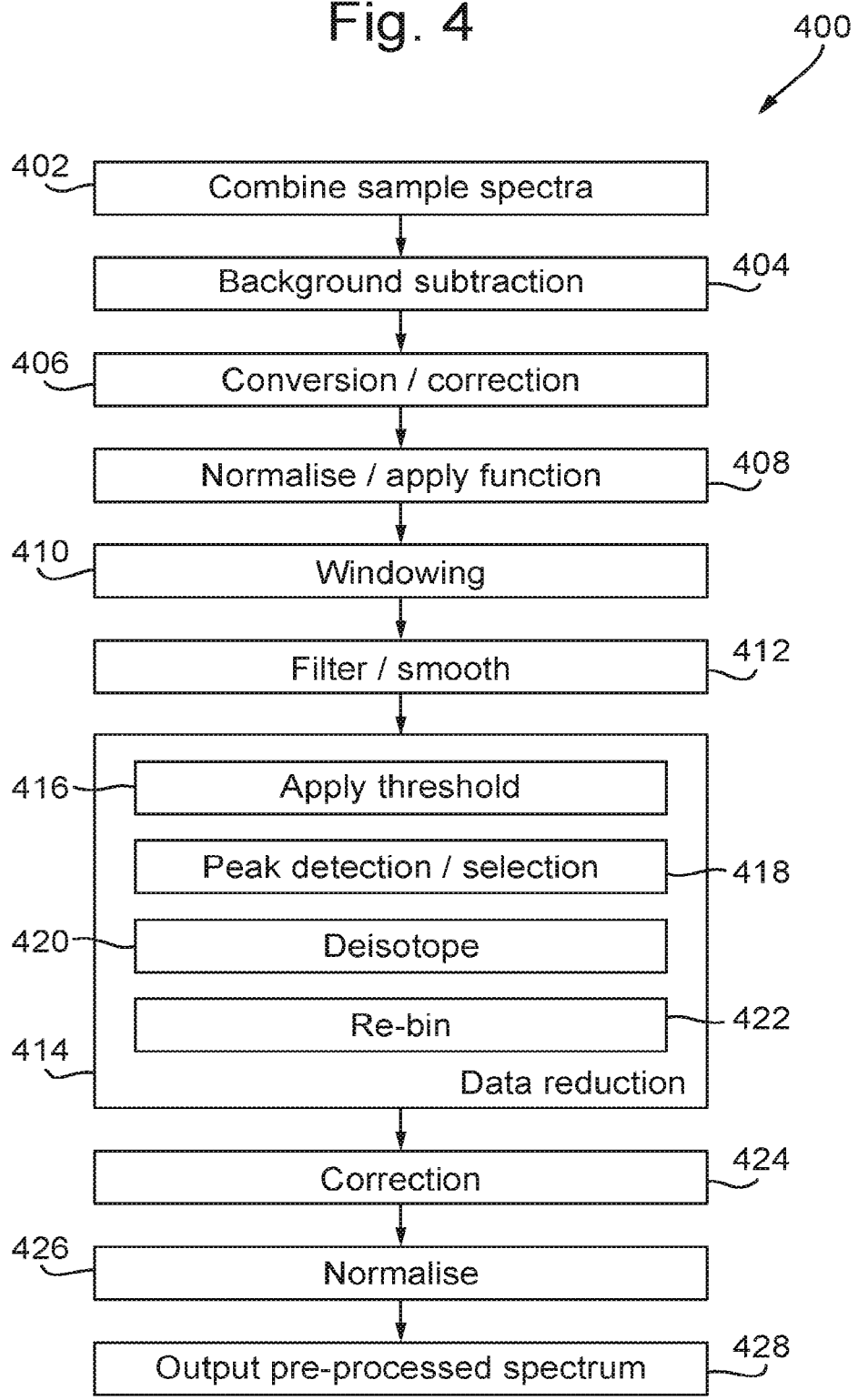
FIG. 4 shows a method of pre-processing sample spectra according to various embodiments.

FIG. 4 shows a method 400 of pre-processing plural sample spectra according to various embodiments.

The pre-processing method 400 comprises a step 402 of combining plural sample spectra. In some embodiments, ion detections or intensity values in corresponding bins of plural spectra are summed to produce a combined sample spectrum for a sample. In other embodiments, the plural spectra may have been obtained using different degrees of ion attenuation, and a suitably weighted summation of ion detections or intensity values in corresponding bins of the plural spectra can be used to produce a combined sample spectrum for the sample. In other embodiments, plural sample spectra may be concatenated, thereby providing a larger dataset for pre-processing and/or analysis.

The pre-processing method 400 then comprises a step 404 of background subtraction. The background subtraction process comprises obtaining background noise profiles for the sample spectrum and subtracting the background noise profiles from the sample spectrum to produce one or more background-subtracted sample spectra. A background subtraction process is described in more detail below.

The pre-processing method 400 then comprises a step 406 of converting and correcting ion arrival times for the sample spectrum to suitable masses and/or mass to charge ratios and/or ion mobilities. In some embodiments, the correction process comprises offsetting and scaling the sample spectrum based on known masses and/or ion mobilities corresponding to known spectral peaks for lockmass and/or lockmobility ions that were provided together with the analyte ions. A lockmass and/or lockmobility process is described in more detail below.

The pre-processing method 400 then comprises a step 408 of normalizing the intensity values of the sample spectrum. In some embodiments, this normalization comprises offsetting and scaling the intensity values base on statistical property for the sample spectrum, such as total ion current (TIC), a base peak intensity, an average intensity value, or quantile. In some embodiments, step 408 also includes applying a function to the intensity values in the sample spectrum. The function can be a variance stabilizing function that removes a correlation between intensity variance and intensity in the sample spectrum. The function can also enhance particular masses and/or mass to charge ratios and/or ion mobilities in the sample spectrum that may be useful for classification.

The pre-processing method 400 then comprises a step 410 of windowing in which parts of the sample spectrum are selected for further pre-processing. In some embodiments, parts of the sample spectrum corresponding to masses or mass to charge ratios in the range of 600-900 Da or Th are retained since this can provide particularly useful sample spectra for classifying tissues. In other embodiments, parts of the sample spectrum corresponding to masses or mass to charge ratios in the range of 600-2000 Da or Th are retained since this can provide particularly useful sample spectra for classifying bacteria.

The pre-processing method 400 then comprises a step 412 of filtering and/or smoothing process using a Savitzky-Golay process. This process removes unwanted higher frequency fluctuations in the sample spectrum.

The pre-processing method 400 then comprises a step 414 of a data reduction to reduce the number of intensity values to be subjected to analysis. Various forms of data reduction are contemplated. Any one or more of the following data reduction steps may be performed. The one or more data reduction steps may also be performed in any desired and suitable order.

The data reduction process can comprise a step 416 of retaining parts of the sample spectrum that are above an intensity threshold or intensity threshold function. The intensity threshold or intensity threshold function may be based on statistical property for the sample spectrum, such as total ion current (TIC), a base peak intensity, an average intensity value, or quantile.

The data reduction process can comprise a step 418 of peak detection and selection. The peak detection and selection process can comprise finding the gradient of the sample spectra and using a gradient threshold in order to identify rising and falling edges of peaks.

The data reduction process can comprise a step 420 of deisotoping in which isotopic peaks are identified and reduced or removed from the sample spectrum. A deisotoping process is described in more detail below.

The data reduction process can comprise a step 422 of re-binning in which ion intensity values from narrower bins are accumulated in a set of wider bins. In this embodiment, each bin has a mass or mass to charge ratio equivalent width of 1 Da or Th.

The pre-processing method 400 then comprises a further step 424 of correction that comprises offsetting and scaling the selected peaks of the sample spectrum based on known masses and/or ion mobilities corresponding to known spectral peaks for lockmass and/or lockmobility ions that were provided together with the analyte ions.

The pre-processing method 400 then comprises a further step 426 of normalizing the intensity values for the selected peaks of the one or more sample spectra. In some embodiments, this normalization comprises offsetting and scaling the intensity values based on statistical property for the selected peaks of the sample spectrum, such as total ion current (TIC), a base peak intensity, an average intensity value, or quantile. This normalization can prepare the intensity values of the selected peaks of the sample spectrum for analysis. For example, the intensity values can be normalized so as to have a particular average (e.g., mean or median) value, such as 0 or 1, so as to have a particular minimum value, such as −1, and so as to have a particular maximum value, such as 1.

The pre-processing method 400 then comprises a step 428 of outputting the pre-processed spectrum for analysis.

In some embodiments, plural pre-processed spectra are produced using the pre-processing method 400 of FIG. 4. The plural pre-processed spectra can be combined or concatenated.

Background Subtraction

As discussed above, the pre-processing method 400 of FIG. 4 comprises a step 404 of background subtraction. This step can comprise obtaining a background noise profile for a sample spectrum.

The background noise profile for a sample spectrum may be derived from the sample spectrum itself. However, it can be difficult to derive adequate background noise profiles for sample spectra themselves, particularly where relatively little sample or poor quality sample is available such that the sample spectrum for the sample comprises relatively weak peaks and/or comprises poorly defined noise.

To address this issue, background noise profiles can instead be derived from reference sample spectra and stored in electronic storage for later use. The reference sample spectra for each class of sample will often have a characteristic (e.g., periodic) background noise profile due to particular ions that tend to be generated when generating ions for the samples of that class. A background noise profile can therefore be derived for each class of sample. A well-defined background noise profile can accordingly be derived in advance for each class using reference sample spectra that are obtained for a relatively higher quality or larger amount of sample. The background noise profiles can then be retrieved for use in a background subtraction process prior to classifying a sample.

By way of example, methods of deriving and using background noise profiles will now be described in more detail.

Figure 5:
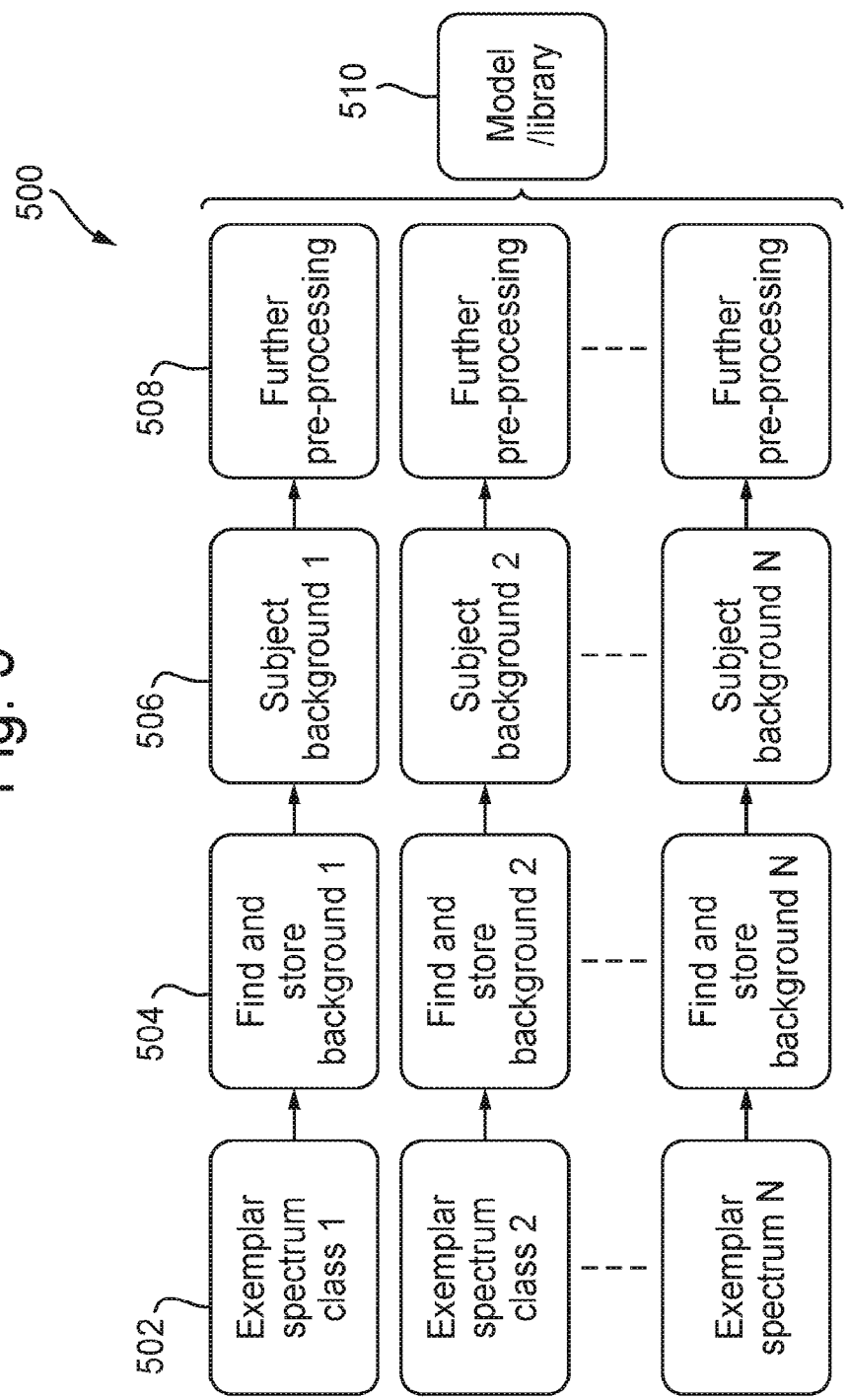
FIG. 5 shows a method of generating background noise profiles from plural reference sample spectra and then using background-subtracted reference sample spectra to develop a classification model and/or library.

FIG. 5 shows a method 500 of generating background noise profiles from plural reference sample spectra and then using background-subtracted sample spectra to develop a classification model and/or library.

The method 500 comprises a step 502 of inputting plural reference sample spectra. The method then comprises a step 504 of deriving and storing a background noise profile for each of the plural reference sample spectra. The method then comprises a step 506 of subtracting each background noise profile from its corresponding reference sample spectrum. The method then comprises a step 508 of performing further pre-processing, for example as described above with reference to FIG. 4, on the background-subtracted sample spectra. The method then comprises a step 510 of developing a classification model and/or library using the background-subtracted sample spectra.

A method of generating a background noise profile from a sample spectrum will now be described in more detail with reference to an example.

Figure 6:
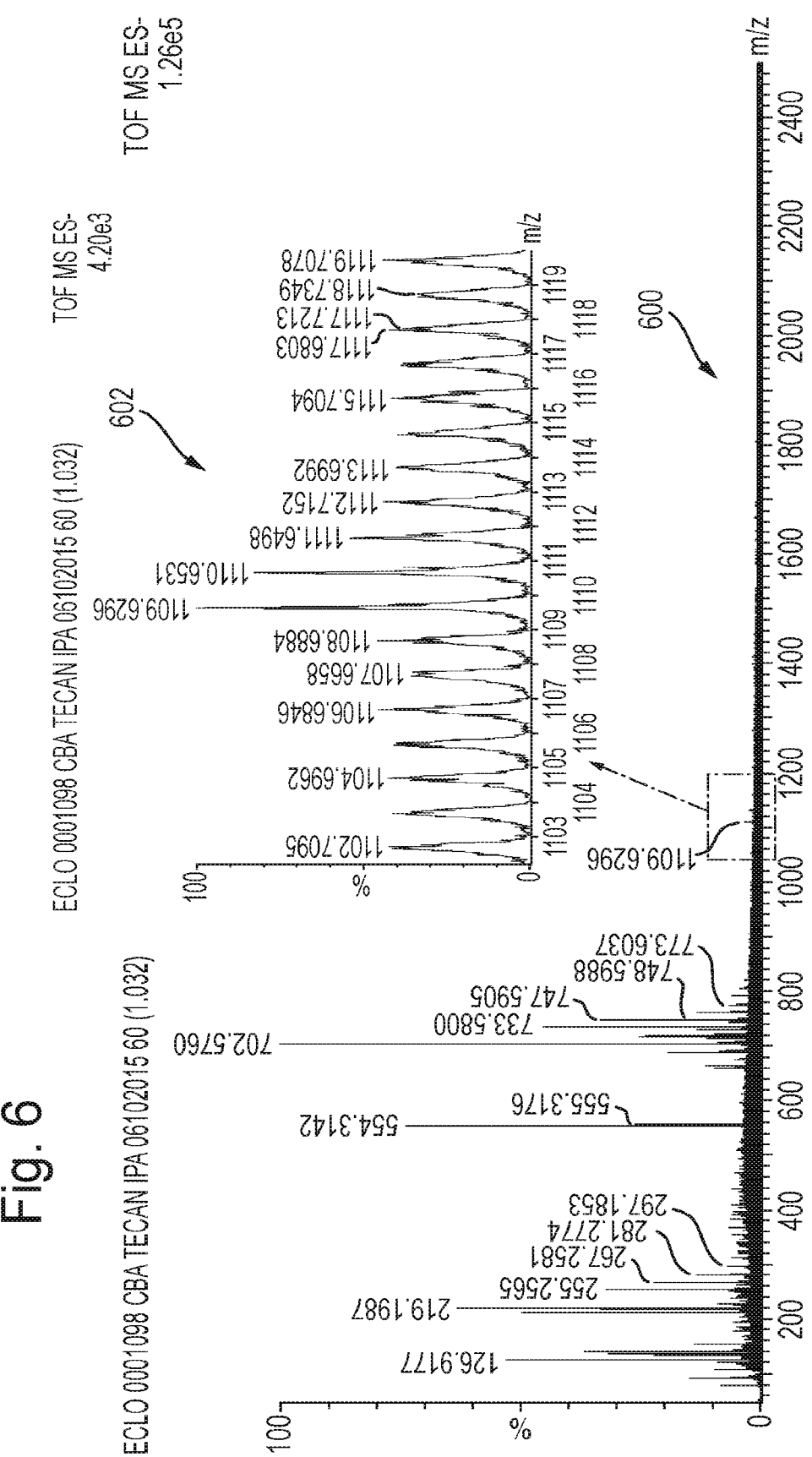
FIG. 6 shows a sample mass spectrum for which a background noise profile is to be derived.

FIG. 6 shows a sample spectrum 600 for which a background noise profile is to be derived. The sample spectrum 600 is divided into plural overlapping windows that are each processed separately. Alternatively, a translating window may be used.

Figure 7:
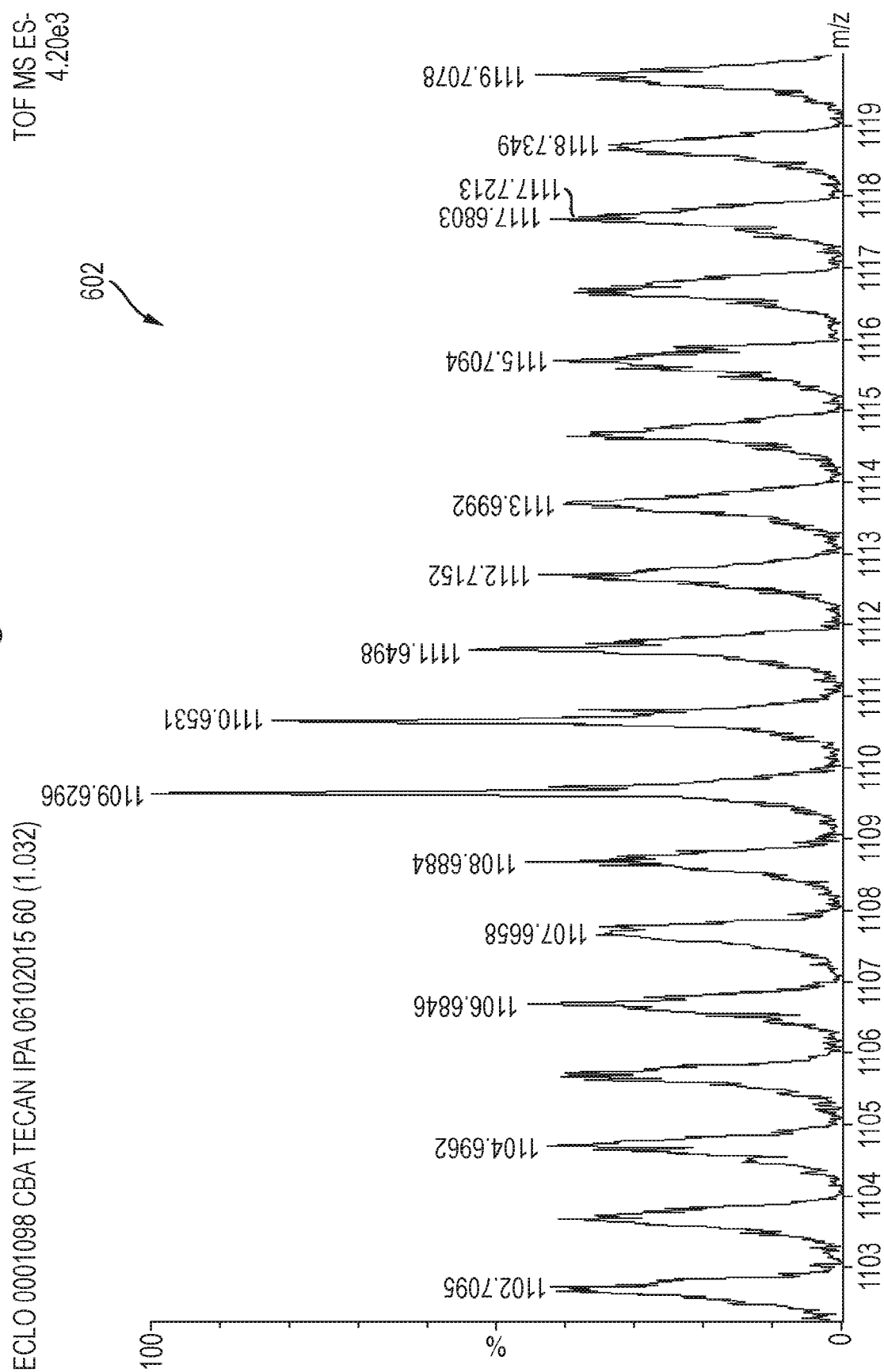
FIG. 7 shows a window of the sample mass spectrum of FIG. 6 that is used to derive a background noise profile.

FIGS. 6 and 7 show a window 602 of the sample spectrum 600 in more detail. In this embodiment, the window is 18 Da or Th wide.

Figure 8:
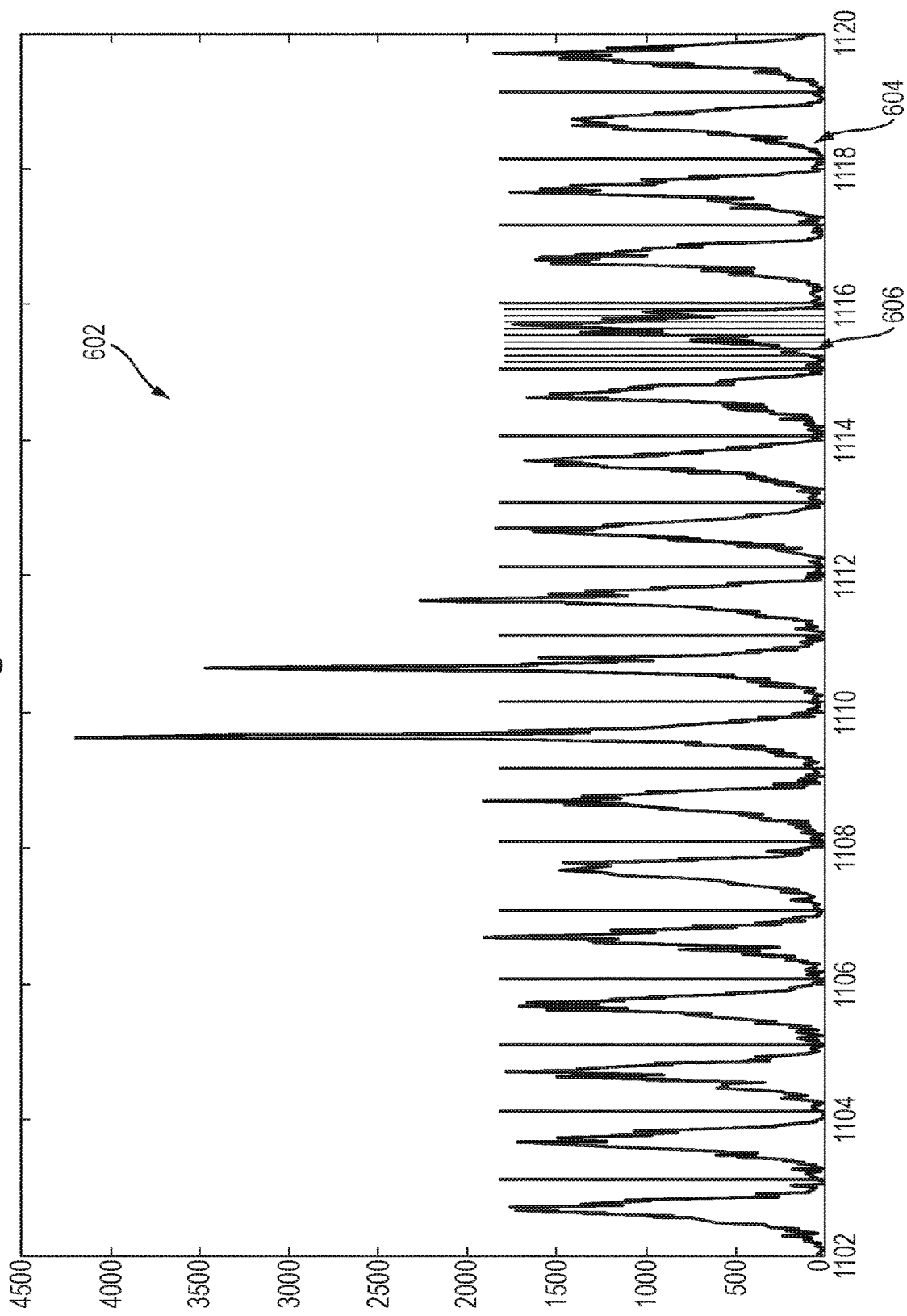
FIG. 8 shows segments and sub-segments of the window of the sample mass spectrum of FIG. 7 that are used to derive a background noise profile.

As is shown in FIG. 8, in order to derive the background noise profile, the window 602 is divided into plural segments 604. In this embodiment, the window 602 is divided into 18 segments, which each segment being 1 Da or Th wide.

Each segment 604 is further divided into plural sub-segments 606. In this embodiment, each segment 604 is divided into 10 sub-segments, which each sub-segment being 0.1 Da or Th wide.

The background noise profile value for a given sub-segment 606 is then a combination of the intensity values for the sub-segment 606 and the other sub-segments of the segments 604 in the window 602 that correspond to the sub-segment 606. In this embodiment, the combination is a 45% quantile of the intensity values for the corresponding sub-segments.

Figure 9:
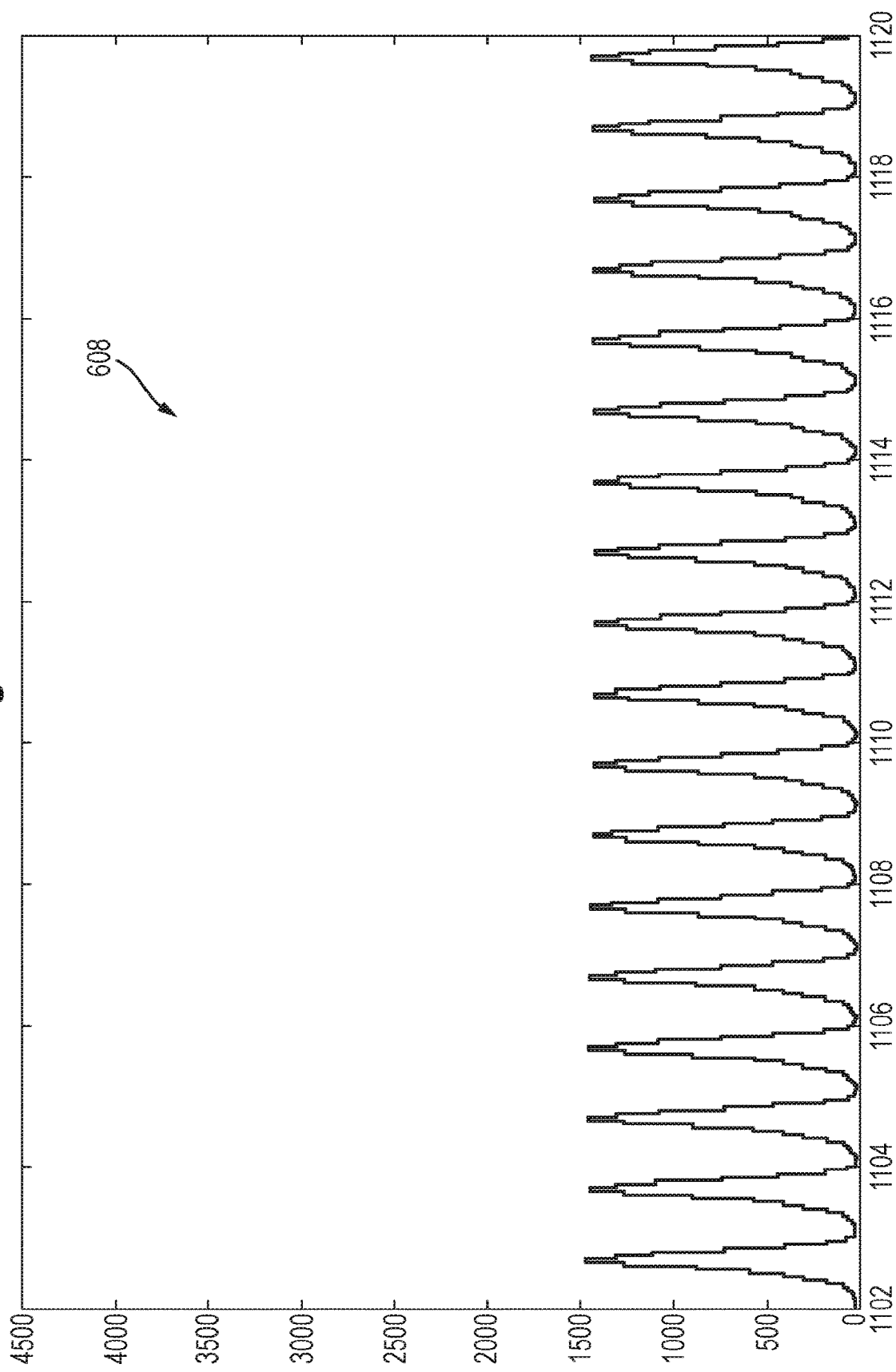
FIG. 9 shows a background noise profile derived for the window of the sample mass spectrum of FIG. 7.

FIG. 9 shows the resultant background noise profile derived for the window 602 of FIGS. 6 and 7. As is shown in FIG. 9, the window 602 comprises a periodic background noise profile having a period of 1 Da or Th.

Figure 10:
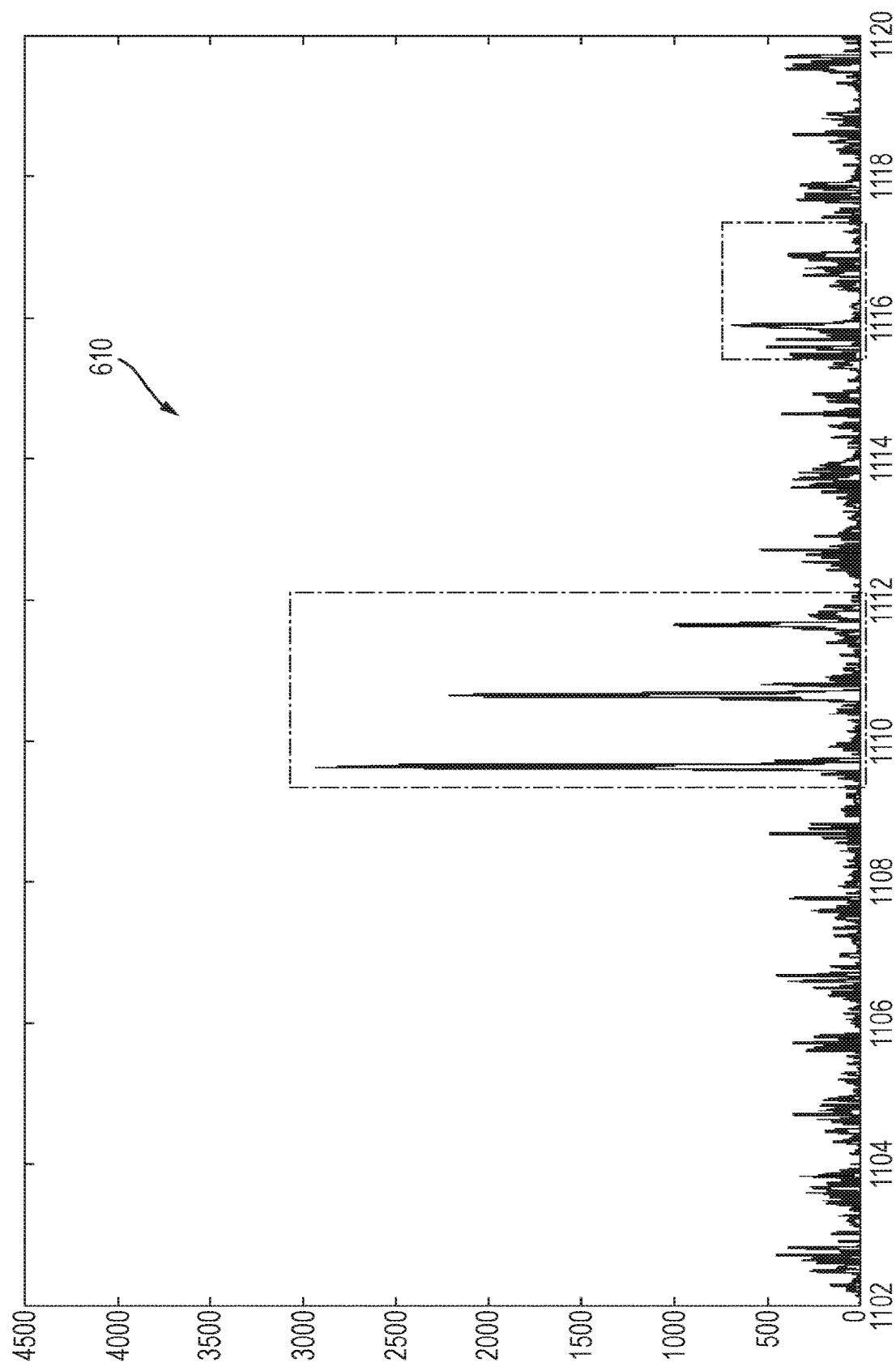
FIG. 10 shows the window of the sample mass spectrum of FIG. 7 with the background noise profile of FIG. 9 subtracted.

FIG. 10 shows the window 602 of FIG. 7 with the background noise profile of FIG. 9 subtracted. Comparing FIG. 10 to FIG. 7, it is clear that the background-subtracted spectrum of FIG. 10 has improved mass accuracy and additional identifiable peaks. Subsequent processing (e.g., peak detection, deisotoping, classification, etc.) can provide improved results following the background subtraction process.

In other embodiments, the background noise profile may be derived by fitting a piecewise polynomial to the spectrum. The piecewise polynomial describing the background noise profile may be fitted such that a selected proportion of the spectrum lies below the polynomial in each segment of the piecewise polynomial.

In other embodiments, the background noise profile may be derived by filtering in the frequency domain, for example using (e.g., fast) Fourier transforms. The filtering can remove components of the spectrum that vary relatively slowly or that are periodic.

A method of using background noise profiles from reference sample spectra will now be described in more detail with reference to an example.

Figure 11:
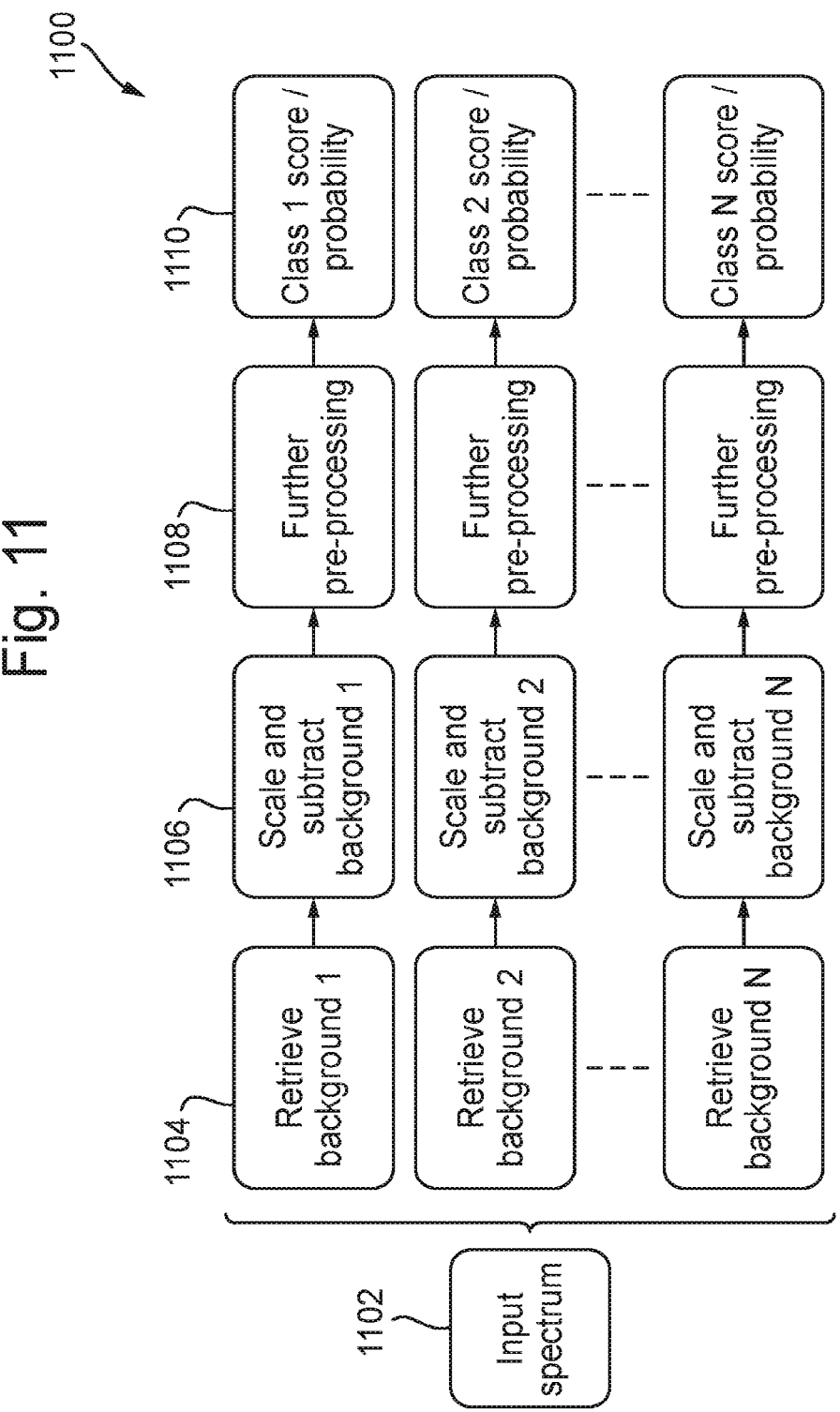
FIG. 11 shows a method of background subtraction and classification for a sample spectrum according to various embodiments.

FIG. 11 shows a method 1100 of background subtraction and classification for a sample spectrum.

The method 110 comprises a step 1102 of inputting a sample spectrum. The method then comprises a step 1104 of retrieving plural background noise profiles for respective classes of sample from electronic storage. The method then comprises a step 1106 of scaling and then subtracting each background noise profile from the sample spectrum to produce plural background subtracted spectra. The method then comprises a step 1108 of performing further pre-processing, for example as described above with reference to FIG. 4, on the background-subtracted sample spectra. The method then comprises a step 1110 of using a classification model and/or library so as to provide a classification score or probability for each class of sample using the background-subtracted sample spectra corresponding to that class.

The sample spectrum may then be classified as belonging to the class having the highest classification score or probability.

Deisotoping

As discussed above, the pre-processing method 400 of FIG. 4 comprises a step 420 of deisotoping. By way of example, a method of deisotoping will now be described in more detail.

Figure 12:
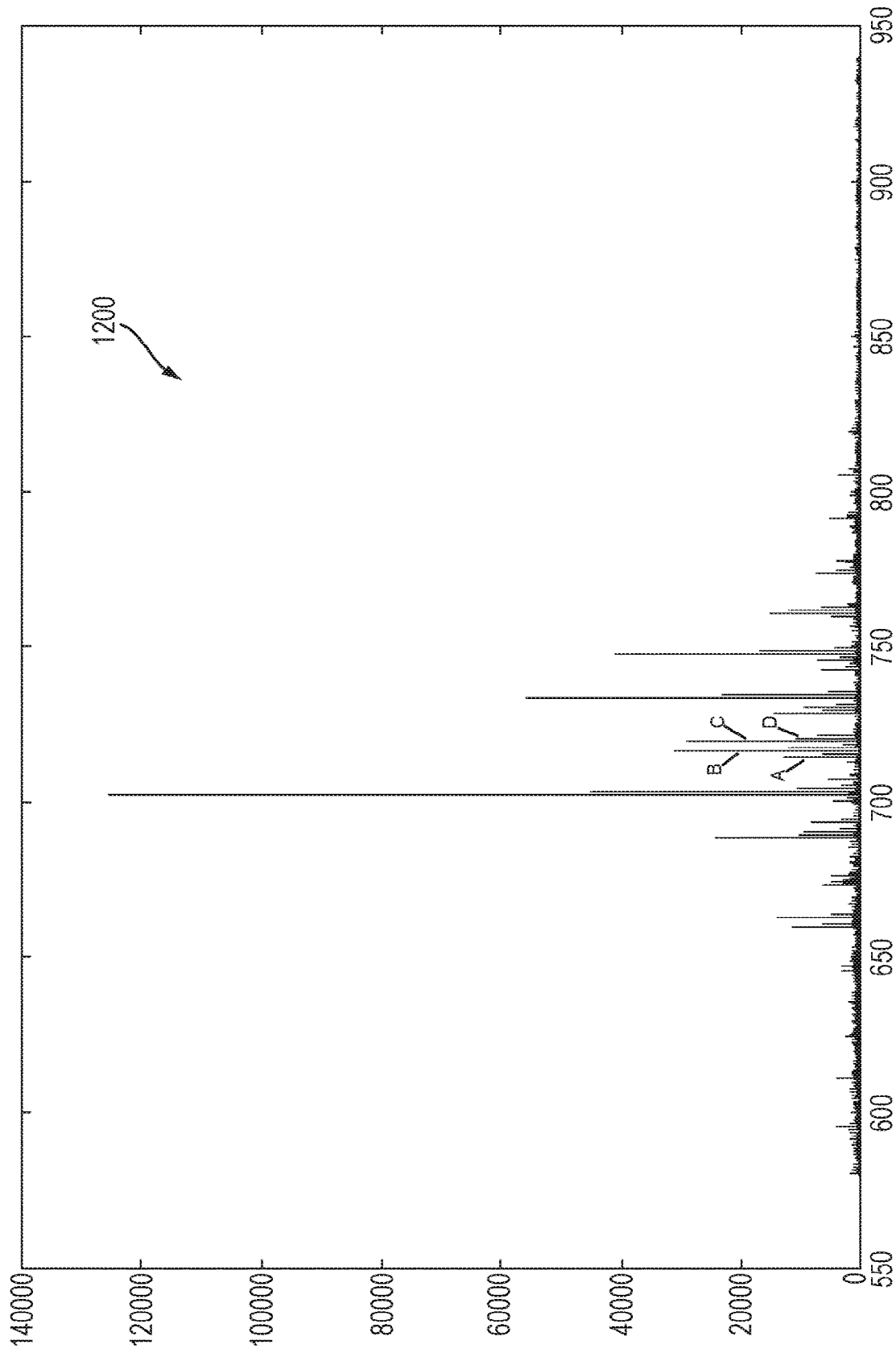
FIG. 12 shows a sample mass spectrum to which a deisotoping process is to be applied.

FIG. 12 shows a sample mass spectrum 1200 to which a deisotoping process will be applied. The sample mass spectrum 1200 was obtained by Rapid Evaporative Ionisation Mass Spectrometry analysis of a microbe culture.

The range of mass to charge (m/z) shown contains a series of phospholipids whose relative intensities can be used to differentiate between different species of microbes.

The sample mass spectrum 1200 contains at least three distinct singly charged species with masses of approximately $M_A$=714.5, $M_B$=716.5 and $M_c$=719.5, each accompanied by a characteristic isotope distribution giving rise to peaks at M+1, M+2, etc.

In this embodiment, the peaks at $M_A$=714.5, $M_B$=716.5 relate to species A and B that are chemically closely related. Because of this, the isotopic peak of species A at m/z 716.5 lies on top of the monoisotopic peak of species B. The peak at 716.5 therefore receives contributions from both species A and species B.

If the relative abundance of species A and B is different for different microbes, then the intensity of the peak with m/z 716.5 relative to the surrounding peaks is complicated.

Situations may arise in which a single mass spectral peak may receive contributions from more than two species, and also species having different charge states. This complexity complicates the classification problem, and may require the use of more sophisticated and/or computationally demanding algorithms than would be required if every peak in the spectrum originated from a single molecular species.

Another related problem that arises is the presence of partially resolved peaks such as the peak at $M_D=720.5$ for species D.

Although the identity of the molecular species represented in a spectrum such as this may not be known, it is often the case that their composition is sufficiently well constrained that the isotope distribution can be predicted with good accuracy given only knowledge of their molecular weight and charge state. This is true especially from molecules built from a common set of components or repeating units (e.g., polymers, oligo-nucleotides, peptides, proteins, lipids, carbohydrates etc.) for which molecular weight and composition are strongly correlated.

It is possible to process mass spectral data containing species of this type to produce a simplified spectrum containing only monoisotopic peaks (in other words a single representative peak for each species). It is also possible for the charge state of each species to be identified from isotopic spacing and for the output of the deisotoping process to be a reconstructed singly charged or neutral spectrum. Although these methods may be used in embodiments, they are more suitable for processing relatively simple spectra as they may fail to deal with overlapping isotope clusters. This can result in assignment of the wrong mass to species, quantitative errors and complete failure to classify some species.

The term "isotopic deconvolution" is used herein to describe deisotoping methods that can deconvolve complicated spectra containing overlapping/interfering or partially resolved species. In these embodiments, the relative intensities of species may be preserved during the deisotoping process, even when isotopic peaks overlap.

In the following embodiment, the deisotoping process is an isotopic deconvolution process in which overlapping and/or interfering isotopic peaks can be removed or reduced, rather than simply being removed.

In this embodiment, the deisotoping process is an iterative forward modelling process using a Monte Carlo, probabilistic (Bayesian inference) and nested sampling method.

Firstly, a set of trial hypothetical monoisotopic sample spectra X are generated. The set of trial monoisotopic sample spectra X are generated using known probability density functions for mass, intensity, charge state and number of peaks for the suspected class of sample to which the sample spectra relates.

A set of modelled sample spectra having isotopic peaks are then generated from the trial monoisotopic sample spectra X using known average isotopic distributions for the suspected class of sample to which the sample spectra relates.

Figure 13:
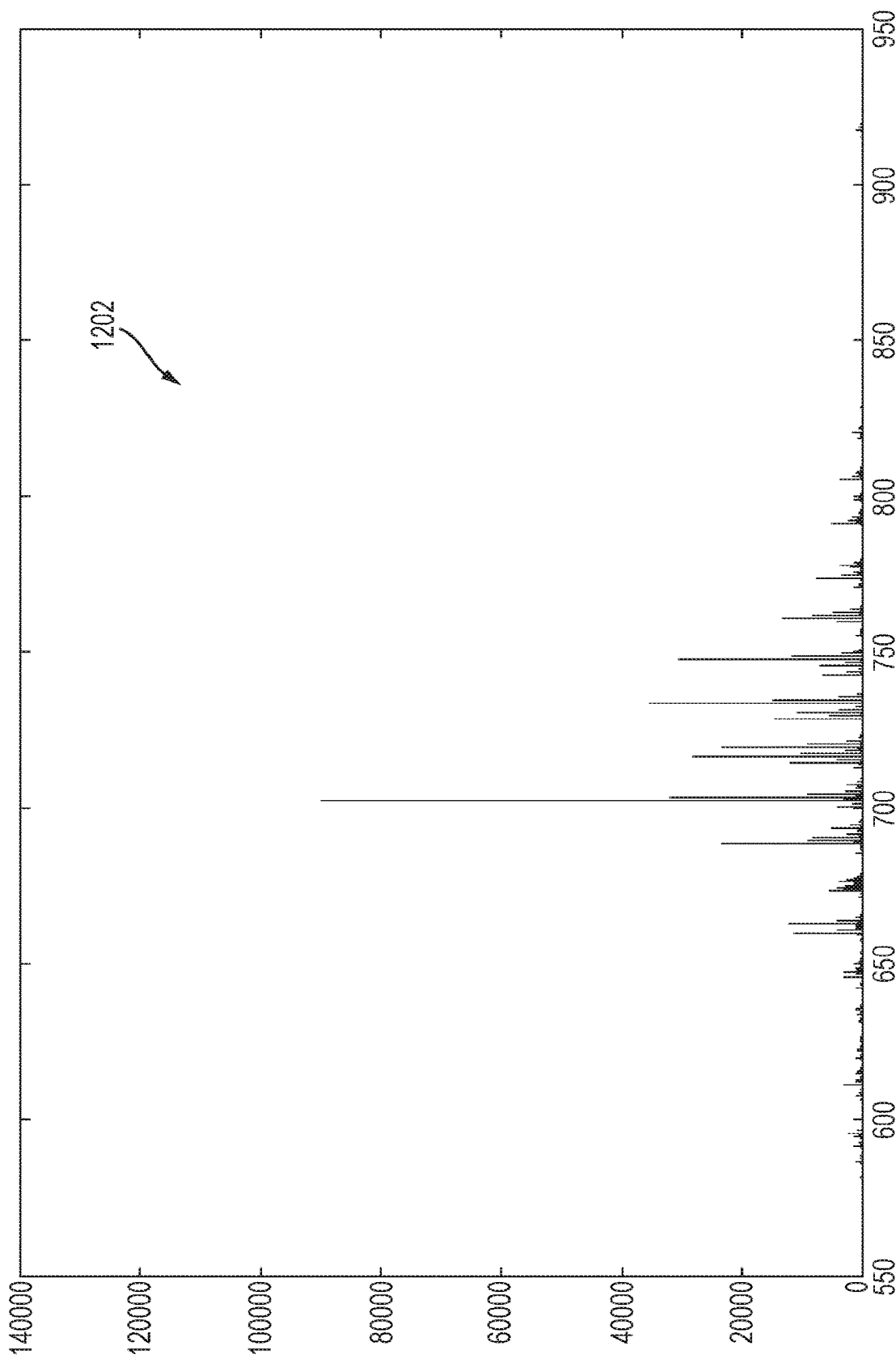
FIG. 13 shows a modelled isotopic version of a trial monoisotopic sample mass spectrum.

FIG. 13 shows one example of a modelled sample spectrum 1202 generated from a trial monoisotopic sample spectrum.

A likelihood L of the sample spectrum 1200 given each trial monoisotopic sample spectrum 1202 is then derived by comparing each model sample spectrum to the sample spectrum 1200.

The trial monoisotopic sample spectrum $x_0$ having the lowest likelihood $L_0$ is then re-generated using the known probability density functions for mass, intensity, charge state and number of peaks until the re-generated trial monoisotopic sample spectrum $x_1$ gives a likelihood $L_1 > L_0$.

The trial monoisotopic sample spectrum $x_2$ having the next lowest likelihood $L_2$ is then re-generated using the known probability density functions for mass, intensity, charge state and number of peaks until the re-generated trial monoisotopic sample spectrum $x_3$ gives a $L_3 > L_2$.

This iterative process of regenerating trial monoisotopic sample spectra continues for each subsequent trial monoisotopic sample spectra $x_n$ having the next lowest likelihood $L_n$, requiring that $L_{n+1} > L_n$, until a maximum likelihood $L_m$ is or appears to have been reached for all the trial monoisotopic sample spectra X.

Figure 14:
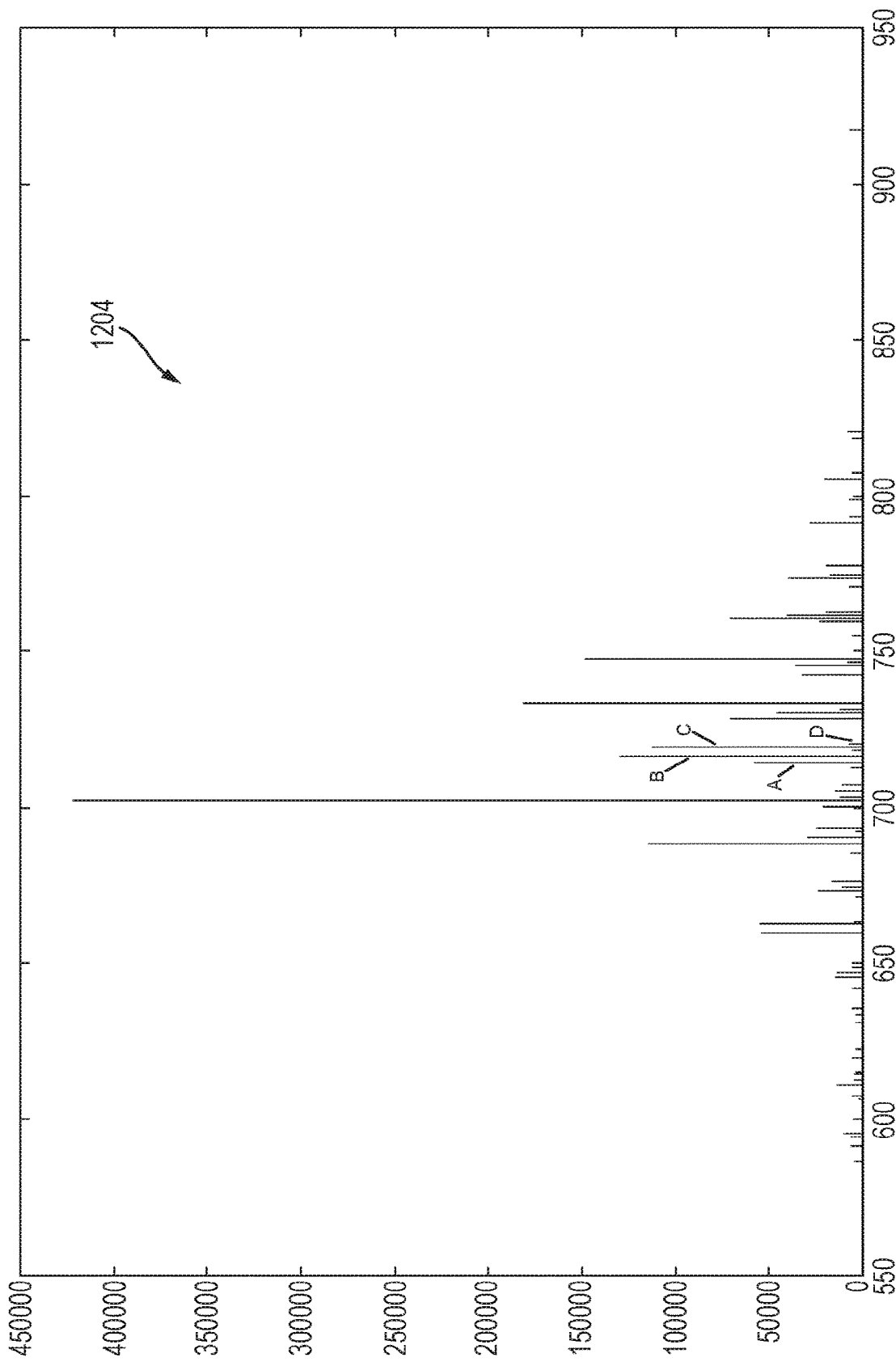
FIG. 14 shows a deisotoped sample mass spectrum for the sample mass spectrum of FIG. 12.

FIG. 14 shows a deisotoped spectrum 1204 for the sample spectrum 1200 of FIG. 12 that is derived from the final set of trial monoisotopic sample spectra X.

In this embodiment, each peak in the deisotoped version 1204 has: at least a threshold probability of presence (e.g., occurrence rate) in a representative set of deisotoped sample spectra generated from the final set of trial monoisotopic sample spectra X; less than a threshold monoisotopic mass uncertainty in the representative set of deisotoped sample spectra; and less than a threshold intensity uncertainty in the representative set of deisotoped sample spectra.

In other embodiments, an average of peak clusters identified across a representative set of deisotoped sample spectra generated from the final set of trial monoisotopic sample spectra X may be used to derive peaks in a deisotoped spectrum.

It will be apparent that the deisotoped spectrum 1204 is considerably simpler than the original spectrum 1200 of FIG. 12, and that a lower dimensional representation of the data is provided (e.g., involving fewer data channels, bins, detected peaks, etc.). This is particularly useful when carrying out multivariate and/or library-based analysis of sample spectra so as to classify a sample. In particular, simpler and/or less resource intensive analysis may be carried out.

Furthermore, deisotoping can help to distinguish between spectra by removing commonality due to isotopic distributions. Again, this is particularly useful when carrying out multivariate and/or library-based analysis of sample spectra so as to classify a sample. In particular, a more accurate or confident classification may be provided, for example due to greater separation between classes in multivariate space and greater differences between classification scores or probabilities in library based analysis.

In other embodiments, other iterative forward modelling processes such as massive inference or maximum entropy may be used. These are also typically isotopic deconvolution approaches.

In other embodiments, other approaches, such as least squares, non-negative least squares and (fast) Fourier transforms may be used These are also typically isotopic deconvolution approaches.

In some embodiments, when one or more species with known elemental composition are known to be present or likely to be present in the spectrum, they may be included in the deconvolution process with the correct mass and an exact isotope distribution based on their true composition rather than an estimate of their composition based on their mass.

Analysing Sample Spectra

As discussed above, the spectrometric analysis method 100 of FIG. 1 comprises a step 106 of analyzing the one or more sample spectra so as to classify an aerosol, smoke or vapour sample.

Also, as discussed above, the spectrometric analysis system 200 of FIG. 2 comprises analysis circuitry 208 arranged and adapted to analyze the one or more sample spectra so as to classify an aerosol, smoke or vapour sample.

Analyzing the one or more sample spectra so as to classify an aerosol, smoke or vapour sample can comprise building a classification model and/or library using reference sample spectra and/or using a classification model and/or library to identify sample spectra. The classification model and/or library can be developed and/or modified for a particular target or subject (e.g., patient). The classification model and/or library can also be developed, modified and/or used whilst a sampling device that is being used to obtain the sample spectra is in use.

By way of example, a number of different analysis techniques will now be described.

A list of analysis techniques which are intended to fall within the scope of the present invention are given in the following table:

Analysis Techniques
Univariate Analysis
Multivariate Analysis
Principal Component Analysis (PCA)
Linear Discriminant Analysis (LDA)
Maximum Margin Criteria (MMC)
Library Based Analysis
Soft Independent Modelling Of Class Analogy (SIMCA)
Factor Analysis (FA)
Recursive Partitioning (Decision Trees)
Random Forests
Independent Component Analysis (ICA)
Partial Least Squares Discriminant Analysis (PLS-DA)
Orthogonal (Partial Least Squares) Projections To Latent Structures (OPLS)
OPLS Discriminant Analysis (OPLS-DA)
Support Vector Machines (SVM)
(Artificial) Neural Networks
Multilayer Perceptron
Radial Basis Function (RBF) Networks
Bayesian Analysis
Cluster Analysis
Kernelized Methods
Subspace Discriminant Analysis
K-Nearest Neighbours (KNN)
Quadratic Discriminant Analysis (QDA)
Probabilistic Principal Component Analysis (PPCA)
Non negative matrix factorisation
K-means factorisation
Fuzzy c-means factorisation
Discriminant Analysis (DA)

Combinations of the foregoing analysis approaches can also be used, such as PCA-LDA, PCA-MMC, PLS-LDA, etc.

Analysing the sample spectra can comprise unsupervised analysis for dimensionality reduction followed by supervised analysis for classification.

By way of example, a number of different analysis techniques will now be described in more detail.

Multivariate Analysis—Developing a Model for Classification

By way of example, a method of building a classification model using multivariate analysis of plural reference sample spectra will now be described.

Figure 15:
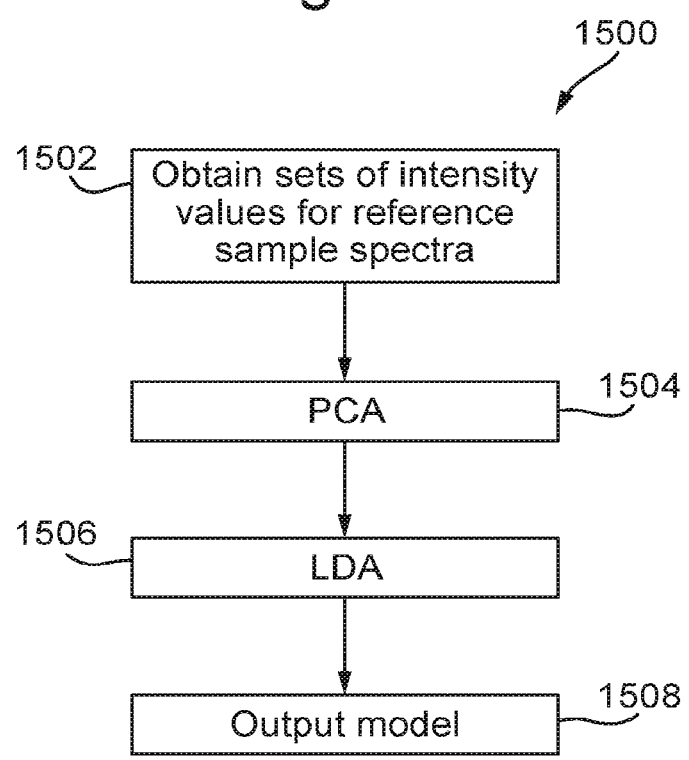
FIG. 15 shows a method of analysis that comprises building a classification model according to various embodiments.

FIG. 15 shows a method 1500 of building a classification model using multivariate analysis. In this example, the method comprises a step 1502 of obtaining plural sets of intensity values for reference sample spectra. The method then comprises a step 1504 of unsupervised principal component analysis (PCA) followed by a step 1506 of supervised linear discriminant analysis (LDA). This approach may be referred to herein as PCA-LDA. Other multivariate analysis approaches may be used, such as PCA-MMC. The PCA-LDA model is then output, for example to storage, in step 1508.

The multivariate analysis such as this can provide a classification model that allows an aerosol, smoke or vapour sample to be classified using one or more sample spectra obtained from the aerosol, smoke or vapour sample. The multivariate analysis will now be described in more detail with reference to a simple example.

Figure 16:
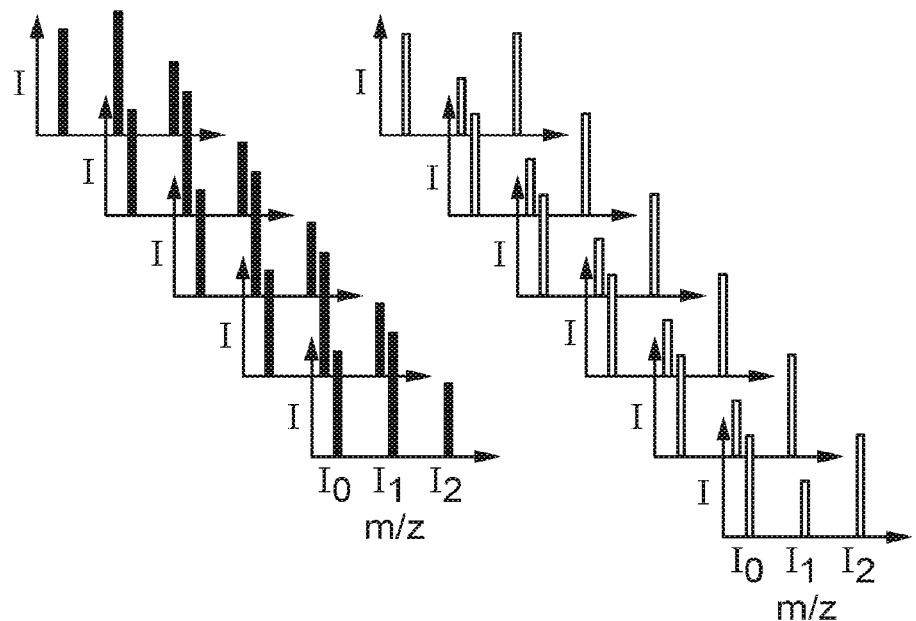
FIG. 16 shows a set of reference sample spectra obtained from two classes of known reference samples.

FIG. 16 shows a set of reference sample spectra obtained from two classes of known reference samples. The classes may be any one or more of the classes of target described herein. However, for simplicity, in this example the two classes will be referred as a left-hand class and a right-hand class.

Each of the reference sample spectra has been pre-processed in order to derive a set of three reference peak-intensity values for respective mass to charge ratios in that reference sample spectrum. Although only three reference peak-intensity values are shown, it will be appreciated that many more reference peak-intensity values (e.g., ~100 reference peak-intensity values) may be derived for a corresponding number of mass to charge ratios in each of the reference sample spectra. In other embodiments, the reference peak-intensity values may correspond to: masses; mass to charge ratios; ion mobilities (drift times); and/or operational parameters.

Figure 17:
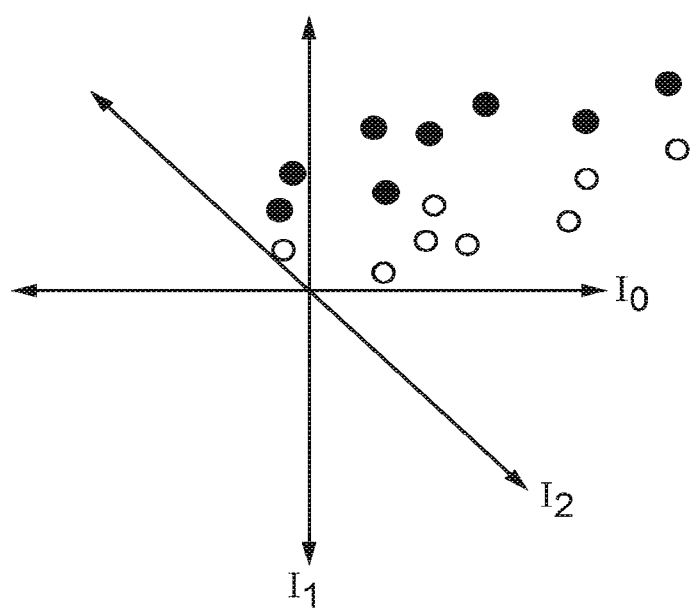
FIG. 17 shows a multivariate space having three dimensions defined by intensity axes, wherein the multivariate space comprises plural reference points, each reference point corresponding to a set of three peak intensity values derived from a reference sample spectrum.

FIG. 17 shows a multivariate space having three dimensions defined by intensity axes. Each of the dimensions or intensity axes corresponds to the peak-intensity at a particular mass to charge ratio. Again, it will be appreciated that there may be many more dimensions or intensity axes (e.g., ~100 dimensions or intensity axes) in the multivariate space. The multivariate space comprises plural reference points, with each reference point corresponding to a reference sample spectrum, i.e., the peak-intensity values of each reference sample spectrum provide the co-ordinates for the reference points in the multivariate space.

The set of reference sample spectra may be represented by a reference matrix D having rows associated with respective reference sample spectra, columns associated with respective mass to charge ratios, and the elements of the matrix being the peak-intensity values for the respective mass to charge ratios of the respective reference sample spectra.

In many cases, the large number of dimensions in the multivariate space and matrix D can make it difficult to group the reference sample spectra into classes. PCA may accordingly be carried out on the matrix D in order to calculate a PCA model that defines a PCA space having a reduced number of one or more dimensions defined by principal component axes. The principal components may be selected to be those that comprise or "explain" the largest variance in the matrix D and that cumulatively explain a threshold amount of the variance in the matrix D.

Figure 18:
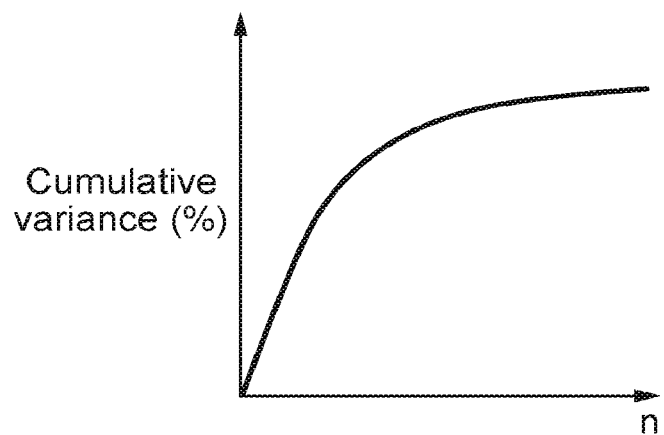
FIG. 18 shows a general relationship between cumulative variance and number of components of a PCA model.

FIG. 18 shows how the cumulative variance may increase as a function of the number n of principal components in the PCA model. The threshold amount of the variance may be selected as desired.

The PCA model may be calculated from the matrix D using a non-linear iterative partial least squares (NIPALS) algorithm or singular value decomposition, the details of which are known to the skilled person and so will not be described herein in detail. Other methods of calculating the PCA model may be used.

The resultant PCA model may be defined by a PCA scores matrix S and a PCA loadings matrix L. The PCA may also produce an error matrix E, which contains the variance not explained by the PCA model. The relationship between D, S, L and E may be:

$$D = SL^T + E \quad (1)$$

Figure 19:
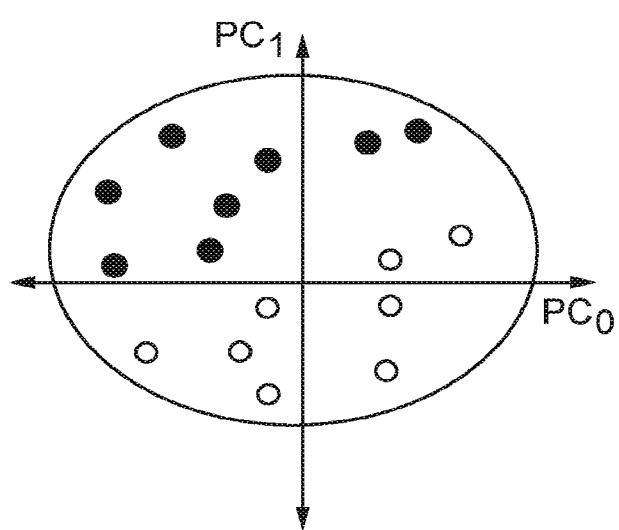
FIG. 19 shows a PCA space having two dimensions defined by principal component axes, wherein the PCA space comprises plural transformed reference points or scores, each transformed reference point corresponding to a reference point of FIG. 17.

FIG. 19 shows the resultant PCA space for the reference sample spectra of FIGS. 16 and 17. In this example, the PCA model has two principal components $PC_0$ and $PC_1$ and the PCA space therefore has two dimensions defined by two principal component axes. However, a lesser or greater number of principal components may be included in the PCA model as desired. It is generally desired that the number of principal components is at least one less than the number of dimensions in the multivariate space.

The PCA space comprises plural transformed reference points or PCA scores, with each transformed reference point or PCA score corresponding to a reference sample spectrum of FIG. 16 and therefore to a reference point of FIG. 17.

As is shown in FIG. 19, the reduced dimensionality of the PCA space makes it easier to group the reference sample spectra into the two classes. Any outliers may also be identified and removed from the classification model at this stage.

Further supervised multivariate analysis, such as multi-class LDA or maximum margin criteria (MMC), in the PCA space may then be performed so as to define classes and, optionally, further reduce the dimensionality.

As will be appreciated by the skilled person, multi-class LDA seeks to maximise the ratio of the variance between classes to the variance within classes (i.e., so as to give the largest possible distance between the most compact classes possible). The details of LDA are known to the skilled person and so will not be described herein in detail.

The resultant PCA-LDA model may be defined by a transformation matrix U, which may be derived from the PCA scores matrix S and class assignments for each of the transformed spectra contained therein by solving a generalised eigenvalue problem, for example using regularisation (e.g., Tikhonov regularisation or pseudoinverses) if required to make the problem well conditioned.

The transformation of the scores S from the original RCA space into the new LDA space may then be given by:

$$Z = SU \quad (2)$$

where the matrix Z contains the scores transformed into the LDA space.

Figure 20:
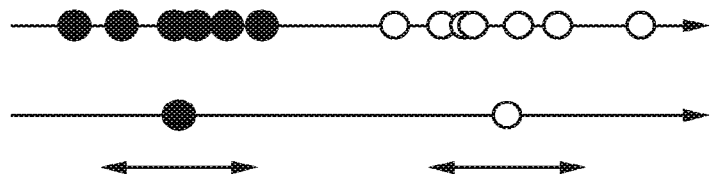
FIG. 20 shows a PCA-LDA space having a single dimension or axis, wherein the LDA is performed based on the PCA space of FIG. 19, the PCA-LDA space comprising plural further transformed reference points or class scores, each further transformed reference point corresponding to a transformed reference point or score of FIG. 19.

FIG. 20 shows a PCA-LDA space having a single dimension or axis, wherein the LDA is performed in the PCA space of FIG. 19. As is shown in FIG. 20, the LDA space comprises plural further transformed reference points or PCA-LDA scores, with each further transformed reference point corresponding to a transformed reference point or PCA score of FIG. 19.

In this example, the further reduced dimensionality of the PCA-LDA space makes it even easier to group the reference sample spectra into the two classes. Each class in the PCA-LDA model may be defined by its transformed class average and covariance matrix or one or more hyperplanes (including points, lines, planes or higher order hyperplanes) or hypersurfaces or Voronoi cells in the PCA-LDA space.

The PCA loadings matrix L, the LDA matrix U and transformed class averages and covariance matrices or hyperplanes or hypersurfaces or Voronoi cells may be output to a database for later use in classifying an aerosol, smoke or vapour sample.

The transformed covariance matrix in the LDA space $V'_g$ for class g may be given by $$V'_g = U^T V_g U \quad (3)$$

where $V_g$ are the class covariance matrices in the PCA space.

The transformed class average position $z_g$ for class g may be given by $$s_g U = z_g \quad (4)$$

where $s_g$ is the class average position in the PCA space.

Multivariate Analysis—Using a Model for Classification

By way of example, a method of using a classification model to classify an aerosol, smoke or vapour sample will now be described.

Figure 21:
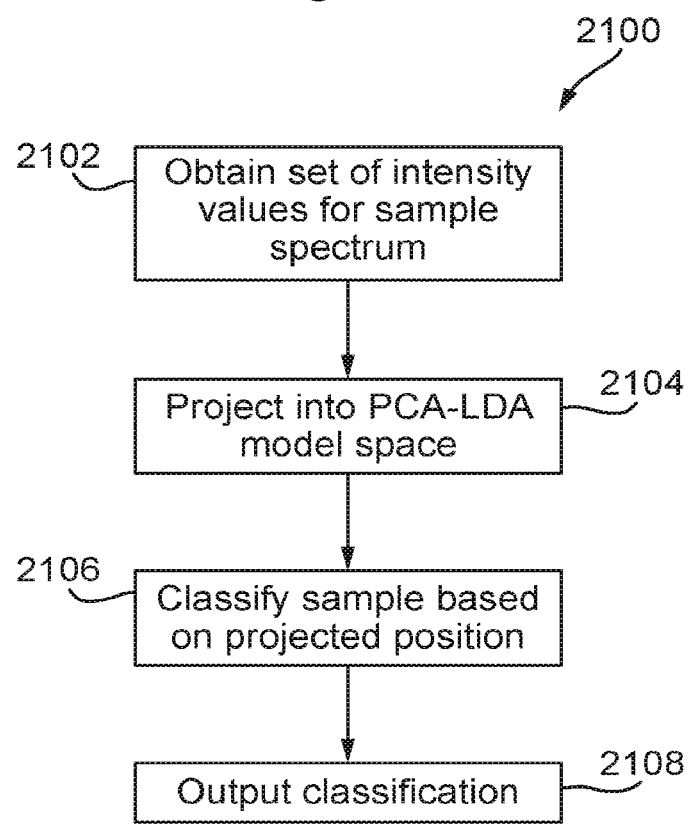
FIG. 21 shows a method of analysis that comprises using a classification model according to various embodiments.

FIG. 21 shows a method 2100 of using a classification model. In this example, the method comprises a step 2102 of obtaining a set of intensity values for a sample spectrum. The method then comprises a step 2104 of projecting the set of intensity values for the sample spectrum into PCA-LDA model space. Other classification model spaces may be used, such as PCA-MMC. The sample spectrum is then classified at step 2106 based on the project position and the classification is then output in step 2108.

Classification of an aerosol, smoke or vapour sample will now be described in more detail with reference to the simple PCA-LDA model described above.

Figure 22:
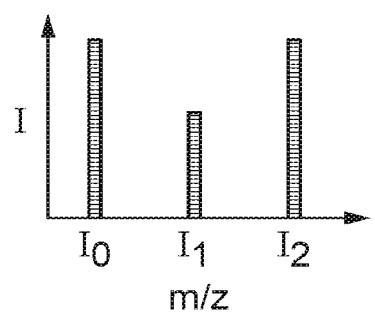
FIG. 22 shows a sample spectrum obtained from an unknown sample.

FIG. 22 shows a sample spectrum obtained from an unknown aerosol, smoke or vapour sample. The sample spectrum has been pre-processed in order to derive a set of three sample peak-intensity values for respective mass to charge ratios. As mentioned above, although only three sample peak-intensity values are shown, it will be appreciated that many more sample peak-intensity values (e.g., ~100 sample peak-intensity values) may be derived at many more corresponding mass to charge ratios for the sample spectrum. Also, as mentioned above, in other embodiments, the sample peak-intensity values may correspond to: masses; mass to charge ratios; ion mobilities (drift times); and/or operational parameters.

The sample spectrum may be represented by a sample vector $d_x$, with the elements of the vector being the peak-intensity values for the respective mass to charge ratios. A transformed PCA vector $s_x$ for the sample spectrum can be obtained as follows:

$$d_x L = s_x \quad (5)$$

Then, a transformed PCA-LDA vector $z_x$ for the sample spectrum can be obtained as follows:

$$s_x U = z_x \quad (6)$$

Figure 23:
FIG. 23 shows the PCA-LDA space of FIG. 20, wherein the PCA-LDA space further comprises a PCA-LDA projected sample point derived from the peak intensity values of the sample spectrum of FIG. 22.

FIG. 23 again shows the PCA-LDA space of FIG. 20. However, the PCA-LDA space of FIG. 23 further comprises the projected sample point, corresponding to the transformed PCA-LDA vector $z_x$, derived from the peak intensity values of the sample spectrum of FIG. 22.

In this example, the projected sample point is to one side of a hyperplane between the classes that relates to the right-hand class, and so the aerosol, smoke or vapour sample may be classified as belonging to the right-hand class.

Alternatively, the Mahalanobis distance from the class centres in the LDA space may be used, where the Mahalanobis distance of the point $z_x$ from the centre of class g may be given by the square root of:

$$(z_x - z_g)^T (V'_g)^{-1} (z_x - z_g) \quad (8)$$

and the data vector $d_x$ may be assigned to the class for which this distance is smallest.

In addition, treating each class as a multivariate Gaussian, a probability of membership of the data vector to each class may be calculated.

As discussed above, a different set of class-specific background-subtracted sample intensity values may be derived for each class of one or more classes of aerosol, smoke or vapour sample. Step 2100 may therefore comprise obtaining a set of class-specific background-subtracted intensity values for each class of aerosol, smoke or vapour sample. Steps 2102 and 2104 may then be performed in respect of each set of class-specific background-subtracted intensity values to provide a class-specific projected position. The sample spectrum may then be classified at step 2106 based on the class-specific projected positions. For example, the sample spectrum may be assigned to the class having a class-specific projected position that gives the shortest distance or highest probability of membership to its class.

Library Based Analysis—Developing a Library for Classification

By way of example, a method of building a classification library using plural input reference sample spectra will now be described.

Figure 24:
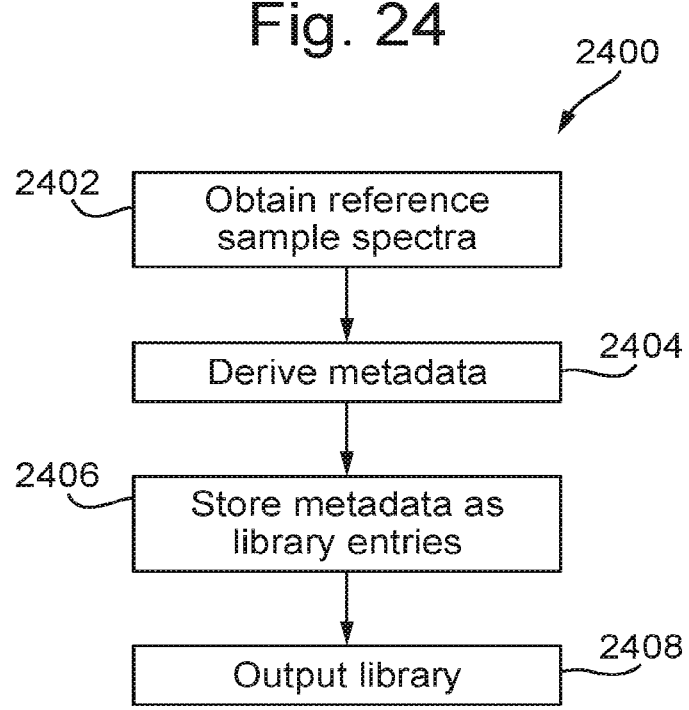
FIG. 24 shows a method of analysis that comprises building a classification library according to various embodiments.

FIG. 24 shows a method 2400 of building a classification library. In this example, the method comprises a step 2402 of obtaining reference sample spectra and a step 2404 of deriving metadata from the plural input reference sample spectra for each class of sample. The method then comprises a step 2406 of storing the metadata for each class of sample as a separate library entry. The classification library is then output, for example to electronic storage, in step 2408.

A classification library such as this allows an aerosol, smoke or vapour sample to be classified using one or more sample spectra obtained from the aerosol, smoke or vapour sample. The library based analysis will now be described in more detail with reference to an example.

In this example, each entry in the classification library is created from plural pre-processed reference sample spectra that are representative of a class. In this example, the reference sample spectra for a class are pre-processed according to the following procedure:

First, a re-binning process is performed, for example as discussed above. In this embodiment, the data are resampled onto a logarithmic grid with abscissae:

$$x_i = \lfloor N_{chan} \log \frac{m}{M_{min}} / \log \frac{M_{max}}{M_{min}} \rfloor$$

where $N_{chan}$ is a selected value and $\lfloor x \rfloor$ denotes the nearest integer below x. In one example, $N_{chan}$ is $2^{12}$ or 4096.

Then, a background subtraction process is performed, for example as discussed above. In this embodiment, a cubic spline with k knots is then constructed such that p % of the data between each pair of knots lies below the curve. This curve is then subtracted from the data. In one example, k is 32. In one example, p is 5. A constant value corresponding to the q % quantile of the intensity subtracted data is then subtracted from each intensity. Positive and negative values are retained. In one example, q is 45.

Then, a normalisation process is performed, for example as discussed above. In this embodiment, the data are normalised to have mean $\bar{y}_i$. In one example, $\bar{y}_i = 1$.

An entry in the library then consists of metadata in the form of a median spectrum value $\mu_i$ and a deviation value $D_i$ for each of the $N_{chan}$ points in the spectrum.

The likelihood for the i'th channel is given by:

$$Pr(y_i | \mu_i, D_i) = \frac{1}{D_i} \frac{C^{C-1/2} \Gamma(C)}{\sqrt{\pi} \Gamma(C - 1/2)} \frac{1}{\left(C + \frac{(y_i - \mu_i)^2}{D_i^2}\right)^C}$$

where $\frac{1}{2} \leq C < \infty$ and where $\Gamma(C)$ is the gamma function.

The above equation is a generalised Cauchy distribution which reduces to a standard Cauchy distribution for C=1 and becomes a Gaussian (normal) distribution as C→∞. The parameter $D_i$ controls the width of the distribution (in the Gaussian limit $D_i = \sigma_i$ is simply the standard deviation) while the global value C controls the size of the tails.

In one example, C is 3/2, which lies between Cauchy and Gaussian, so that the likelihood becomes:

$$Pr(y_i | \mu_i, D_i) = \frac{3}{4} \frac{1}{D_i} \frac{1}{(3/2 + (y_i - \mu_i)^2 / D_i^2)^{3/2}}$$

For each library entry, the parameters $\mu_i$ are set to the median of the list of values in the i'th channel of the input reference sample spectra while the deviation $D_i$ is taken to be the interquartile range of these values divided by √2. This choice can ensure that the likelihood for the i'th channel has the same interquartile range as the input data, with the use of quantiles providing some protection against outlying data.

Library-Based Analysis—Using a Library for Classification

By way of example, a method of using a classification library to classify an aerosol, smoke or vapour sample will now be described.

Figure 25:
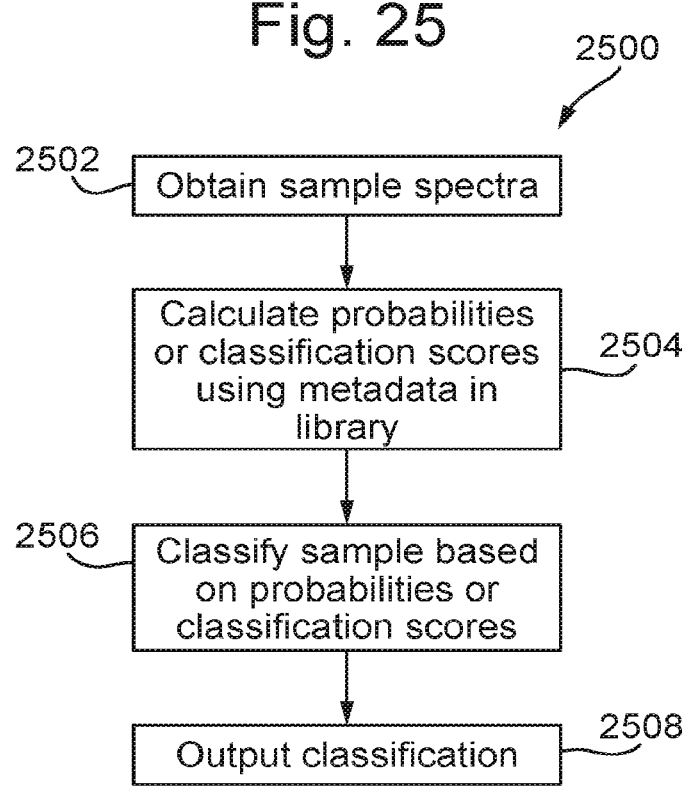
FIG. 25 shows a method of analysis that comprises using a classification library according to various embodiments.

FIG. 25 shows a method 2500 of using a classification library. In this example, the method comprises a step 2502 of obtaining a set of plural sample spectra. The method then comprises a step 2504 of calculating a probability or classification score for the set of plural sample spectra for each class of sample using metadata for the class entry in the classification library. This may comprise using a different set of class-specific background-subtracted sample spectra for each class so as to provide a probability or classification score for that class. The sample spectra are then classified at step 2506 and the classification is then output in step 2508.

Classification of an aerosol, smoke or vapour sample will now be described in more detail with reference to the classification library described above.

In this example, an unknown sample spectrum y is the median spectrum of a set of plural sample spectra. Taking the median spectrum y can protect against outlying data on a channel by channel basis.

The likelihood $L_s$ for the input data given the library entry s is then given by:

$$L_s = Pr(y | \mu, D) = \prod_{i=1}^{N_{chan}} Pr(y_i | \mu_i, D_i)$$

where $\mu_i$ and $D_i$ are, respectively, the library median values and deviation values for channel i. The likelihoods $L_s$ may be calculated as log likelihoods for numerical safety.

The likelihoods $L_s$ are then normalised over all candidate classes 's' to give probabilities, assuming a uniform prior probability over the classes. The resulting probability for the class $\bar{s}$ is given by:

$$Pr(\tilde{s} \mid y) = \frac{L_s^{(1/F)}}{\sum_s L_s^{(1/F)}}$$

The exponent (1/F) can soften the probabilities which may otherwise be too definitive. In one example, F=100. These probabilities may be expressed as percentages, e.g., in a user interface.

Alternatively, RMS classification scores $R_s$ may be calculated using the same median sample values and derivation values from the library:

$$R_s(y, \mu, D) = \sqrt{\frac{1}{N_{chan}} \sum_{i=1}^{N_{chan}} \frac{(y_i - \mu_i)^2}{D_i^2}}$$

Again, the scores $R_s$ are normalised over all candidate classes 's'.

The aerosol, smoke or vapour sample may then be classified as belonging to the class having the highest probability and/or highest RMS classification score.

Confirmation of Classification

Figure 26:
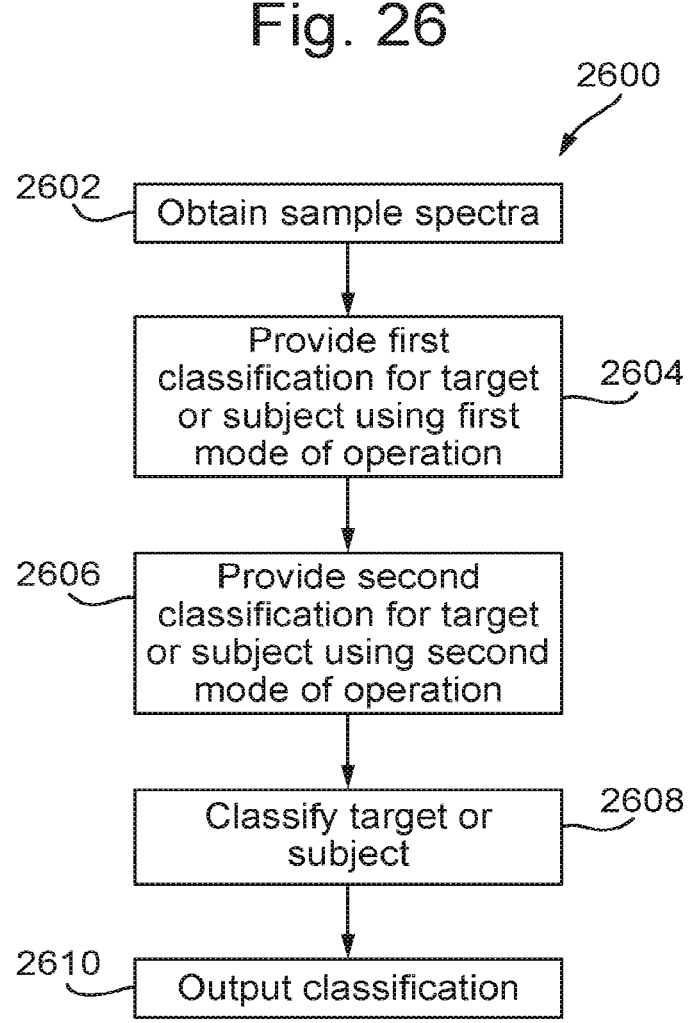
FIG. 26 shows a method of analysis that comprises using first and second modes of operation to provide first and second classifications according to various embodiments.

FIG. 26 shows a method of analysis 2600 in which a first and second different modes of operation are used to provide first and second classifications for a target or subject (e.g., patient).

The method comprises a step 2602 of obtaining sample spectra. The method then comprises a step 2604 of providing a first classification for a target or subject using a first mode of operation. The method then comprises a step 2606 of providing a second classification for the target or subject using a second mode of operation. The mode of operation may be changed from the first mode of operation to the second mode of operation whilst a sampling device that is being used to obtain the sample spectra is in use. The target is then classified at step 2608.

In various embodiments, the first and second modes of operation can differ in the way in which sample spectra are obtained, pre-processed and/or analysed. Various differences between the first and second modes of operation are contemplated.

For example, the first and second modes differ with respect to: the condition of the target or subject that is sampled when obtaining an aerosol, smoke or vapour sample (e.g., stressed, hypoxic, medicated, etc.); the type of device used to obtain an aerosol, smoke or vapour sample (e.g., needle, probe, forceps, etc.); the device settings used when obtaining an aerosol, smoke or vapour sample (e.g., the potentials, frequencies, etc., used); the device mode of operation when obtaining an aerosol, smoke or vapour sample (e.g., probing mode, pointing mode, cutting mode, resecting mode, coagulating mode, desiccating mode, fulgurating mode, cauterising mode, etc.); the type of ambient ion or ionisation source used; the sampling time over which an aerosol, smoke or vapour sample is obtained; the ion mode used to generate analyte ions for an aerosol, smoke or vapour sample (e.g., positive ion mode and/or negative ion mode); the spectrometer settings used when obtaining the one or more sample spectra (e.g., potentials, potential waveforms (e.g., waveform profiles and/or velocities), frequencies, gas types and/or pressures, dopants, etc., used); the use, number and/or type of fragmentation or reaction steps (e.g., MS/MS, MS$^n$, MS$^E$, higher energy or lower energy fragmentation or reaction steps, Electron-Transfer Dissociation (ETD), etc.); the use, number and/or type of mass or mass to charge ratio separation or filtering steps (e.g., the range of masses or mass to charge ratios that are scanned, selected or filtered); the use, number and/or type of ion mobility separation or filtering steps (e.g., the range of drift times that are scanned, selected or filtered, the gas types and/or pressures, dopants, etc., used); the use, number and/or type of charge state separation or filtering steps (e.g., the charge states that are scanned, selected or filtered); the type of ion detector used when obtaining one or more sample spectra; the ion detector settings (e.g., the potentials, frequencies, gains, etc., used); and the binning process (e.g., bin widths) used.

The first and second modes of operation can also differ with respect to: the number and type of spectra that are combined; the background subtraction process; the conversion/correction process; the normalising, offsetting, scaling and/or function application process; the windowing process (e.g., range(s) of masses, mass to charge ratios, or ion mobilities that are retained or selected); the filtering/smoothing process; the data reduction process; the thresholding process; the peak detection/selection process; the deisotoping process; the binning process; the peak alignment process; and the (further) normalising, offsetting, scaling and/or function application process.

The first and second modes of operation can also differ with respect to: the type of classification method (e.g., multivariate, univariate, library-based, supervised, unsupervised, etc.) used; the particular classification model and/or library used; the particular reference sample spectra used in the classification model and/or library; the particular classes or class definitions used.

In one embodiment, the first mode of operation comprises library based analysis and the second mode of operation comprises PCA-LDA multivariate analysis.

In some embodiments, the first classification can be used to select the second mode of operation. In some embodiments, the first classification can be used to decide to change to the second mode of operation, for example if the first classification is ambiguous. In these embodiments, the second classification alone may be used to classify the target or subject and can be output in step 2610.

In other embodiments, both the first and second classification may be used to classify the target or subject. In these other embodiments, the second classification may be the same as the first classification or may be a sub-classification within the first classification, and thus may confirm the first classification. The confirmed classification or sub-classification can then then output in step 2610.

Alternatively, the second classification may not be the same as the first classification and may not be a sub-classification within the first classification, and thus may contract the first classification. In these alternative embodiments, it may be necessary to provide one or more further classifications using one or more further modes of operation, for example until a suitably confirmed classification or sub-classification is provided.

Target or Subject Tailored Classification Model and/or Library

Figure 27:
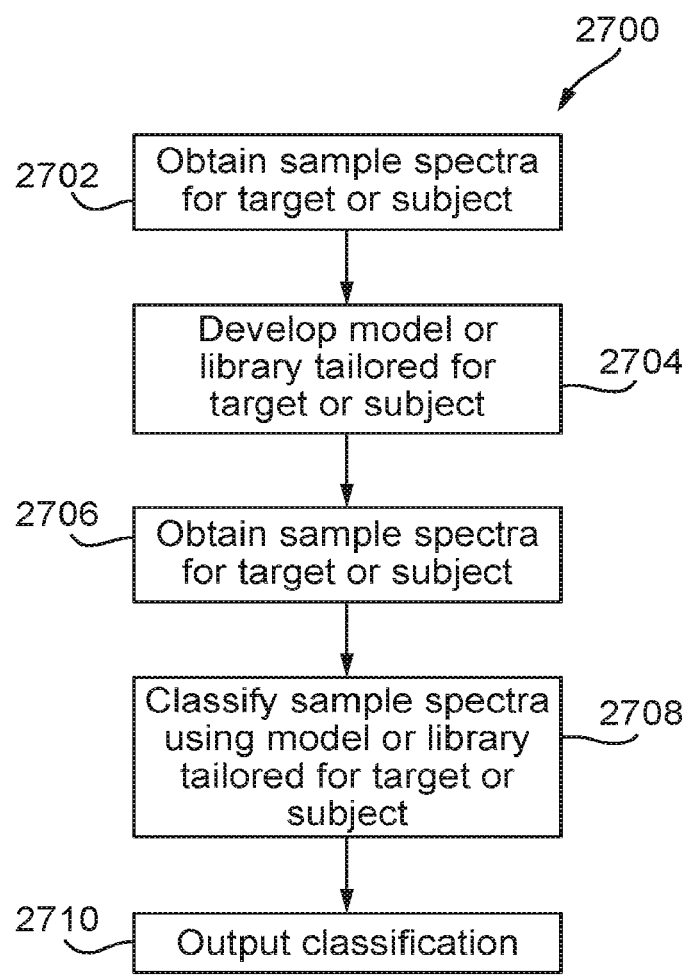
FIG. 27 shows a method of analysis that comprises developing and using a classification model and/or library that is tailored for a particular subject according to various embodiments.

FIG. 27 shows a method 2700 of analysis that comprises developing and using a classification model and/or library that is tailored for a particular target or subject (e.g., patient). The classification model and/or library can be developed and used for classification whilst a sampling device that is being used to obtain the sample spectra is in use.

In this example, the method comprises a step 2702 of obtaining reference sample spectra for a target or subject.

The reference sample spectra may be obtained from regions of the target or subject that are known to comprise normal or healthy tissue. The reference sample spectra may also be obtained from regions of the target or subject that are suspected or known to comprise abnormal or unhealthy target tissue.

The method then comprises a step 2704 of developing a classification model and/or library specifically tailored for the subject using the reference sample spectra, for example in a manner as discussed above.

The method then comprises a step 2706 of obtaining sample spectra for the target or subject. The sample spectra may be obtained from regions of the target or subject that potentially comprise abnormal or unhealthy target tissue.

The sample spectra may then classified at step 2708 using the classification model and/or library specifically tailored for the target or subject. The classification is then output in step 2710.

Using Results of Analysis

As discussed above, the spectrometric analysis method 100 of FIG. 1 comprises a step 108 of using the results of the analysis. The results can be used and/or provided whilst a sampling device that is being used to obtain the sample spectra is in use.

This may comprise, for example, displaying the results of the classification using the feedback device 210 and/or controlling the operation of the sampling device 202, spectrometer 204, pre-processing circuitry 206 and/or analysis circuitry 208.

By way of example, a number of different uses for the results will now be described.

Use of Results in Guiding Surgery

In various embodiments, the results of the analysis can be used to guide a surgeon intra-operatively.

In some embodiments, the results can be used to guide a surgeon in debulking or resection, for example debulking or resection of cancerous, diseased or infected tissue in a subject. These embodiments may comprise obtaining sample spectra for aerosol, smoke or vapour samples generated from the region of the subject containing the potentially cancerous, diseased or infected tissue. The sample spectra may be analysed so as to classify the samples either as being healthy or as being cancerous, diseased or infected. The results may be provided to the surgeon, for example via the feedback device 210, in order to indicate the location of cancerous, diseased or infected tissue so that the surgeon can debulk or resect an appropriate region of tissue.

In other embodiments, the results can be used to guide a surgeon in amputation, for example amputation of a necrotic lower limb and foot of a diabetic subject. These embodiments may comprise obtaining sample spectra for aerosol, smoke or vapour samples generated from the lower limb and foot of the subject. The sample spectra may be analysed so as to classify the samples as being either necrotic or non-necrotic. The results may be provided to the surgeon, for example via the feedback device 210, in order to indicate the location of necrotic tissue so that the surgeon can then amputate an appropriate amount of the lower limb and foot.

Use of Genotype and/or Phenotype Based Results

In various embodiments, sample spectra may be analysed so as to classify an aerosol, smoke or vapour sample in terms of target or subject genotype and/or phenotype. The classification can be used to inform treatment decisions.

In these embodiments, plural reference sample spectra may be obtained for aerosol, smoke or vapour sample generated from tissue of subjects having different genotypes and/or phenotypes. In one example, plural reference sample spectra may be obtained for aerosol, smoke or vapour sample generated from the breast tissue of subjects having either genotype/phenotype A or genotype/phenotype B, where subjects having genotype/phenotype A have or are more susceptible to developing severe forms of breast cancer than subjects having genotype/phenotype B.

A classification model and/or library may be built based on the plural reference sample spectra for the subjects and the plural reference sample spectra may then be classified accordingly based genotype and/or phenotype. The classification model and/or library can then be used when diagnosing or treating another subject. For example, plural sample spectra may be obtained for aerosol, smoke or vapour sample generated from the tissue of the subject and classified using the classification model and/or library. The classification of the aerosol, smoke or vapour sample may indicate the genotype and/or phenotype of the tissue. Treatment decisions may then be made on the basis of the classification. For example, when the aerosol, smoke or vapour sample is classified as relating to genotype/phenotype A, a potentially more effective but extreme breast cancer treatment may be used. Conversely, when the aerosol, smoke or vapour sample is classified as relating to genotype/phenotype B, a potentially less effective but less extreme breast cancer treatment or no breast cancer treatment may be used.

Use of Outcome Based Results

In various embodiments, sample spectra may be analysed so as to classify an aerosol, smoke or vapour sample in terms of an actual or expected outcome. The classification can be used to inform treatment decisions or further treatment decisions. In these embodiments, plural reference sample spectra may be obtained for aerosol, smoke or vapour sample generated from tissue of subjects that have undergone or are undergoing a particular treatment. In one example, plural reference sample spectra may be obtained for aerosol, smoke or vapour sample generated from cancerous bowel tissue of subjects undergoing bowel resections. In another example, plural reference sample spectra may be obtained for aerosol, smoke or vapour sample generated from the skin tissue of subjects that is to be used or has been used for a skin graft.

A classification model and/or library may be built based on the plural reference sample spectra for the subjects and the subjects may be monitored to see whether or not the particular treatment was successful and/or to what degree the treatment was successful. The plural reference sample spectra may then be classified accordingly based on the outcome. The outcome classification may be based, for example, on: life expectancy; life quality; recovery time; remission rate; surgery success rate; complication rate; complication type; need for further treatment rate; and/or further treatment type typically needed.

The classification model and/or library can then be used for another subject undergoing the particular treatment in question. For example, plural sample spectra may be obtained for aerosol, smoke or vapour sample generated from tissue of the subject and classified using the classification model and/or library. The classification of the aerosol, smoke or vapour sample may indicate whether or not the removal or use of that tissue is likely to result in a positive outcome, such as longer life expectancy; better life quality; shorter recovery time; higher remission rate; higher surgery success rate; lower complication rate; less severe complication type; lower need for further treatment rate; and/or less severe further treatment type typically needed. If a positive outcome is indicated, then the tissue (e.g., bowel tissue or skin) may be removed or used.

Analysis of Analyte Ions

Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly (or vice versa) ion mobility analysis (IMS) and/or differential ion mobility analysis (DMA) and/or Field Asymmetric Ion Mobility Spectrometry (FAIMS) analysis followed by secondly (or vice versa) mass analysis by a mass analyser such as a quadrupole mass analyser or a Time of Flight mass analyser. Various embodiments also relate to an ion mobility spectrometer and/or mass analyser and a method of ion mobility spectrometry and/or method of mass analysis. Ion mobility analysis may be performed prior to mass to charge ratio analysis or vice versa.

Various references are made in the present application to mass analysis, mass analysers, mass analysing, mass spectrometric data, mass spectrometers and other related terms referring to apparatus and methods for determining the mass or mass to charge of analyte ions. It should be understood that it is equally contemplated that the present invention may extend to ion mobility analysis, ion mobility analysers, ion mobility analysing, ion mobility data, ion mobility spectrometers, ion mobility separators and other related terms referring to apparatus and methods for determining the ion mobility, differential ion mobility, collision cross section or interaction cross section of analyte ions. Furthermore, it should also be understood that embodiments are contemplated wherein analyte ions may be subjected to a combination of both ion mobility analysis and mass analysis i.e. that both (a) the ion mobility, differential ion mobility, collision cross section or interaction cross section of analyte ions together with (b) the mass to charge of analyte ions is determined. Accordingly, hybrid ion mobility-mass spectrometry (IMS-MS) and mass spectrometry-ion mobility (MS-IMS) embodiments are contemplated wherein both the ion mobility and mass to charge ratio of analyte ions generated e.g., by an ambient ionisation ion source are determined. Ion mobility analysis may be performed prior to mass to charge ratio analysis or vice versa. Furthermore, it should be understood that embodiments are contemplated wherein references to mass spectrometric data and databases comprising mass spectrometric data should also be understood as encompassing ion mobility data and differential ion mobility data etc. and databases comprising ion mobility data and differential ion mobility data etc. (either in isolation or in combination with mass spectrometric data).

Applications

Various different applications are contemplated.

According to some embodiments the methods disclosed above may be performed on in vivo, ex vivo or in vitro tissue. The tissue may comprise human or non-human animal tissue.

Various surgical, therapeutic, medical treatment and diagnostic methods are contemplated. However, other embodiments are contemplated which relate to non-surgical and non-therapeutic methods of spectrometry which are not performed on in vivo tissue. Other related embodiments are contemplated which are performed in an extracorporeal manner such that they are performed outside of the human or animal body.

Further embodiments are contemplated wherein the methods are performed on a non-living human or animal, for example, as part of an autopsy procedure.

Further non-surgical, non-therapeutic and non-diagnostic embodiments are contemplated.

Several more specific examples will now be described.

Chemical Guidance

Combination of Raman Spectroscopy with Rapid Evaporative Ionisation Mass Spectrometry ("REIMS") and Other Ambient Ionisation Techniques for the In Situ Identification of Tumours During Surgery According to an embodiment Raman spectroscopy may be combined with rapid evaporative ionization mass spectrometry ("REIMS") (or other ambient ionisation techniques) for the identification of tumours either during surgery or when analysing ex vivo tissue. Experimental data is presented below taken from the context of in vivo brain surgery. However, the approach of combining Raman spectroscopy with ambient ionisation techniques such as rapid evaporative ionization mass spectrometry ("REIMS") may be applied to other situations including other types of surgery and non-surgical applications.

Figure 28:
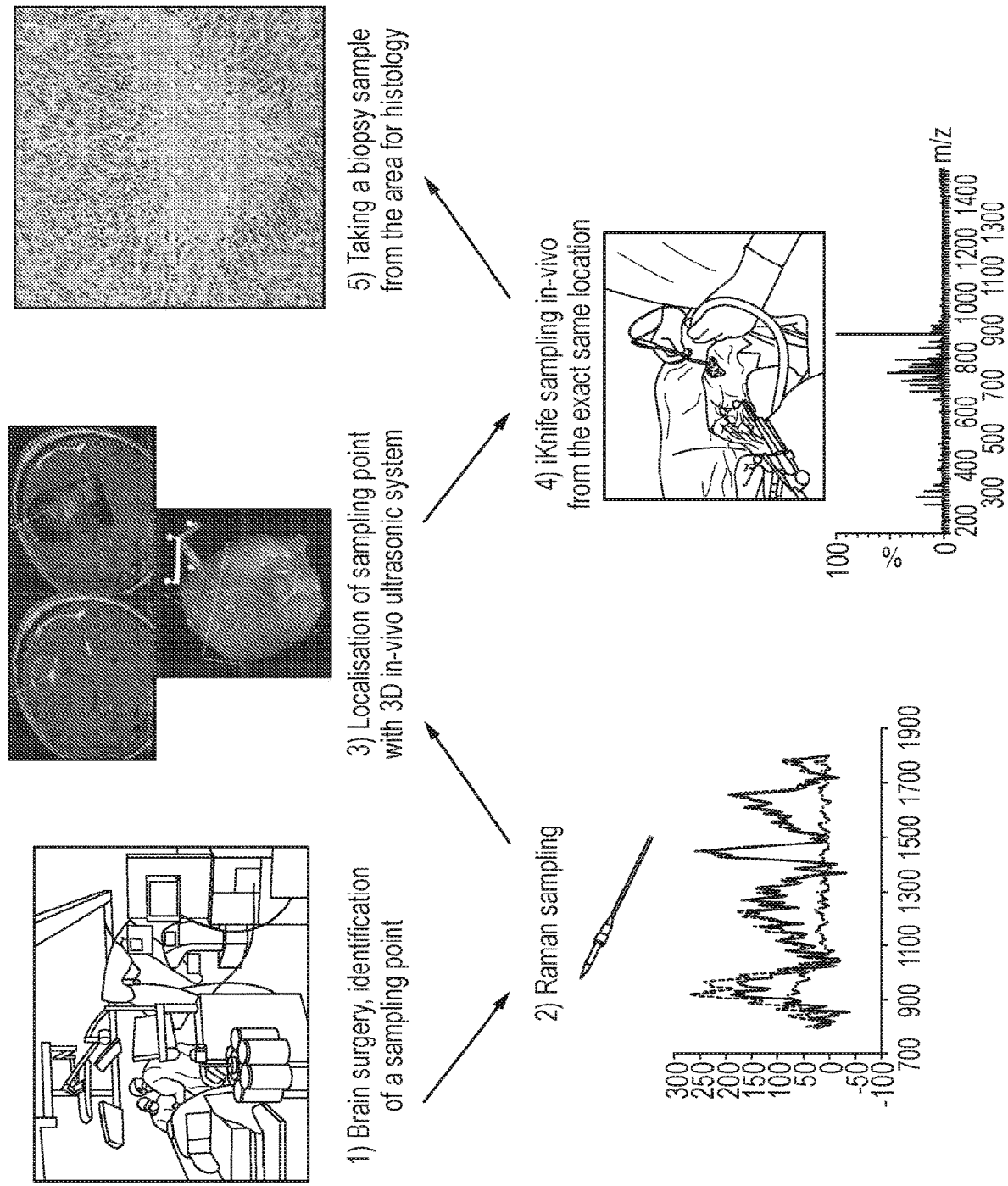
FIG. 28 shows an embodiment wherein various sampling points during brain surgery were subjected to Raman sampling and wherein the sampling points were then localised using a 3D in vivo ultrasonic system and rapid evaporative ionisation mass spectrometry ("REIMS") sampling was then performed at the same sampling points.

A sampling and validation method is summarized in FIG. 28. According to an embodiment one or more Raman sampling points may be identified. Raman sampling may then be performed at the sampling points. Localisation of the one or more Raman sampling points may then be performed using a 3D in vivo ultrasonic visualisation system. Rapid evaporative ionisation mass spectrometry ("REIMS") sampling (or sampling using a different type of ambient ionisation ion source) may then be performed in vivo from exactly the same locations as the Raman sampling points. Furthermore, a biopsy sample may optionally be taken from the area for histological validation.

The target (e.g., surgical site) may first be sampled by Raman spectroscopy, followed by an ultrasonic reading and localization of the area. As a subsequent step rapid evaporative ionisation mass spectrometry ("REIMS") sampling (or another method of ambient ionisation) may then be performed using e.g., bipolar forceps or a laser ablation device. The rapid evaporative ionisation mass spectrometry ("REIMS") sampling (or other method of ambient ionisation) may then be followed by taking a core biopsy of the area for ex vivo analysis and histopathology.

According to an embodiment a number of different sampling points may be used during a surgical procedure. For example, according to an experiment which was performed and which is described in more detail below, 14 sampling points were used. However, it will be understood to those skilled in the art and a fewer or greater number of sampling points may be used.

A total of 24 patients were enrolled in one particular patient study involving rapid evaporative ionisation mass spectrometry ("REIMS") analysis of brain tumours during which additional Raman sampling was performed in nine cases.

Figure 29:
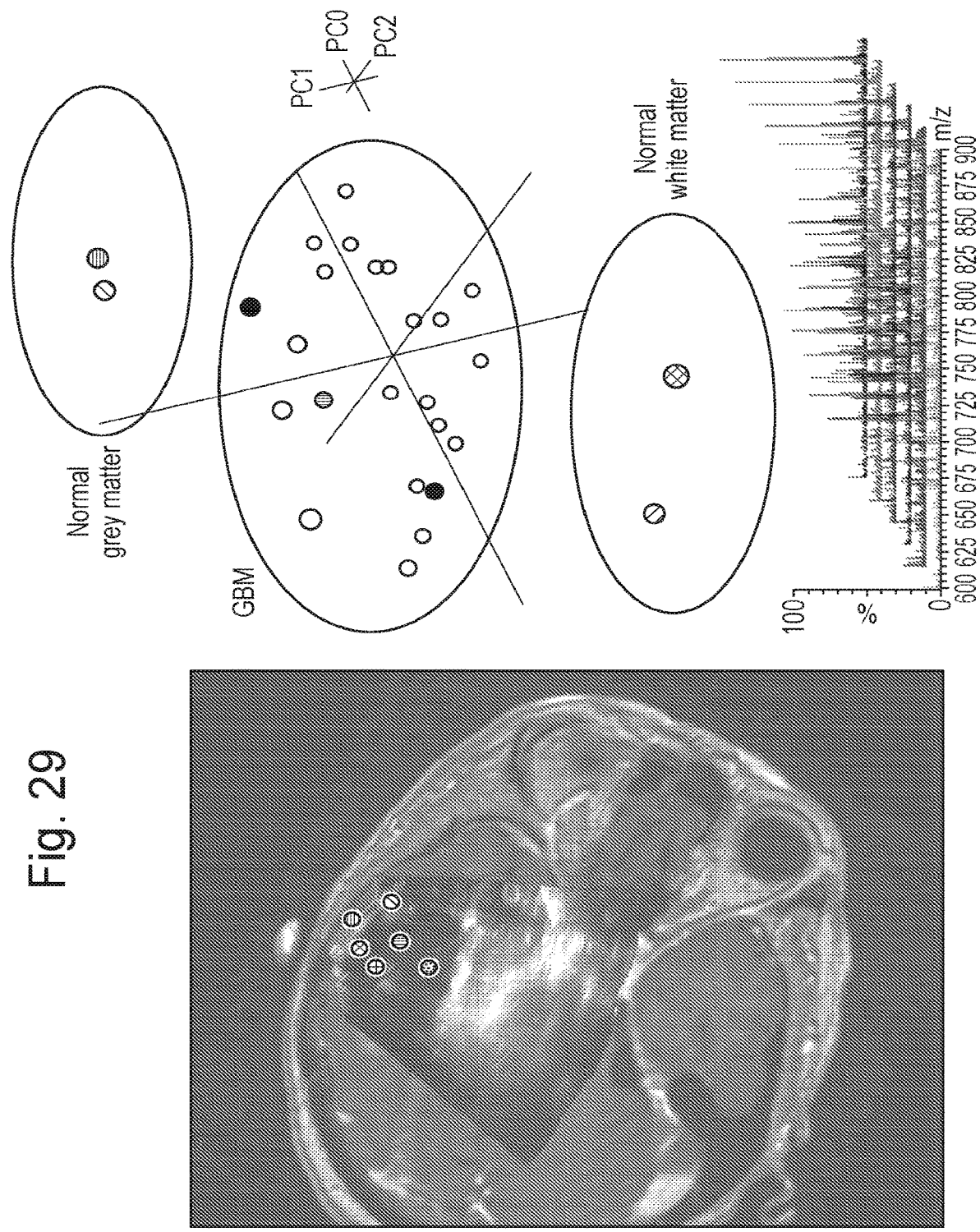
FIG. 29 shows on the left-hand side a case study of a patient suffering from Glioblastoma multiforme ("GBM") and shows a 3D image of the patient's brain which is overlayed by real time ultrasonic image and wherein an aerosol was generated by rapid evaporative ionisation mass spectrometry ("REIMS") from six sampling points (which are shown on the image) during surgery, wherein corresponding mass spectra which were recorded at each sampling point are shown (right bottom) together with a 3D PCA plot of all sampling point taken during the surgery and as labelled by a neuropathologist.

FIG. 29 relates to a case study of one out of the 24 patients who were all suffering from different types of brain tumours. The particular patent who was the subject of the case study presented in FIG. 29 was patient #4 (IKBRA04) who had grade IV Glioblastoma multiforme ("GBM"). A full list of patients and their associated tumour type is given in the following table:

| Patient | Tumour type | WHO grade |
|---|---|---|
| IKBRA01 | low grade oligodendroglioma | Grade II |
| IKBRA02 | low grade fibrillary astrocytoma | Grade II |
| IKBRA03 | Anaplastic astrocytoma | Grade III |
| IKBRA04 | Glioblastoma multiforme | Grade IV |
| IKBRA05 | Glioblastoma multiforme | Grade IV |
| IKBRA06 | Diffuse astrocytoma | |
| IKBRA07 | Anaplastic astrocytoma | Grade III |
| IKBRA08 | Meningioma | Grade I |
| IKBRA09 | Cystic gliosarcoma | |
| IKBRA10 | Anaplastic oligodendroglioma | Grade III |
| IKBRA11 | Glioblastoma multiforme | Grade IV |
| IKBRA12 | Glioblastoma multiforme | Grade IV |
| IKBRA13 | Fibrillary and gemistocytic astrocytoma | Grade II |
| IKBRA14 | Diffuse astrocytoma | Grade II |
| IKBRA15 | Ependymoma, cellular type | Grade II |
| IKBRA16 | Glioblastoma multiforme | Grade IV |
| IKBRA17 | Glioblastoma multiforme | Grade IV |
| IKBRA18 | Oligodendroglioma | Grade II |
| IKBRA19 | Giant Cell Glioblastoma | Grade IV |
| IKBRA20 | Anaplastic astrocytoma | Grade III |
| IKBRA21 | Low grade astrocytoma | Grade II |
| IKBRA22 | Low grade astrocytoma | Grade II |
| IKBRA23 | Recurrent glioblastoma | Grade IV |
| IKBRA24 | Anaplastic astrocytoma | Grade III |

The left-hand portion of FIG. 29 shows a 3D image of the brain of patient #4 which has been overlayed with a real time ultrasonic image. Six sampling points were taken using a rapid evaporative ionisation mass spectrometry ("REIMS") probe during surgery and are also depicted on the image shown in FIG. 29.

FIG. 29 also shows six corresponding mass spectra which were recorded wherein each mass spectrum corresponds to a different sampling point.

FIG. 29 also shows a 3D PCA plot of all sampling point taken during the surgery. The 3D PCA plot was labelled by a neuropathologist.

All in vivo and ex vivo sampling points are shown on the PCA plot shown in FIG. 29. It is apparent from FIG. 29 that normal grey and white matter group separately both from the cancerous samples and from each other.

Figure 30:
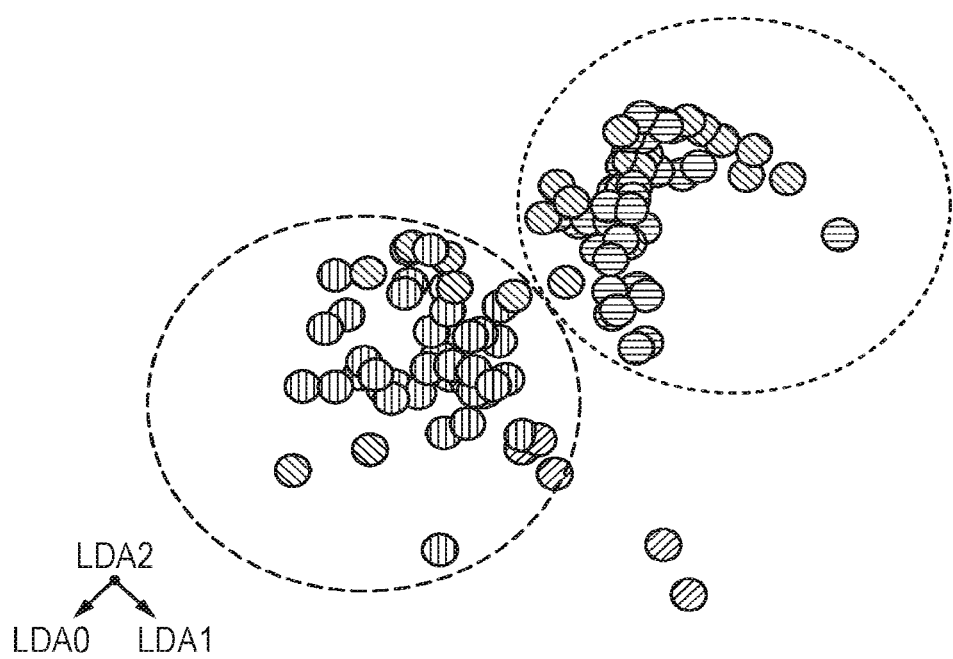
FIG. 30 shows a 3D pseudo LDA plot of ten patients who were suffering from four different tumour types and shows that high and low grade tumours separate well on the space although some grade III oligodendroglioma tumours group with low grade tumours.

Tumour Typing and Grading Using a Rapid Evaporative Ionisation Mass Spectrometry ("REIMS") Probe FIG. 30 shows the result according to an embodiment of comparing patients with high grade (grade IV) Glioblastoma multiforme (e.g., Glioblastoma, giant cell Glioblastoma and recurrent Glioblastoma) and low grade (grade II and III) tumours (e.g., anaplastic astrocytoma, oligodendroglioma and diffuse astrocytoma).

It is apparent from FIG. 30 that high grade (grade IV) and low grade (grade II and III) tumours separated well on a 3D pseudo LDA plot.

Patients having intermediate grade III tumours grouped either with the high grade area of the space or with the low grade area of the space.

Embodiments are contemplated wherein the positioning of a sample in the 3D space may be used to predict the possible progression of an anaplastic astrocytoma in the future.

Comparison of Healthy and Cancerous Samples with Both Raman Spectroscopy and Rapid Evaporative Ionisation Mass Spectrometry ("REIMS") Sampling Patient #21 (IKBRA21) was suffering from a low grade (grade II) astrocytoma. The patient was subjected to a combination of Raman spectroscopy sampling and rapid evaporative ionisation mass spectrometry ("REIMS") sampling. Raman data from a total of 32 sampling points were recorded. 13 of these 32 sampling points corresponded with normal tissue, 18 of these 32 sampling points corresponded with cancerous tissue and 1 corresponded with background.

Rapid evaporative ionisation mass spectrometry ("REIMS") sampling was also performed at 14 of the 32 sampling points.

FIG. 31 shows rapid evaporative ionisation mass spectrometry ("REIMS") mass spectra from two sampling points. Sampling point S4 corresponded with tumour tissue having a low cellularity. In particular, sampling point S4 corresponded with posterior medial superficial tumour. Fragments of the tumour tissue had low cellularity and some degree of reactive gliosis. Sampling point S14 corresponded with normal white matter have single cell infiltration. In particular, sampling point S14 corresponded with posterior base pot. Multiple fragments of white matter with reactive gliosis and single-cell tumour infiltration are present.

FIG. 31 also shows a 3D PCA plot corresponding to all sampling points taken throughout the surgery.

Figure 32:
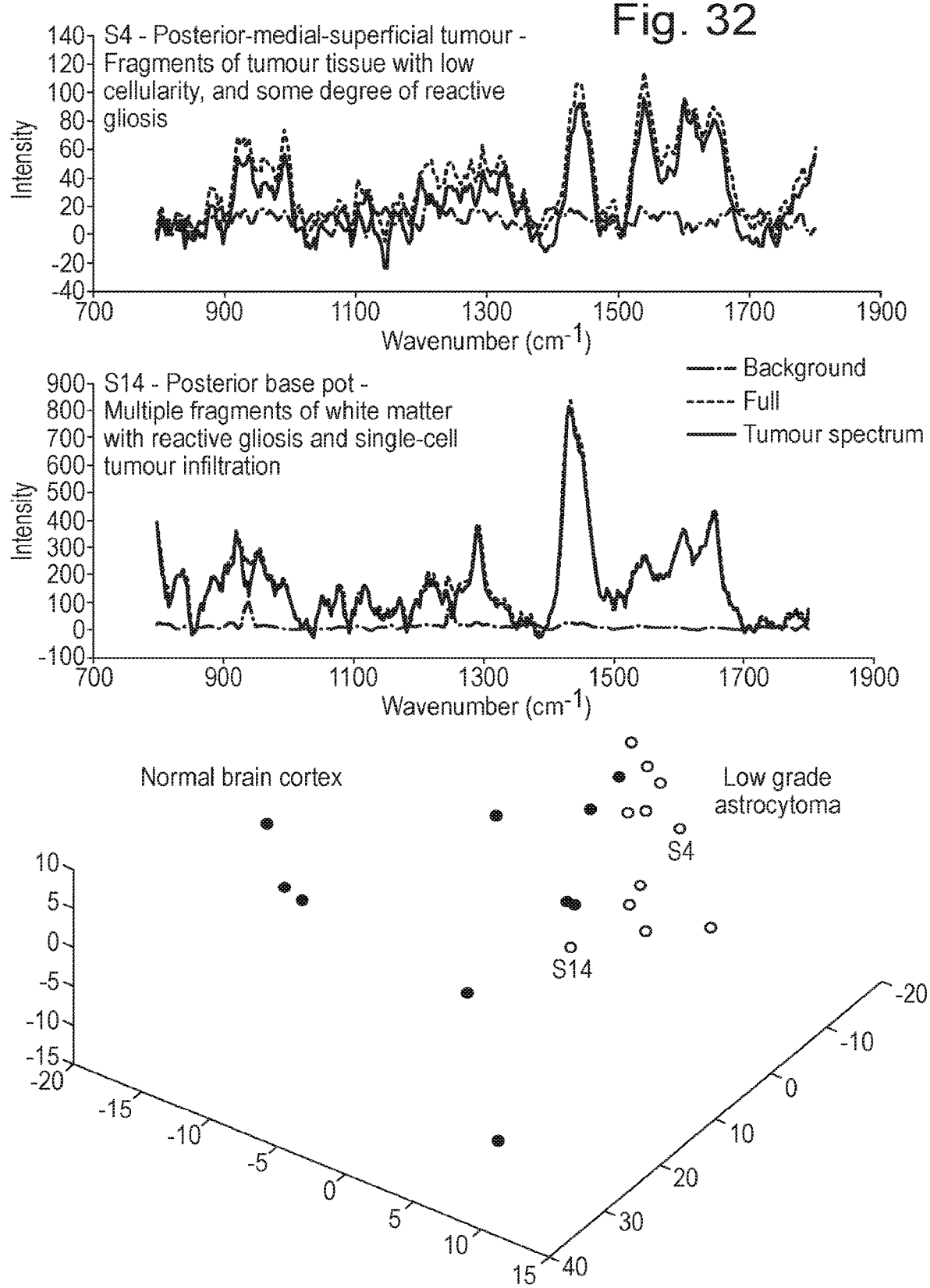
FIG. 32 shows Raman spectra (above) and a 3D PCA plot (below) from the same sampling points, one consisting mainly from the tumour, the other from normal white matter wherein the main differences observed on the PCA plot are due to the lipid vibration region.

FIG. 32 shows corresponding Raman spectra from sampling points S4 (tumour) and S14 (normal white matter) together with a 3D PCA plot from all sampling points taken throughout the surgery.

Both the Raman spectra and mass spectra obtained using an ambient ionisation ion source such as a rapid evaporative ionisation mass spectrometry ("REIMS") ion source have a tissue specific "fingerprint" in the phospholipid range. The main differences observed on the PCA plot are due to the lipid vibration region.

There are a number of sulfatides which are very specific for normal white matter of brain. For example, the following sulfatides are specific for normal white matter of the brain:

| m/z (calculated) | compound | formula |
|---|---|---|
| 888.624 | C24:1 sulfatide | $C_{48}H_{91}NO_{11}S$ |
| 906.635 | C24—OH sulfatide | $C_{48}H_{92}NO_{12}S$ |
| 916.655 | C26:1 sulfatide | $C_{50}H_{94}NO_{11}S$ |

The above described embodiments represent a novel protocol for intraoperative tissue identification and validation in surgical applications wherein both rapid evaporative ionisation mass spectrometry ("REIMS") technology and Raman spectroscopy are utilised. The various embodiments disclosed above show that both technologies are feasible for the distinction of healthy tissue and different brain cancers during an operation.

Raman spectroscopy, used as a non-invasive probe, is particularly suitable for providing initial information to a surgeon about where to start cutting, operating or resecting.

Rapid evaporative ionisation mass spectrometry ("REIMS") can provide more detailed and continuous information about the dissected tissue and may also be used to predict if a low grade tumour (e.g., grade II or III) has a high likelihood of progressing to a high grade tumour (e.g., grade IV) in the future or not.

The combination of Raman spectroscopy and rapid evaporative ionisation mass spectrometry ("REIMS") technologies enables molecular navigation in real-time and the combination of these two technologies enables important information to be provided to a surgeon in the assessment of tumour margins and tumour types (which can lead to an increase in the survival rate of patients).

DESI Imaging
Prediction of Tissue Types in Breast Cancer Biopsies

Manual histological evaluation of the stained biopsy tissue sections has been the gold standard method when it comes to providing a diagnosis for breast cancers. However, the accuracy of this morphology-based tissue diagnosis is often compromised as it is dependent on the pathologists' interpretation resulting in poor prognosis for a given patient.

Desorption electrospray ionisation mass spectrometry imaging (MSI) enables visualisation of spatial distribution of lipid species across tissue sections allowing direct correlation with the histological features. Therefore, breast cancer tissues were analysed with desorption electrospray ionisation mass spectrometry imaging (MSI) to obtain lipidomic data. 45 samples were analysed in positive and negative ion mode.

Figure 33A:
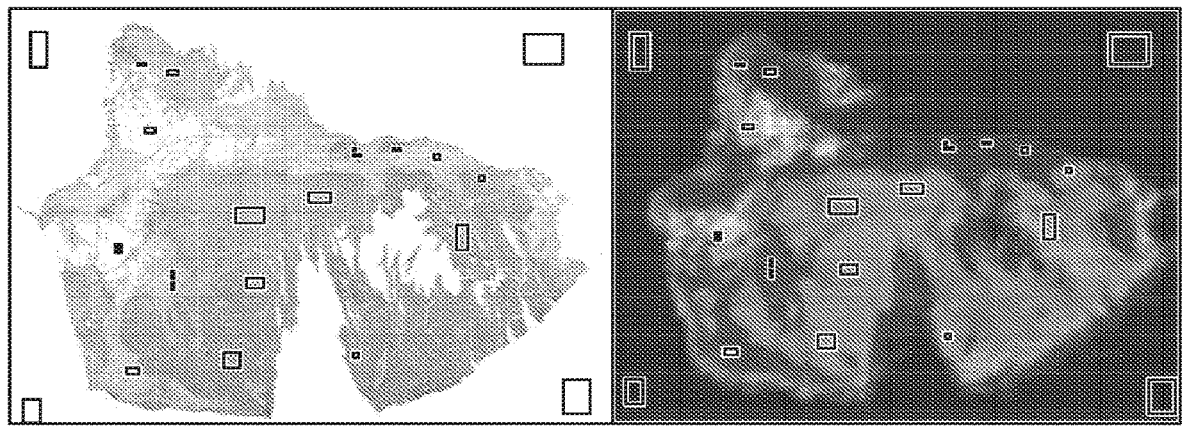
FIG. 33A shows images of PCA components 1, 2 and 3 in negative ion mode along with a respective histological image of a Grade II Invasive Ductal Carcinoma (IDC)
Figure 33B:
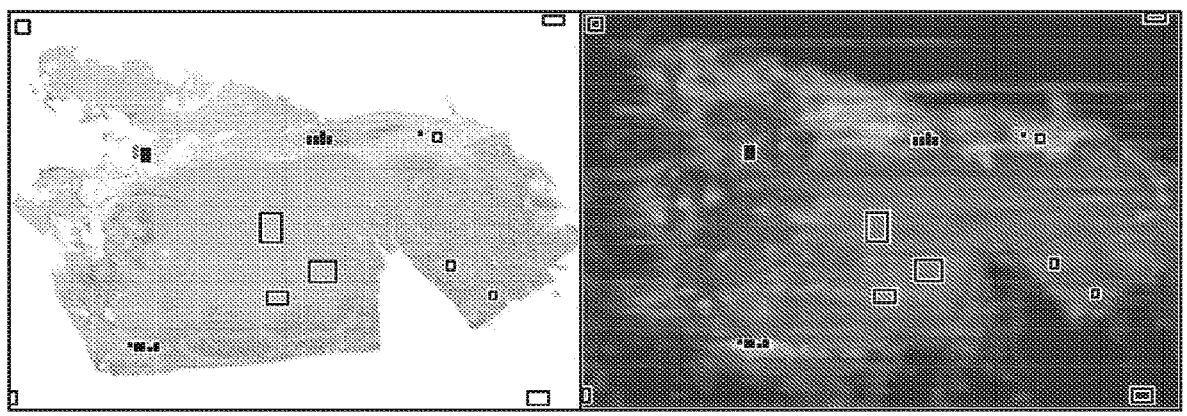
FIG. 33B shows images of PCA components 1, 2 and 3 in positive ion mode along with a respective histological image of a Grade II Invasive Ductal Carcinoma (IDC)

FIG. 33A shows RGB images of PCA components 1, 2 and 3 in negative ion mode and FIG. 33B shows in positive ion mode with the respective histological images of a Grade II Invasive Ductal Carcinoma (IDC).

An ovarian cancer dataset with different epithelial carcinomas (endometrioid, serous and clear cell carcinomas), borderline tumours, and healthy ovary and fallopian tube has been analysed. A total of 109 samples were collected and acquired by desorption electrospray ionisation-MS in positive and negative ion mode.

Figure 34A:
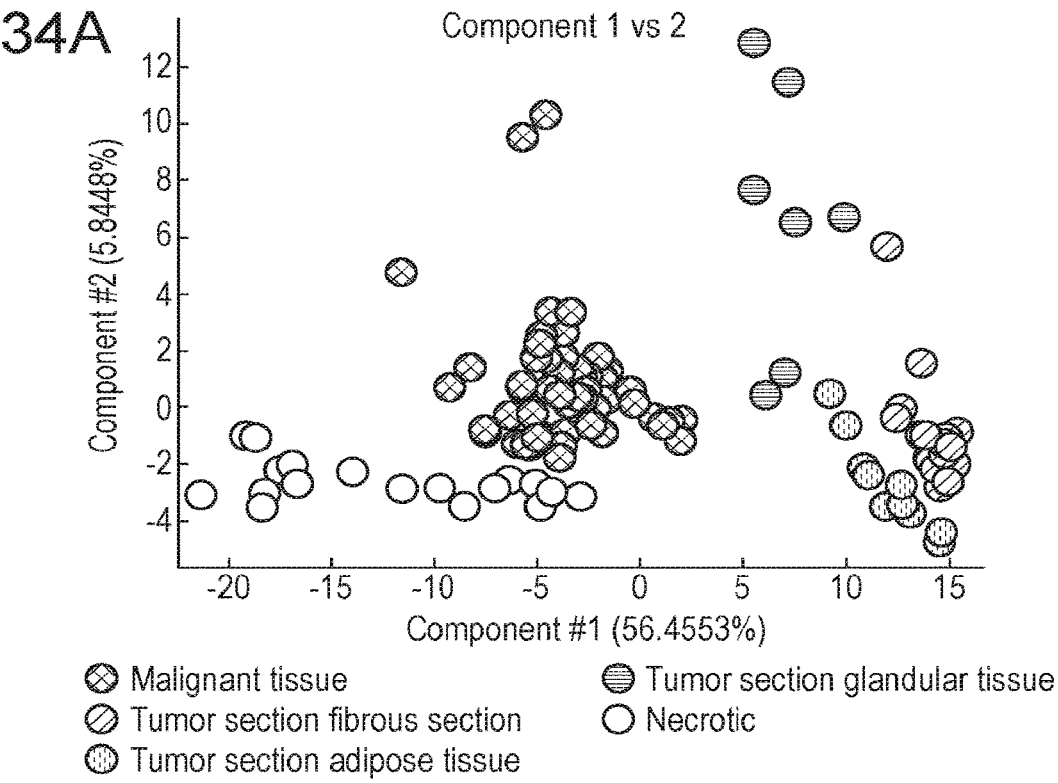
FIG. 34A shows PCA analysis of a Grade II Invasive Ductal Carcinoma in negative ion mode and FIG. 34B shows MMC analysis of a Grade II Invasive Ductal Carcinoma in negative ion mode.

FIG. 34A shows PCA analysis of Grade II IDC in negative ion mode.

Figure 34B:
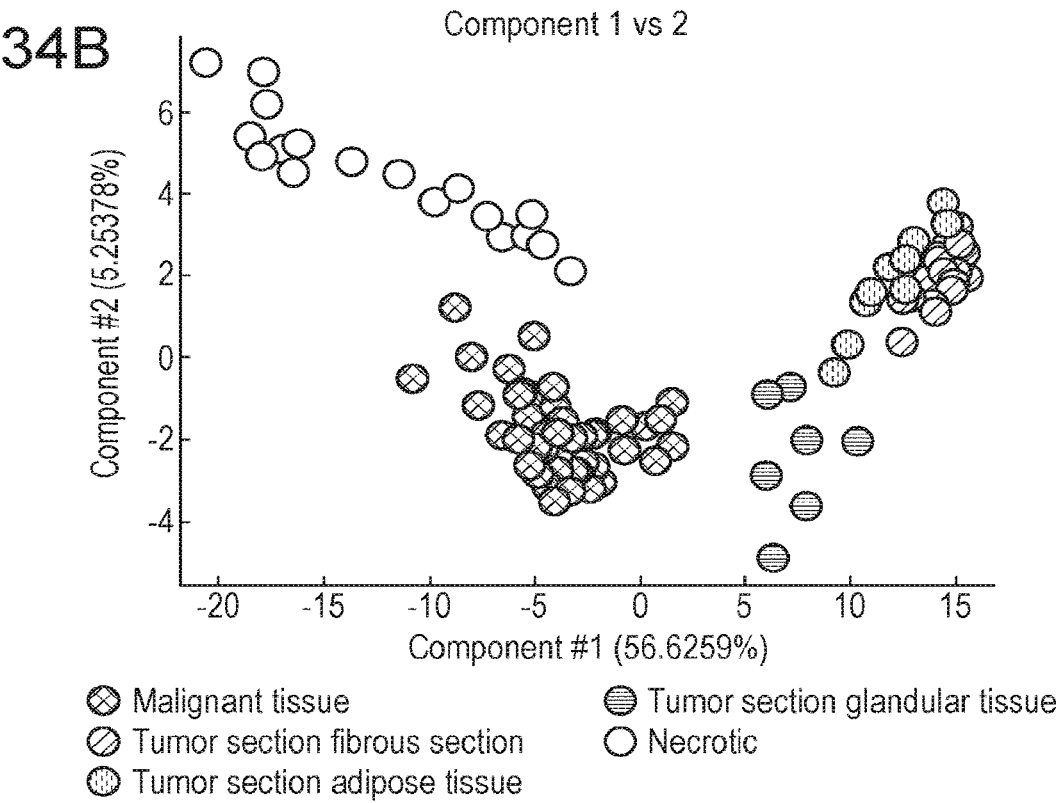

FIG. 34B shows MMC analysis of Grade II IDC negative ion mode.

Figure 35A:
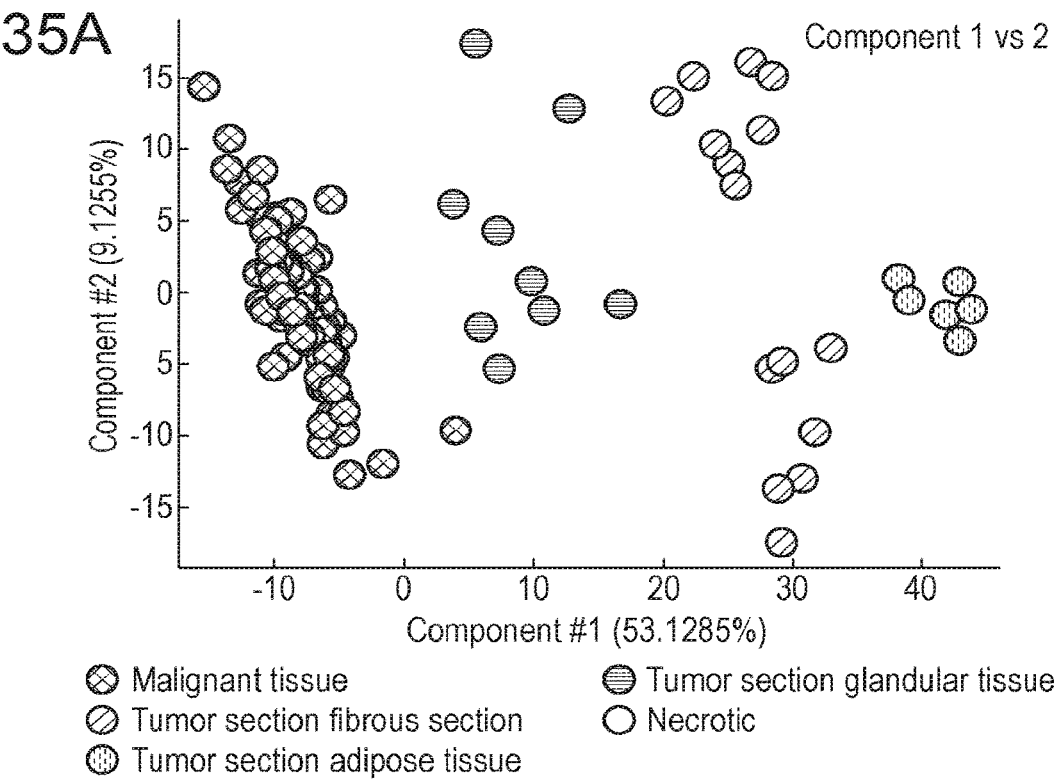
FIG. 35A shows PCA analysis of a Grade II Invasive Ductal Carcinoma in positive ion mode and FIG. 35B shows MMC analysis of a Grade II Invasive Ductal Carcinoma in positive ion mode.

FIG. 35A shows PCA analysis of Grade II IDC in positive ion mode.

Figure 35B:
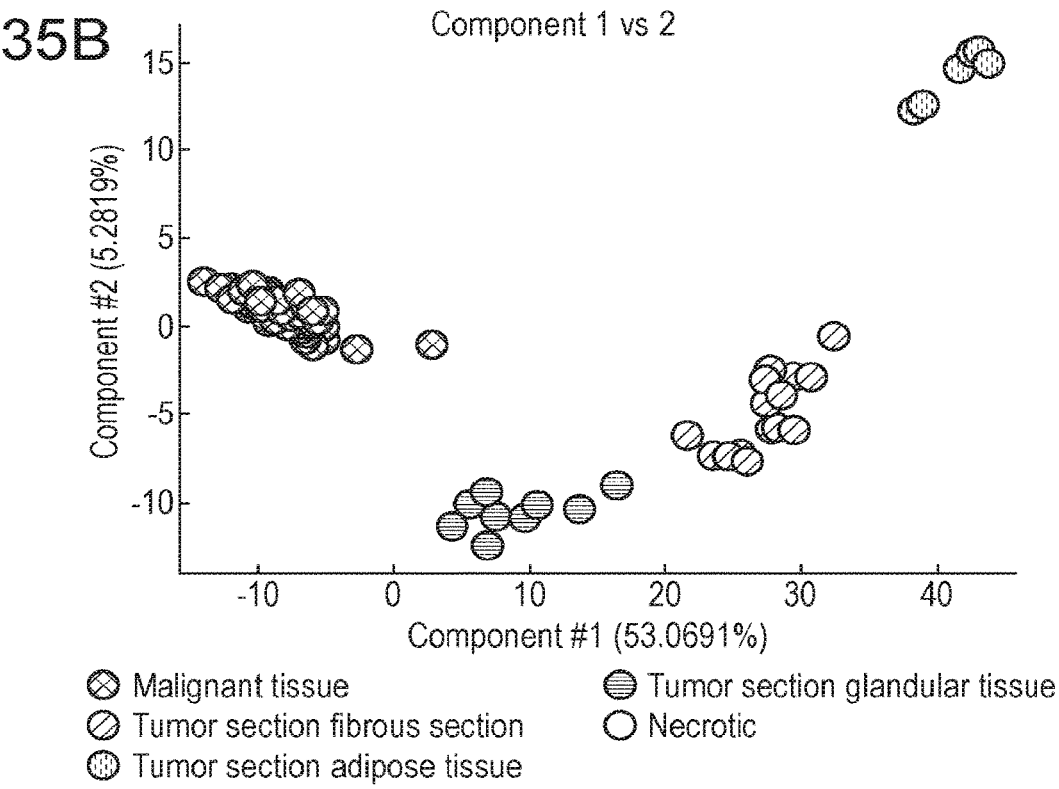

FIG. 35B shows MMC analysis of Grade II IDC positive ion mode.

Figure 36A:
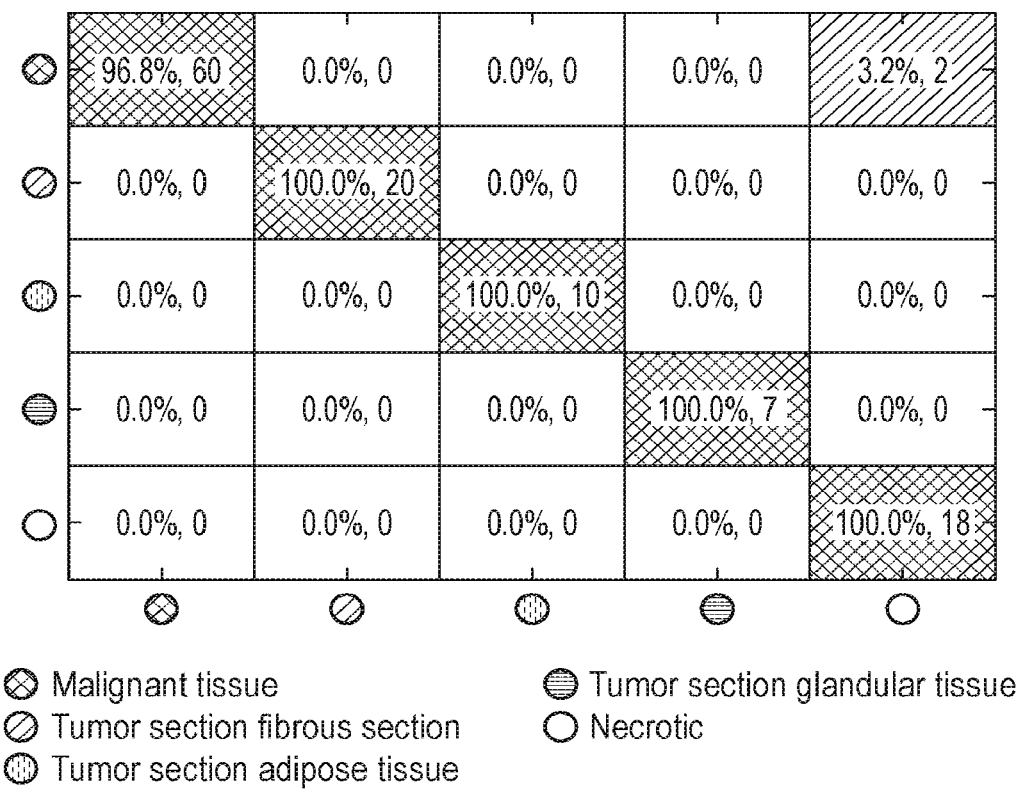
FIG. 36A shows leave one out cross validation of different tissue types in a Grade II Invasive Ductal Carcinoma in negative ion mode and FIG. 36B shows leave one out cross validation of different tissue types in a Grade II Invasive Ductal Carcinoma in positive ion mode.
Figure 36B:
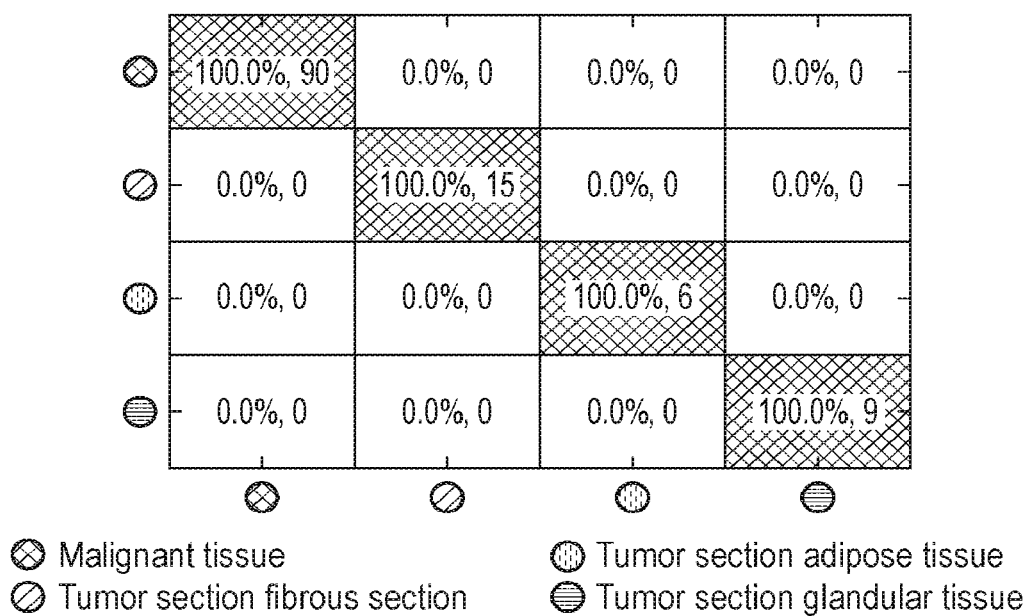

FIG. 36A shows leave one out cross validation of different tissue types in a Grade II IDC in negative ion mode and FIG. 36B shows in positive ion mode.

Each individual breast sample was subjected to unsupervised principal component analysis (PCA) to visualize differences between different tissue types. In both positive and negative ion mode, a clear distinction could be observed between the stroma and the tumour tissue in almost all of the samples (FIG. 34A and FIG. 35A). Recursive maximum margin criterion (RMMC) analysis was used for supervised classification (FIG. 34B and FIG. 35B).

Tissue types in each sample and their spatial distribution were determined by an independent histopathologist based on the H&E (haematoxylin and eosin) stained optical image. Based on this information, a small number of representative mass spectra per tissue were selected from the integrated MS ion image to build a sample-specific RMMC model which was used to classify all pixels in the different tissue types. This data was submitted to cross validation, which exceeded 95% accuracy generally for all tissue types in all samples in both negative and positive ion mode (FIG. 36A and FIG. 36B).

Development of Spatially Resolved Shotgun Lipidomic Methods for Histology-Level Cancer Diagnostics Using Ovarian Cancer Dataset A dataset was initially pre-processed and multivariate statistical analysis was performed on each individual sample's dataset in order to compile a database of histologically authentic lipidomic profiles. The morphological regions of interest were assigned by a qualified histopathologist and automatically co-registered and aligned with the MSI dataset.

Figure 37:
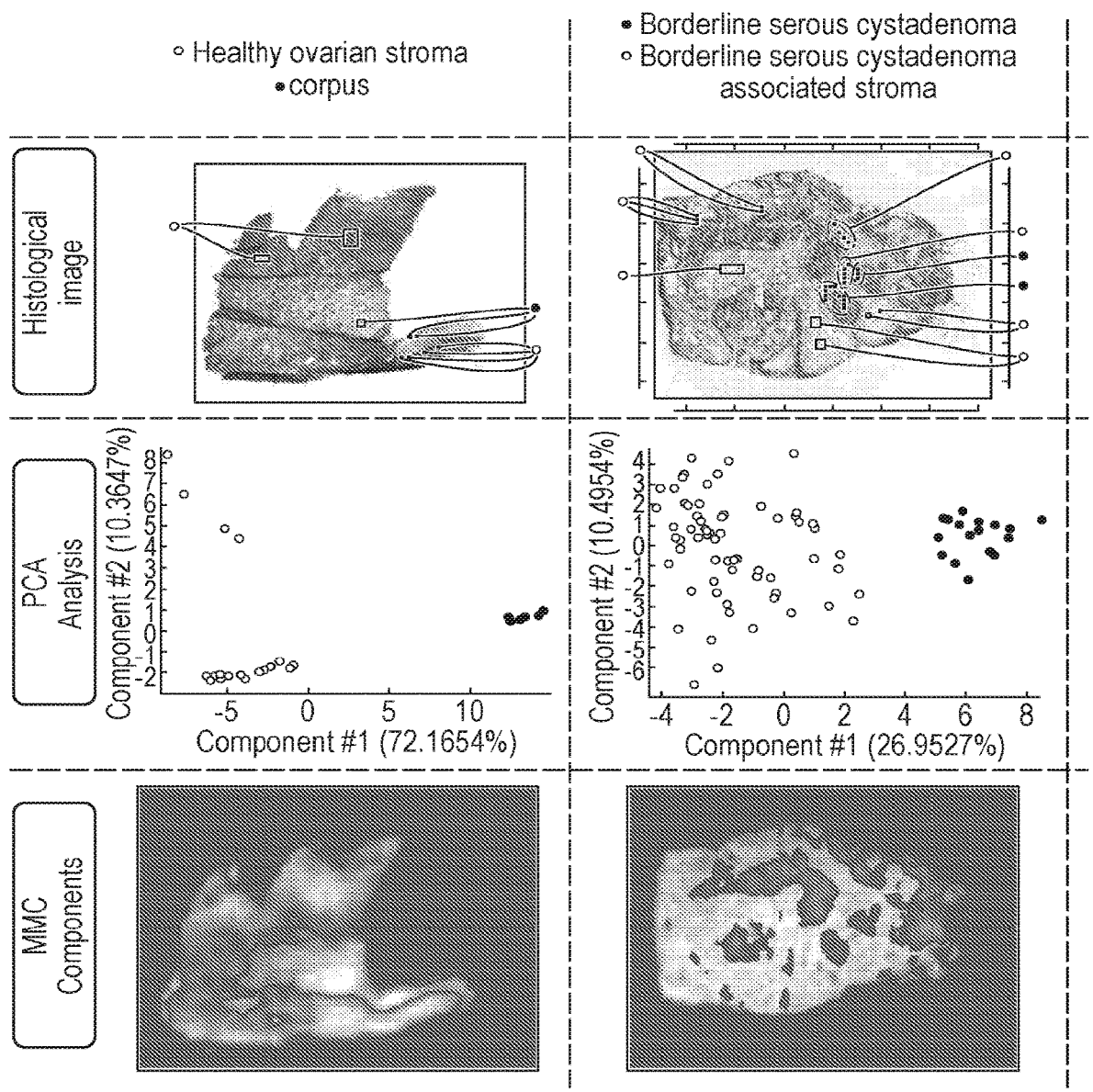
FIG. 37 shows histological images with annotated regions of interest by a histopathologist together with PCA analysis of these assigned regions and MMC supervised analysis components from samples analysed in the negative ion mode.
Figure 37:
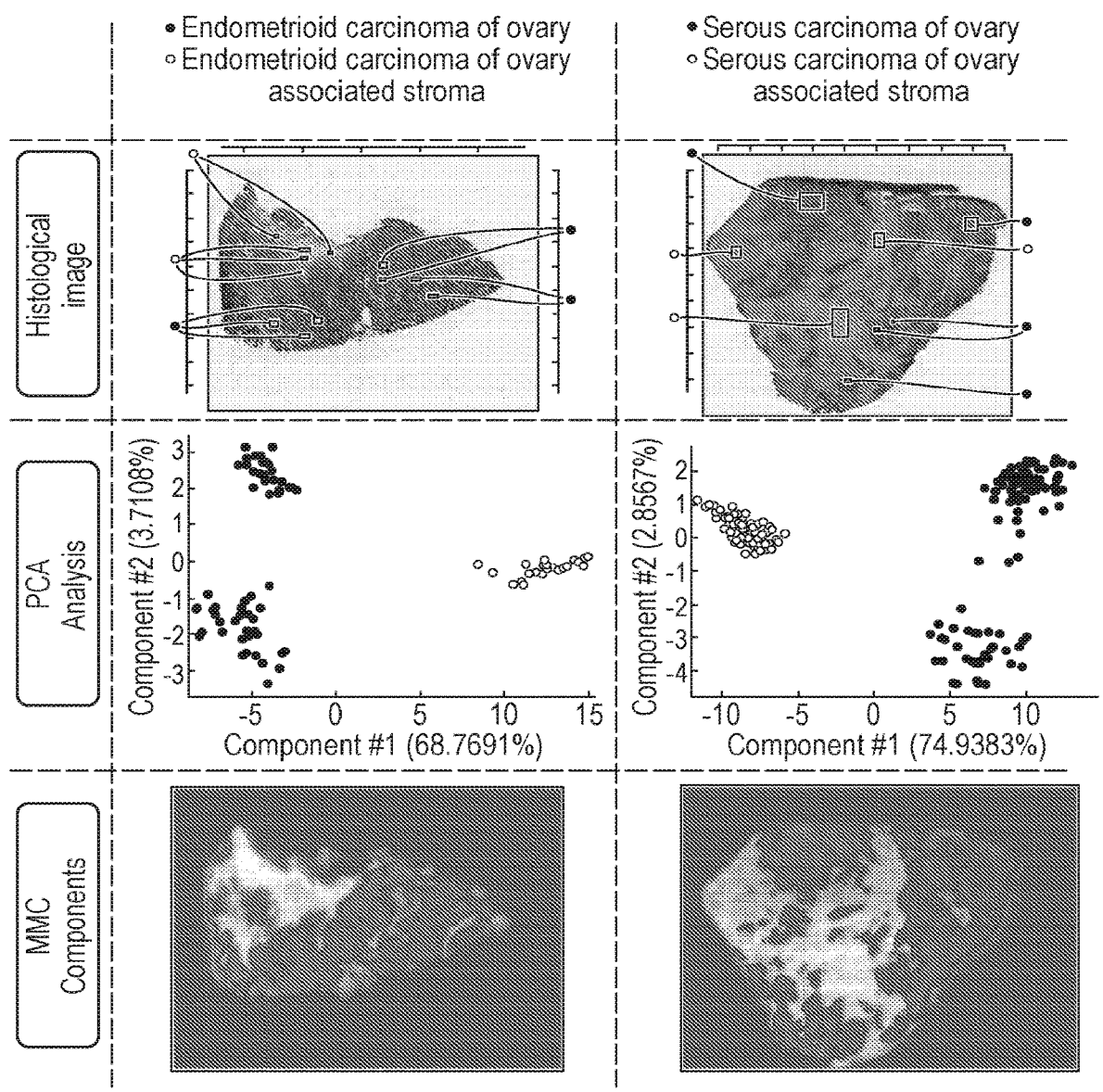

FIG. 37 shows histological images with the annotated regions of interest by histopathologist. The PCA analysis of these assigned regions together with the MMC supervised analysis components from samples analysed in the negative ion mode.

Using principal component analysis (PCA) it was observed that different tissue types within the same sample show different lipid profiles. For example, normal ovary contains corpus and stroma tissue, and these are completely separated in PCA.

In the borderline and cancer samples it was possible to distinguish two different tissue types, the tumour cells and the surrounding stroma cells presenting large differences in their lipidomic profile.

When supervised maximum margin criteria (MMC) analysis was applied and a colour map according to the MMC components was applied it was possible to produce tissue maps that reflect the different tissue types identified in the histological image.

This profile database was also used to perform comparative analysis across multiple samples. PCA was used to perform unsupervised tissue segmentation based on the lipidomic profiles, without taking into account histological assignment. A supervised analysis was then performed and a respective leave-one-tissue-per-patient-out cross validation was calculated.

Figure 38A:
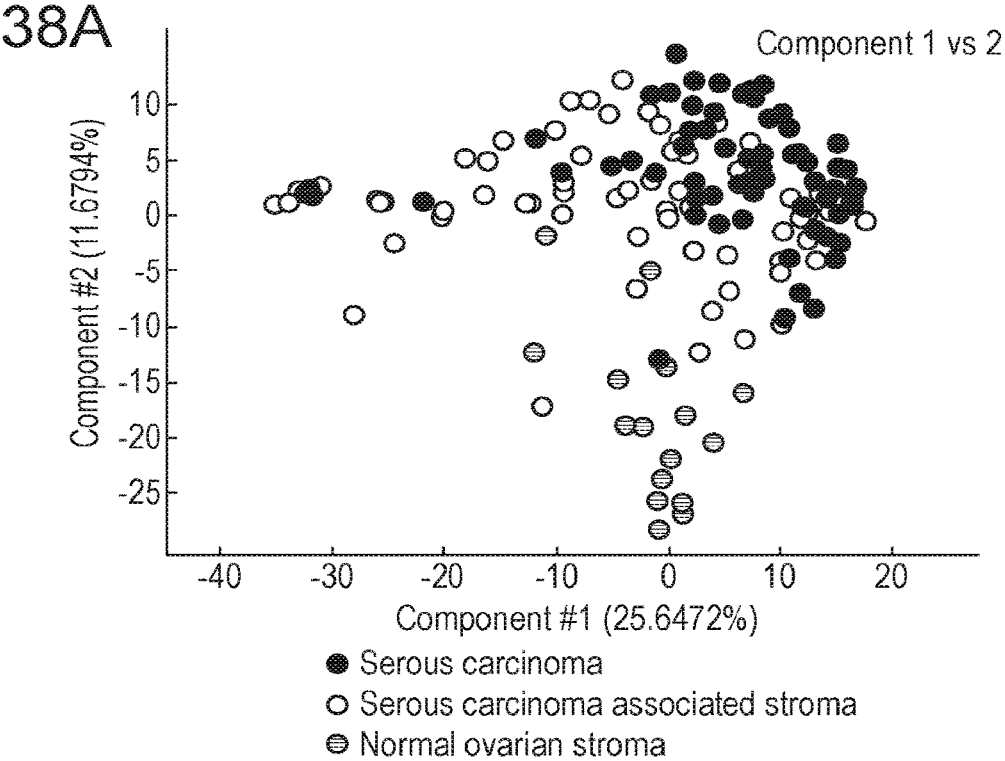
FIG. 38A shows analysis of a combined dataset from multiple samples (negative ion mode) of PCA of identified regions.
Figure 38B:
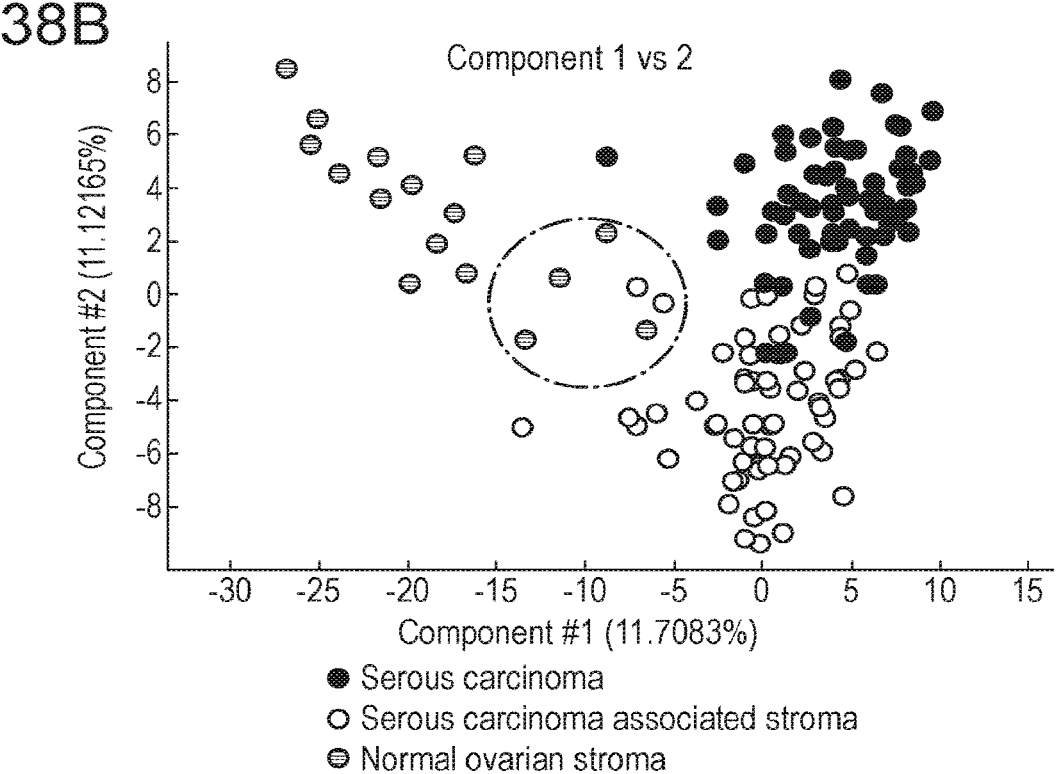
FIG. 38B shows MMC supervised analysis.
Figure 38C:
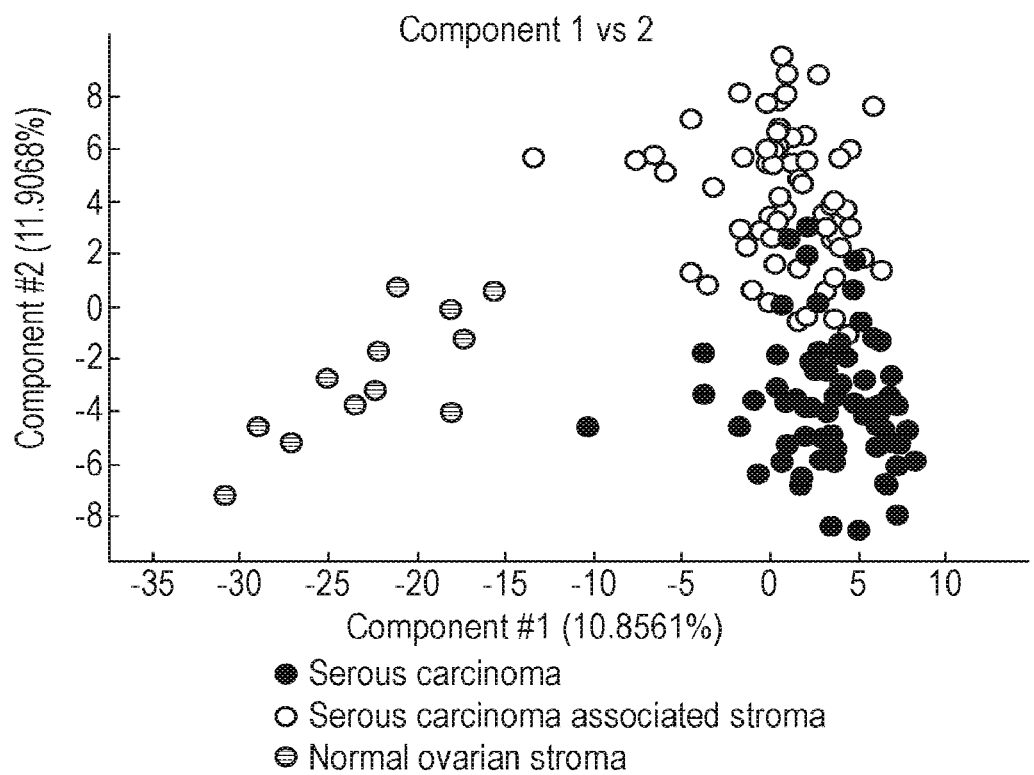
FIG. 38C shows MMC analysis excluding the samples with outliers identified in FIG. 38B
Figure 38D:
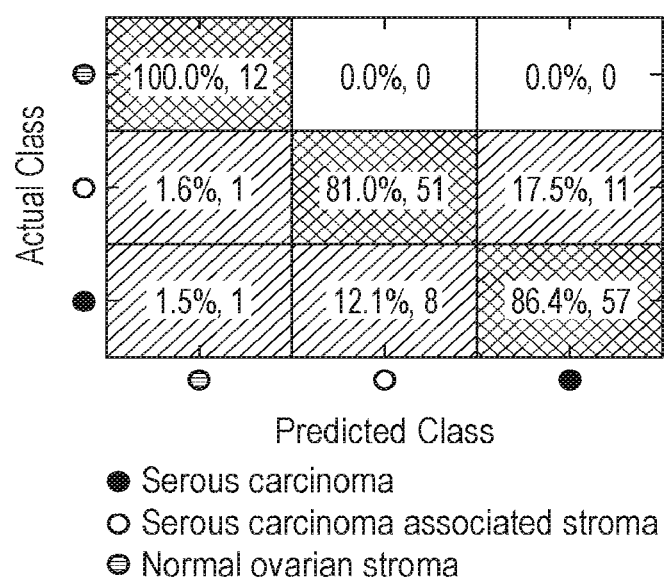
FIG. 38D shows respective leave-one-region-per-patient-out cross validation.

FIG. 38A shows analysis of a combined dataset from multiple samples (negative ion mode using PCA of identified regions, FIG. 38B shows corresponding MMC supervised analysis, FIG. 38C shows MMC analysis excluding the samples with outliers identified in FIG. 38B and FIG. 38D shows respective leave-one-region-per-patient-out cross validation. PCA shows some separation between normal ovary, serous carcinoma, and serous carcinoma associated stroma. The supervised MMC analysis shows good separation between all three tissue types with six outliers (circles in FIG. 38B). All four misclassified normal samples were samples which were classified as normal ovary but were taken from an ovary with a tumour distant from the sampling area. This suggests that the biochemistry of this tissue is altered, even though this cannot be detected in a morphological examination.

MMC analysis was repeated under exclusion of the outliers and leave-one-region-per-patient-out cross validation was performed, showing a complete separation of normal tissue and an overall accuracy of 85%.

The same analysis was performed for the positive ion mode data shown in FIGS. 35A-35B.

Figure 39A:
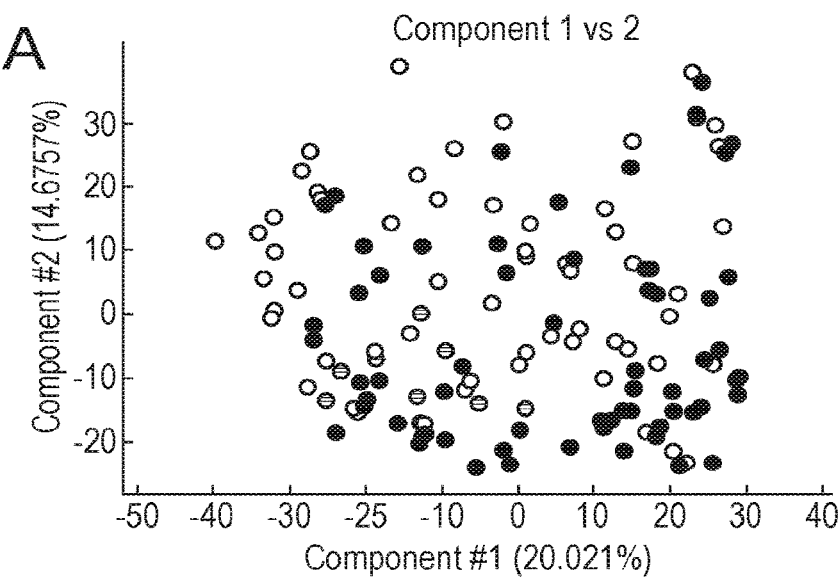
FIG. 39A shows PCA of identified regions.
Figure 39B:
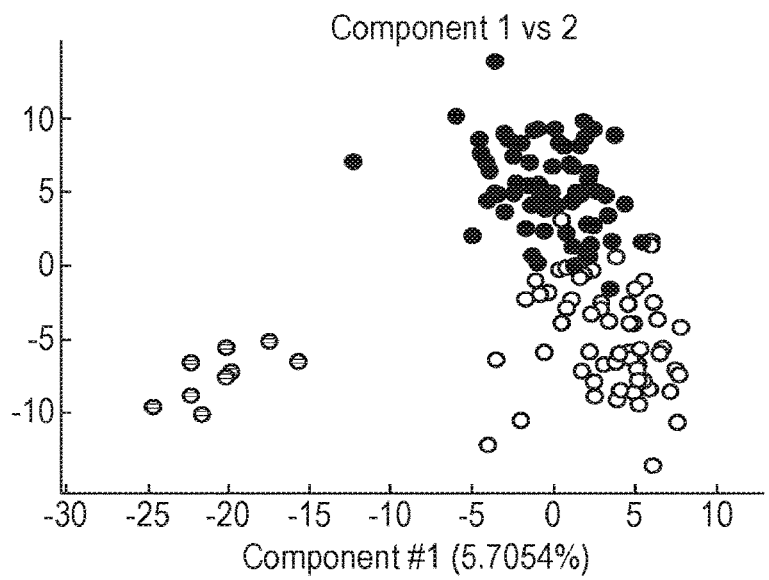
FIG. 39B shows MMC supervised analysis and FIG. 39C shows leave-one-region-per-patient-out cross validation for the positive ion mode data.
Figure 39C:

FIG. 39A shows PCA of identified regions, FIG. 39B shows MMC supervised analysis and FIG. 39C shows leave-one-region-per-patient-out cross validation for the positive ion mode data.

In the positive ion mode, the cross validation shows lower scores then in negative ion mode, the different tissue types being classified with an average cross validation accuracy of around 80%.

The variances between different types of samples were also examined. For example, it was evaluated how well negative ion mode desorption electrospray ionisation mass spectrometry imaging (MSI) can separate cancer tissues, borderline and healthy ovary.

Figure 40A:
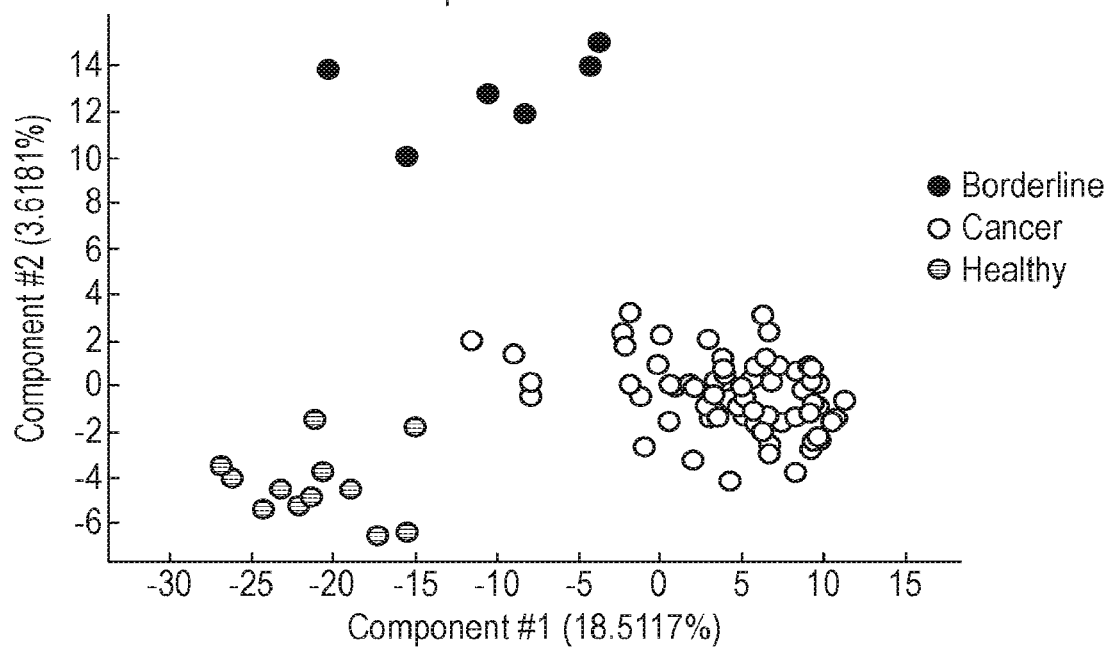
FIG. 40A shows supervised MMC analysis of healthy ovary, borderline tumours and carcinomas
Figure 40B:
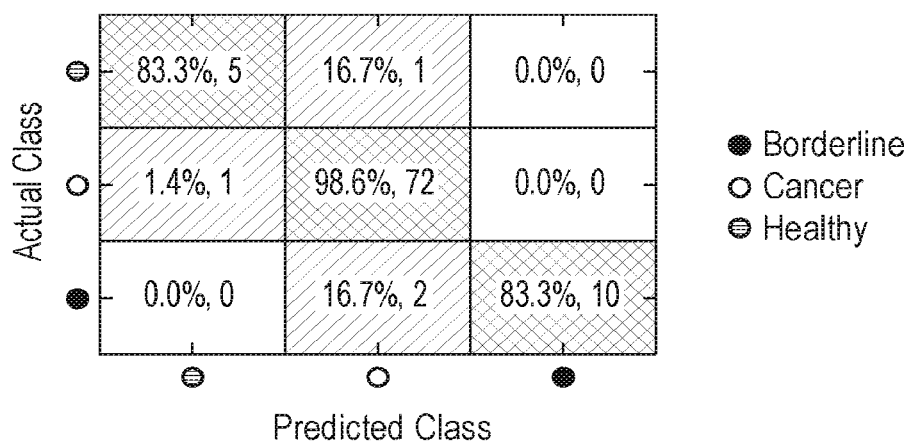
FIG. 40B shows corresponding leave one patient out cross validation for negative ion mode.

FIG. 40A shows supervised MMC analysis of healthy ovary, borderline tumours and carcinomas together with FIG. 40B showing leave one patient out cross validation.

More samples are being analysed to improve the model, but even with this small data set, an overall classification accuracy of 95.6% was achieved.

A further analysis performed was the comparison between different types of epithelial carcinomas in the dataset: endometrioid and serous carcinomas. Using the negative ion mode data, healthy ovary, serous carcinoma, and endometrioid carcinoma could be classified with an overall accuracy of 90% (see FIG. 41A and FIG. 41B).

Figure 41A:
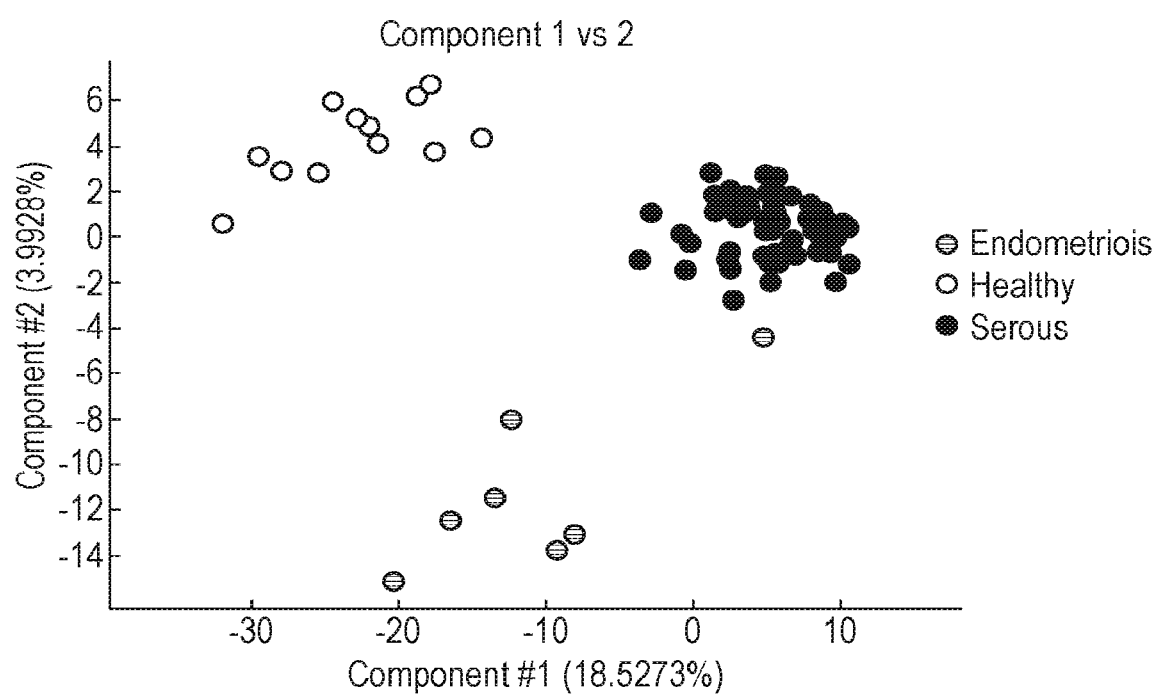
FIG. 41A shows supervised MMC analysis of healthy ovary and different epithelial carcinomas (endometrioid and serous) and FIG. 41B shows corresponding leave one patient out cross validation for negative ion mode.
Figure 41B:
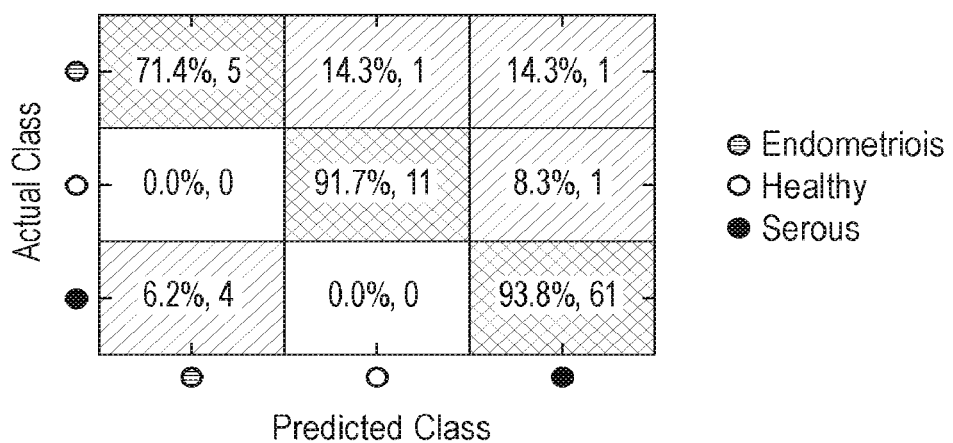

FIG. 41A shows supervised MMC analysis of healthy ovary and different epithelial carcinomas (endometrioid and serous) and FIG. 41B leave one patient out cross validation.

An examination was also performed based on the models created, as to whether it was possible to predict the different tissue types of a blind sample. The number of serous carcinomas analysed provided a robust model to perform this validation using negative ion mode data.

FIG. 42A shows a sample with unknown histology used to predict the different tissue types. Cross validation of this prediction was based on the histological annotation.

The desorption electrospray ionisation data allowed an excellent prediction of the two tissue types present in the sample i.e. stroma and cancer. A cross validation as shown in FIG. 42B was performed based on histological annotation performed after this analysis and a classification accuracy of almost 100% was achieved.

Biopsy and Swabs

Swabs may be used in the various embodiments described herein as both a sampling probe and ionisation probe.

Figure 43A:
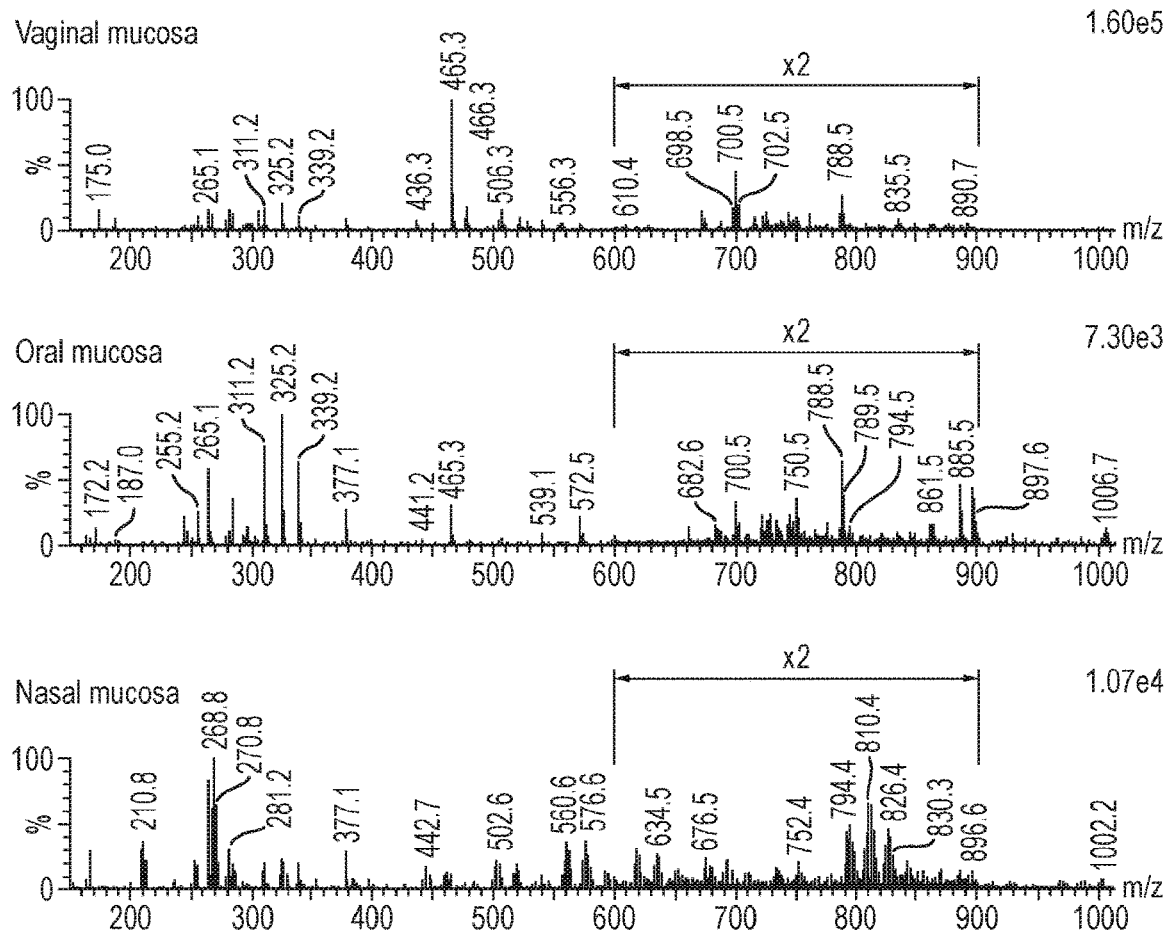
FIG. 43A shows averaged negative-ion desorption electrospray ionisation ("DESI") mass spectra from vaginal, oral and nasal mucosa recorded using a Xevo G2-S Q-Tof® mass spectrometer
Figure 43B:
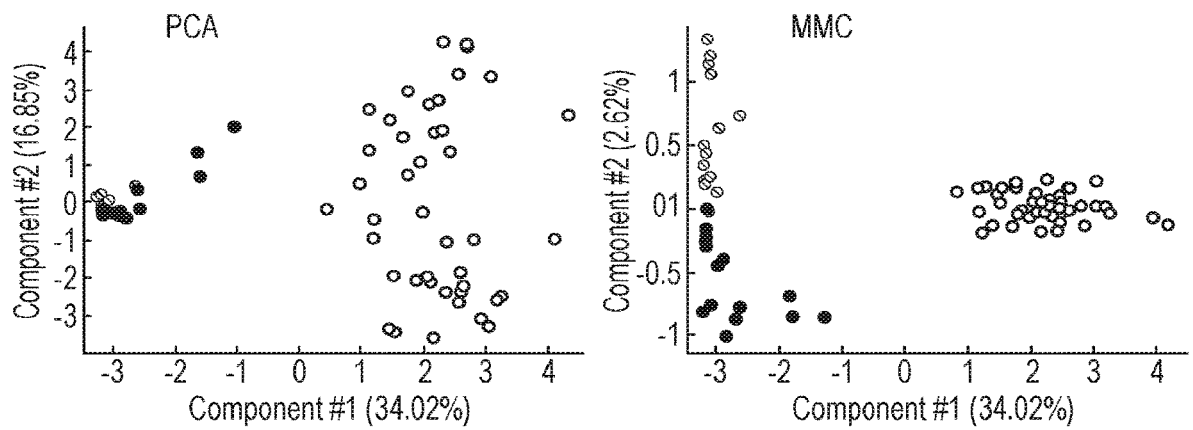
FIG. 43B shows a PCA and MMC score plot for vaginal (n=68), oral (n=15) and nasal (n=20) mucosa acquired with desorption electrospray ionisation ("DESI") mass spectrometry.

FIGS. 43A and 43B show the results of desorption electrospray ionisation ("DESI") mass spectrometry analysis of swabs, and multivariate statistical analysis including principal component analysis (PCA) and recursive maximum margin criterion (RMMC), which were used to identify lipid patterns characteristic of different mucosal models.

FIG. 43A shows averaged negative-ion mode desorption electrospray ionisation ("DESI") mass spectra from vaginal, oral and nasal mucosa recorded using a Xevo G2-S Q-Tof® mass spectrometer.

FIG. 43B shows a principal component analysis ("PCA") and a maximum margin criterion ("MMC") score plots for vaginal (n=68), oral (n=15) and nasal (n=20) mucosa acquired with desorption electrospray ionisation ("DESI") mass spectrometry.

As shown in FIG. 43A, unique lipid patterns were observed between different mucosal membrane models. The spectra for vaginal mucosa and oral mucosa featured predominately glycerophospholipids, e.g., [PS(34:1)-H]− having a mass to charge ratio ("m/z") of 760.4, [PS(36:2)-H]− having a m/z of 788.5 and [PI (36:1)-H]− having a m/z of 863.4.

As shown in FIG. 43A, nasal mucosa featured mainly chlorinated adducts [PC(36:2)+Cl]− m/z 820.5, [PC(34:1)+Cl]− m/z 794.5 and [PI(36:2)-H]− m/z 826.4 in the m/z 700-900 range.

A characteristic feature of vaginal mucosa was deprotonated cholesterol sulphate at a m/z of 465.3, which was consistently observed to be the most dominant peak in the spectrum. Chemical assignment of this peak was confirmed by tandem mass spectrometry experiments. This compound is an important component of cell membranes with regulatory functions including a stabilizing role, e.g., protecting erythrocytes from osmotic lysis and regulating sperm capacitation.

Leave-one-patient-out cross validation of the multivariate model containing spectra obtained by the analyses of three mucosal models resulted in a high classification accuracy. This shows that MS based profiling of different mucosal membranes allows stratification of patients based upon bacterial diversity.

Figure 44:
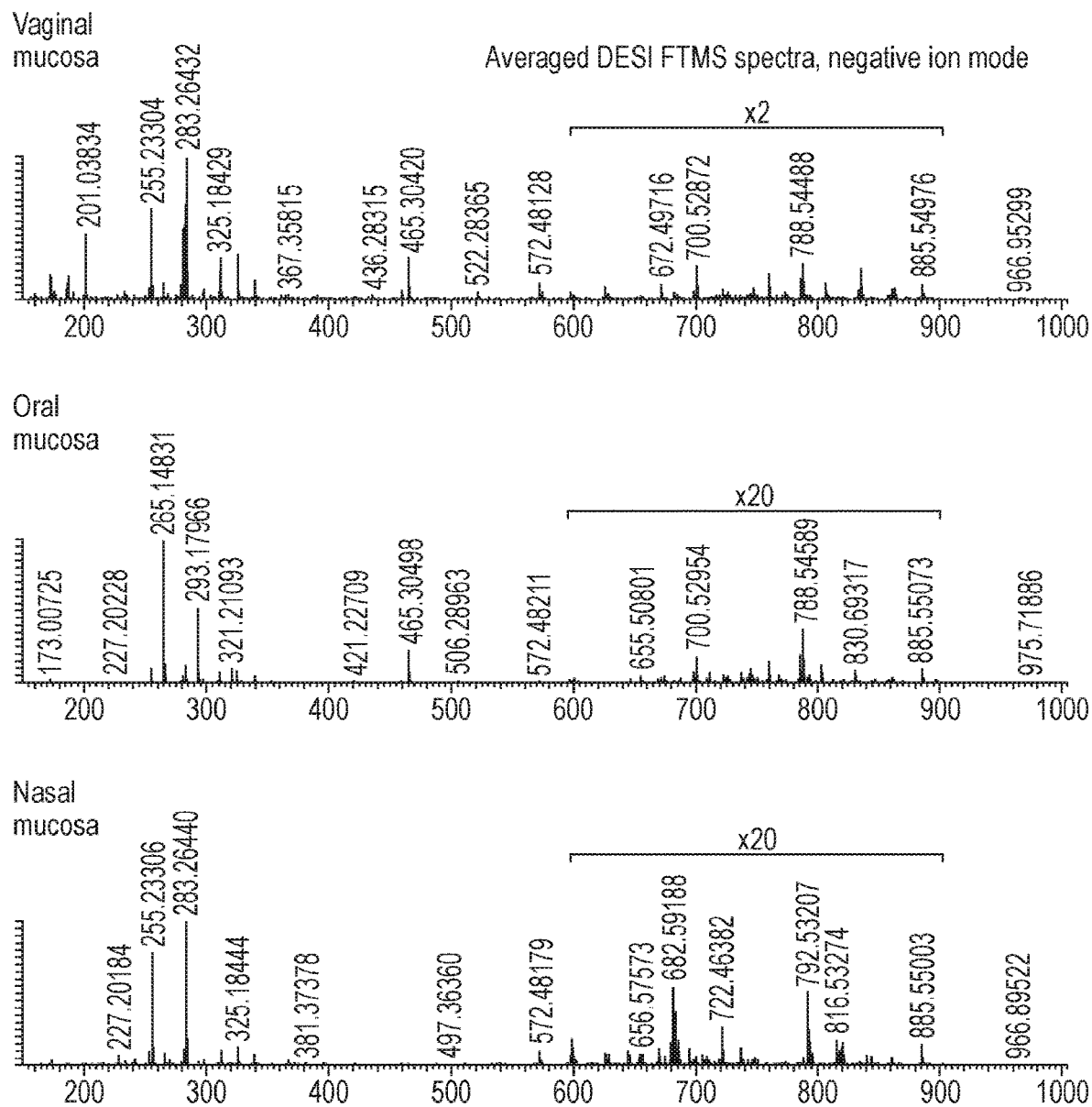
FIG. 44 shows desorption electrospray ionisation ("DESI") mass spectrometry spectra of vaginal, oral and nasal mucosal membranes in a negative ion mode obtained from medical cotton swabs, together with principal component analysis (PCA) and maximum margin criterion analysis providing a separation between different mucosal classes (nasal, oral, vaginal) with a prediction accuracy ranging from 92-100% obtained by leave one out cross validation.
Figure 44:
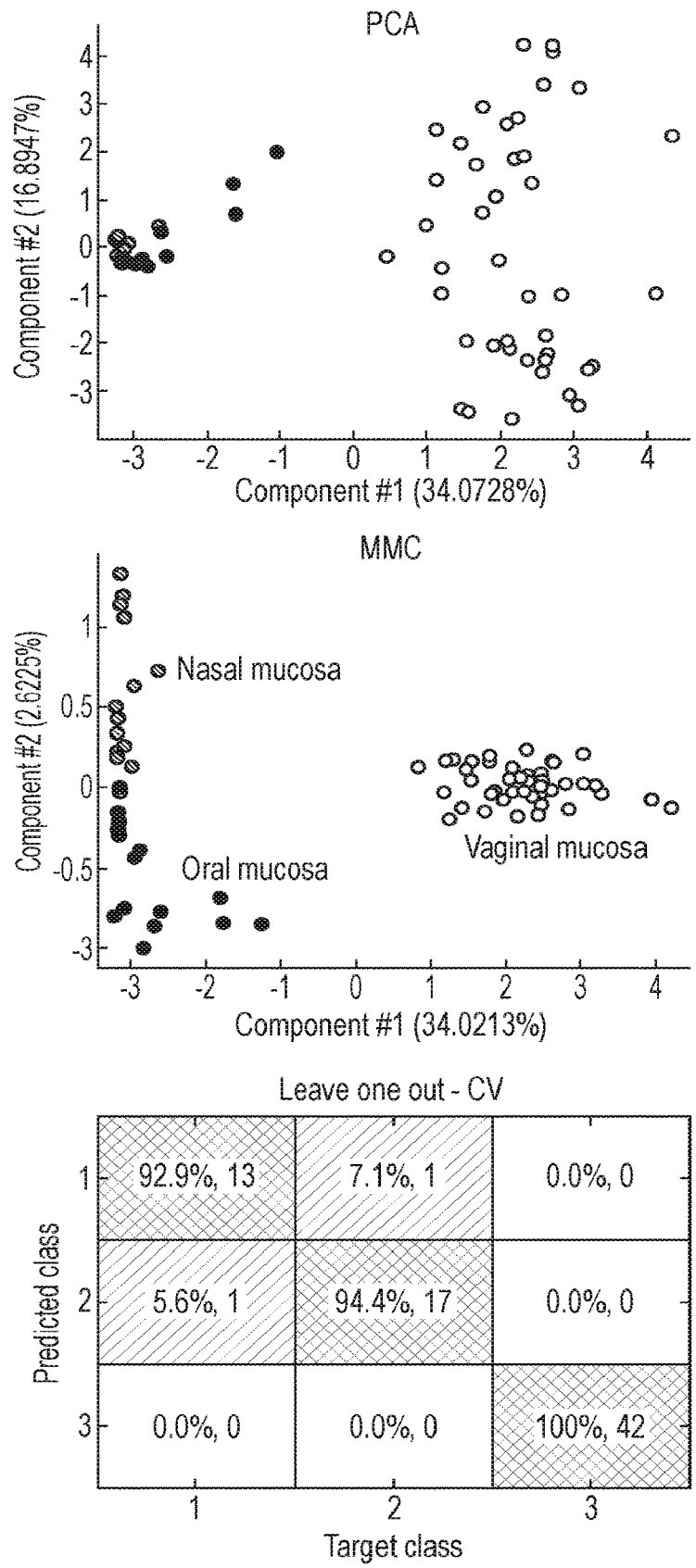

Similarly, FIG. 44 shows Fourier transform mass spectrometry ("FTMS") mass spectral data obtained from vaginal, oral and nasal mucosa on medical cotton swabs in negative ion mode in the mass range of m/z 150-1000. Again, different metabolic signatures were observed in each mucosal membrane model.

In total, 300 to 1000 spectral features found without isotopes and adducts including small human primary metabolites such as cholesterol sulphate, bacterial secondary metabolites including lactate as well as glycerophospholipids were tentatively identified by exact mass, isotope cluster distribution and tandem mass spectrometry experiments in the mucosal membrane.

Figure 45:
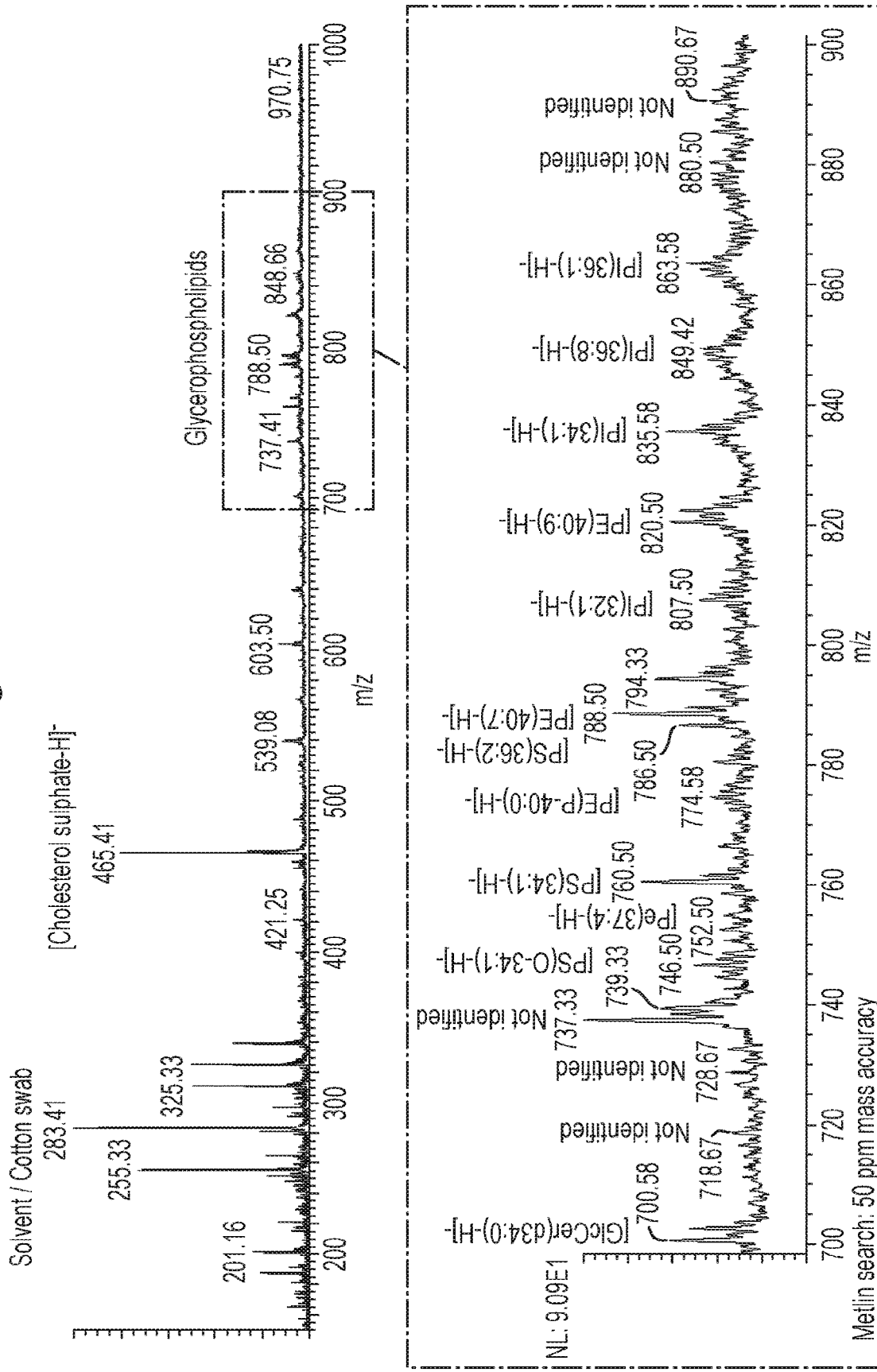
FIG. 45 shows a desorption electrospray ionisation ("DESI") mass spectrum of pregnant vaginal mucosal membrane obtained in negative ion mode from a medical cotton swab, wherein the urogenital mucosa was found to produce cholesterol sulphate [M-H]– having a mass to charge ratio of 465.41 as the most abundant lipid species as well as a different glycerophospholipids species such as glycerophosphoethanolamine (PE) [PE(40:7)-H]– having a mass to charge ratio of 788.50, glycerophosphoserine (PS) [PS(34:1)-H]– having a mass to charge ratio of 760.50 and glycerophosphoinositol (PI) [PI(36:1)-H]– having a mass to charge ratio of 863.58.
Figure 45:
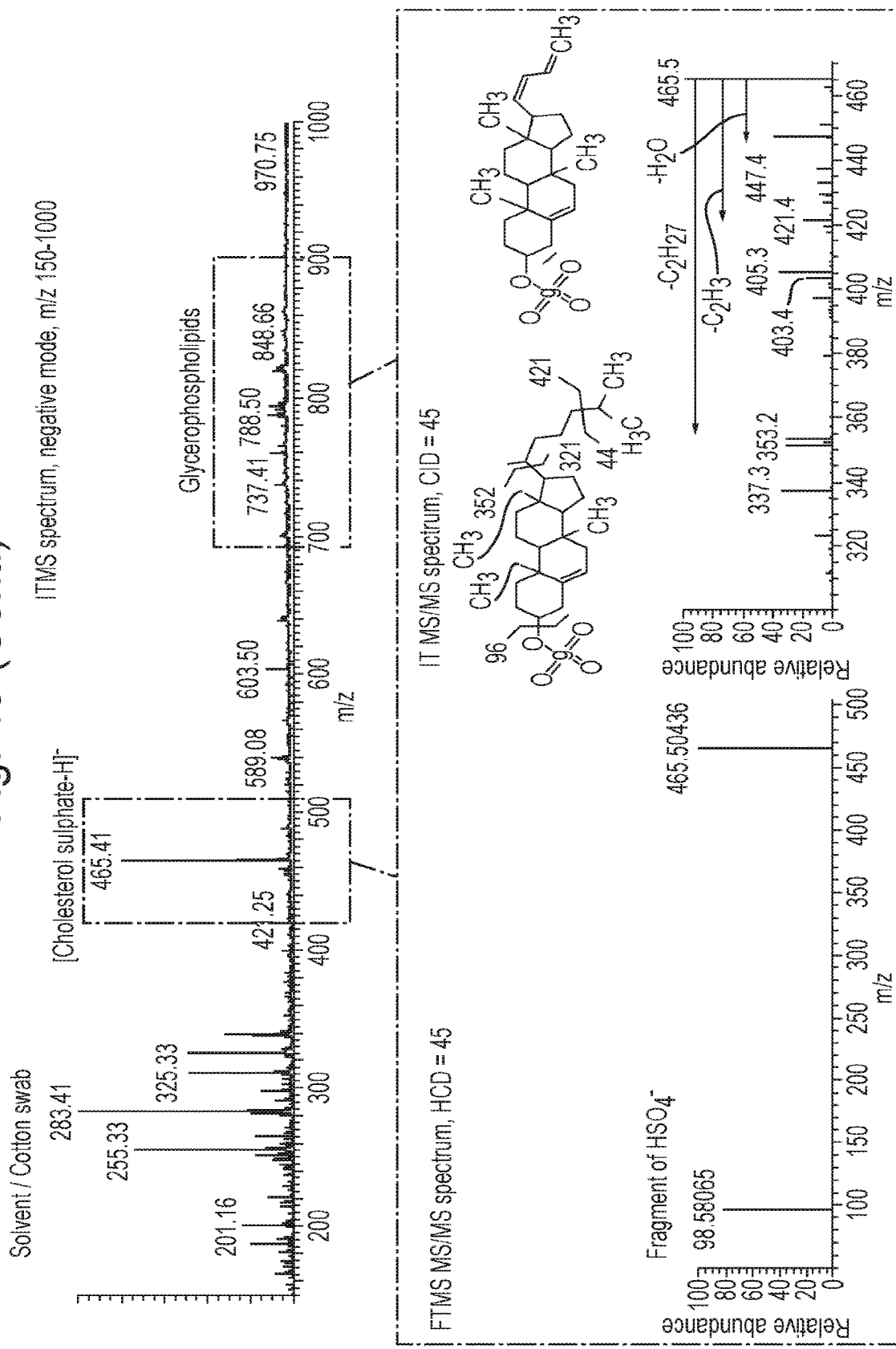

FIG. 45 shows a desorption electrospray ionisation ("DESI") mass spectrum relating to a pregnant vaginal mucosal membrane in more detail which was obtained in negative ion mode using a medical cotton swab. The urogenital mucosa was found to produce cholesterol sulphate [M-H]− at a m/z of 465.41 as the most abundant lipid species as well as a different glycerophosholipids species such as glycerophosphoethanolamine (PE) [PE(40:7)-H]− at a m/z of 788.50, glycerophosphoserine (PS) [PS(34:1)-H]− at a m/z of 760.50 and glycerophosphoinositol (PI) [PI(36:1)-H]− at a m/z of 863.58. As shown in FIG. 45, chemical assignment of the cholesterol sulphate peak was confirmed by tandem mass spectrometry experiments.

The mass spectral data of FIG. 45 were further processed using median normalization, background subtraction, Savitzky-Golay peak detection, peak alignment and log-transformation. Following data processing, multivariate statistical analysis was applied on the data set to characterise distinct mucosa models based on their metabolic profile. Multivariate statistical analysis tools including principal component analysis (PCA) and maximum margin criterion (MMC) were used to analyse the data set.

As shown in FIG. 44, the PCA score plot as well as the MMC score plot reveal a separation of the different mucosal membrane types within the first two components with a prediction accuracy between 92-100% obtained by leave one out cross validation.

It will be appreciated that analysis according to various embodiments results in characteristic profiles for the various sample types that can be clearly distinguished e.g., by using PCA, MMC and/or leave one out cross validation analyses. These results show the use of desorption electrospray ionisation ("DESI") mass spectrometry to characterise human mucosal membrane models, e.g., based on their metabolic signatures excreted by characteristic bacteria, as a fast bacterial identification method, e.g., compared to 16S rRNA sequencing.

Further embodiments are contemplated wherein chemical biomarkers in human mucosal membranes may be measured, which are reliable predictors e.g., in the cases of dysbiotic, inflammatory, cancerous and/or infectious diseases.

Pregnancy involves major changes in circulating hormone (e.g., estrogen and progesterone) levels as well as their secondary metabolites. Moreover, pregnancy is associated with a reduction in vaginal microbial diversity and an increase in stability. As described below, differences in the chemical signature of vaginal mucosa in normal pregnancy and the non-pregnant state can be readily determined using desorption electrospray ionisation ("DESI") mass spectrometry according to various embodiments. A clinical set of pregnant (n=22, in a gestational age between 26 and 40 weeks) and non-pregnant mucosal membrane (n=22) were evaluated in more detail in order to reveal metabolic signature differences caused by a change in the vaginal microbiome during pregnancy. Desorption electrospray ionisation ("DESI") mass spectrometry spectra were acquired from both groups in negative ion mode in the mass range of m/z 150-1000. A number of different metabolites were detected in the vaginal mucosal membrane.

FIG. 46A shows averaged desorption electrospray ionisation ("DESI") mass spectra from pregnant and non-pregnant group acquired in the negative ion mode in the mass range m/z 150-1000. A comparison of the averaged spectra shown in FIG. 46A shows spectral differences between non-pregnant and pregnant mucosa metabolic profiles, especially in the lipid mass range from m/z 550-900.

Further data analysis comprising unsupervised PCA and RMMC analysis revealed clear separation between the two groups with a high (80%) classification accuracy as determined using leave-one-out cross validation.

FIGS. 468 and 46C show the results of multivariate statistical analysis of pregnant (n=22) and non-pregnant (n=22) vaginal mucosal membrane using desorption electrospray ionisation ("DESI") mass spectrometry.

FIG. 46B shows principal component analysis and discriminatory analysis using RMMC and FIG. 46C shows analysis with leave-one-out cross-validation.

Figure 46D:
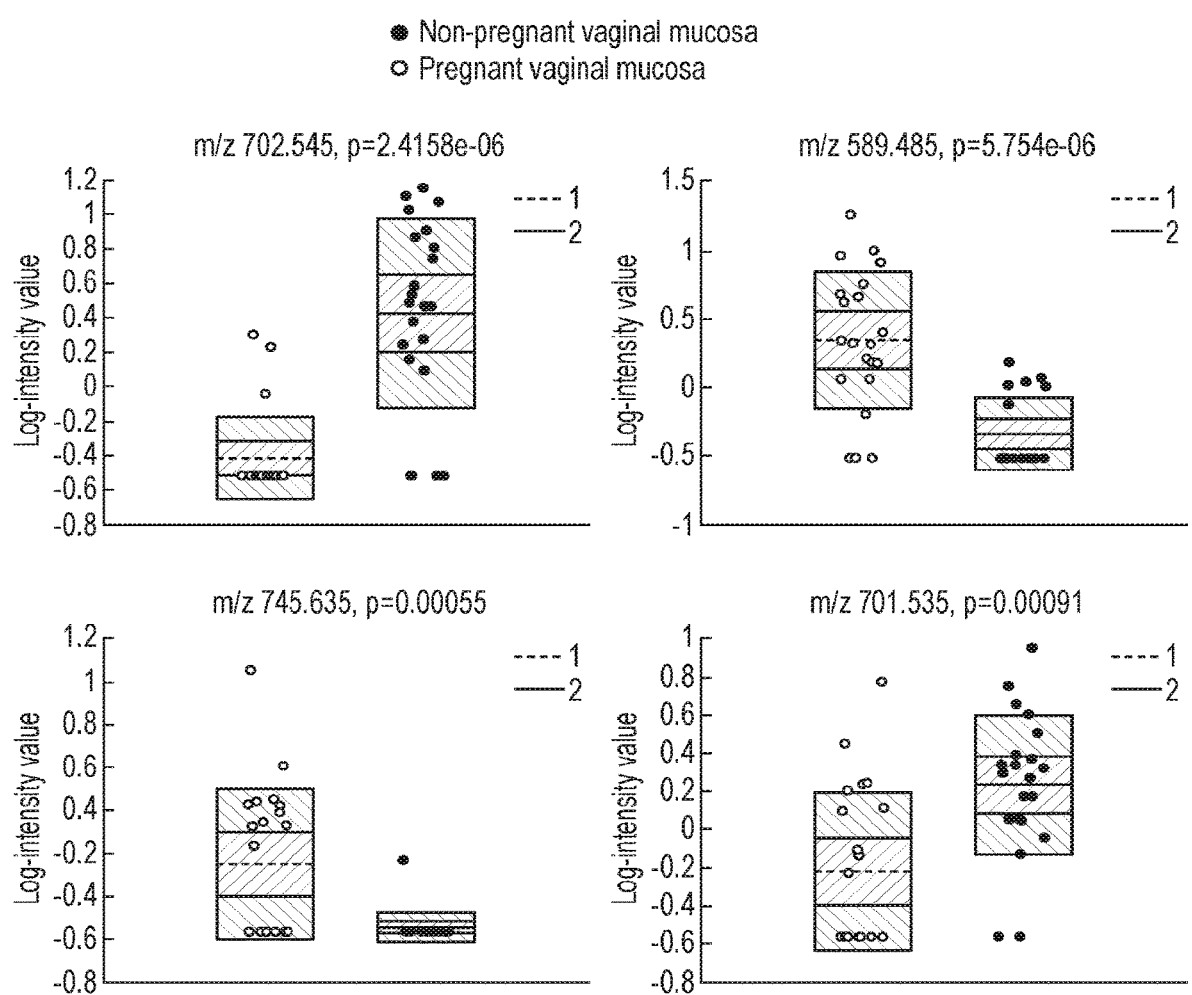
FIG. 46D shows box plots indicating significant differences of the abundance for selected peaks between non-pregnant and pregnant vaginal mucosal membranes mainly in the mass to charge ratio ("m/z") range 550-1000 and FIG. 46E shows the leave-one-out cross-validation.

FIG. 46D shows box plots which indicate significant differences in the abundance of selected lipid peaks between non-pregnant and pregnant vaginal mucosal membrane mainly in the range from m/z 550-1000 obtained by Kruskal-Wallis ANOVA, p≤0.005.

Figure 46E:
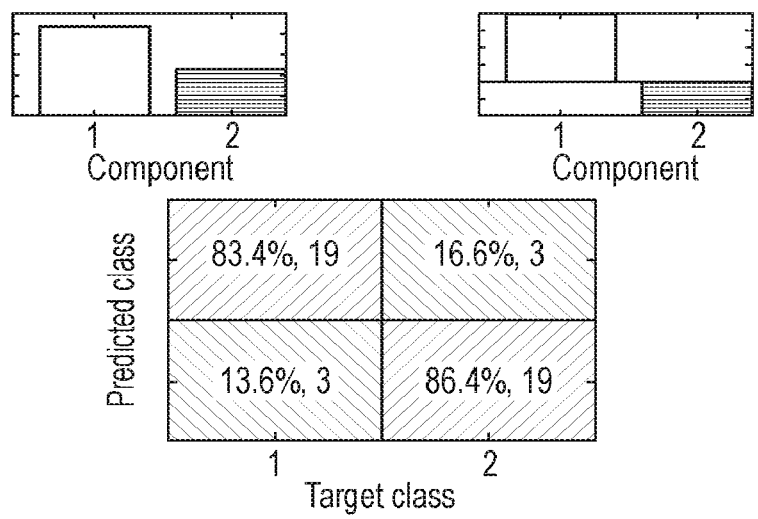

As shown in FIG. 46E, using RMMC both groups separate well in the RMMC space with a high (≥80%) classification accuracy according to distinct metabolic signatures obtained by leave-one-patient-out cross validation.

Clinical studies have shown that vaginal microbial, e.g., bacterial diversity is associated with specific vaginal mucosal metabolites. For example, during healthy pregnancy the vaginal mucosa is colonized mainly by the *Lactobacillus* species. However, importantly, a shift towards vaginal dysbiosis during pregnancy may be a causal trigger for preterm birth.

Using the desorption electrospray ionisation ("DESI") mass spectrometry based technique disclosed herein allows females, e.g., women who have had a spontaneous preterm birth to be evaluated and compared to controls in order to identify biomarkers that can be used to predict preterm delivery. Moreover, the vaginal mucosa of pregnant females may be analysed using the desorption electrospray ionisation ("DESI") mass spectrometry based technique disclosed herein to analyse, e.g., diagnose or predict the risk of, a (spontaneous) preterm birth.

Mass spectral profiling of vaginal mucosa can enable an early identification of females, e.g., women who are at risk of infection during pregnancy based upon microbial, e.g., bacterial diversity in the vaginal mucosa. Furthermore, this enables targeted treatment response strategies.

Various embodiments are contemplated and include: (i) identification of vaginal mucosa metabolite biomarkers that are related to specific microbial, e.g., bacterial communities, optionally as determined using sequencing microbiome analysis; (ii) profiling of vaginal mucosal membrane during healthy pregnancy wherein microbe, e.g., bacteria-specific metabolites and signatures that are excreted during healthy pregnancy may be characterised in detail; and (iii) identification of diagnostic and prognostic metabolic signatures from vaginal mucosa membranes with poor pregnancy outcomes (e.g., preterm delivery).

FIG. 47A shows desorption electrospray ionisation ("DESI") mass spectrometry analysis of a bacteria (*Klebsiella pneumonia*) sample on a swab in accordance with an embodiment. The data illustrated in FIG. 47A shows that bacterial samples can be detected using desorption electrospray ionisation ("DESI") mass spectrometry on swabs, according to various embodiments. FIG. 47B shows for comparison rapid evaporative ionisation mass spectrometry ("REIMS") time of flight ("TOF") mass spectrometry data of a corresponding bacterial sample measured directly from an agar plate. The peaks highlighted by stars were detected with both ionisation techniques.

Desorption electrospray ionisation ("DESI") swab analysis for microorganism detection was further tested on six cultivated species including *Candida albicans, Pseudomonas montelli, Staphylococcus epidermis, Moraxella catarrhalis, Klebsiella pneumonia* and *Lactobacillus* sp. These are all important bacteria and fungi species that were isolated from vaginal mucosal membranes of pregnant patients and which were identified by sequence analysis such as 16S rRNA gene sequencing.

A swab was quickly dipped into a solution of diluted biomass from each species in 10 μL methanol, followed by desorption electrospray ionisation ("DESI") mass spectrometry analysis of the swab surface.

Figure 48A:
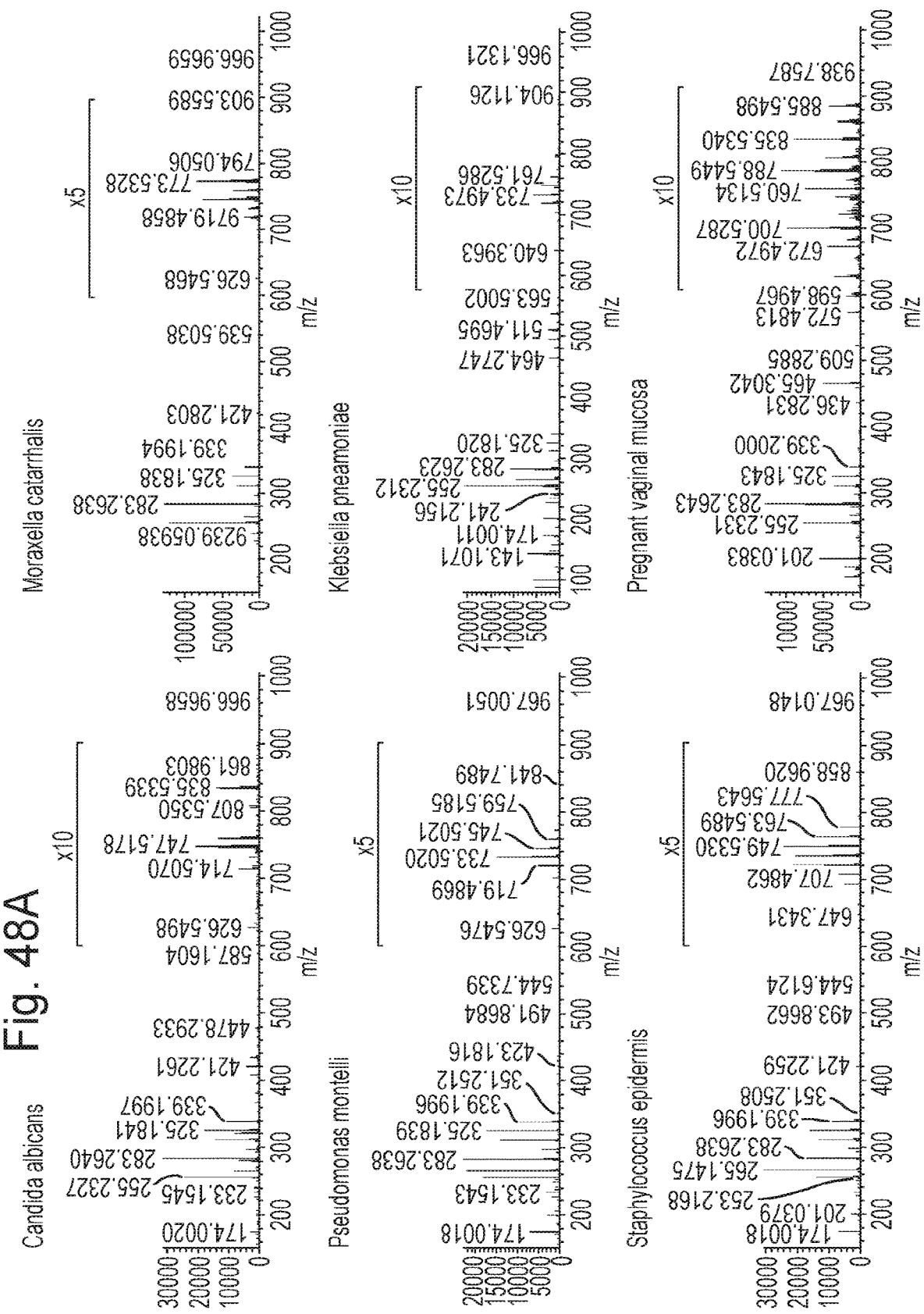
FIG. 48A shows averaged desorption electrospray ionisation ("DESI") mass spectra of diverse analysed microorganism species including *Candida albicans, Pseudomonas montelli, Staphylococcus epidermis, Moraxella catarrhalis, Klebsiella pneumonia* and *Lactobacillus* sp as well as pregnant vaginal mucosa.
Figure 48B:
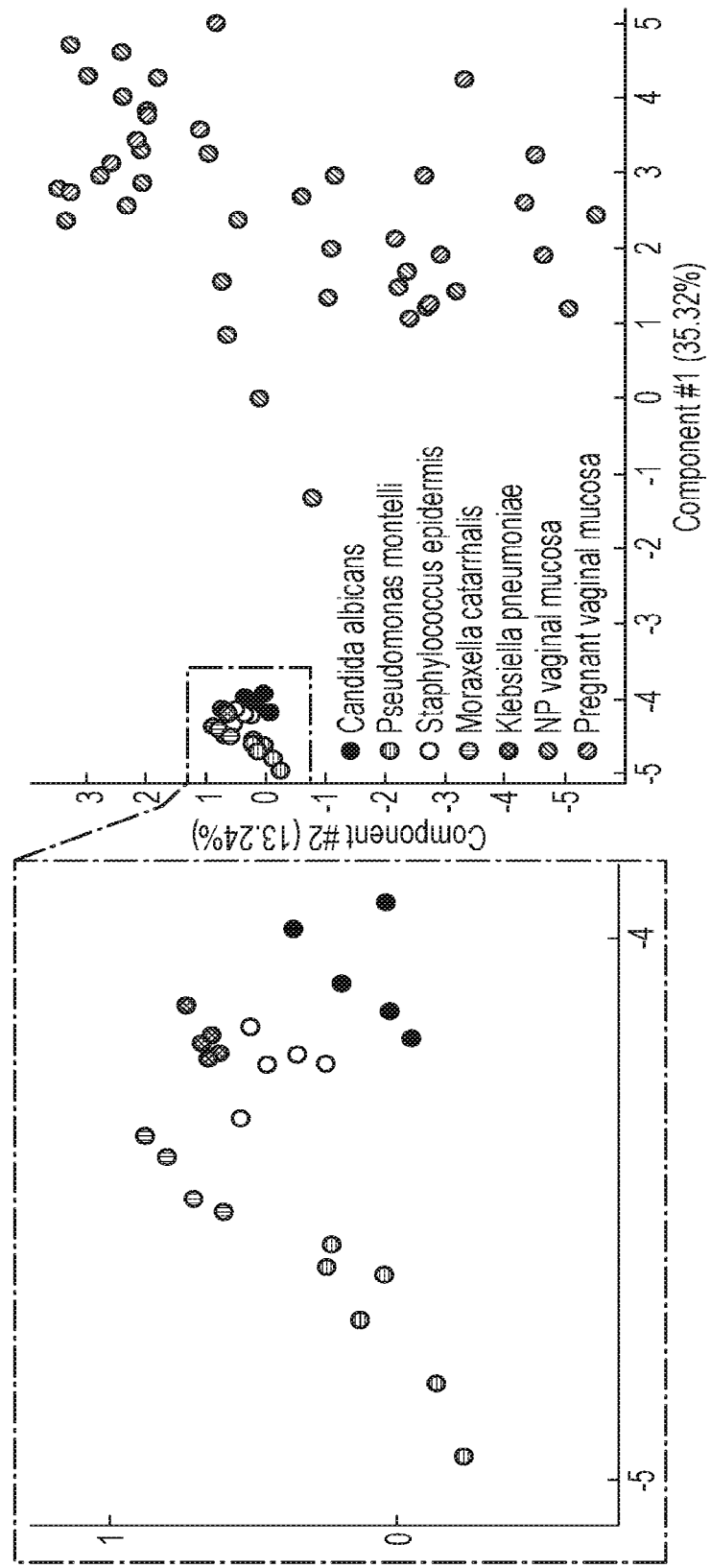
FIG. 48B shows a PCA plot showing a separation between the vaginal mucosa (pregnant and non-pregnant group) from the microorganism species within the first two components and FIG. 48C shows a separation between the different bacteria and fungi species.
Figure 48C:
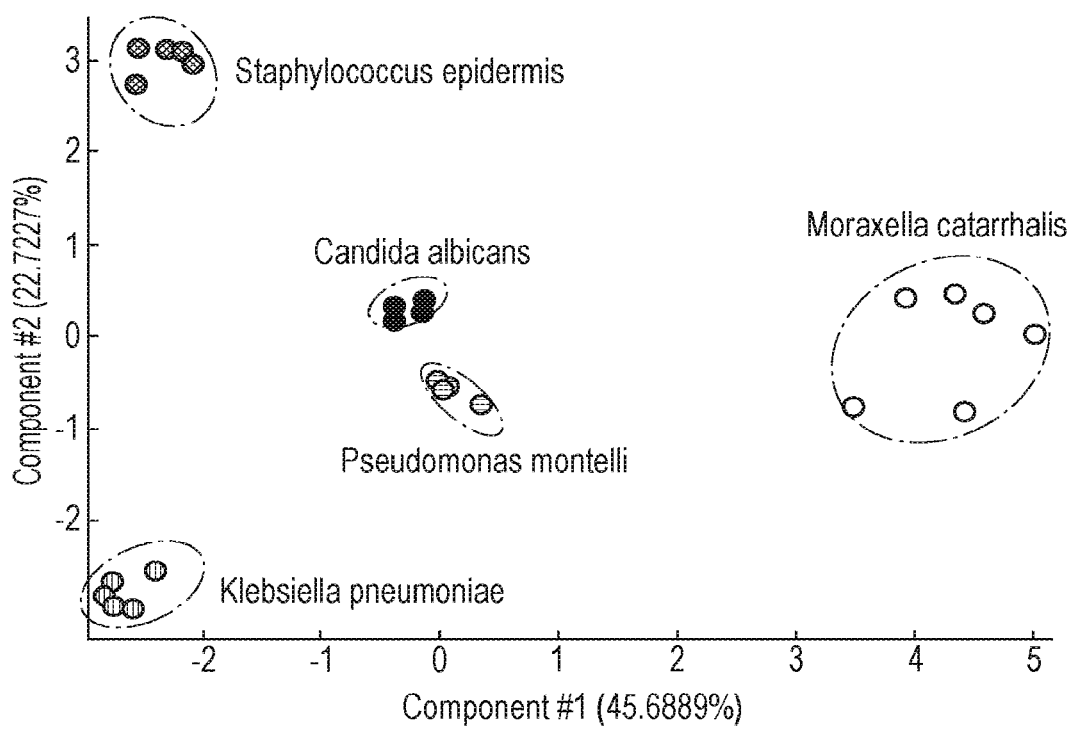

FIGS. 48A-C show microorganism analysis using desorption electrospray ionisation ("DESI") mass spectrometry on swabs.

FIG. 48A shows averaged desorption electrospray ionisation ("DESI") mass spectra of diverse analysed microorganism species including *Candida albicans, Pseudomonas montelli, Staphylococcus epidermis, Moraxella catarrhalis, Klebsiella pneumonia* and *Lactobacillus* sp.

FIGS. 48B and 48C show PCA plots showing a separation between the vaginal mucosa (pregnant and non-pregnant group) and the microorganism species within the first two components. In addition, a separation can be observed between the different bacteria and fungi species.

Unique spectral features were observed in the mass spectra as shown in FIG. 48A resulting in the ability to separate between different microorganism classes as well as from the vaginal mucosa in the PCA score plots (FIGS. 48B and 48C) within the first two components.

This result shows the potential to characterise microbe, e.g., bacteria-specific and host-response metabolite biomarkers and signatures from specific microbial, e.g., bacterial communities from the animal, e.g., human mucosal membrane using desorption electrospray ionisation ("DESI") mass spectrometry on medical swabs.

It will be appreciated that various embodiments provide a new desorption electrospray ionisation ("DESI") mass spectrometry setup for non-invasive and fast analysis of the mucosal metabolome profile from the surface of medical swabs. This arrangement has been successfully shown to be capable of differentiating animal, e.g., human, mucosal membrane models and to enable microorganism identification. The method is capable of readily distinguishing different mucosal sites, biochemical alterations induced by physiological events such as pregnancy, and permits rapid identification of intact bacterial and fungal species.

Since desorption electrospray ionisation ("DESI") mass spectrometry analysis causes minimal sample destruction to the majority of the sample surface material, according to various embodiments the medical swab can optionally be sent directly after desorption electrospray ionisation ("DESI") analysis, e.g., to a microbiological lab, for further assessment such as cultivation, microbe identification/confirmation, and/or next generation sequencing analysis. As the resultant desorption electrospray ionisation mass spectrometry spectral profiles according to various embodiments harbour information descriptive of mucosal biochemistry as well as microbal-host interactions, the method according to various embodiments is applicable to a wide range of clinical applications.

Various embodiments provide a new point of care mucosal screening diagnostic method which uses standard cotton medical swabs as both the sampling probe for mucosal membrane uptake and ionisation probe for desorption electrospray ionisation ("DESI") mass spectrometry analysis. After data acquisition the obtained spectra may be compared with spectra collected in a database to provide a rapid diagnosis to the patient, e.g., within several seconds.

Various embodiments relate to the application of the desorption electrospray ionisation ("DESI") technique for direct metabolomic profiling of specific mucus models (nasal, vaginal, pharyngeal, bronchial, oesophageal) from the surface of standard medical swabs. Various embodiments relate to a rapid point-of-care diagnostic method for diseases, optionally selected from any of the diseases mentioned herein, e.g., inflammatory and pathogen-related diseases such as in immunological disorders, dysbiosis in the microflora (which may, e.g., be indicative of the risk of pre-term delivery during pregnancy), microbial, e.g., bacterial infections, or the detection of cancer or pre-cancerous states. The metabolomic profiling of animal, e.g., human mucosal membrane followed by detailed statistical analysis permits the identification of disease-specific metabolic profiles and/or taxon specific microbial, e.g., bacterial markers in a rapid, robust manner conducive to a point-of-care diagnostic method.

As shown in FIG. 49, according to various embodiments, desorption electrospray ionisation ("DESI") mass spectral analysis 160 of a sample sampled 161 onto a swab may be subjected to statistical analysis 162 in order to provide a diagnosis 163 (or prognosis). The sample may be additionally or alternatively be analysed by rapid evaporative ionisation mass spectrometry ("REIMS") mass spectrometry 164.

Embodiments are contemplated wherein multiple different analysis techniques may be applied to the same swab (or another swab) so as to additionally perform analyses that rely on culturing 165, such as DNA extraction and PCR analysis, e.g., to produce complementary 16S rRNA microbiome data.

As shown in FIG. 49, any one or more or all of the additional analyses may be used to validate the desorption electrospray ionisation ("DESI") based diagnosis 163.

Calibration/Lockmass/Lock Mobility Compounds

Calibration/lockmass/lock mobility compounds may be used in the various techniques described herein for calibrating a mass spectrometer or providing a reference mass to the mass spectrometer.

Figure 50A:
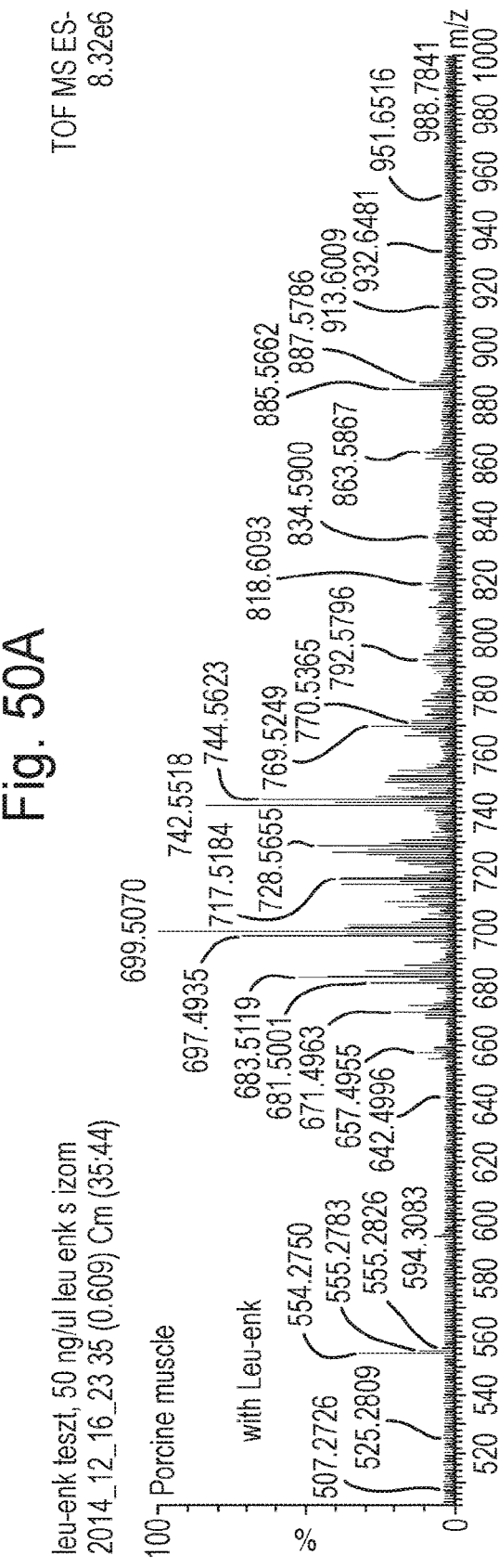
FIG. 50A shows a mass spectrum obtained using a lockmass compound and FIG. 50B shows a mass spectrum obtained without using a lockmass compound.
Figure 50B:
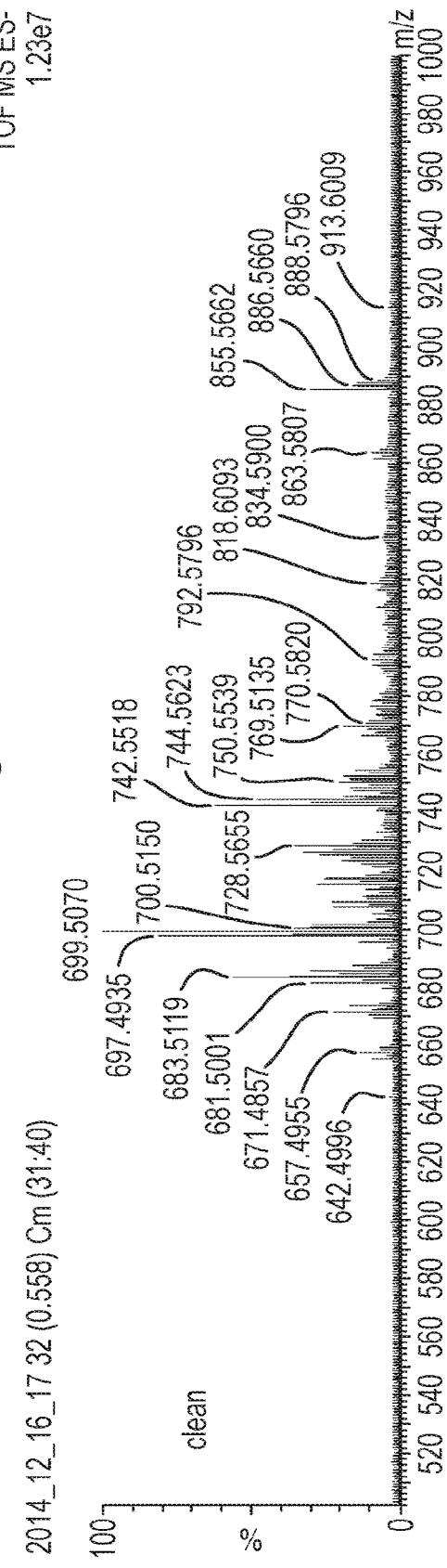

FIG. 50A and FIG. 50B show two mass spectra obtained by analysing a sample of porcine muscle according to an embodiment. The spectrum of FIG. 50A was obtained whilst introducing a lockmass compound (Leu-enk) into a mass spectrometer. The peaks for the lockmass compound can be observed as the first peaks in the mass spectrum. The mass to charge ratios of the lockmass ions are known in advance and can be used to calibrate the mass spectrometer such that the mass to charge ratios of the other ions detected can be determined more accurately. The mass spectrum shown in FIG. 50B was obtained using the same method as the spectrum in FIG. 50A, except that no lockmass compound was used in the analysis. It can be seen that the two mass spectra are substantially identical, except for the detection of the lockmass ions in the mass spectrum of FIG. 50A. It is therefore apparent that the introduction of a lockmass compound in the technique does not affect the mass spectra measured by the mass spectrometer.

Figure 51:
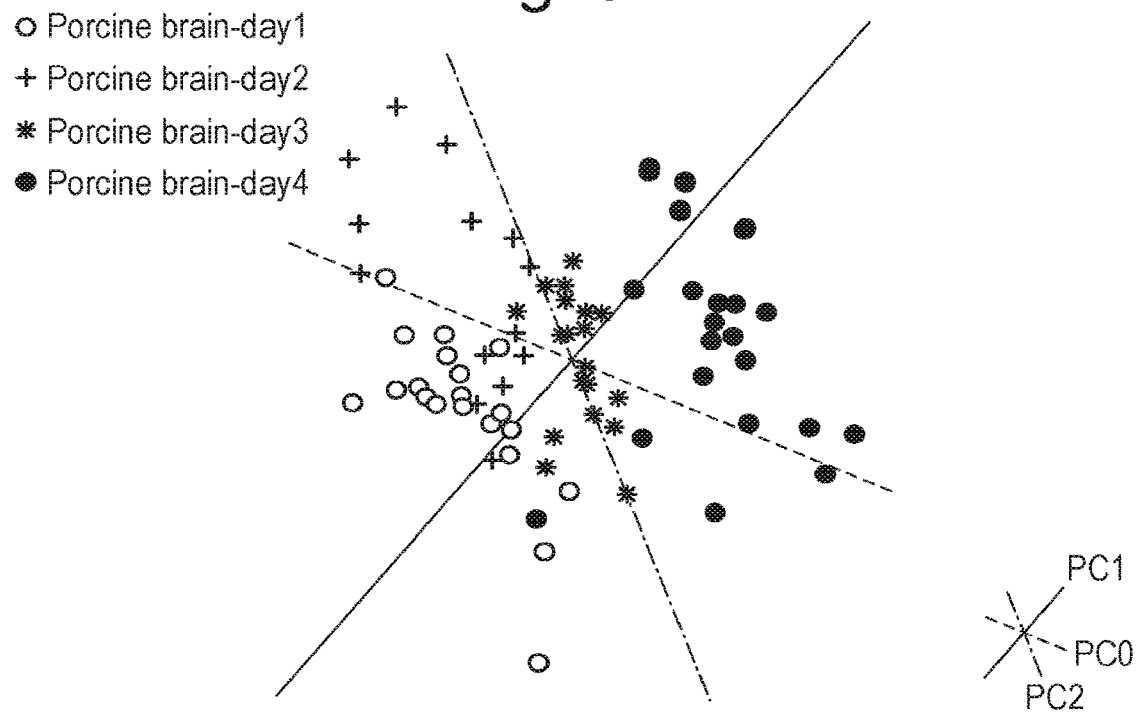
FIG. 51 shows the results of a principle component analysis on data obtained over different days, both with and without the use of lockmass ions.

FIG. 51 shows a plot resulting from a principle component analysis of porcine brain over four days. The data for Day 1 and Day 4 was obtained without the use of a lockmass compound, whereas the data for Day 2 and Day 3 was obtained with the use of a lockmass compound. The analysis was performed over the range of 600-900 mass units and so the lockmass ions are not shown in the plot, as the lockmass ions are outside of this range (see FIG. 50A). The principle component analysis shows that the data obtained with use of the lockmass compound is not separable from the data obtained without use of the lockmass compound, and that the variance due to the data being from different days is significantly greater than any variance due to the inclusion of the lockmass compound.

Figure 52:
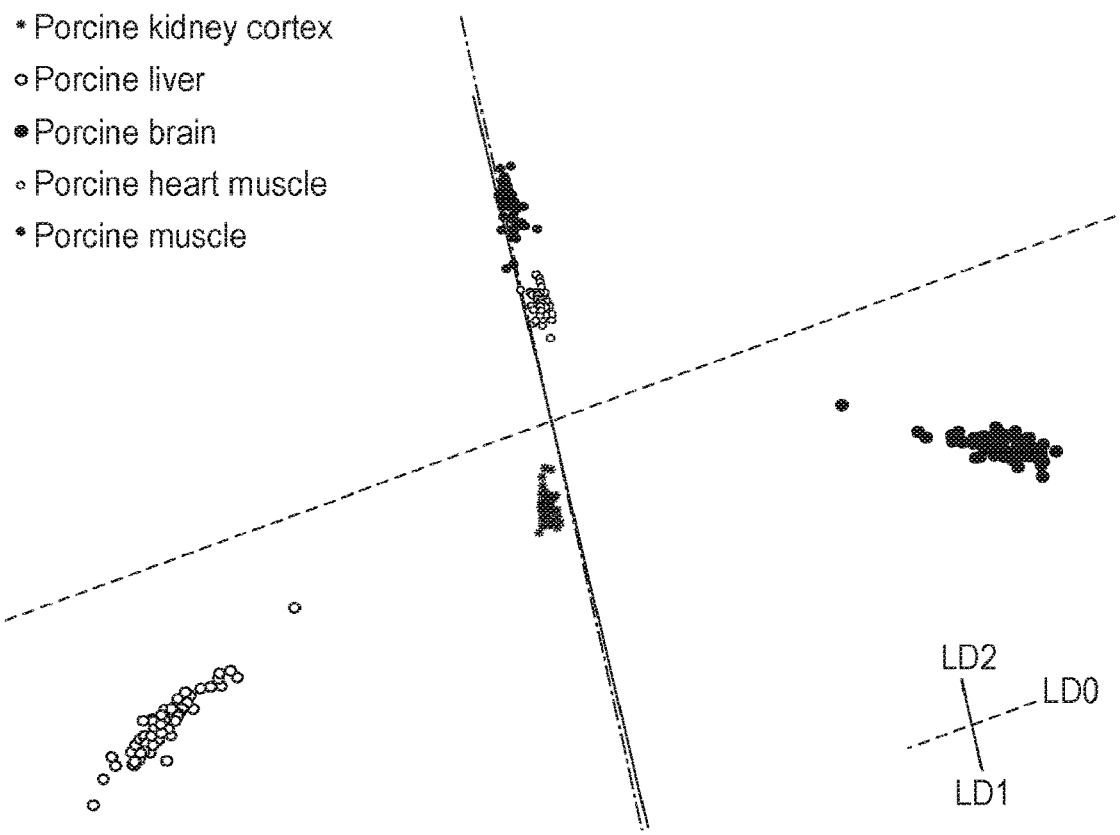
FIG. 52 shows the results of a principle component analysis on data obtained for different tissue types, both with and without the use of lockmass ions.

FIG. 52 shows the results of a principle component analysis for the analysis of data obtained from porcine kidney cortex, porcine liver, porcine brain, porcine heart muscle and other porcine muscle. Some of the data was obtained using a lockmass compound and some of the data was obtained without the use of a lockmass compound. However, the data for each of the types of tissue is well clustered in a particular region of the plot, demonstrating that the use of a lockmass compound does not affect the analysis and tissue classification.

It has been determined that more than one different known lock mass compound may be used without adversely affecting analysis of the sample. Exact lock mass compound(s) may be used and/or external lock mass compound(s) may be used.

Endoscopy

In various embodiments, a rapid evaporative ionisation mass spectrometry compatible endoscope may be used to obtain one or more sample spectra.

Colonoscopic procedures involving electrocautery are associated with a 9× increase in perforation risk compared to a purely diagnostic procedure. It has also been reported that endomucosal resection ("EMR") of ulcerated lesions are at higher risk of perforation. According to an embodiment the rapid evaporative ionisation mass spectrometry endoscopic method may include an alert feature such that any diathermy device is immediately stopped if there is a breach of the submucosal layer during polypectomy or endomucosal resection.

Real time and/or delayed information may be provided to a user of the electrosurgical tool that may comprise mass spectral information and/or tissue classification information. A feedback device and/or an alarm and/or an alert may also may be provided to provide a user of the electrosurgical tool with feedback and/or an alarm and/or an alert that analyte from an undesired target region or area is being analysed by the analyser or that the electrosurgical tool is operating in and/or is located in an undesired target region or area.

Electrical power to the electrosurgical tool may be reduced and/or stopped in the event that analyte from an undesired target region or area is being analysed by the analyser and/or the electrosurgical tool is operating in and/or is located in an undesired target region or area.

Development of the rapid evaporative ionisation mass spectrometry technology for this purpose advantageously helps in decreasing perforation rates and the significant morbidity associated with this complication.

A rapid evaporative ionisation mass spectrometry compatible endoscope and snare has been tested in both ex vivo and in vivo settings.

Analysis of ex vivo human colonic adenocarcinoma (n=43) and healthy colonic mucosa (n=45) acquired from seven patients was conducted using a LTQ Velos® mass spectrometer at the University of Debrecen, Hungary.

Figure 53A:
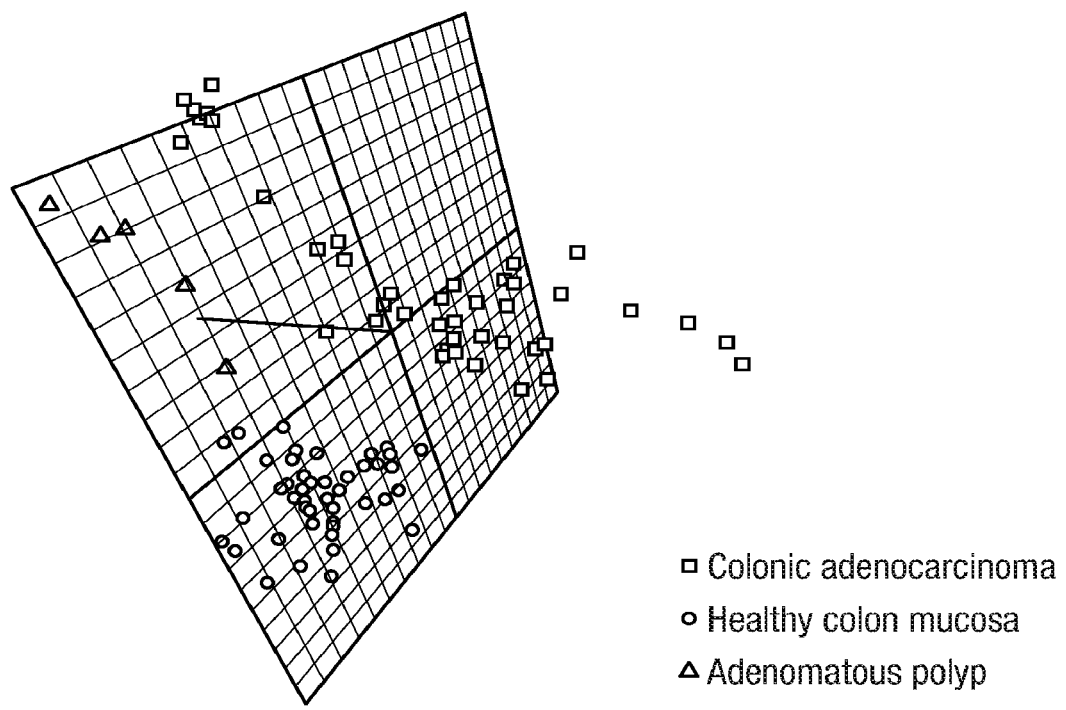
FIG. 53A shows a 3-dimensional PCA plot of human colon adenocarcinoma (n=43) and healthy colon mucosal data (n=45) acquired from seven patients using an LTQ Velos® mass spectrometer wherein the adenomatous polyps (n=5) collected from two patients were sampled ex vivo after their removal and wherein a significant difference can be observed in the PCA space between all three groups and FIG. 53B shows a 3-dimensional PCA plot of healthy gastric mucosa (n=32), gastric submucosa (n=10) and adenocarcinoma of the stomach (n=29) acquired from three patients ex vivo using a Xevo G2-S® Q-Tof mass spectrometer (Waters®) wherein significant differences between submucosa and the other two layers may be used to provide a perforation risk alert system for interventional endoscopy according to an embodiment.
Figure 53B:
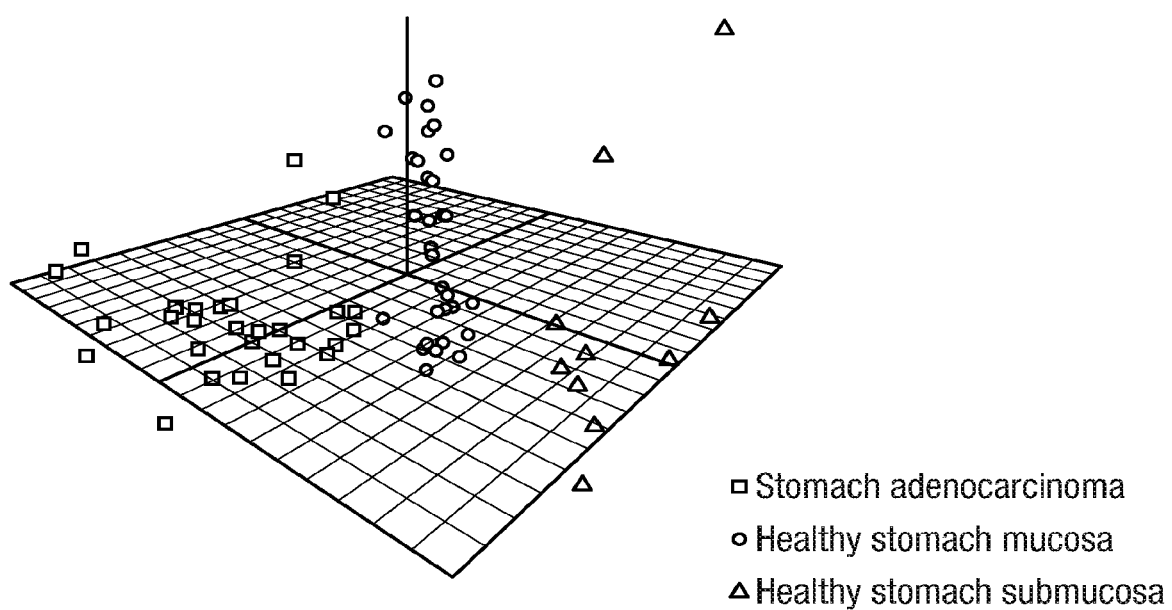

Adenomatous polyps (n=5) from two patients were also sampled ex vivo and the resulting rapid evaporative ionisation mass spectrometry data was analysed using multivariate statistical tools as shown in FIGS. 53A and 53B. In agreement with previously published rapid evaporative ionisation mass spectrometry studies, the spectra acquired from healthy mucosa and adenocarcinoma of both the stomach and colon were discovered to separate well in 3-dimensional PCA space as can be seen from FIGS. 53A and 53B. The sampled adenomatous polyps also demonstrate good separation from both healthy mucosa and malignant tissue from the colon as shown in FIG. 53A.

Following the proof of concept analysis of ex vivo samples, the rapid evaporative ionisation mass spectrometry endoscopic method was also tested in vivo on three consecutive patients referred for colonoscopy. FIG. 54A shows in vivo utilization of a rapid evaporative ionisation mass spectrometry compatible endoscope system according to an embodiment and sampling points taken from three patients undergoing colonoscopy and FIG. 54B shows the sampling points depicted on a 3-dimensional PCA plot wherein the spectra acquired in vivo when the polyps were removed localize in a different part of space whilst all other mucosal spectra are quasi uniformly independent from the sampling location.

Different regions of the colon and rectum were sampled during the colonoscopy procedures. The first and third patients had evidence of colonic polyps and these were confirmed to be benign. The second patient had evidence of a normal colon with no visible polyps. The mucosal layer showed uniform spectral pattern independently from anatomical location. However, colonic polyps showed marked differences from the healthy mucosal layer as shown in FIG. 54B. This is in agreement with the findings of previous ex vivo studies.

The data presented herewith demonstrates the significant advantages in using the rapid evaporative ionisation mass spectrometry technique as a real-time diagnostic tool in endoscopy in accordance with an embodiment.

Rapid evaporative ionisation mass spectrometry technology has also been demonstrated to be able to identify microorganisms. Accordingly, a rapid evaporative ionisation mass spectrometry endoscope may be used to analyser in situ bacteria. This is of particular interest since the composition and metabolic activity of gut microbiota has been associated with the pathogenesis of cancer, diabetes, obesity, hypertension and autism.

The techniques described above are presented in the context of an embodiment utilising rapid evaporative ionisation mass spectrometry. However, it will be appreciated that the techniques and apparatus described herein are not limited to rapid evaporative ionisation mass spectrometry devices and may also be extended to other ambient ion sources. For example, a tool having fenestrations or aspiration ports may be provided as part of a laser surgery probe for aspirating aerosol, smoke or vapour generated using the laser. Further details of known ambient ion sources that may be suitable for use with the techniques and apparatus described herein are presented above.

An endoscopic tool may be used to help distinguish between healthy, potentially cancerous, cancerous, potentially diseased or diseased biological tissue or the margins or bounds of a tumour.

The cancerous biological tissue or the tumour may comprise: (i) grade I, grade II, grade III or grade IV cancerous tissue; (ii) metastatic cancerous tissue; (iii) mixed grade cancerous tissue; or (iv) a sub-grade cancerous tissue.

An endoscopic tool may also be used to identify whether or not a patient is suffering from irritable bowel syndrome ("IBS"), inflammatory bowel disease ("IBD"), Chron's disease or ulcerative colitis ("UC").

Cell Lines

Shotgun Lipidomic Characterization of the NCI-60 Cell Line Panel Using Rapid Evaporative Ionization Mass Spectrometry A methodological background was established for fundamental studies aimed at the exploration of the molecular background of REIMS-based tissue identification. Furthermore, comprehensive shotgun lipidomics data on the NCI-60 cell line collection was also obtained.

According to an embodiment Rapid Evaporative Ionization Mass Spectrometry (REIMS) may be applied to the shotgun lipidomic fingerprinting of cancer cell lines. Experimental data relating to various embodiments and details of the experimental scheme are presented below.

According to an embodiment spectral reproducibility was assessed for a set of three different cell lines.

The NCI-60 cell line panel was then subjected to REIMS analysis and the resulting dataset was investigated for its distinction of different tissue types of origin and the correlation with publicly available gene and protein expression profiles. Significant correlations between REIMS spectral features and gene expression profiles were identified and are exemplified in case of fads2 and ugcg genes.

REIMS is an attractive means to study cell lines as it involves minimal sample preparation and analysis times in the range of several seconds.

Culturing of Cell Lines

Cells were cultured in RPMI 1640 medium, with the exception of HEK and HeLa cells in the Mycoplasma study which were cultured in Gibco DMEM medium (Invitrogen, Carlsbad, Calif., USA). In all cases, media were supplemented with 10% (v/v) fetal bovine serum and with 2 mM glutamine, 100 units/mL penicillin, and 100 mg/mL streptomycin (Invitrogen-Gibco, Carlsbad, Calif., USA). Cells were incubated in 75 cm$^2$ tissue culture flasks at 37° C. under conditions of humidified 37° C., 5% carbon dioxide atmosphere. Cell lines were regularly screened for mycoplasma contamination using the MycoAlert™ Mycoplasma Detection Kit (Lonza Group Ltd, Basel Switzerland). At 80%-90% confluence in 75 cm$^2$ tissue culture flasks, cells were rinsed with Phosphate Buffered Saline (PBS, pH: 7.2) solution, and were detached using 0.1% trypsin/EDTA for 10 minutes. The trypsin was subsequently neutralized with excess culture medium (RPMI). The cell suspension was centrifuged at 250×g for five minutes. After centrifugation the cells were re-suspended and washed two times in 10 mL PBS. A third wash was performed in an Eppendorf tube with only 1 mL PBS. The cell pellets were frozen and stored at −80° C. until further analysis.

Mycoplasma Infection and Treatment

Mycoplasma-infected HEK and HeLa cell lines were treated with 25 µg/mL Plasmocin™ Mycoplasma Elimination Reagent (InvivoGen, San Diego, Calif., USA) for 14 days.

REIMS Analysis

For REIMS analysis, two handheld electrodes in the form of a forceps were used as the sampling probe (irrigated bipolar forceps, obtained from Erbe Elektromedizin, Tubingen, Germany). A Valleylab Force EZc power-controlled electrosurgical unit (Covidien, Dublin, Ireland) was used at 60 W power setting in bipolar mode as radiofrequency alternating current power supply (470 kHz, sinusoidal). An approximately 1.5 m long ⅛ inch outer diameter, 1/16 inch inner diameter PTFE tubing (Fluidflon PTFE tubing; LIQ-UID-scan GmbH Co. KG, Uberlingen, Germany) was employed to connect the embedded fluid transfer line of the bipolar forceps with the inlet capillary of a mass spectrometer. The inherent vacuum system of the mass spectrometer was used for aspiration of the analyte-containing aerosol created during analysis. This setup is shown in FIGS. 55A-55C.

Figure 55A:
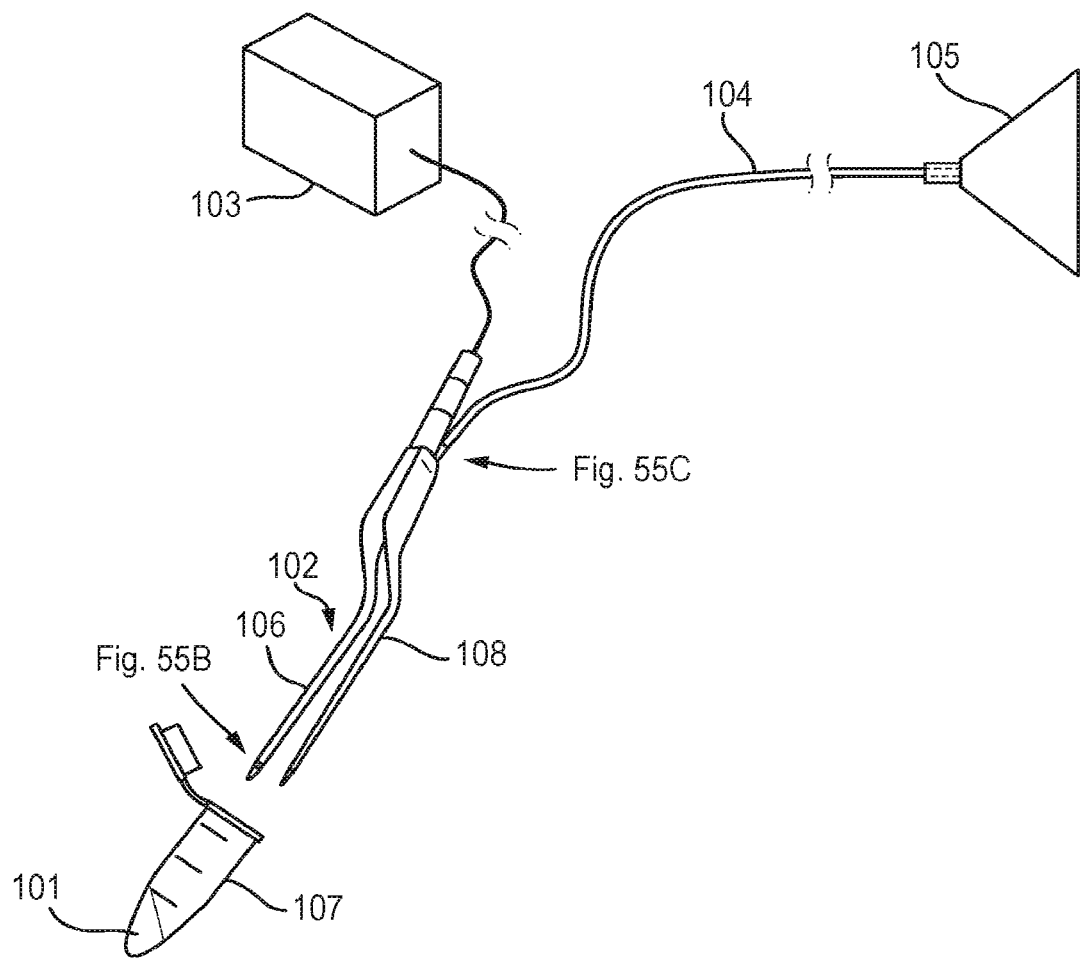
FIGS. 55A-55C show an experimental setup used for REIMS analysis of a cell population.
Figure 55B:
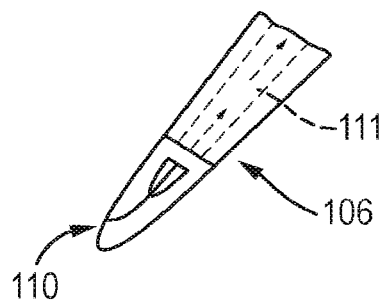
Figure 55C:
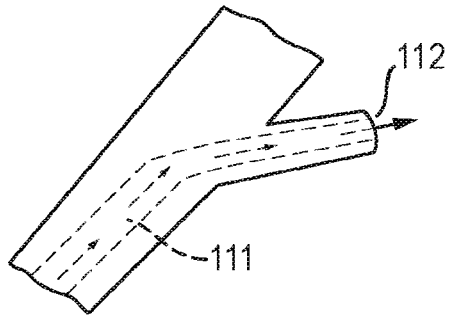
Figure 55D:
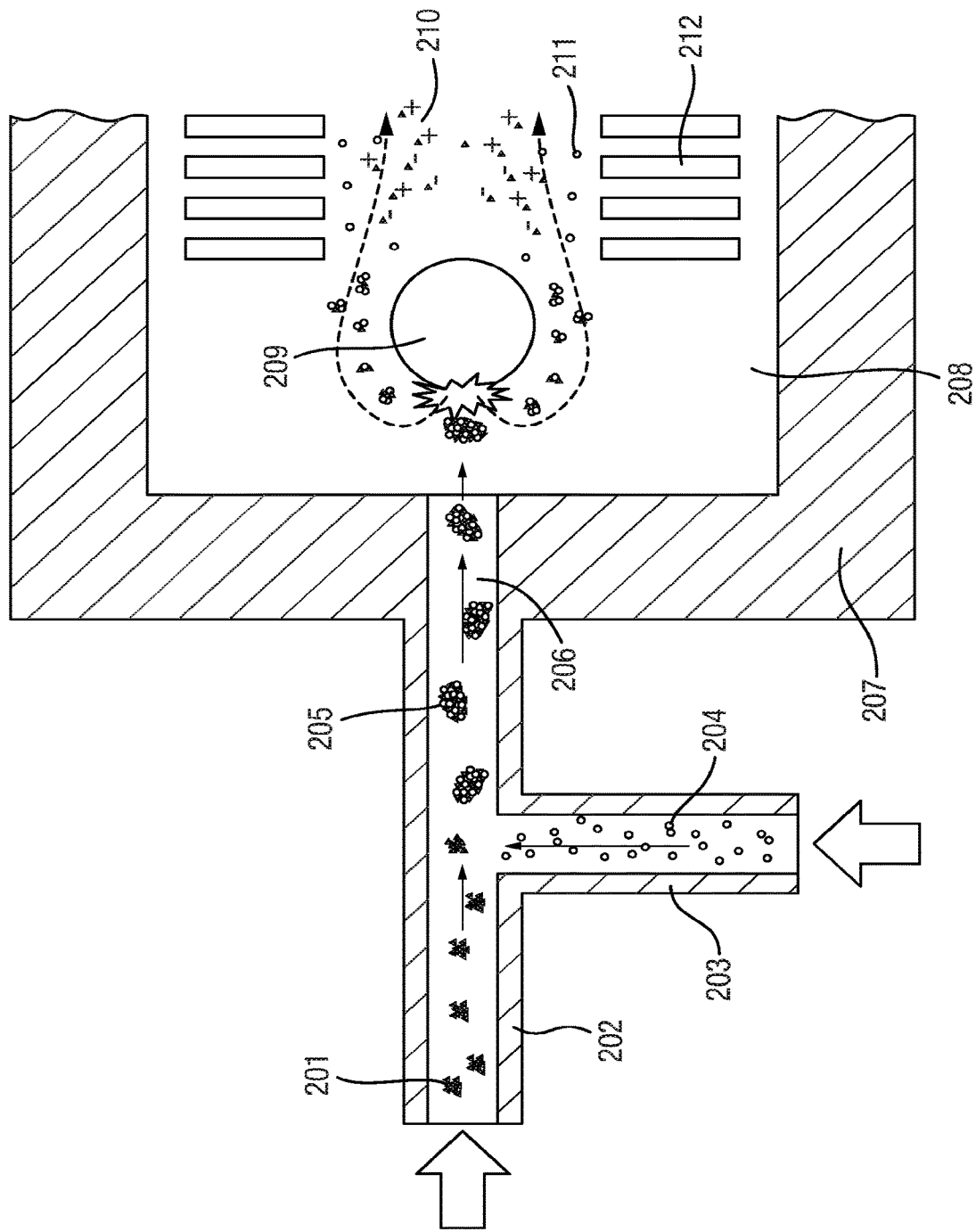
FIG. 55D shows an interface for ionising aerosol from the target cells.
Figure 55E:
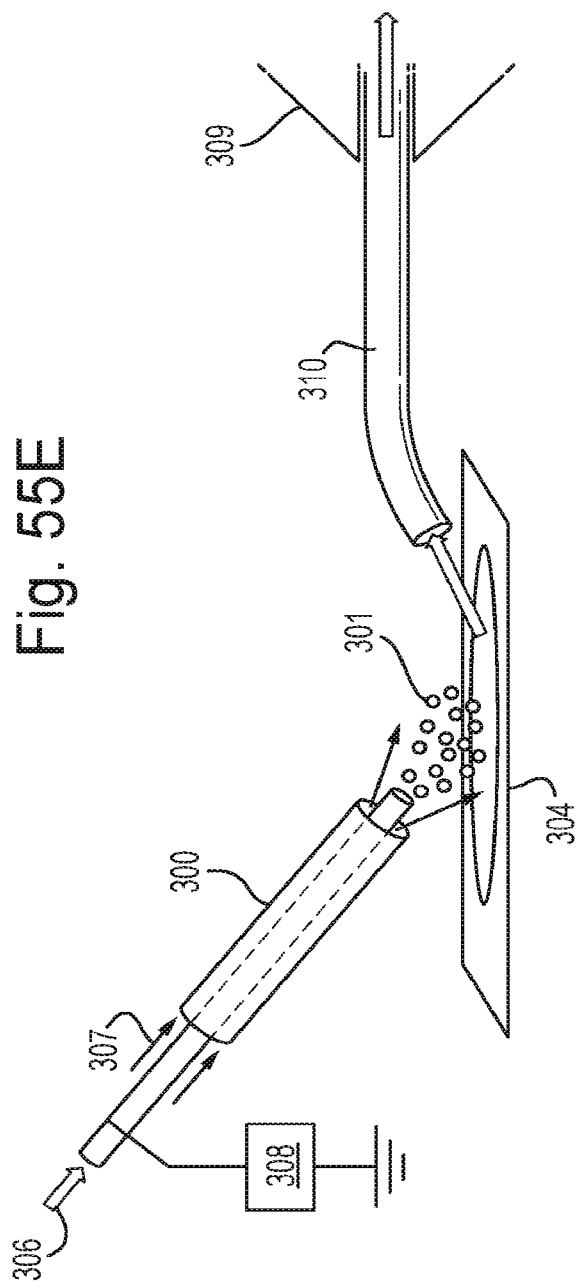
FIG. 55E-55F show a DESI method for analysing target cells.
Figure 55F:
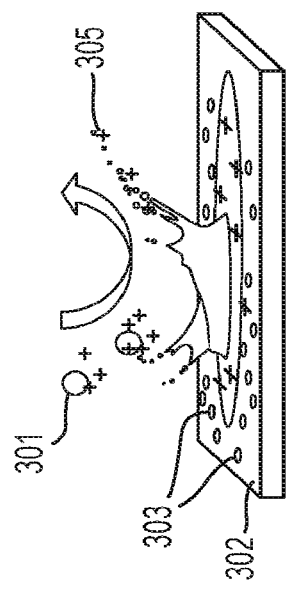

As shown in FIGS. 55A-55C a sample may be provided in the form of a cell pellet 101 in an Eppendorf tube. A sampling probe 102 may be used to sample the cell pellet 101. The sampling probe 102 may be energized by a RF power supply 103. Application of a RF voltage to the sampling probe 102 results in the generation of an aerosol which is transmitted via transfer tubing 104 to the inlet 105 of a mass spectrometer.

The particular instrumental settings which were used are given in the table below:

| Parameter | Setting |
| --- | --- |
| Injection time | 1000 ms |
| Microscans | 1 |
| Ion mode | negative |
| Mass range | 150-2000 |
| Tube Lens Voltage | −160 V |
| Capillary Voltage | −50 V |
| Skimmer Voltage | −24 V |
| Capillary Temperature | 250° C. |
| Automatic Gain Control | On |
| AGC Target | High dynamic range |
| Resolution | 50,000 at m/z 200 |

Mass spectrometric analysis of the cell line biomass was performed directly on a thawed cell pellet without further sample pre-processing steps. 0.1-1.5 mg of cell biomass was taken up between the tips of the forceps and the two electrodes were subsequently brought into close proximity (i.e. by pinching the biomass between the tips of the forceps). The RF power supply was triggered using a foot switch. The cell line biomass is rapidly heated up due to its non-zero impedance and an aerosol containing charged molecular species of the analytes is produced and transferred directly into the mass spectrometer. Multiple technical replicates were recorded for each cell line.

Data Analysis

Raw mass spectrometric files were converted into mzML format using the MSConvert tool (part of the ProteoWizard 3.0.4043 suite) and subsequently imported as imzML format into MATLAB (Mathworks, Natick, Mass.; http://www.mathworks.co.uk/) for data pre-processing. All REIMS spectra were linearly interpolated to a common sampling interval of 0.01 Da. Recursive segment wise peak alignment was then used to remove small mass shifts in peak positions across spectral profiles. The aligned data were subjected to total ion count (TIC) data normalization and log-based transformation. Pattern recognition analysis and visualization were performed either in Matlab or in RStudio (Boston, Mass., USA, see also www.r-project.com). The mass range of m/z 150-1000 was used for data analysis. For self-identity experiments, the data set was filtered to keep a reduced set of m/z values: a m/z value was kept, if the difference between the available samples were significantly different at alpha=0.01 threshold level based on the Kruskal-Wallis test.

Ionic species in the mass spectra were identified based on exact mass measurements (mass deviation 3 ppm) and MS/MS fragmentation patterns.

Spectral Content

Spectral content comprises fatty acids and all glycerophospholipid species undergoing ionization in negative ion mode, including phosphatidic acids (PAs), phosphatidylethanolamines (PEs), phosphatidylglycerols (PGs), phosphatidylserines (PSs), phosphatidylinositols (PIs) in agreement with earlier REIMS studies performed on bulk tissue samples. All observed ions displayed a single negative charge, the vast majority by forming the quasi-molecular [M-H]− ion. In addition, [M-NH3-H]− was observed in case of PEs. Various ceramide and glycosylated ceramide species were detected as [M+Cl]− ions.

Reproducibility Dataset

For each cross-validation run, a principal component analysis (PCA) transformation of the training data set with pre-determined number of principal components (PCs) was calculated in R and a prediction score was calculated for each test sample using the 3 nearest neighbor (3-NN) method. The training data in the 'reproducibility set' was selected as follows: for each measurement day, a cell line with defined passage (p) and flask number (A/B) was kept as part of the training data (e.g., HeLa p4 A) if samples were available from at least two different biological replicates (i.e. A1-3). Such sets from each of the three cell lines were combined randomly to produce balanced training data where each cell line is represented by similar number of samples. All of the remaining samples constituted the test set.

Figure 56:
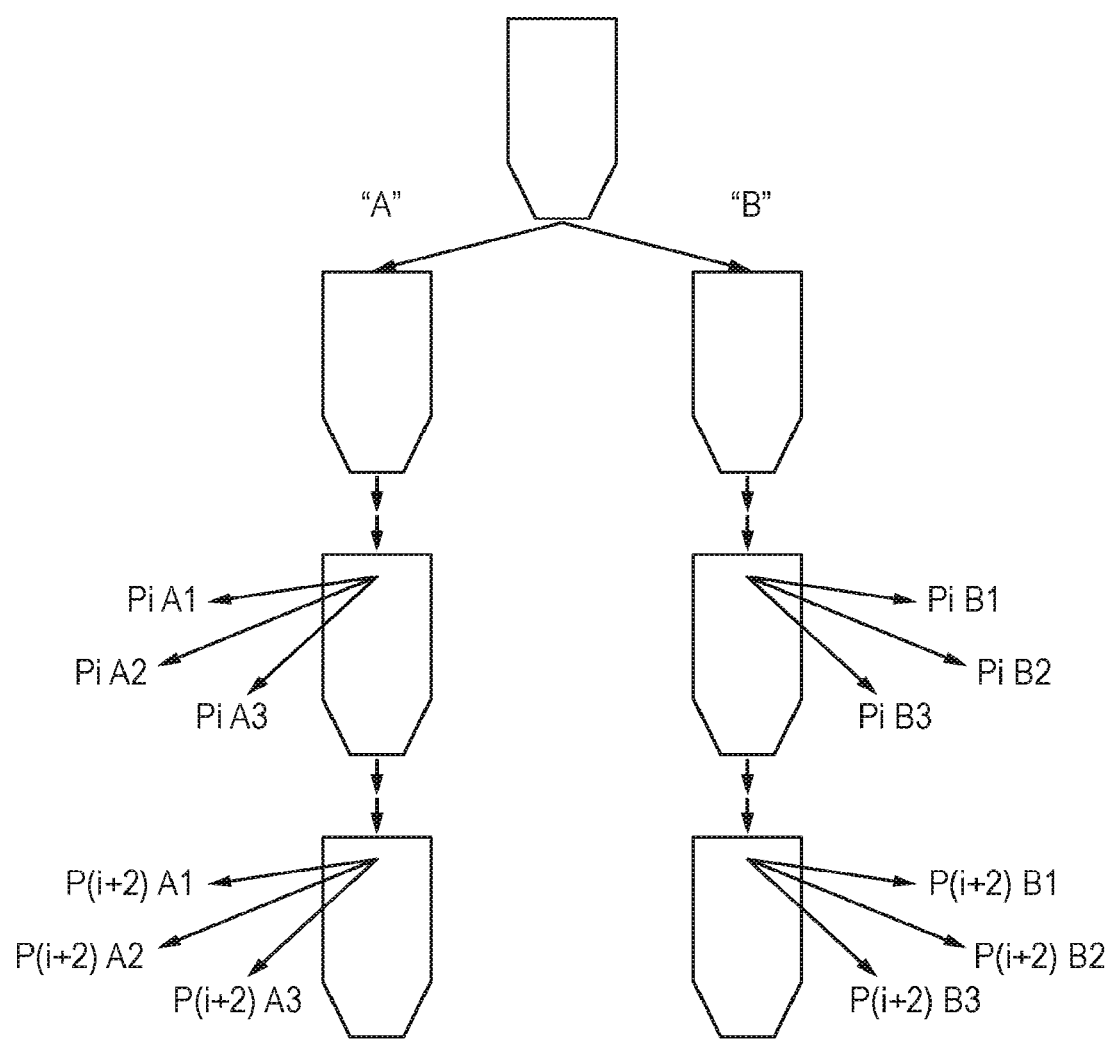
FIG. 56 shows the experimental scheme used for assessment of REIMS spectral reproducibility.

FIG. 56 shows the experimental scheme used for assessment of REIMS spectral reproducibility. In particular, flasks A and B are shown.

All of the remaining samples constituted the test set. The resulting cross-validation results can be seen in the table below.

The table below shows cross-validation results for SNB-19, HeLa and MES-SA cell lines based on PCA model comprising the first 4 principal components and using 3 nearest neighbour as classifier:

| | predicted | | | |
| --- | --- | --- | --- | --- |
| kept in test set | HeLa | MES-SA | SNB-19 | correct |
| HeLa p6 A day 2 (9 samples) | 63 | — | — | 100% |
| MES-SA p8 A day 1 (9 samples) | 2 | 57 | — | 97% |
| SNB-19 p4 A day 1 (9 samples) | — | — | 54 | 100% |
| HeLa p4 B day 2 (9 samples) | 62 | 1 | — | 98% |
| MES-SA p10 B day 1 (9 samples) | 17 | 42 | — | 71% |
| SNB-19 p4 B day 2 (7 samples) | — | — | 56 | 100% |
| HeLa p4 A day 1 (9 samples) | 49 | 14 | — | 78% |
| MES-SA p10 A day 3 (12 samples) | — | 56 | — | 100% |
| SNB-19 p6 A day 2 (7 samples) | — | 1 | 55 | 98% |

Cross-validations were performed based on a PCA model created of a training set as described elsewhere herein. Following this procedure, three different training sets were generated and subjected to PCA analysis. These training sets comprised between 25-28 sampling points, which represent ≤15% of the overall sample points (n=203). The composition of the training sets and corresponding cross-validation results are shown in the Table above. Consistently, the cross-validation results show ≥98% correct classification for SNB-19 samples, with only a single misclassification observed in case of the third training set, which was tentatively associated with the unequal sample size for MES-SA (n=12) and SNB-19 (n=7). Unequal sample size is known to lead to a bias in PCA calculations towards the larger sample subset, which explains the misclassification of SNB-19 cells as MES-SA.

Spectral Reproducibility in NCI-60 Cell Line Panel

The table below shows the different cell lines present in the NCI-60 cell line panel and respective number of replicates which were used.

| Tissue of origin | Cell line | No of biological replicates | No of technical replicates |
|---|---|---|---|
| Breast | BT549 | 1 | 4 |
| | HS-578-T | 1 | 6 |
| | MCF-7 | 1 | 12 |
| | MDA-MB-231 | 2 | 10 (6 + 4) |
| | MDA-MB-468 | 1 | |
| | TD-47-D | 1 | 11 |
| CNS | SF268 | 2 | 18 (8 + 10) |
| | SF295 | 2 | 18 (8 + 10) |
| | SF539 | 1 | 8 |
| | SNB-19 | 1 (3) | 10 (10 + ? + ?) |
| | SNB-75 | not measured | |
| | U251 | 1 | 9 |
| Colon | COLO-205 | 1 | 10 |
| | HCC2998 | 1 | 7 |
| | HCT-15 | 1 | 7 |
| | HCT-116 | 1 | 11 |
| | HT-29 | 2 | 9 (5 + 4) |
| | KM-12 | 1 | 7 |
| | SW-620 | 1 | 12 |
| Leukaemia | CCRF-CEM | 1 | 10 |
| | HL-60 | 1 | 7 |
| | K562 | 1 (2) | 9 |
| | MOLT-4 | 1 | 6 |
| | RPMI-8226 | 1 | 5 |
| | SR | 1 | 8 |
| Melanoma | LOX-IMVI | 1 | 9 |
| | M14 | 2 | 15 (7 + 8) |
| | Malme-3M | 1 | 6 |
| | MDA-MB-435 | 2 | 14 (4 + 10) |
| | SK-MEL-2 | 1 | 10 |
| | SK-MEL-5 | 1 | 8 |
| | SK-MEL-28 | 1 | 9 |
| | UACC62 | 1 | 6 |
| | UACC257 | 1 | 9 |
| Non small cell lung cancer | A549 | 1 | 10 |
| | EKVX | 1 | 9 |
| | HOP-62 | 1 | 6 |
| | HOP-92 | 1 | 13 |
| | NCI-H23 | 1 | 11 |
| | NCI-H226 | 1 | 9 |
| | NCI-H322M | 1 | 7 |
| | NCI-H460 | 1 | 9 |
| | NCI-H522 | 1 | 9 |
| Ovarian | IGROV-1 | 2 | 8 (5 + 3) |
| | NCI-ADR-RES | 1 | 9 |
| | OVCAR-3 | 1 | 6 |
| | OVCAR-4 | 1 | 7 |
| | OVCAR-5 | 1 | 10 |
| | OVCAR-8 | 1 | 8 |
| | SK-OV-3 | 1 | 9 |
| Prostate | DU-145 | 1 | 9 |
| | PC-3 | 1 | 11 |
| Renal | 786-0 | 1 | 9 |
| | A498 | 1 | 11 |
| | ACHN | 1 | 10 |
| | CAKI-1 | 1 | 6 |
| | RXF393 | 1 | 6 |
| | SN-12-C | 1 | 8 |
| | TK-10 | 1 | 9 |
| | UO31 | 1 | 7 |

Biological replicates were analysed in of six out of the 58 cell lines used in this study. To assess the specificity of the REIMS spectral patterns toward individual cell lines, cross-validations were performed by omitting one replicate from the PCA model building process, and then projecting it into the resulting data space and classifying each data point based on its three nearest neighbour.

Figure 57:
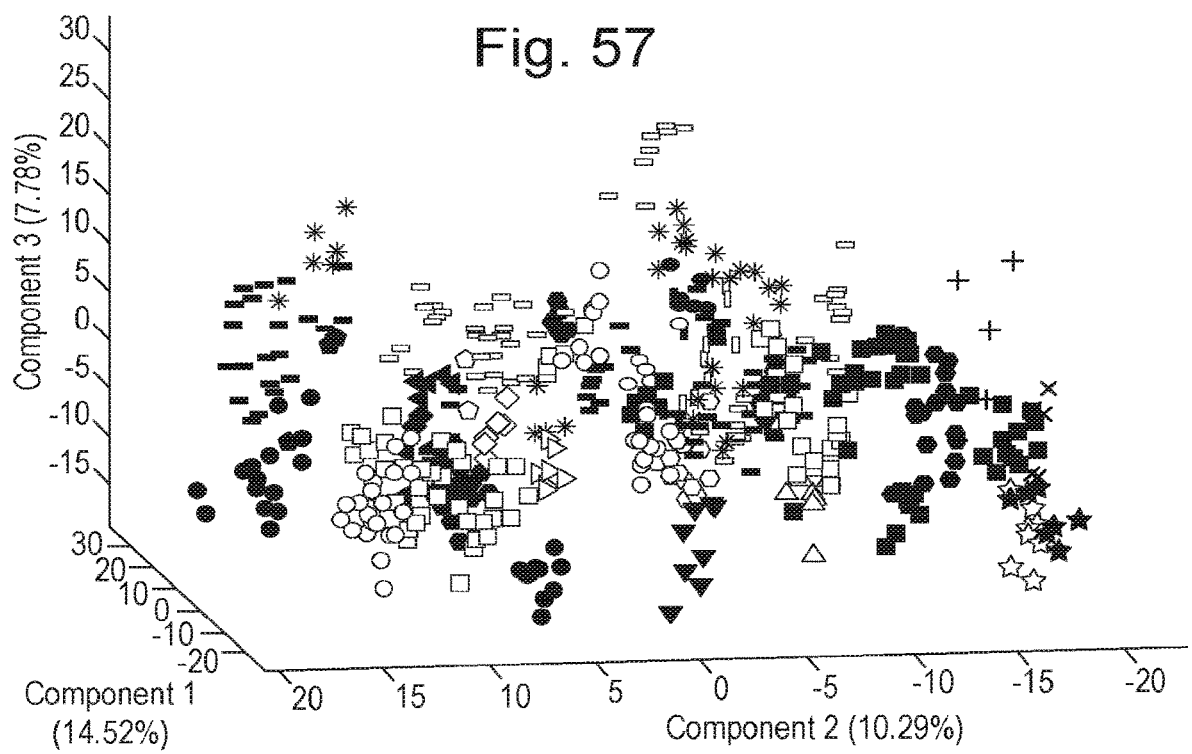
FIG. 57 shows a PCA plot of NCI-60 cell line panel, m/z 150-1000, with replicates highlighted.

FIG. 57 shows a PCA plot of NCI-60 cell line panel, m/z 150-1000, with replicated highlighted.

The table below shows the results of cross-validation results of the PCA model shown in FIG. 57. Cross-validations were performed as described above leaving a whole biological replicate out at a time. Good identification results (100%) were obtained for leukemia K562, melanoma MDA-MB-231 and MDA-MB-435 cell lines. One replicate of CNS SF295 was classified correctly. However, a second one is only correctly assigned in case of 50% of the data points. The misclassified samples were all wrongly assigned as SNB-19, another CNS cell line. The same is true for IGROV-1, of which the misclassified replicate falls into OVCAR-8, another ovarian cancer cell line. In the case of small sample number, correct classification becomes more difficult, but still the cell identity of a large proportion of HT-29 samples were correctly predicted.

Overall, the good prediction results further supports that REIMS spectral profiles can be used characterise and classify human cell line samples.

Cross-Validation Results for Replicates in NCI-60 Dataset

In the case of some cell lines, two biological replicates have been measured. For these cell lines both replicate was retained one by one and supplemented with samples from all other cell lines as the training set. The other biological replicate constituted the test set.

The table below shows cross-validation results for replicated NCI-60 cell lines based on PCA model of the entire NCI-60 dataset comprising the first 10 principal components. Three nearest neighbour as classifier:

| kept in test set | predicted | correct |
|---|---|---|
| K562 P5 (9 samples) | LE:K562 (9) | 100% |
| K562 P11 (9 samples) | LE:K562 (9) | 100% |
| MDA-MB-231 (6 samples) | BR:MDAMB231 (4) | 100% |
| MDA-MB-231 P10 (4 samples) | BR:MDAMB231 (6) | 100% |
| SF295 1 (10 samples) | CNS:SF295 (4), CNS:SNB19 (4) | 50% |
| SF295 2 (8 samples) | CNS:SF295 (10) | 100% |
| M14 (7 samples) | ME:M14 (5), ME:MDAMB435 (1), ME:SKMEL28 (2) | 63% |

-continued

| kept in test set | predicted | correct |
|---|---|---|
| M14 (2) (8 samples) | ME:M14 (1), ME:MDAMB435 (6) | 14% |
| MDA-MB-435 (10 samples) | ME:MDAMB435 (4) | 100% |
| MDA-MB-435 P6 (4 samples) | ME:MDAMB435 (10) | 100% |
| HT-29 (5 samples) | CO:HT29 (3), OV:OVCAR5 (1) | 75% |
| HT-29 P3 (4 samples) | CO:HT29 (4) CO:COLO205 (1) | 80% |
| IGROV-1 (5 samples) | OV:IGROV1 (3) | 100% |
| IGROV-1 P9 (3 samples) | OV:OVCAR8 (4) RE:UO31 (1) | 0% |

Correlation with Gene Expression Data

Gene expression for the NCI-60 cell line panel was obtained from the CellMiner online data query tool. For each available gene and filtered m/z value the gene expression and the binned signal intensity across the cell lines was correlated using Pearson's correlation coefficient with 1000 iterations. The bootstrapped correlation value was defined as the lower 95% confidence interval level of the 1000 iterations, resulting in a total of 26065 (genes)×17878 (filtered m/z)=465990070 values.

Bootstrapped Correlation Analysis

For each available gene and binned m/z value with sufficient variance a bootstrapped correlation coefficient was calculated, resulting in a total of 26065×5452=142106380 correlation values. In the case of each gene—m/z value pair, the gene expression and the binned signal intensity across the 58 cell lines was correlated using Pearson's correlation coefficient with 1000 iterations. The bootstrapped correlation value was defined as the lower 95% confidence interval level of the 1000 iterations.

Comparison of Cell Line and Bulk Cancer Tissue Spectra

Figure 58:
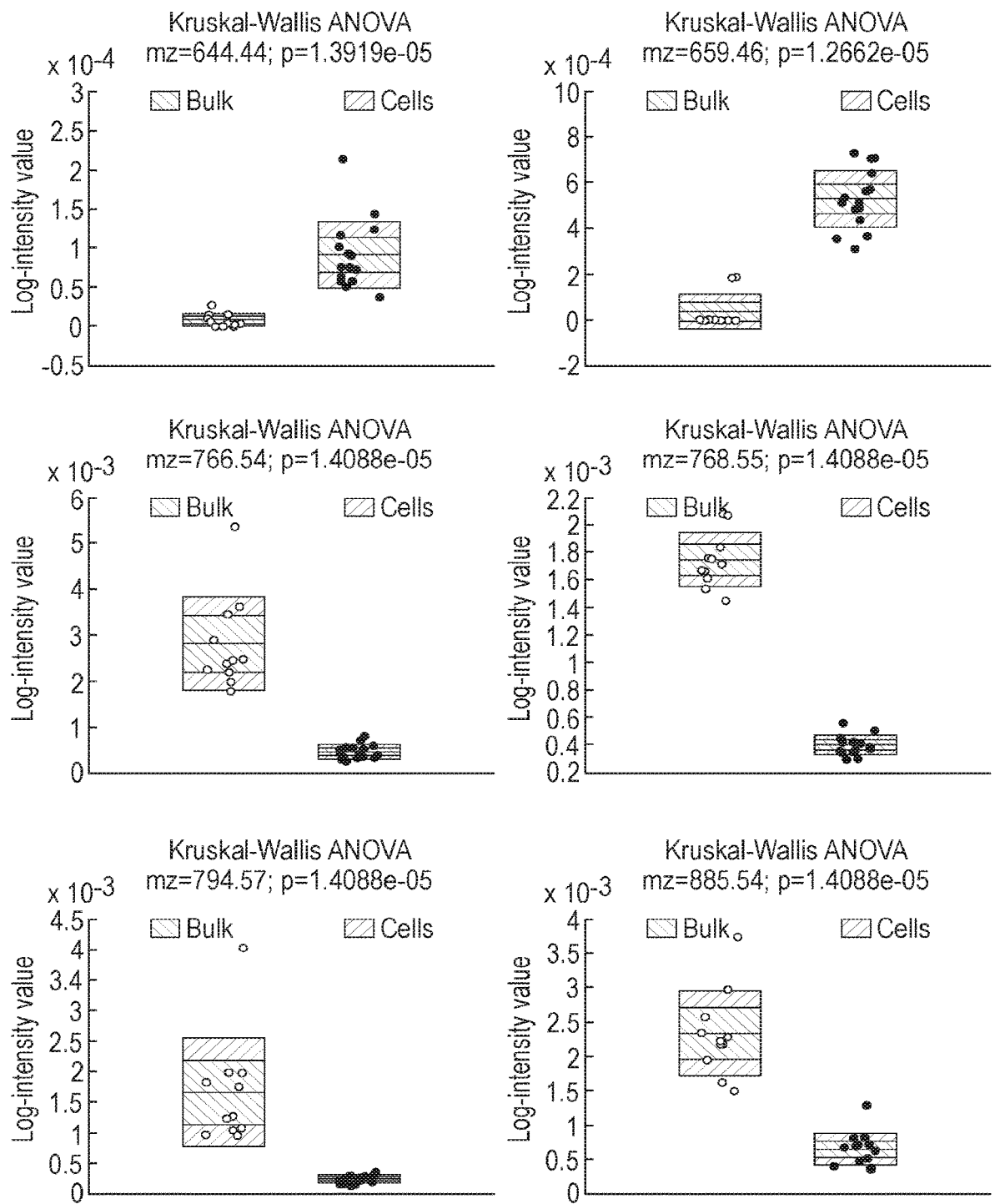
FIG. 58 shows a comparison of cell line and bulk cancer tissue spectra. m/z values that were found to be significantly increased in either bulk cancerous tissue or cancer cell lines.

FIG. 58 shows a comparison of cell line and bulk cancer tissue spectra. Mass to charge ratio values that were found to be significantly increased in either bulk cancerous tissue or cancer cell lines.

Correlation of REIMS Spectral Data with Protein Expression Data

Protein expression data was obtained from online source of the Technische Universität München, Germany (Gholami et al., supra). The fads2 gene encodes the fatty-acid desaturase 2 protein. However, for this protein data was only available in case of 29 members of the NCI-60 cell line panel.

To assess the agreement of data for gene and protein expression, both were plotted as a function of phospholipid species PE(38:3) and the ratio of PE(38:3)/PE(38:2).

Figure 59A:
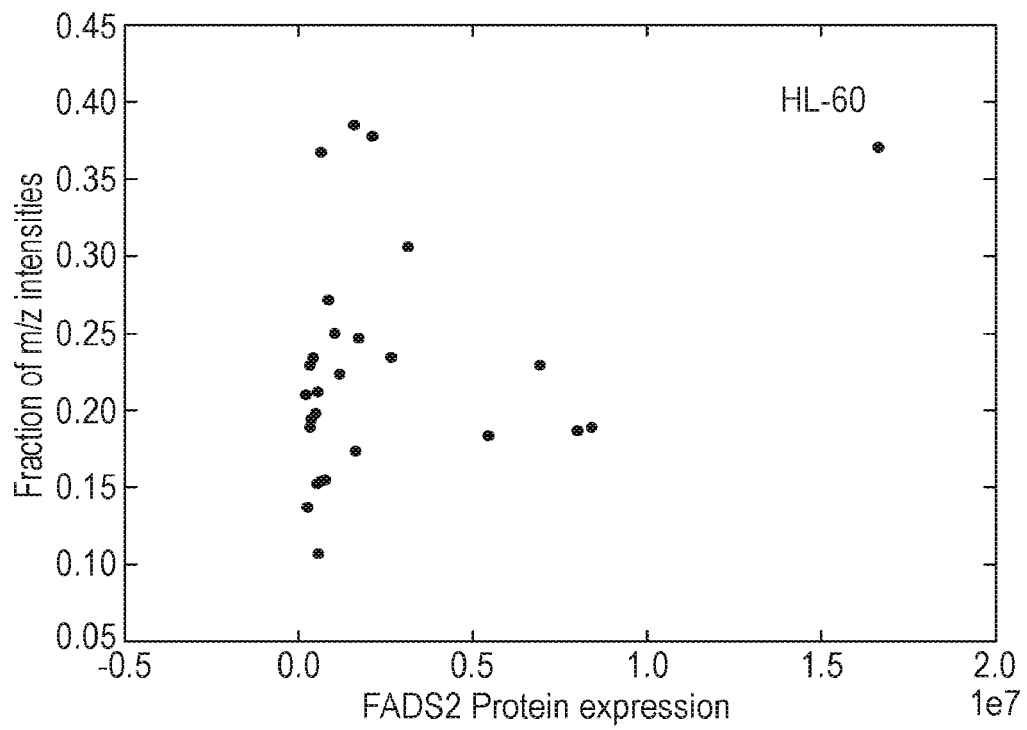
FIG. 59A shows PE(38:3)/PE(38:2) peak intensity ratio
Figure 59B:
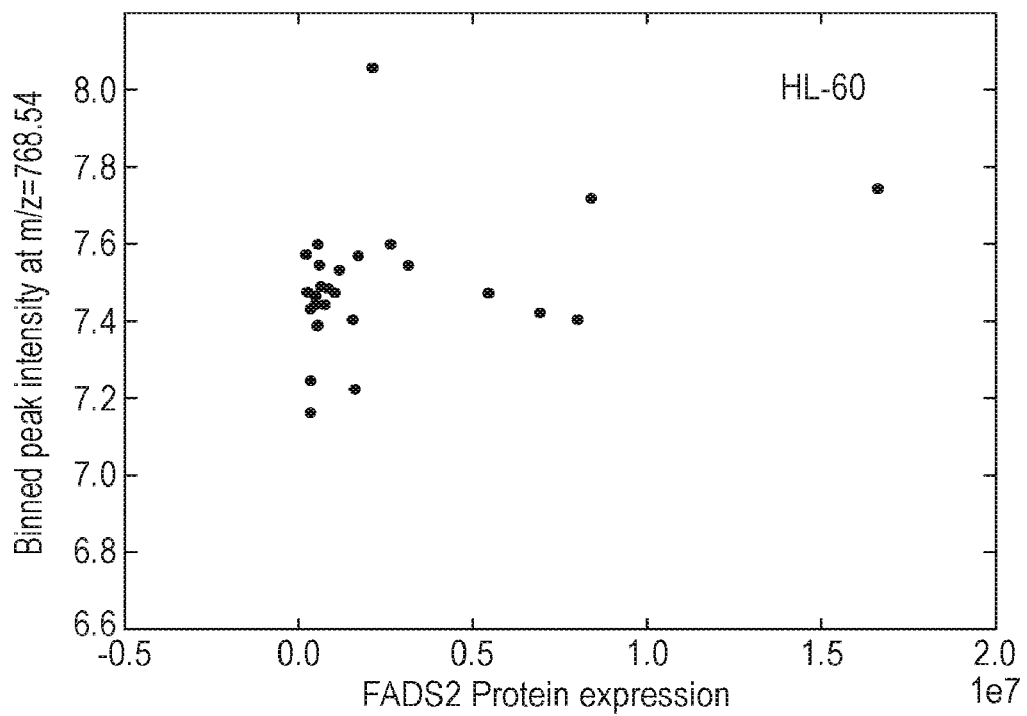
FIG. 59B shows PE(38:3) peak intensity as a function of FADS2 protein expression (for FADS2 protein expression see Gholami, Amin M., et al., *Global Proteome Analysis of the NCI-60 Cell Line Panel*. Cell Reports, 2013. 4(3): p. 609-620)

FIG. 59A shows phospholipid species PE(38:3)/PE(38:2) peak intensity ratio and FIG. 59B shows PE(38:3) peak intensity as a function of fads2 protein expression.

Correlation of Glycosylated Lipids with Ugcg Gene

Fragmentation spectra were recorded for peak set at m/z=842-846 recorded using a Waters Xevo G2-XS Q-ToF® instrument with a collision energy set at 35 eV. Fragmentation spectra showed similar behaviour and thus similar structural backbone. The main fragments observed are due to loss of HCl ($\Delta m=36$ Da) and loss of a hexose moiety HCl ($\Delta m=198$ Da). The loss of the hexose moiety as major fragmentation pathway agrees well with spectra of reference standards as found at Lipid Maps for the corresponding [M-H]$^-$ ion. No differentiation can be made between glycosylated and galactosylated ceramides.

Safety Considerations

To avoid any negative health impact originating from aerosolized cancer cells, the analysis site was enclosed into a Class II safety level glove box compartment equipped with UV light source and HEPA filters.

Robustness of RE/MS Spectral Profiles

In order to show that REIMS spectral patterns are reproducible and sufficiently specific to differentiate between different human cancer cell lines, three different cell lines (HeLa—cervical adenocarcinoma, MES-SA—uterine sarcoma and SNB-19—glioblastoma) were analyzed in an experiment designed to test spectral reproducibility.

The experimental scheme accounts for variance introduced by different culture batches or the passage number and for analytical variance introduced by the multiple measurements. Reference is made to FIG. 56.

Replicates were randomly analyzed over three analysis days in order to assess the analytical variance and robustness of a REIMS-based lipid profiling method. In addition, the influence of freeze-thaw cycles on spectral variance was investigated and was found to be insignificant.

Raw REIMS mass spectrometric profiles of the three cell lines show significant similarities as is apparent from FIG. 60A. The main spectral content comprises predominantly glycerophospholipid-type membrane lipid components such as phosphatidylethanolamines (PEs), phosphatidylinositols (PIs), phosphatidylglycerols (PGs), phosphatidic acids (PAs) and phosphatidylserines (PSs) as well as other complex lipids including ceramides and glycosylated ceramide species. All observed ions displayed a single negative charge, the vast majority by forming the quasi-molecular [M-H]$^-$ ion. In addition, [M-NH$_3$—H]$^-$ was observed in case of PEs. Sphingolipid species were detected as [M+Cl]$^-$ ions.

For clinically oriented applications, REIMS spectral profiles were largely analyzed using supervised multivariate statistical analyses such as linear discriminant analysis (LDA) to explore the differentiation of various tissue types or healthy and diseased tissues.

In the experimental results presented below the analysis was restricted to exploratory unsupervised analysis methods to confirm that REIMS profiles would reproducibly cluster into different groups corresponding to cell line identities.

PCA of the REIMS profiles defined three clusters, as shown in FIG. 60B, corresponding to the three cell lines. SNB-19 cells are clearly differentiated from HeLa and MES-SA cells along the first principal component. The second and the third principal component allow the full separation of HeLa and MES-SA cell lines from each other. A slight separation along the second principal component due to passage numbers was observed for HeLa and SNB-19, however, analytical and biological variances were found to be small compared to the inherent spectral differences of the cell lines. These results suggest that although there is an expected biological and analytical variance, the REIMS spectral profiles obtained from cell line pellets show sufficient reproducibility and specificity to characterize and distinguish human cancer cell lines.

RE/MS Profile of the NCI-60 Cell Line Panel

Following confirmation that REIMS spectral patterns are able to distinguish between three cancer cell lines, the entire NCI-60 panel consisting of 60 human different cancer cell lines was profiled. Based on amount of available biomass after culture, 4 to 15 individual measurement points were made for each cell line. Several biological replicates were also included (the detailed sample set is given in a table above).

Figure 61:
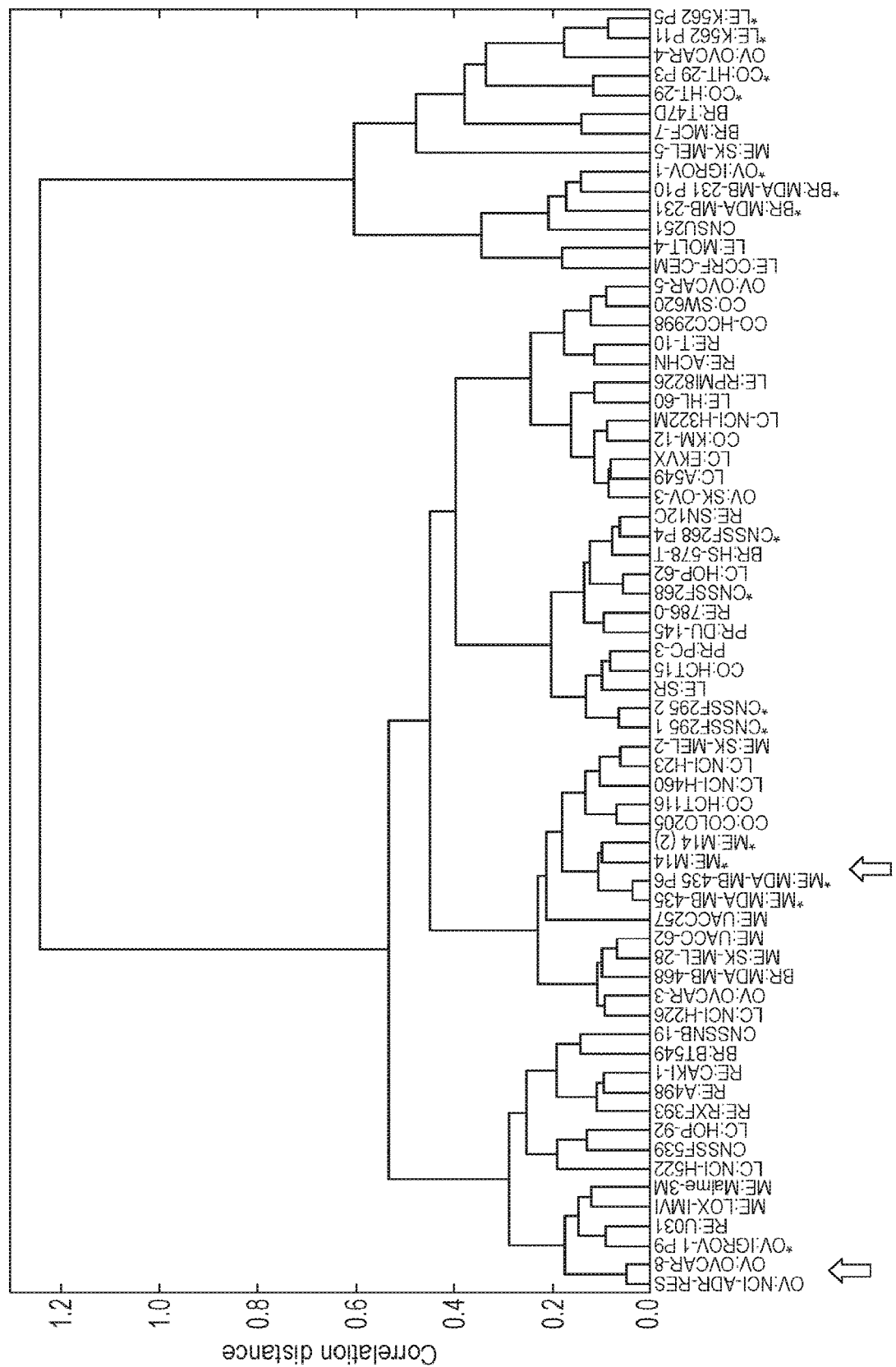
FIG. 61 shows a hierarchical cluster analysis and shows how lipidomic profiles revealed by REIMS distinguish cell lines of the NCI-60 panel consisting of ovarian (OV, green), renal (RE, brown), melanoma (ME, light blue), central nervous system (CNS, light green), breast (BR, black), lung (LC, blue), colon (CO, red), leukemia (LE, magenta) and prostate (PR, yellow) origin, wherein the cluster dendrogram of the NCI-60 panel includes independently cultured replicates (highlighted by asterisks) or biologically related cell lines (blue arrows) and wherein distance was calculated using Pearson correlation and agglomeration via the Ward metric.

Hierarchical cluster analysis as shown in FIG. 61 and principal component analysis (as shown in FIG. 57) of the filtered sample averages indicated that the 60 cells are characterized by unique REIMS profiles.

Biological replicates showed the expected level of similarity as indicated by the cluster analysis (FIG. 61) or the cross-validation results given in table above.

Profiling studies revealed that the MDA-MB-435 cells more closely resembled melanoma cell lines than the other breast tumor lines (Ross, Nat Genet 2000).

Consistent with gene expression, SNP and karyotype analyses, the REIMS profiles also confirmed that MDA-MB-435 and M14 are of the same origin (FIG. 61, arrows).

Karyotyping has also found that the NCI-ADR-RES is in fact a drug resistant derivative of OVCAR-8.

As shown in FIG. 61, these cell lines (indicated by arrows) also show close similarity based on their REIMS profiles. Taken together, these results confirm that REIMS profiles are strongly associated with the biological identity of cancer cell lines.

Gene and protein expression patterns of the NCI-60 panel were found to correlate with tissue types whereas metabolomic signatures did not differentiate between tissue origins.

Clustering of the cell lines based on their REIMS lipid profile showed extensive heterogeneity within most tissue types, except for melanoma samples (FIG. 61, light colored cell lines).

REIMS profiles of the NCI60 panel were subsequently compared to bulk cancer samples of ovarian and colon adenocarcinomas analyzed using the same experimental setup. A PCA plot of the resulting dataset is shown in FIG. 62 and reveals clear differences between cell lines and bulk tissue specimens along the first principal component suggesting strong differences among their membrane lipid composition. A tentative separation according to tissue type of origin can be observed for both cell lines and tissue specimens, although more pronounced in the latter. Only a small number of tissue specimens (n=4) were available in case of ovarian tumors, but based on previous studies a significant increase in separation power can be expected for larger sample sets. Nevertheless, the direction of separation is similar in both cases, indicating similar lipidomic differences.

Representative spectral profiles of both ovarian and colon cancer tissue and cell line samples are shown in FIGS. 63A-63D.

Figure 63A:
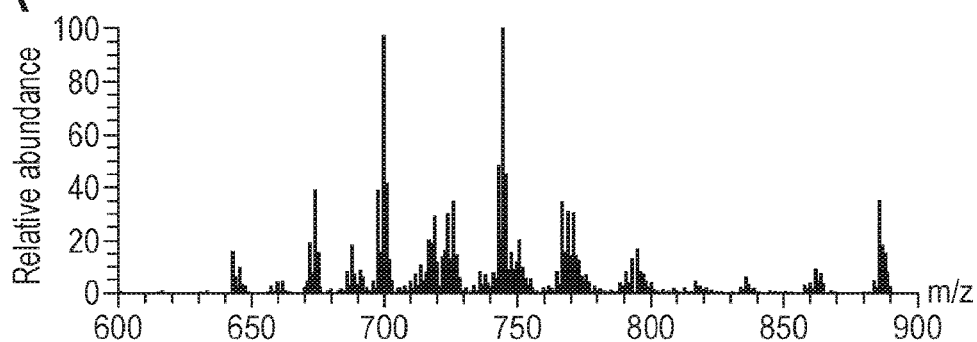
FIG. 63A-63D show a comparison of spectral profiles for bulk tissue samples and cell lines of the corresponding tissue type of origin.
Figure 63B:
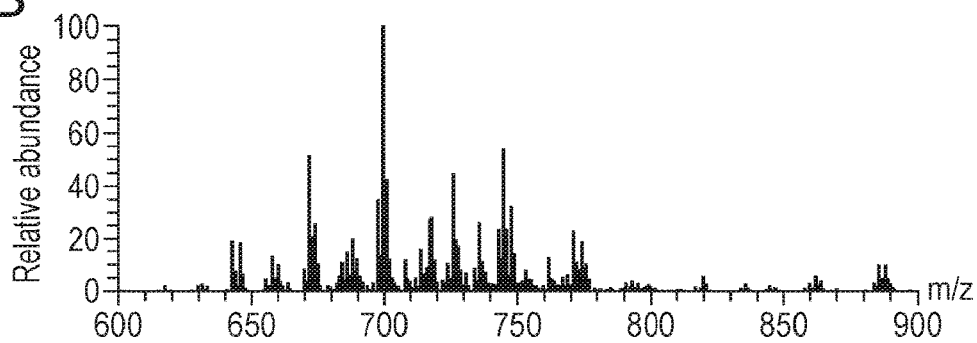
Figure 63C:
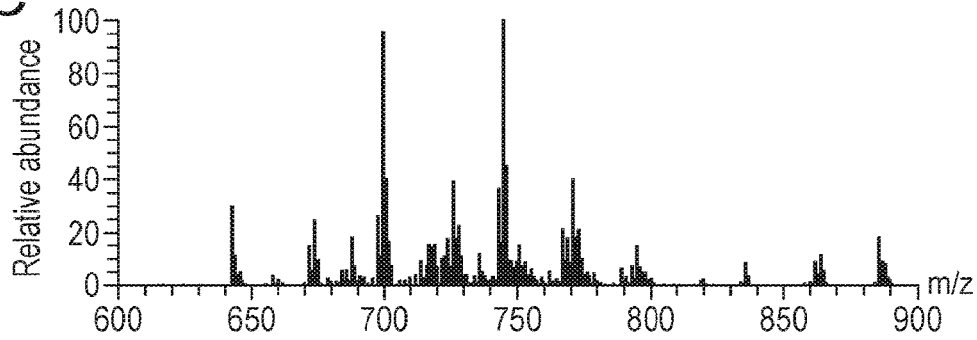
Figure 63D:
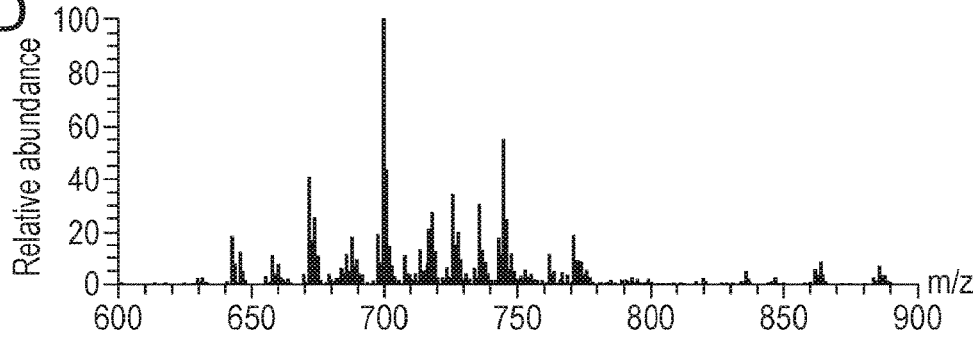

FIG. 63A shows the mass spectral profile for bulk ovarian cancer tissue, FIG. 63B shows a corresponding mass spectral profile for ovarian cancer cell line OVCAR-3, FIG. 63C shows a mass spectral profile for bulk colorectal cancer tissue and FIG. 63D shows a mass spectral profile for colon cancer cell line HCT-15.

Bulk tissue samples (c.f. in vitro cultured cell lines) display larger amounts of long-chain phosphatidylinositols such as PI(38:4) at m/z 885.55. Similar trends were observed in case of certain phosphatidylethanolamines. For example, the peaks detected in the mass range of m/z 790-794 corresponding to PE(40:6)-PE(40:4) species or those occurring at m/z 766.54 and 768.55 corresponding to PE(38:4) and PE(38:3), respectively. On the other hand, m/z 645.45, corresponding to PA(32:1), was found in significantly higher proportions in cell lines.

The characteristic differences in lipid composition may be due to the uniform lipid content of the culturing medium, which does not recapitulate the complex lipid source of real tumors that rely on dietary and liver-synthesized lipids as well as de-novo lipid synthesis (see FIG. 62 for a statistical analysis of distinct spectral features associated with cell lines and bulk tumors).

Conclusion

The above described experiments demonstrate the applicability of a REIMS-based shot-gun lipidomic characterization approach for human cancerous cell lines. Individual cancer cell lines were found to exhibit reproducible and cell line-specific spectral profiles while spectra could be acquired in less than five seconds. This does not only allow rapid identification of cell lines based on their spectral fingerprint, but also detailed characterization of membrane lipid composition in order to study the changes in the cell membrane composition in different cancer phenotypes.

Tissues

Breast Cancer Diagnosis Ex Vivo Using REIMS Technology

About 227 samples from tumour, normal and fibroadenoma human tissue were obtained and analysed. The distribution of the samples is shown in the table below. The samples were histologically validated.

| Sample type | Number of subjects |
| --- | --- |
| Normal | 120 |
| Tumour | 73 |
| Fibroadenoma | 34 |

Sampling took place with either diathermy or plasmablade taking measurements in separate files using cut or coagulation modes if the amount of tissue allowed. Diathermy cut mode was the preferred method if the tissue collected was small. Regardless of whether diathermy or plasmablade were used, and regardless of whether cut or coagulation mode were used, each sample was correctly identified as being normal, tumour or fibroadenoma.

Figure 64:
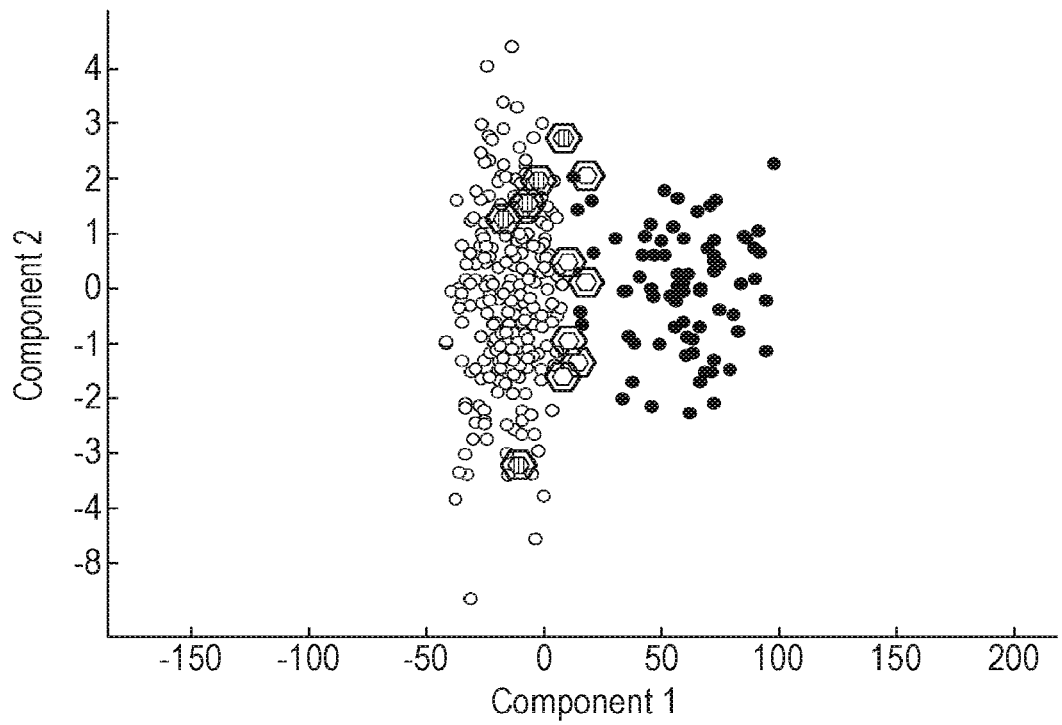
FIG. 64 shows data from Breast cancer diagnosis ex vivo using REIMS technology: cut mode (normal tissue from 61 patients, 280 spectra, tumour tissue from 37 patients, 80 spectra)
Figure 65:
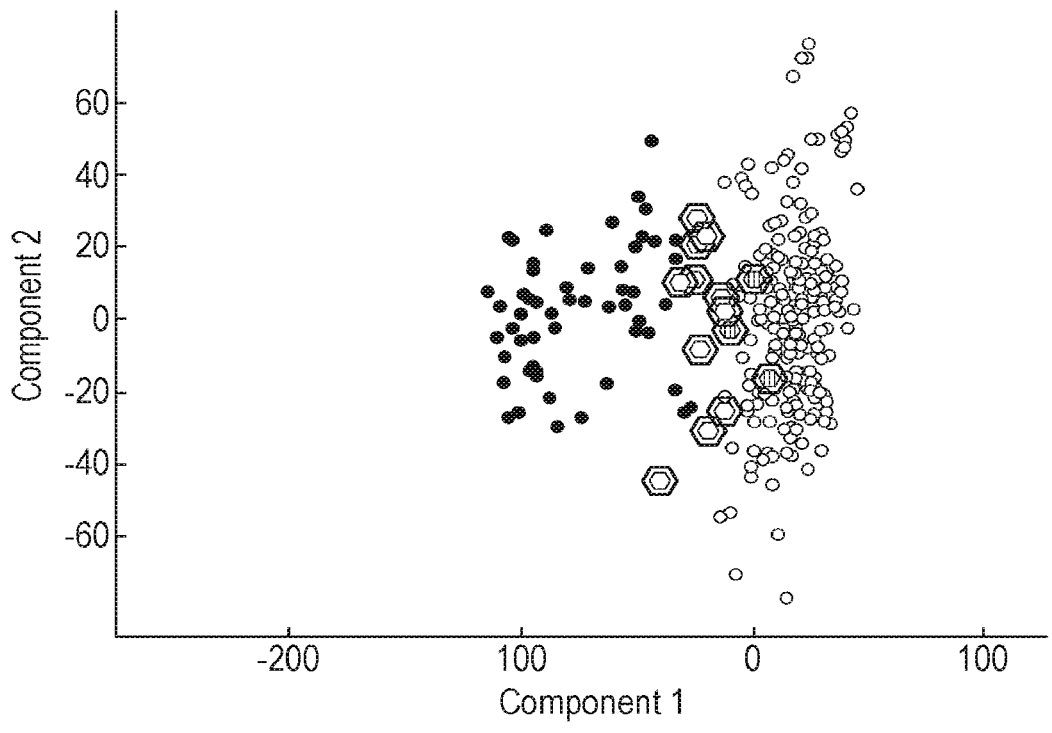
FIG. 65 shows data from Breast cancer diagnosis ex vivo using REIMS technology: Coagulation mode (normal tissue from 66 patients, 281 spectra, tumour tissue from 31 patients, 59 spectra)

Principal component analysis and linear discriminant analysis with cross validation have been done separately for samples run in cut and coagulation modes. See FIGS. 64 and 65.

Ovarian Cancer Analysis Using RE/MS Technology

In this ex vivo data study, a total of 146 samples were analysed as shown in the table below.

| | |
| --- | --- |
| Total Samples | 146 |
| Ovarian Cancer | 67 |
| Normal (15 ovary, 15 peritoneum, 15 fallopian tube) | 45 |
| Borderline tumour of ovary | 15 |
| Benign ovarian lesions | 14 |
| Non-ovarian tumours | 4 |
| Non-ovarian smooth muscle tumour of uncertain malignant potential (STUMP) | 1 |

The samples were histologically validated and analysed by mass spectrometry. Statistical analysis using supervised linear discriminant analysis showed excellent separation of cancer and borderline tissue on the margins of cancer and normal tissue. Good separation was also seen when including benign lesions. See FIG. 66.

Analysis of Necrosis

The method may be used to analyse necrosis, e.g., to detect necrotic tissue. This was exemplified in human lung tissue samples of two different patients. Samples were analysed using histopathology, which identified 100% necrotic cancer tissue. The samples were also analysed using MS and it was possible to distinguish between necrotic and non-necrotic tissue using MS.

Figure 67A:
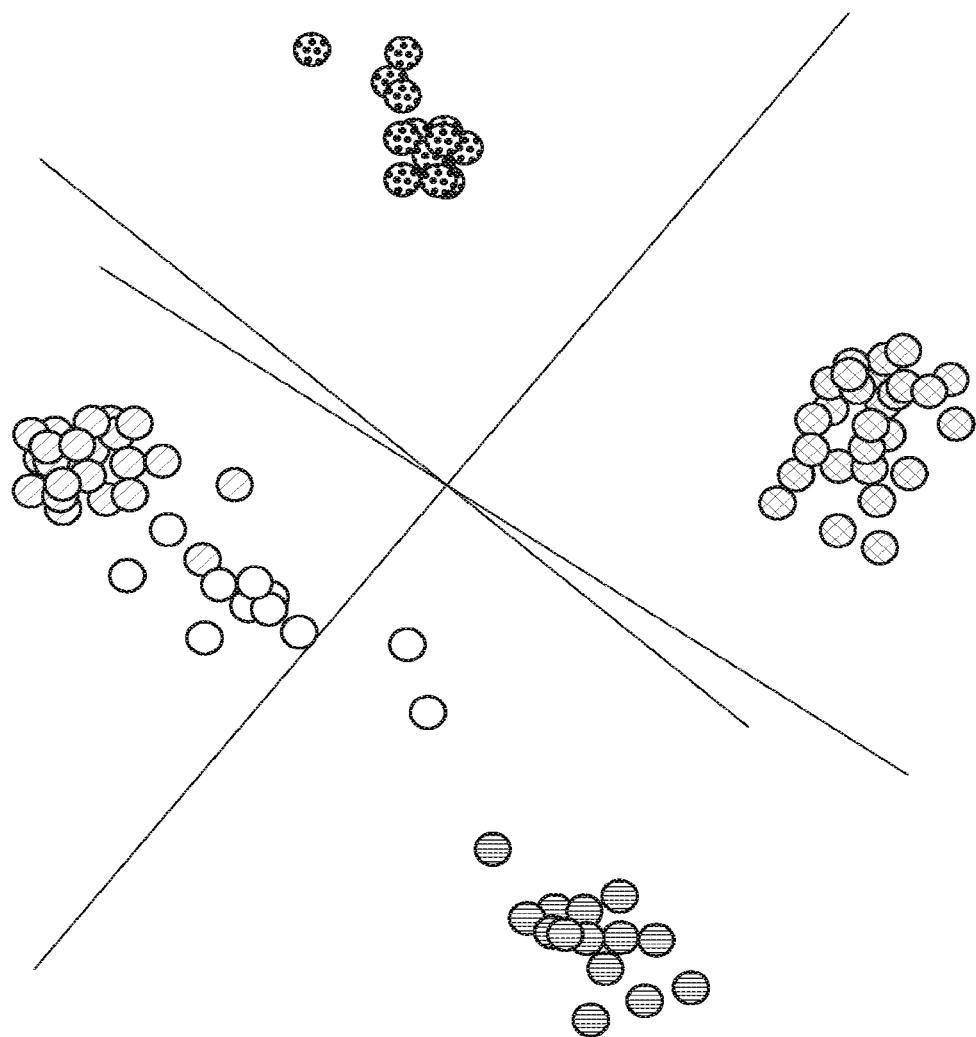
FIGS. 67 (*a*) and (*b*) show results from analysis of necrosis.

The second PC component separates necrosis from the other tissue, this can be seen in FIG. 67. Adenocarcinoma, normal lung, cancer border, squamous cell carcinoma and necrotic tissue was analysed and could clearly be distinguished.

Analysis of Ovarian Cancer

Ovarian cancer (OC) is common and five-year survival is 21.9% and 5.6% for stage 3 or stage 4 disease respectively, which is when 60% of women first present. Intra-operative tissue identification typically relies on frozen section histopathological analysis, which is time-consuming and expensive. Macroscopic non-descript lesions, which may be cancer, can be difficult to correctly identify intra-operatively, especially after neo-adjuvant chemotherapy.

Methods

Fresh frozen ovarian samples (normal, benign, borderline, OC), plus fallopian tube and peritoneum were cut with the Covidien diathermy hand-piece. Surgical smoke was extracted and ionised in a Water's Xevo G2-S mass spectrometer. Resultant mass spectra underwent pre-processing and background subtraction with lock-mass. Processed tissue samples were re-reported by histopathologists to confirm histology. These data were used to create an authentic spectral database, which was histologically ratified. Data were processed with principal component and linear discriminant analyses and leave one patient out cross-validation.

In total 144 different samples were collected from 130 individual patients (some patients provided more than one tissue type), which is summarised in the table below.

| Organ group | Tissue type | Sub-type | No of samples | Spectra |
|---|---|---|---|---|
| Ovary | Normal | | 15 | 64 |
| | Benign | | 8 | 32 |
| | Borderline | | 8 | 30 |
| | Cancer | Serous | 32 | 115 |
| | | Endometrioid | 9 | 35 |
| | | Clear cell | 7 | 24 |
| | | Mucinous | 5 | 21 |
| | No tumour seen | | 11 | 37 |
| | Inconclusive | | 15 | 49 |
| | Excluded | | 5 | 18 |
| Fallopian tube | Normal | N/A | 14 | 49 |
| Peritoneum | Normal | N/A | 15 | 55 |
| | | | 144 | 529 |

Fresh tissue samples had been snap frozen and stored at −80° c. Data including age of sample, International Federation of Gynaecology and Obstetrics (FIGO) stage and grade of disease, histopathology as reported in medical records and sample site was recorded on a National Health Service (NHS) networked computer and only accessed by clinically authorised personnel.

Batches of tissue were issued from the tissue bank and logged to the study accordingly. The samples were thawed and cut with a Covidien ForceTriad™ energy generator coupled with a modified electrosurgical knife. Samples were processed in cut mode using 25 watts and the resultant smoke analysed with a Waters® G2-S TOF mass spectrometer in negative-ion mode.

Figure 68:
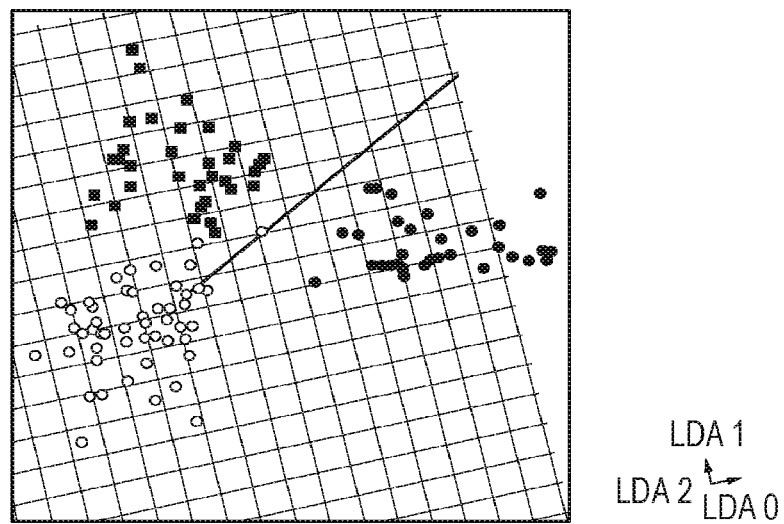
FIG. 68 shows results from analysis of ovarian cancer.

144 tissue samples were processed, producing 529 spectra. Normal ovary and OC could be distinguished in principal component and linear discriminant analyses. Cross-validation resulted in 100% sensitivity and 100% specificity in the separation of normal ovary from viable OC (n=189). A further analysis comparing OC with fallopian tube, normal ovary and peritoneum resulted in 100% sensitivity and 97.8% specificity with cross validation (n=291). Results are shown in FIG. 68.

This study has shown that normal ovarian, peritoneal and fallopian tube tissues have unique spectral signatures, which may be used to accurately determine tissue type. The method may be used intra-operatively (in-vivo). The method's ability to rapidly determine tissue type may shorten operations and reduce morbidity and mortality, potentially improving patient care and survival.

Bacteria

Automatic Ion Imaging of Bacterial Samples

For the analysis of human samples, ethical approval was obtained from the National Healthcare Service Research Ethics Committee (Study ID 11/LO/1686).

According to various embodiments an automatic ion imager was provided which was arranged to automatically sample different locations of a target (e.g., a bacterial or fungal sample which had been culture on a culture medium).

Figure 69:
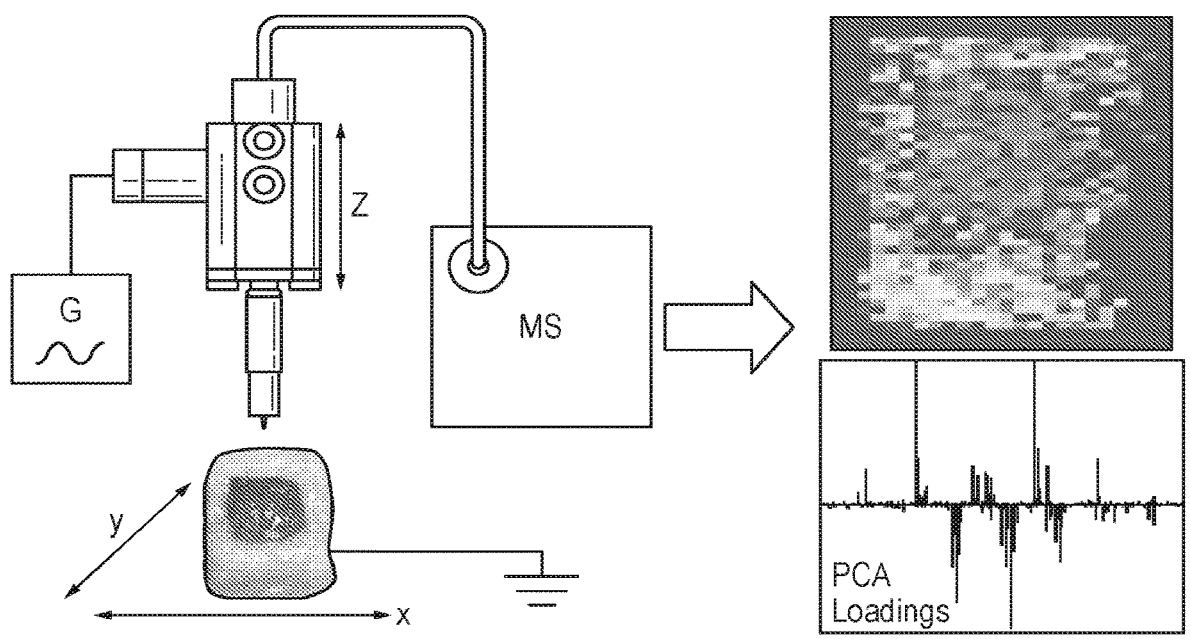
FIG. 69 shows an embodiment wherein a REIMS imaging platform is located above a sample, e.g., tissue sample to be imaged.

FIG. 69 shows a related embodiment wherein a REIMS imaging platform is located above a tissue sample to be imaged.

Figure 70:
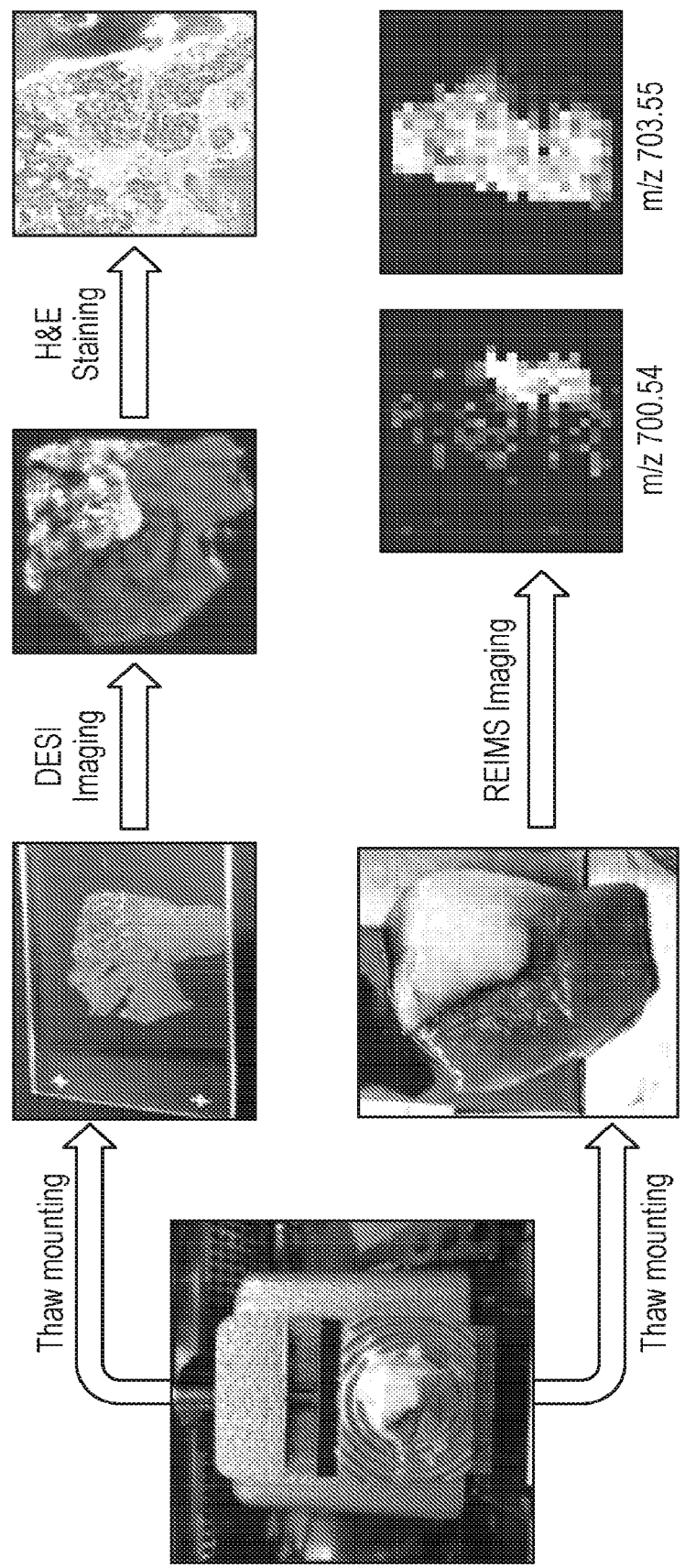
FIG. 70 shows a workflow of a combined DESI and REIMS imaging platform analysis for co-registration of histological features between an optical image and DESI and REIMS data.

FIG. 70 shows a workflow illustrating various aspects an embodiment wherein fresh human liver metastasis samples were obtained from surgical resection specimens and immediately frozen to −80° C. The tissue samples were cryosectioned (Thermo Microm HM550 Cryostat, Thermo Fisher Scientific®, Germany) to 10 µm thickness and thaw mounted onto glass slides for Desorption Electrospray Ionisation ("DESI") analysis. The remaining bulk tissue was used for REIMS analysis.

DESI analysis was carried out using an in-house built DESI stage and REIMS analysis was performed using a modified Prosolia® flowprobe stage (Prosolia®, USA).

DESI analysis of tissues was carried out using a mass spectrometer operated in negative ion mode.

The DESI imaging pixel size was set to 100 µm, the electrospray solvent was methanol:water (95:5 vol/vol) at a solvent flow rate of 1.5 µL/min and zero-grade nitrogen nebulizing gas at a pressure of 4 bar was used. Following DESI analysis, tissue sections were stained with H&E (haematoxylin and eosin) and digitally scanned (Nano-Zoomer 2.0-HT, Hamamatsu®, Japan) to create optical images for comparison with MS images.

A line scan mode (cutting mode) REIMS analysis of one liver metastasis sample was performed on a mass spectrometer and a spot sampling (pointing mode) analysis of another liver metastasis sample and a microorganism culture were performed on a Waters Xevo G2-S Q-TOF Instrument® (Waters Micromass®, U.K.) in negative ion mode.

Figure 71:
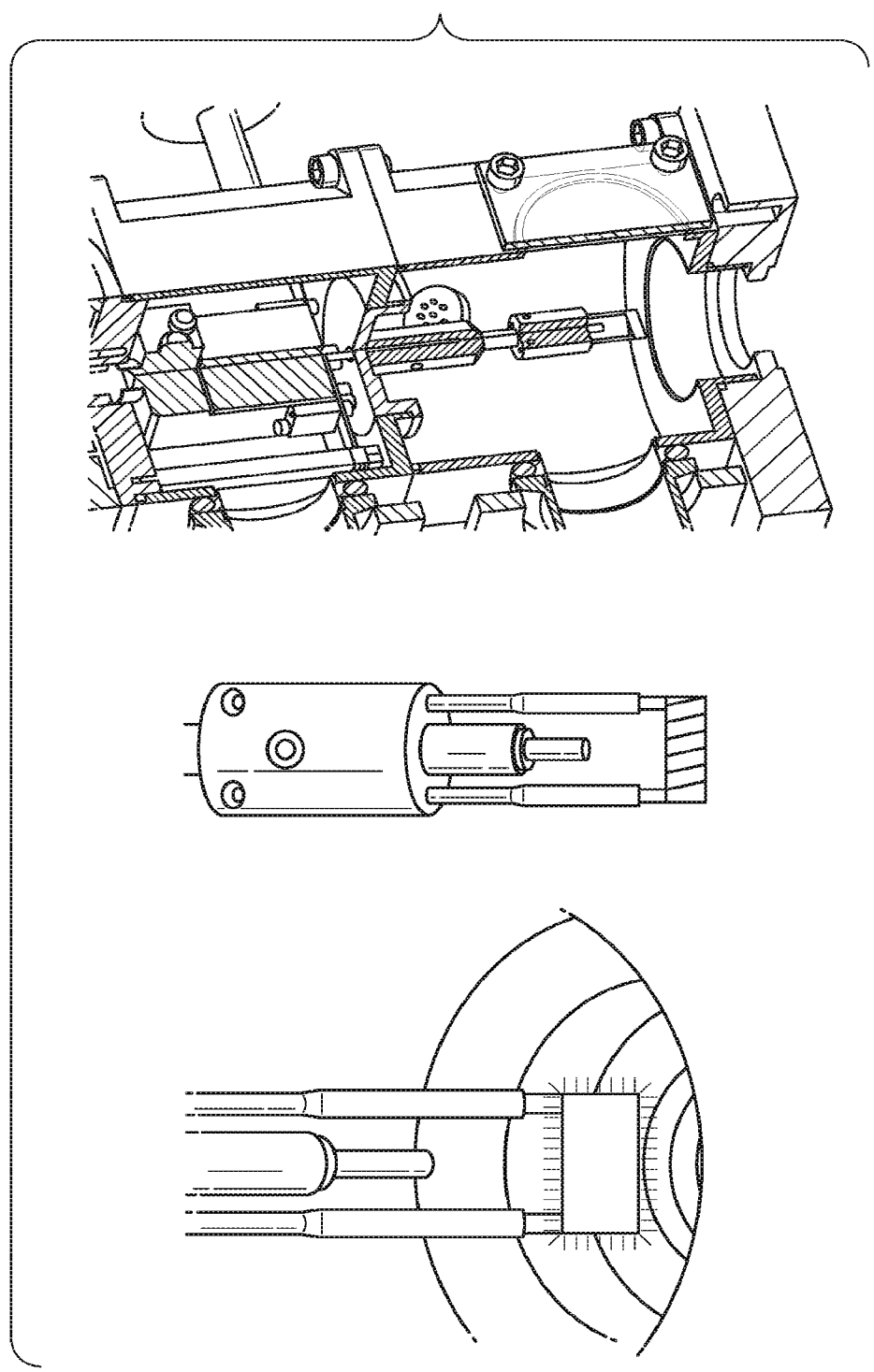
FIG. 71 shows a heated coil interface used on a Waters Xevo G2-S® instrument for improved sensitivity and robustness towards contamination.

The Waters Xevo G2-S® mass spectrometer was equipped with a modified atmospheric interface combining an orthogonal Venturi-pump for aerosol transfer and a heated capillary inlet as shown in FIG. 71.

REIMS imaging analysis of liver metastasis was carried out in a (first) cutting mode at about 1 bar Venturi gas pressure and about 4 kV p-p amplitude at about 50 kHz alternating current frequency (AC). A blade-shaped electrosurgical tip was used, about 500 µm pixel size, about 1 mm/s cutting speed and about 1 mm cutting depth.

Analysis of liver metastasis in a (second) pointing mode was carried out at about 0.25 bar Venturi gas pressure, about 2 kV amplitude at about 50 kHz AC and using a wire-shaped electrosurgical tip at about 750 μm pixel size, about 0.1 s time remaining inside the sample and a pointing depth of about 1 mm.

Aerosol was transferred using a ⅛" OD, 2 mm ID PTFE tubing. Since the used power settings were sufficiently high such as potentially to cause severe injury, the instrumental setup was handled with high caution and insulating gloves were worn.

Parameter optimization of the REIMS imaging platform was carried out using porcine liver samples. For comparison of spectrometric patterns between REIMS imaging and iKnife, porcine liver, porcine kidney cortex, lamb liver and chicken skeletal muscle were analysed using an electrosurgical handpiece (Meyer-Haake GmbH®, Germany) with incorporated PTFE tubing (⅛" OD, 2 mm ID) which was connected to the Venturi pump. Liver, kidney and muscle were food grade and purchased as such. The iKnife was operated in a cutting mode at 4 about 0 W and about 1 bar gas pressure in combination with a Valleylab SurgiStat II® power-controlled electrosurgical generator (Covidien, Ireland).

Data Processing

Raw spectral profiles were loaded into a MATLAB® environment (Version R2014a, Mathworks, USA) for pre-processing, MS-image visualization and pattern recognition analysis. All mass spectra were linearly interpolated to a common interval of 0.1 Da and individually normalized to the total ion count ("TIC") of each mass spectrum. The data was used for univariate comparison of intensity levels across liver tissue types and ionization techniques and for bacterial MS-image visualization of single ions. Peak annotation for liver metastasis samples was based on m/z accuracy obtained from the unprocessed raw files, while bacterial peak annotation was based on mass accuracy and on tandem-MS spectra obtained using bipolar forceps.

Multivariate MS-image visualization was performed on mass spectra additionally binned to 1 Da intervals in the mass range of m/z 600-1000 Da for biological tissue and m/z 400-2000 for bacteria. For multivariate image visualization, MS-images and optical images were co-registered to define regions of interest ("ROIs") for building a supervised training model. Defined ROIs (classes) were healthy and cancerous tissue for the liver samples and one region for each bacterium plus agar, resulting overall in 2 classes for liver samples and 4 classes for bacterial samples.

The training model was used to classify each pixel of the same sample and colour code the obtained score-values into red-green-blue colour scale. This supervised strategy for image visualization is based on an algorithm that combines recursive maximum margin criterion ("RMMC") with linear discriminant analysis ("LDA"). For unsupervised analysis, principal component analysis ("PCA") was performed on the mass spectra defined by the regions of interest.

Concordance correlation coefficients were used to measure the agreement between REIMS imaging platform ("RIP") mass spectra and iKnife mass spectra. This quantitative measure is defined as:

$$\rho_c = \frac{2\rho\sigma_{RIP}\sigma_{iKnife}}{\sigma_{RIP}^2 + \sigma_{iKnife}^2 + (\mu_{RIP} - \mu_{iKnife})^2} \quad (1)$$

wherein $\rho_c$ is the concordance correlation coefficient, $\rho$ is Pearson's correlation coefficient and $\sigma_{RIP/iKnife}$ is the standard deviation of the mean intensity values of $\mu_{RIP/iKnife}$.

A low concordance correlation coefficient close to the value of zero indicates low agreement while a value close to the value of one suggests high similarity between spectral profiles.

Boxplots show the median at the central mark within the box with $25^{th}$ and $75^{th}$ percentiles at the edges of the box. The upper and lower whiskers account for approximately 2.7 standard deviations (99.3% data coverage). Mass spectra were standardized to 100% intensity scale before their data was visualized with boxplots.

Figure 72:
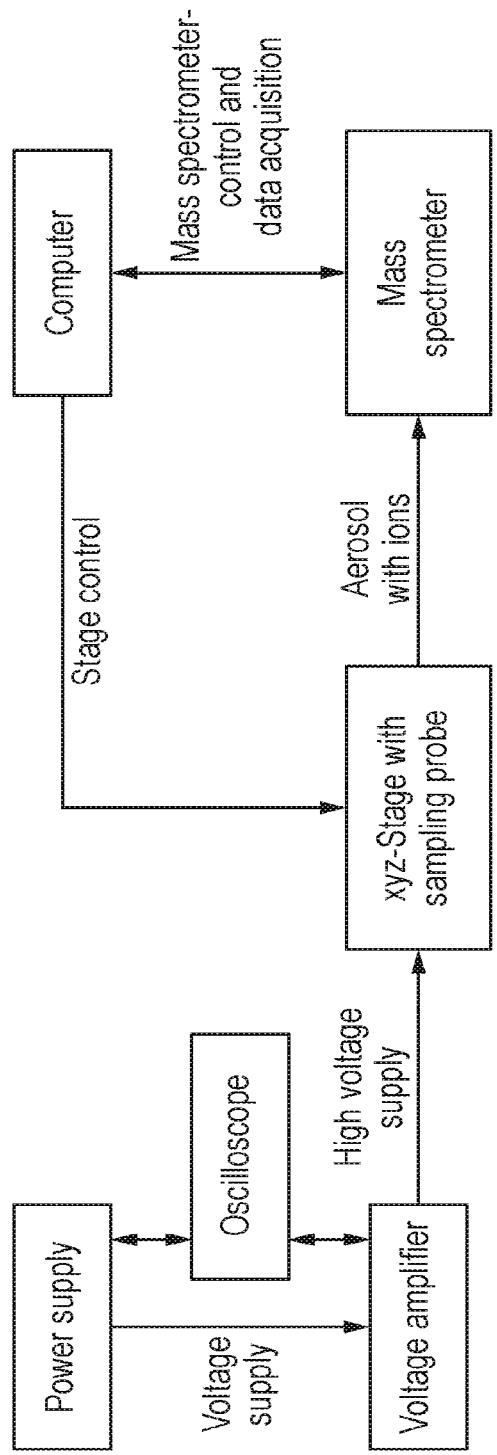
FIG. 72 shows a setup of REIMS imaging instrumentation.

FIG. 72 shows in further detail a REIMS imaging platform which comprises three major functional elements that all influence the quality of mass spectra. The imaging platform comprises a power generator, a xyz-stage with a sampling probe and a mass spectrometer.

The power supply setup used for the platform comprises a Tektronix® AFG 3022 arbitrary function generator (Tektronix®, USA), a Tektronix® DPO 3014 Oscilloscope and a Trek 10/40A High Voltage Amplifier (Trek®, USA).

The arbitrary function generator was used to generate sinus waveforms with amplitudes between about 1 V and 6 V at frequencies in the range of about 10 to 60 kHz. The high voltage power amplifier multiplied the voltage by a factor of about 1000 and supplied the connected sampling probe with the electric current. The oscilloscope provided feedback to ensure correct working parameters.

Figure 73:
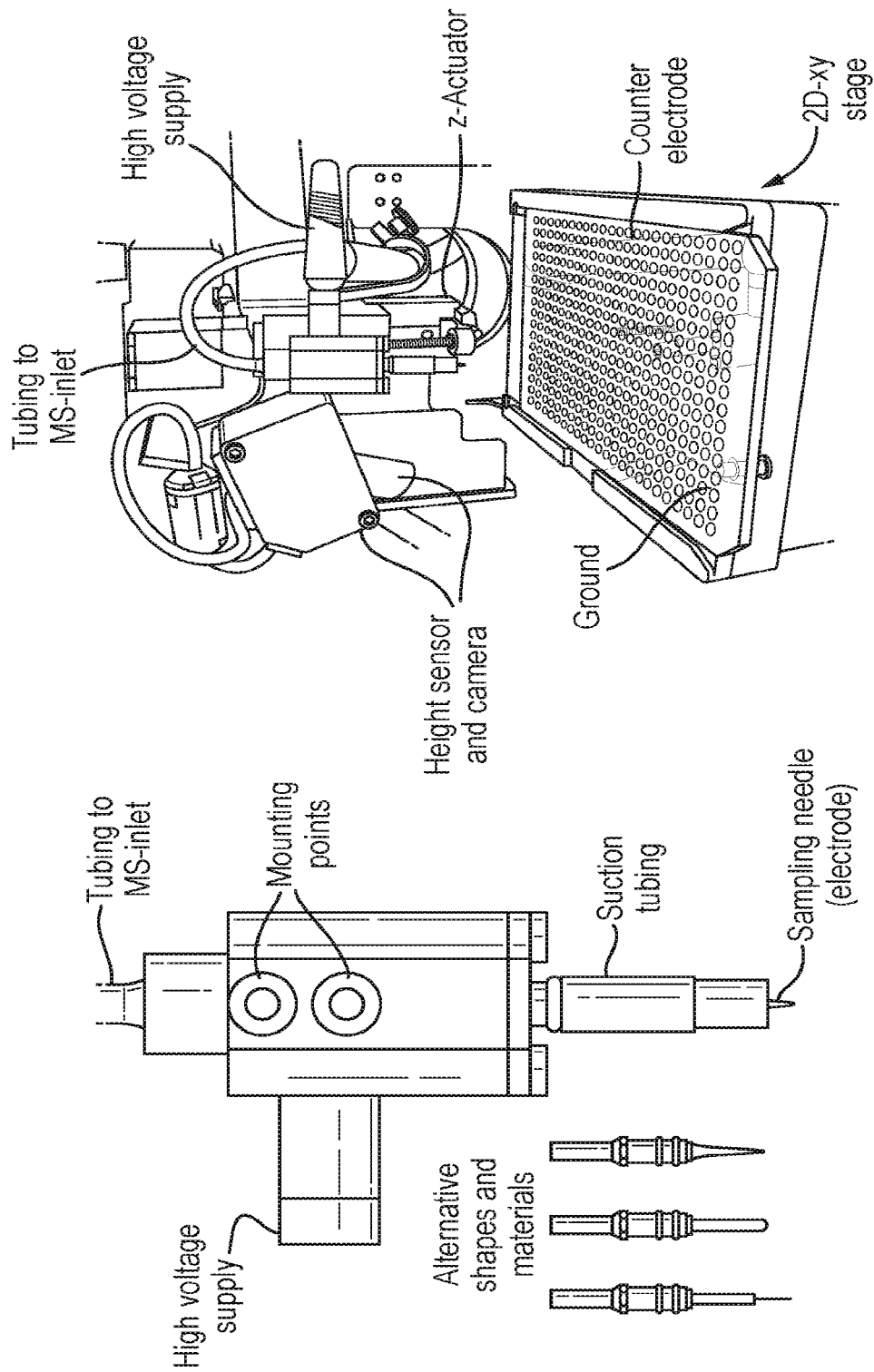
FIG. 73 shows a REIMS imaging sampling probe and setup of a xyz-stage wherein a sampling probe is mounted onto a z-actuator and is connected to a high voltage power supply and wherein evaporated aerosol is captured by suction tubing and is transported to a mass spectrometer.

The xyz-stage comprises a modified Prosolia® 2D DESI stage including Flowprobe® upgrade (Prosolia®, USA) with a high precision z-axis actuator. The sampling probe is mounted onto the actuator and is connected to the power generator setup as well as a MS inlet capillary (as shown in FIG. 73).

A laser height sensor may be provided to measure the distance between the electrosurgical tip and the sample surface and ensures an equal penetration depth of the tip into the sample which is particularly useful for an uneven sample surface. The electrosurgical tip can be exchanged for other materials or shapes depending on the field of application. In case of high precision sampling, a small diameter wire may be used, whereas a large surface tip is suitable to maximize mass spectrometric signal intensity. The electrosurgical tip is surrounded by a tubing which is connected to a Venturi air jet pump.

Bacterial Identification/Imaging

Tissue ion imaging has been described above to assist in the understanding of ion imaging of microbial populations.

REIMS imaging analysis of bacteria was carried out at about 1 bar Venturi gas pressure, about 2 kV, about 40 kHz AC, with a blade-shaped electrosurgical tip, about 1 mm pixel size, about 0.1 s time remaining inside the sample and about 1 mm pointing depth.

Bacterial strains of *P. aeruginosa* ATCC 27853, *B. subtilis* ATCC 6633 and *S. aureus* ATCC 25923 were cultured in a single petri dish on solid agar-based media (Oxoid®, U.K.). Incubation was carried out under atmospheric conditions at 37° C. overnight. REIMS analysis was carried out directly from solid culture medium on the Waters Xevo G2-S® mass spectrometer. Peak identifications were carried out on isolated strains using tandem mass spectrometry and the REIMS bipolar forceps approach.

Imaging mass spectrometric techniques such as MALDI-MSI and (nano-)DESI-MSI are increasingly applied in microbiological context as they offer the unique opportunity to study the spatially-resolved distribution of metabolites in a microbial colony. Additionally, microbial cultures cannot only be studied individually but the interactions of different microorganisms can be analysed directly and in many cases in vivo in 2D and after sectioning of the growth medium in 3D. This can reveal novel insights into defence mechanisms of certain types of bacteria and can be extended to the imaging of microbial infections and the study of microbe-host interactions.

Figure 74:
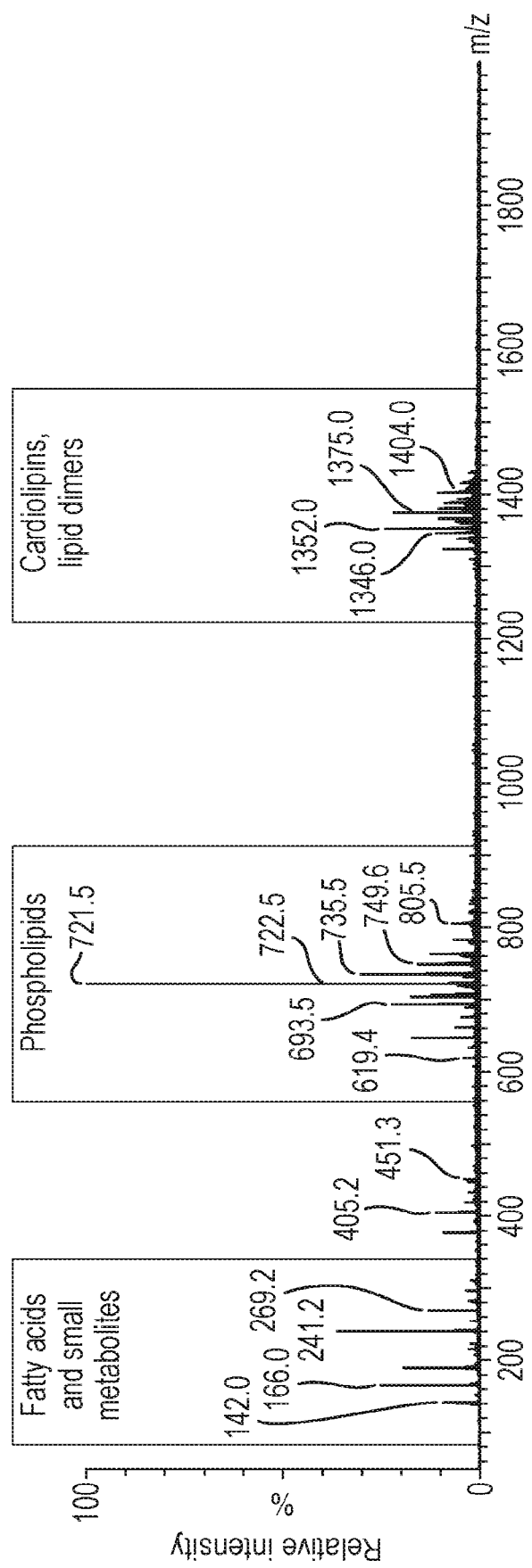
FIG. 74 shows an example mass spectrum of *P. aeruginosa* bacterium with most prominent metabolite classes for distinct mass ranges.
Figure 75:
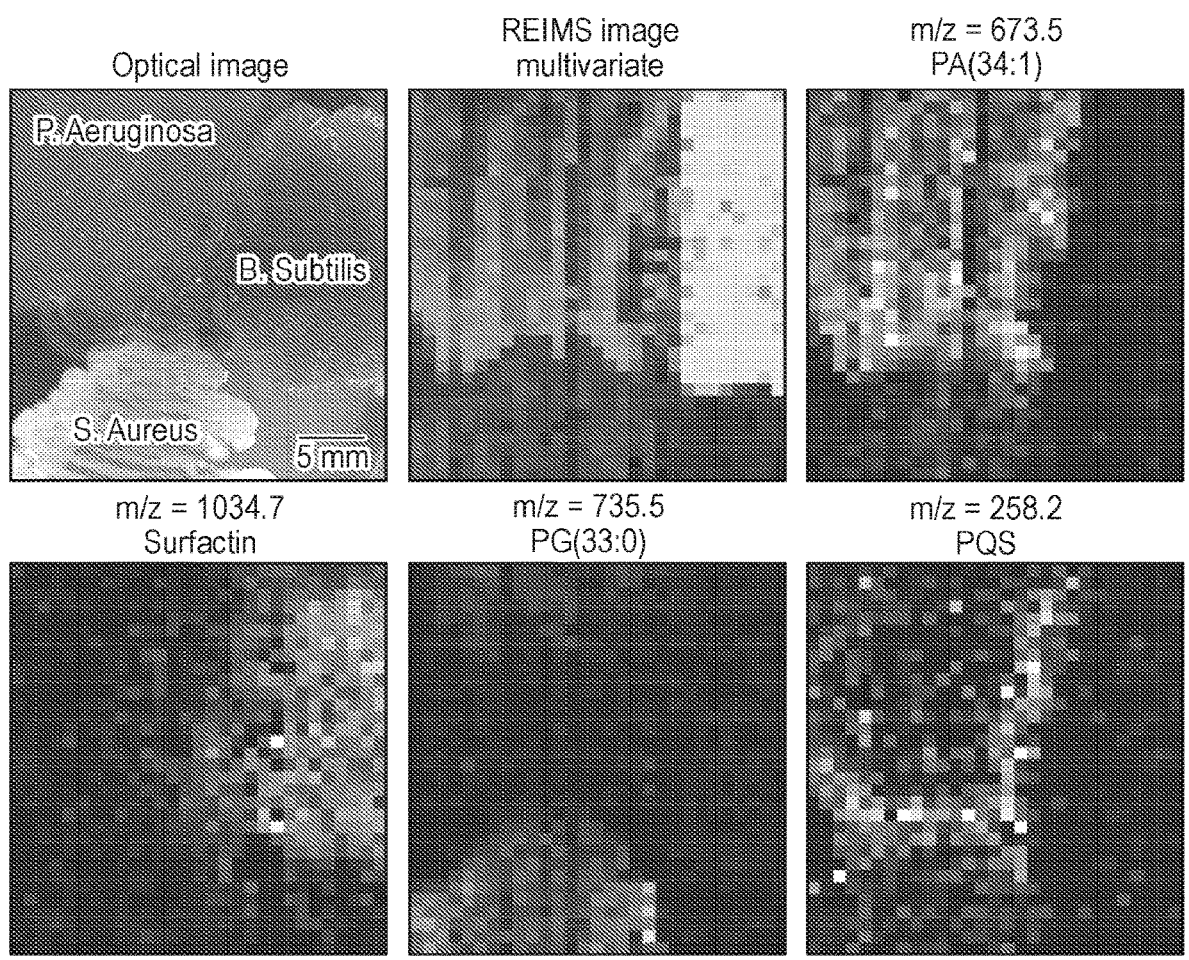
FIG. 75 shows optical, mass spectrometric multivariate and ion images of three different bacterial species wherein the multivariate image shows clear distinction between the species, while ion images show metabolites of current interest, including phospholipids. Molecules were ionized as [M-H] wherein PA: phosphatidic acid, PG: phosphatidylglycerol, PQS: 2-Heptyl-3hydroxy-4(1H)-quinolone.
Figure 76:
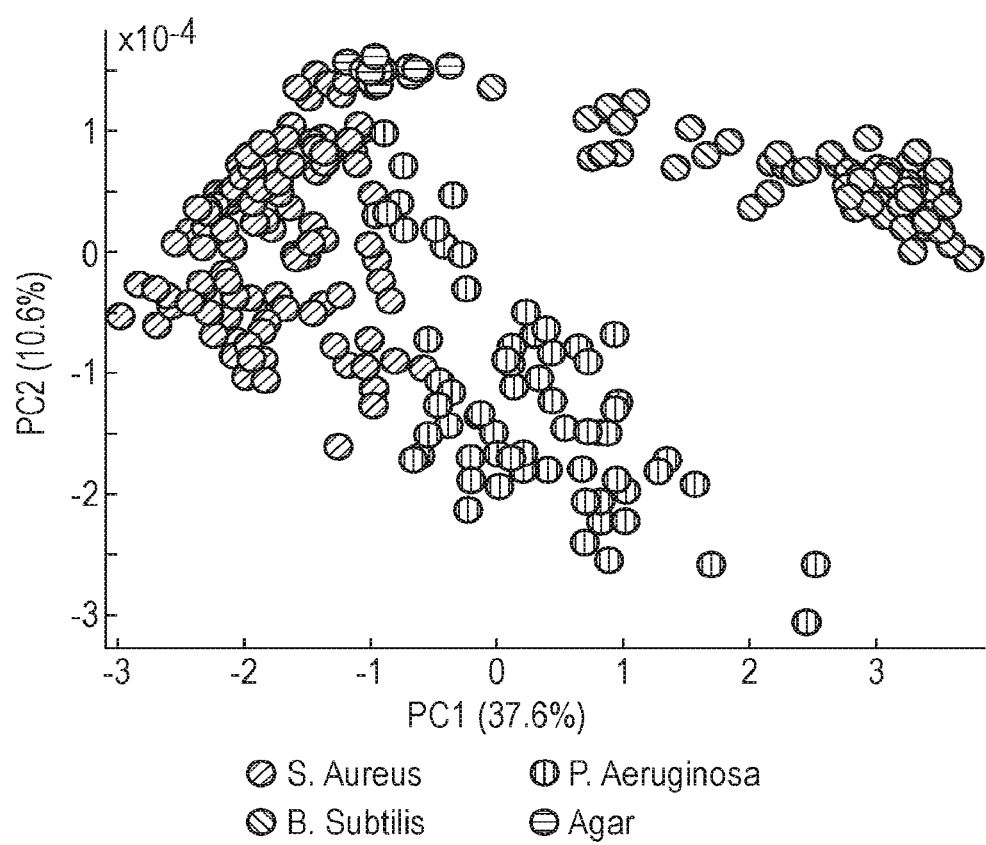
FIG. 76 shows a principal components analysis plot of three different bacterial strains together with agar medium and wherein PC is the principal component and percentage values are explained variance.

REIMS imaging analysis of the bacterial strains P. aeruginosa, B. subtilis and S. aureus was carried out directly from the colonies growing on agar plates in vivo. The detected spectrometric species show high resemblance with those of the same strains obtained using bipolar REIMS. The mass spectra are each dominated by intact phospholipid species in the mass range of m/z 600 to 1000, identified as phosphatidic acid ("PA"), phosphatidyl-glycerol ("PG") and phosphatidyl-ethanolamine ("PE") species. Fatty acids are mostly present in the lower mass range, whereas cardiolipins give strong signal in the higher mass range (see FIG. 74). Using the mass range of m/z 400 to 2000, all three strains are distinguishable from each other using both supervised and unsupervised multivariate methods (see FIGS. 75 and 76). The multivariate images show distinct separation of each of the three species, with agar not grouping into any of the three strains.

Unlike in bipolar REIMS, where the agar surface remains intact, with a monopolar REIMS imaging setup the sampling probe is directly immersed into the agar culturing medium during analysis. However, the ion yield from agar was generally low, devoid of all the lipid peaks observed in bacteria. This low ion yield might be associated with the carbohydrate-based agar matrix undergoing condensation reactions by losing water, resulting in charring and therefore hindering ion formation via the REIMS mechanism.

Single ion images reveal the spatial distribution of excreted metabolites such as the lipopeptide surfactin in B. subtilis. Surfactin was reported to exhibit antibacterial, antiviral and antifungal properties. The surfactin signal was equally distributed over the B. subtilis culture. However, excretion of surfactin into neighbouring areas not directly inhabited by B. subtilis can be observed in FIG. 75.

In the case of Pseudomonas aeruginosa, a range of PQS-derived quorum sensing molecules were observed with similar distributions to each other.

Figure 77:
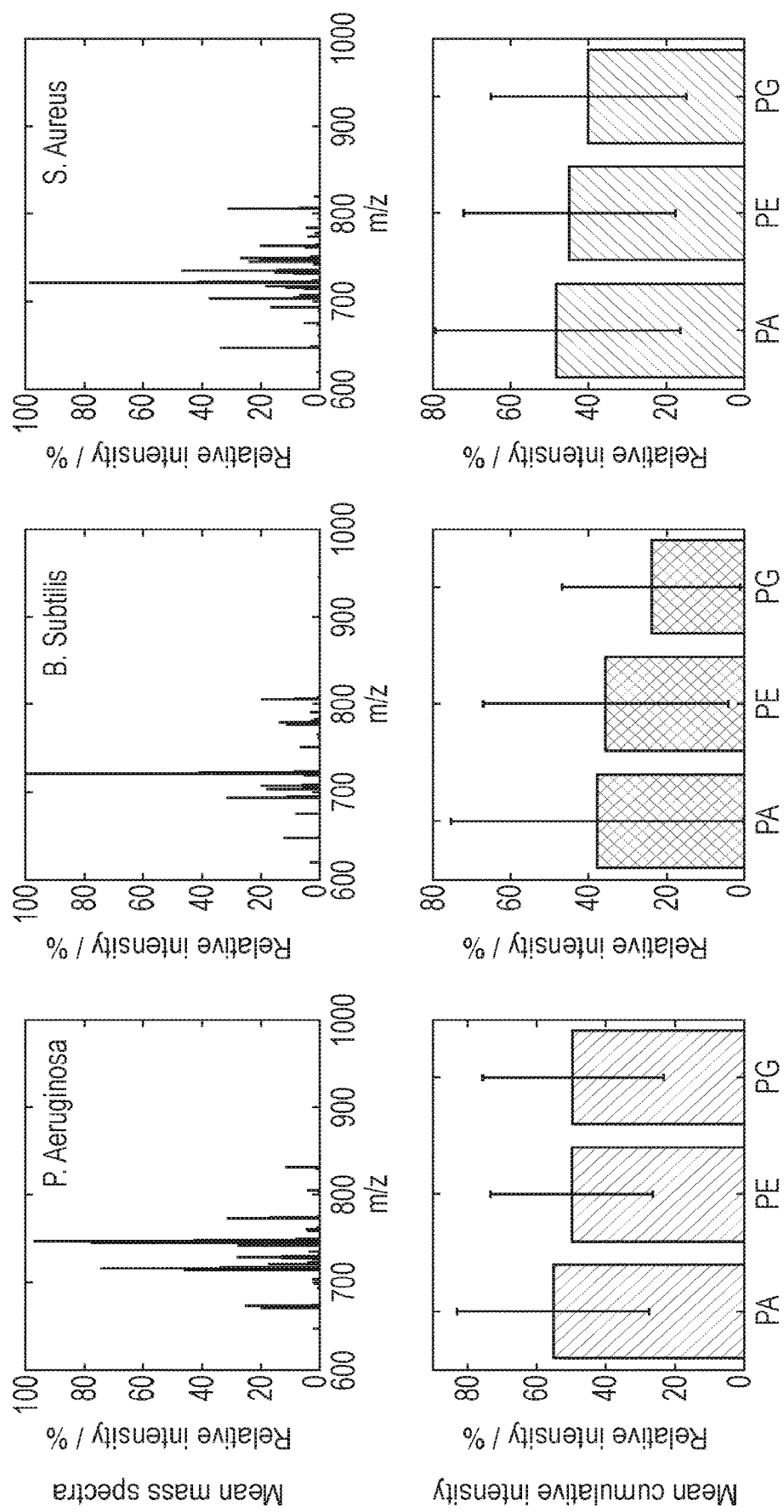
FIG. 77 shows mean mass spectra and mean phospholipid-class intensity levels for each lipid species wherein mean intensities of phospholipid classes are stable across the species, with highest level for PA class and lowest level for PG class and wherein PA: phosphatidic acid, PE: phosphatidyl-ethanolamine, PG: phosphatidyl-glycerol and wherein n(*P. aeruginosa*)=48, n(*B. subtilis*)=45, n(*S. aureus*)=52.

While structural cell membrane components such as PA(34:1) are equally distributed over the whole area covered by P. aeruginosa, the extracellular quorum-sensing metabolites are found in significantly higher abundance on the outer edge of the P. aeruginosa growth area as visualized for PQS (Pseudomonas quorum signal, 2-Heptyl-3-hydroxy-4(1H)-quinolone) in FIG. 77.

The area with high concentration of quorum-sensing molecules seems to correlate to the P. aeruginosa bacterial cells that were swarming from the main growth area. Quorum sensing molecules such as PQS are excreted by a wide variety of bacteria for both cell-to-cell communication within the same or between bacterial species. Quorum-sensing has been related to a wide variety of behaviours in P. aeruginosa including swarming and biofilm production. A comparison of the mean intensity levels of the phospholipid classes shows similar relative intensity distributions for PA, PE and PG classes across all bacterial strains (see FIG. 77). Cumulative intensity of PA ion species is slightly elevated compared to the other classes, being approximately 5% higher in intensity compared to PG class for P. aeruginosa and S. aureus and about 15% higher for B. subtilis.

The results demonstrate successful multivariate differentiation and identification of endogenous and exogenous bacterial species, while simultaneously allowing the spatially-resolved localization of metabolic features, eventually giving information on biochemical pathways and interactions between microbial species. A REIMS-based imaging platform additionally marks the first step towards an automated sampling system for microbial cultures for colony-to-colony sampling on a plate containing multiple organisms.

The automated nature of the REIMS imaging platform enables the systematic collection of reference mass spectra for use in spectral libraries necessary for classification of unknown tissue or bacteria. In both cases, REIMS imaging technology was able to clearly distinguish between healthy/cancerous tissue and between three bacterial strains. This enables the localization of metabolites within the growth area of bacteria as well as an automated identification system for microorganisms.

The ability to arbitrarily choose the material and the shape of the electrode provides a versatile application of the technology depending on the needs of the user, while the availability of two modes of sampling (pointing and cutting) adds another layer of flexibility. Principally, any conductive material with biological origin can be systematically analysed without pre-preparation by this technology, enabling a wide range of applications such as, tissue matrix analysis, bacterial identification or food quality management. Since REIMS mass spectrometric profiles varies across histological tumour types and bacteria, underlying biochemical information together with a large spectrometric database may provide additional information for future biomarker discovery or bacterial pathway exploration.

Analysis Using RE/MS Technology

In embodiments disclosed herein, for analysis using REIMS technology, two handheld electrodes in form of a forceps were used as the sampling probe (bipolar forceps, obtained from Erbe Elektromedizin, Tubingen, Germany). A Valleylab Force EZc power-controlled electrosurgical unit (Covidien, Dublin, Ireland) was used at 60 W power setting in bipolar mode as RF alternating current power supply (470 kHz, sinusoid). An approximately 1.5 m long ⅛ in. outer diameter, 1/16 in. inner diameter PTFE tubing (Fluidflon PTFE tubing; LIQUID-scan GmbH Co. KG, Überlingen, Germany) was applied to connect the embedded fluid line of the bipolar forceps and the inlet capillary of either an LTQ Orbitrap Discovery instrument (Thermo Scientific GmbH, Bremen, Germany), a Thermo Exactive instrument (Thermo Scientific GmbH), or a Xevo G2-S Q-TOF instrument (Waters Corporation, Manchester, UK). In each case the inherent vacuum system of the mass spectrometer was used for aspiration of the aerosol. This setup is shown in FIG. 55A-C while instrumental settings are given in the table below.

Instrumental Parameters of Orbitrap Discovery and Xevo G2-S Instruments Used in this Study.

| Parameter | Thermo Orbitrap Discovery Setting | Exactive Setting | Waters Xevo G2-S Parameter | Setting |
|---|---|---|---|---|
| Injection time | 1000 ms | 1000 ms | Scan time | 1000 ms |
| Microscans | 1 | 1 | Scan Mode | Sensitivity |
| Mass analyser | FTMS[a] | FTMS[b] | Mass analyser | TOF |
| Ion mode | negative | negative | Ion mode | negative |
| Mass range | 150-2000 | 150-2000 | Mass range | 150-2000 |
| Tube Lens Voltage | −120 V | −160 V | Sampling Cone | 30 V |
| Capillary Voltage | −40 V | −50 V | Source Offset | 80 V |

| Parameter | Thermo Orbitrap Discovery Setting | Exactive Setting | Waters Xevo G2-S Parameter | Setting |
|---|---|---|---|---|
| Skimmer Voltage | na | −24 V | Source Temperature | 150° C. |
| Capillary Temperature | 250° C. | 250° C. | | |
| Automatic Gain Control | Off | On | | |

[a] Orbitrap Discovery instrument is working at a resolution of 30,000 at m/z = 400,
[b] Mass analyser was used at a resolution of 50,000 (m/z = 200)

Mass spectrometric analysis of the microorganisms was typically performed directly from the solid culture medium, in which case about 0.1-1.5 mg of microbial biomass was scraped off the agar surface using one of the electrodes of the bipolar forceps. The two electrodes were subsequently brought into close proximity (i.e. by pinching the biomass between the tips of the forceps) and the RF power supply was triggered using a foot switch. The microbial biomass is rapidly heated up due to its non-zero impedance and an aerosol containing the analytes is produced and transferred directly into the mass spectrometer. Where possible, five individual measurements were performed for each strain and averaged as a database entry.

Culturing of Microorganisms

All clinical isolates analysed in some embodiments disclosed herein were routinely isolated during clinical microbiology work by trained NHS staff. Most of the microorganisms analysed during this study were previously isolated from blood cultures, identified using a Bruker Biotyper instrument, and stored on beads in a −80° C. freezer. For REIMS analysis, microorganisms were, for example, grown on a range of solid agar-based media commonly used in clinical microbiology settings. Media were purchased from Oxoid (Basingstoke, UK) or E&O Laboratories Ltd. (Bonnybridge, UK). The bacteria were incubated under appropriate atmospheric conditions at 37° C. overnight before analysis. Atmospheric conditions included aerobic (hot room), anaerobic (incubator), microaerophilic (jar in hot room), and aerobic containing 5% $CO_2$ (humidified incubator). Microaerophilic conditions were generated using a Whitley Jar Gassing System (Don Whitley Scientific Ltd., Shipley, UK).

Analysis of Bacteria Using REIMS Technology

When using REIMS technology to bacteria, the majority of phospholipid species detected can be ascribed to PAs, PEs and PGs. This can clearly be seen in Table 1, which shows the qualitative phospholipid distribution as obtained for nine different bacterial pathogenic species using exact mass measurements and tandem mass spectrometry measurements acquired during REIMS technology measurements. Only high abundance signals 5% relative abundance) were included. Distinct peak patterns can be obtained for all bacterial species, even for those that are closely related such as different *Streptococcus* spp. or members of the Enterobactereaceae family (*E. coli, C. koseri, K. pneumoniae, S. marcescens, P. mirabilis*). Most spectral patterns for both Gram-negative and Gram-positive species are seen to be dominated by high abundance quasi-molecular PG signals.

Generally, Gram-negative species display a higher amount of unsaturated phospholipid species and a higher relative amount of PEs. This is in good agreement with literature published about the bacterial phospholipid composition. *Staphylococcus aureus* (and other *Staphylococcus* spp.) are clearly distinguished from other bacterial species by the fact that they exclusively show signals arising from saturated phospholipid species.

Metabolite Identification

Bacterial metabolites were primarily identified based on exact mass measurements and literature references on compounds with the same exact mass that were found in the same bacterial species. Mass deviations were calculated using the following formula $$\Delta m[ppm] = \left| \frac{m_{exp} - m_{th}}{m_{th}} 10^6 \right|$$

with Δm=mass deviation (in ppm)
$m_{exp}$=experimental exact mass, 4 decimal places accuracy
$m_{th}$=theoretical exact mass, 4 decimal places accuracy Mass accuracies of 3 ppm were regarded to be confirming the proposed the sum formula. Further structural identifications were only made by additional literature references, confirmed by additional tandem mass spectrometry measurements if signal intensity was found sufficiently high and reference spectra were available. Fragmentation experiments were performed on either on a Thermo LTQ XL or Xevo G2-S instrument and using collision induced dissociation as fragmentation mechanism.

Distinction Between Bacteria and Yeast

There are marked differences in the phospholipid composition between bacteria and fungi. The inventors have determined that REIMS spectral profiles of bacteria differ extensively between different bacteria, whereas the REIMS spectra of fungi have an overall very conserved appearance with differences largely arising from different phospholipid ratios, rather than the presence or absence of certain lipid species. Thus, the method was successfully used to distinguish between bacteria and fungi.

Thus, optionally, the method may be used to detect the presence or absence of bacteria in a sample. Optionally, the method may be used to detect the presence or absence of fungi in a sample. Optionally, the method may be used to determine whether a microbe is a bacterium or a fungus. Optionally, the method may be used to detect the presence of bacterial contamination in a non-bacterial culture, such as, a fungal culture or an animal cell line culture. Optionally, the method may be used to detect the presence of fungal contamination in a non-fungal culture, such as, a bacterial culture or an animal cell line culture.

Candida Speciation

*Candida* species are found within the environment, soil and on surfaces. They can cause a range of infections from thrush to sepsis, and be a problem, e.g., in immune-compromised patients such as those suffering from HIV or cystic fibrosis. In the UK they are the 9th most common cause of bloodstream infections and 90% of these are due to *C. albicans*. It is clinically useful to speciate *Candida* species because *Candida* species other than *C. albicans* are typically more drug resistant and are often intrinsically resistant to azole antifungals.

Identification of yeasts using MALDI TOF MS requires the pre-treatment of the yeast sample prior to mass spectrometric analysis in order to give reliable identification performances (score ≥2.0). While the recommended sample pre-treatment for MALDI TOF MS comprises the complete extraction of the fungal material using formic acid and acetonitrile, intact yeast species can directly be analysed without any modifications in experimental setup or analysis workflow.

Seven different *Candida* species were sampled and examined using the forceps method and REIMS.

Figure 78A:
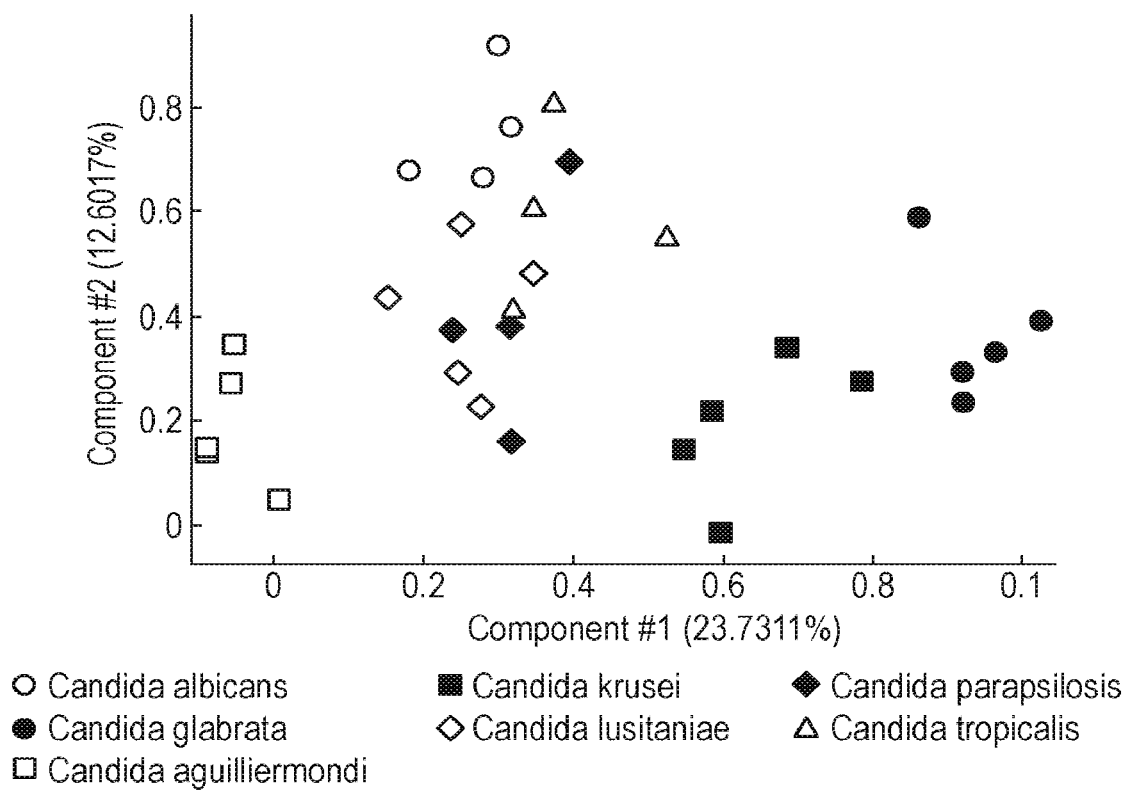
FIG. 78A shows PCA analysis of 7 *Candida* species using REIMS technology.
Figure 78B:
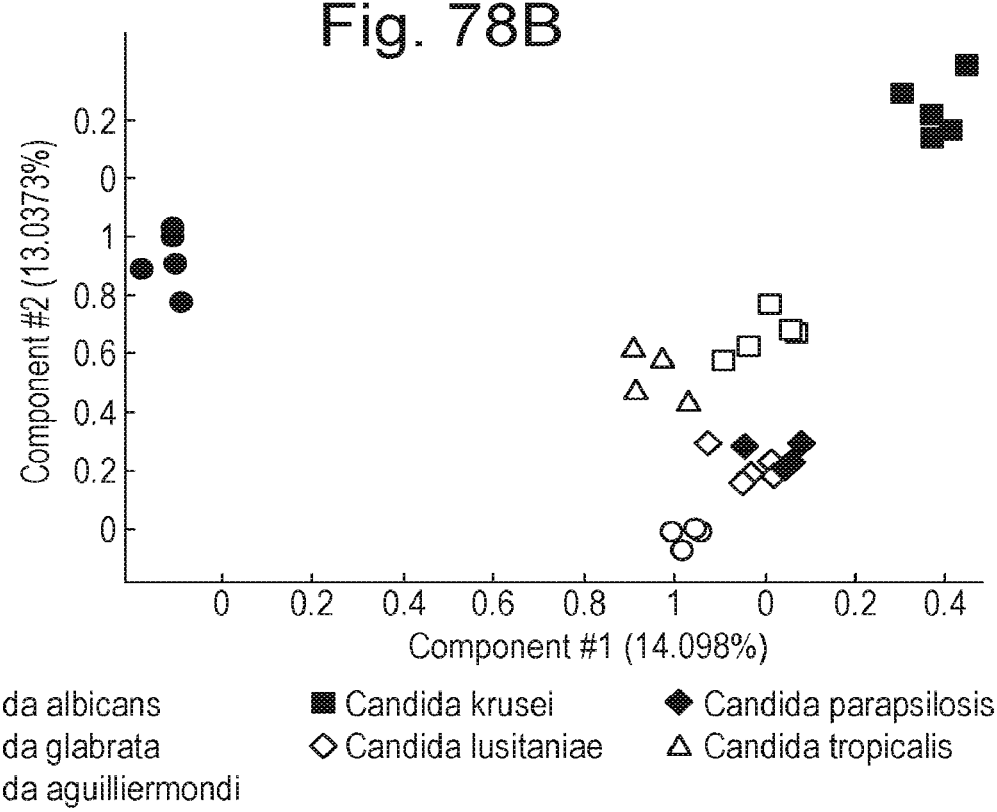
FIG. 78B shows LDA analysis of 7 *Candida* species using REIMS technology.

As shown in FIG. 78, it was possible to distinguish all species. Leave one out cross validation scores were 100%. In this Example, the spectrometric data of any of the tested *Candida* species may serve as a "comparator" spectrometric data with respect of each of the other tested species. Alternatively or in addition, the spectrometric data of any of these species may be compared to "reference" spectrometric data of one or more known *Candida* species.

Thus, optionally, the method may be used to detect, identify and/or characterise one or more *Candida* species. Optionally, the method may be used to detect or confirm the presence or absence of *C. albicans* in a sample, for example by comparing the spectrometric data from the sample to a reference spectrometric data of *C. albicans*.

Optionally, the method may be used to detect or confirm the presence or absence of one or more *Candida* species selected from *C. albicans, C. gaibrata, C. krusei, C. guilliermondii, C. lusitaniae, C. parapsilosis* and/or *C. tropicalis*.

Optionally, the method may be used to detect or confirm the presence or absence of one or more *Candida* species selected from those listed elsewhere herein.

The sample may optionally be known to contain at least one yeast species, e.g., one *Candida* species.

Analysis of Microbial Mixtures

To determine whether species specific peaks could be observed from mixed cultures, known quantities of bacteria were amalgamated and analysed using forceps based REIMS. For example, as shown in FIGS. 79A-C, when 10 µl of *E. coli* and *C. albicans* were mixed together and analysed using REIMS, species specific peaks could be observed within the mixed spectra.

Figure 79C:
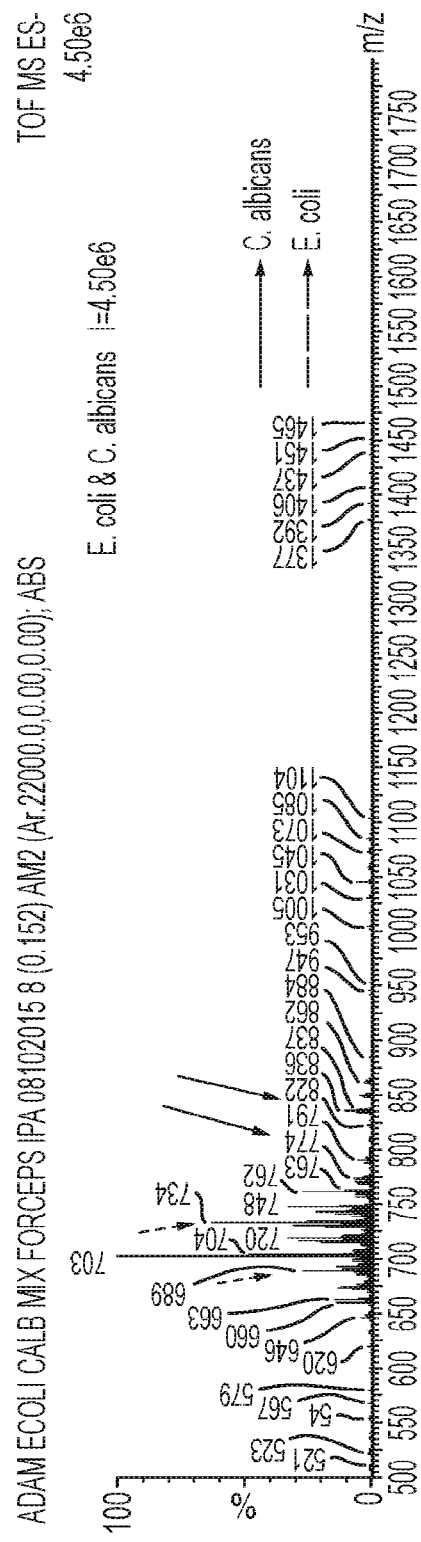
FIG. 79C shows spectral profiles of an amalgamated sample containing an equal ratio of the two, wherein isolate specific peaks are highlighted.

FIG. 79A shows a mass spectrum of *Escherichia coli*, FIG. 79B shows a mass spectrum of *Candida albicans* and FIG. 79C shows a mass spectrum of a mixture of *Escherichia coli* and *Candida albicans*.

Thus, embodiments may comprise detecting, identifying and/or characterising a sample comprising a microbial mixture. By "microbial mixture" is meant that at least 2 different microbes are present in a sample, so a first and a second microbe may be present. Optionally, at least 3, 4, 5, 6, 7, 8, 9 or at least 10 different microbes are present in the sample. Optionally, the different microbes are taxonomically different, e.g., different strains, species, genera, classes or the like. In another embodiment, the different microbes differ at least in one characteristic, such as drug sensitivity or the ability to produce a particular compound. Thus, optionally, the different microbes may be identical or different at a taxomonic level such as Gram stain, class, family, genus, species and/or strain.

Optionally, the method may be used to detect, identify and/or characterise 1, 2, 3, 4, 5, 6, 7, 8, 9 or 10, or at least 1, at least 2, at least 3, at least 4, at least 5, at least 6, at least 7, at least 8, at least 9 or at least 10 of the microbes present in a sample comprising a microbial mixture.

Optionally, embodiments may comprise confirming the presence or absence of *E. coli* and/or *C. albicans* in a sample. Optionally, the sample may comprise a microbial mixture.

Subtyping of Microbes

Microbial typing provides information on the genetic relationships between strains. This process is critical for tracking the spread of infectious diseases, informing infection control practices and, in some instances, providing useful information about the nature of the microbe, for example whether it is a highly pathogenic variant. The suitability using REIMS technology to provide accurate strain level discrimination was shown using various examples as discussed below.

Ribotyping of *C. difficile*

*Clostridium difficile* is a Gram-positive anaerobic bacterium and its derived infections are often nosocomially (i.e. in a hospital) acquired infections obtained after broad-band antibiotic treatment, which allows excessive growth of this more hardy and spore-forming species. *Clostridium difficile* is an important cause of antibiotic associated diarrhoea and has a case fatality rate of up to 30%. Typing information is used clinically to understand the epidemiology of disease and to determine whether an isolate has been transferred from one patient to another. In routine clinical microbiology, severe *C. difficile* outbreaks are often associated with certain ribotypes such as ribotype 027 or 078 which are thought to be especially pathogenic. Therefore, it is especially interesting for clinical microbiology labs to establish whether an infection was acquired during the hospital stay (nosocomial—all patients would be expected to have been infected by a strain of the same ribotype) or whether the infection was caused by a strain acquired before entering the hospital (different patients may be expected to be infected by strains of different ribotypes).

Ribotyping of *C. difficile* is routinely performed by isolating *C. difficile* on specific media, such as Braziers medium, and subsequently performing PCR amplification of the 16S-23S intergenic spacer region to determine the ribotype pattern. This process is very time consuming and labour intensive, so the specificity of the REIMS technique was investigated for this particular problem.

As *C. difficile* sporulates in adverse conditions, this may affect the cell membrane lipids in turn affecting spectral profiles. Culture conditions should be standardised to reduce any confounding factors that may introduce differences in the spectral patterns.

10 strains of each of three different ribotypes of *C. difficile* were cultured on Columbia blood agar for 24 hrs under anaerobic conditions. The ribotypes included 002 and 014 which are thought to be less pathogenic and the more pathogenic ribotype 078. Clear separation trends can be observed (see FIG. 80). Overall cross-validation accuracy was 90%. Thus, using REIMS technology can provide strain level information.

Typing of *Pseudomonas aeruginosa*

*Pseudomonas aeruginosa* (*P. aeruginosa*) is an organism that while ubiquitous and generally not pathogenic, can cause severe infections including sepsis and pneumonia. It is also a significant pathogen for Cystic Fibrosis ("CF") patients where it can lead to exacerbations. Currently *P. aeruginosa* isolates are commonly typed by Variable Number Tandem Repeat (VNTR) testing, e.g., at the Public Health England reference laboratory.

REIMS technology was successfully used to distinguish between two different *P. aeruginosa* strains obtained from CF patients (data not shown).

Typing of *Escherichia coli*

REIMS technology was successfully used to distinguish between two different *E. coli* strains: OP50, derived from parent strain B, and C600 derived from parent strain K-12 (data not shown).

Serotyping of *Streptococcus pneumoniae*

*Streptococcus pneumoniae* is a Gram-positive bacterium that causes a variety of infectious diseases in children and adults, including bacteremia, meningitis and infections of the respiratory tract. Young children and the elderly are most affected and it is estimated that about one million children die of pneumococcal disease every year, especially in developing parts of the world. *Streptococcus pneumoniae* cells are covered with layers of polysaccharides forming a capsule which is an essential factor in virulence. 91 distinct pneumococcal serotypes have been identified, however, only a comparably small number of these serotypes are accounting for most diseases in infants. Identification of *S. pneumoniae* serotypes is most commonly performed using the Quellung reaction which involves adding an antibody solution to a broth of *S. pneumoniae* and observing a positive reaction indicated by "swelling" of the bacterial cells. This test is labourious and time-consuming and consists of a range of subsequent individual tests until a serotype is unambiguously identified. Usually antibody solutions are added in mixtures of several antibodies at a time to reduce amount of tests necessary. Molecular serotyping methods involving PCR are rather expensive and need extensive sample processing. Therefore, a straightforward way to distinguish between different pneumococcal serotypes without the need to introduce further sample processing steps besides those needed for species-level identification would have a huge impact on daily microbiological practice.

REIMS technology was successfully used to distinguish between two different *Streptococcus pneumonia* serotypes, serotype 14 and serotype 3 (data not shown).

Thus, embodiments may comprise microbial typing, such as strain typing, ribotyping and/or serotyping, optionally *C. difficile* ribotyping *Streptococcus pneumonia* serotyping, typing of *E. coli* and/or typing of *P. aeruginosa* strains.

Conventionally, ribotyping is the characterization or classification of bacteria on the basis of their rRNA gene sequences. It can be done, e.g., by 16S rRNA gene PCR-RFLP and sequencing. Optionally, embodiments may comprise analysing, e.g., whether a microbe has a particular ribotype, to distinguish between 2 or more microbes having different ribotypes, to detect a microbe having a particular ribotype, and the like.

Conventionally, serotyping is the characterization or classification of microbes On the basis of particular surface structures. Optionally, embodiments may comprise analysing, e.g., whether a microbe has a particular serotype, to distinguish between 2 or more microbes having different serotypes, to detect a microbe having a particular serotype, and the like.

Antimicrobial Susceptibility Testing ("AST")

Antibiotic resistance of microbes is a global problem of increasing significance that often can significantly complicate treatment of infections. The protein profiles that are acquired during routine MALDI TOF analysis do not contain information on the antibiotic sensitivity and resistance pattern. As discussed elsewhere herein, culture-based methods for testing antibiotic sensitivity are time-consuming.

*Staphylococcus aureus* can cause a range of infections including pneumonia, bacteraemia and skin and soft tissue infections. Methicillin resistant *Staphylococcus aureus* (MRSA) strains are resistant to beta-lactam antimicrobials and result in increased length of hospital stays, higher economic costs and poorer clinical outcomes. Moreover, it is a leading cause of Hospital Acquired Infections (HAIs) and is estimated to account for 44% of HAIs in the EU each year. Because MRSA colonisation has been identified as a major risk factor in the development of an MRSA infection, and to curb nosocomial spread, universal or targeted screening programmes are often adopted.

30 MRSA and 30 methicillin susceptible *S. aureus* (MSSA) isolates were examined using REIMS technology. LDA and cross validation analysis (FIG. 81) revealed a clear separation of MSSA and MRSA isolates indicating that the embodiments can provide a useful tool for MRSA screening.

REIMS technology was also successfully used to distinguish between some antimicrobial-resistant (cabapenemase-producing) and antimicrobial-sensitive (not cabapenemase-producing) strains of *Klebsiella pneumonia*.

Thus, embodiments may comprise detecting, identifying or characterising a microbe having sensitivity to an antimicrobial. Embodiments may comprise detecting, identifying or characterising a microbe having resistance to an antimicrobial. Embodiments may comprise distinguishing between antimicrobial-resistant and antimicrobial-sensitive microbes.

Optionally, the antimicrobial may be selected from any of the antimicrobials disclosed elsewhere herein.

Optionally, the antimicrobial-resistant microbe may be selected from a producer of β-lactamase, such as cabapenemase or TEM-1 β-lactamase; a producer of chloramphenicol acetyltransferase, a producer of a tetracycline efflux system, a producer of AmpC cephalosporinase; and/or an over-producer of DHF (dihydrofolate) reductase.

Optionally, the antimicrobial-resistant microbe may be MRSA and/or the antimicrobial-sensitive microbe may be MSSA.

Imaging Platform

An imaging platform (i.e. ion imager) can enable automated high-throughput collection of reference mass spectra in order to aid real-time classification in MS-guided electrosurgery (iKnife technology) applications. For example, according to an embodiment, the classification algorithm (i.e. sample classification model) may compare mass spectral patterns of spectra created during surgery with mass spectra obtained ex vivo, in vivo or in vitro. Accordingly, it is important that the rapid evaporative ionization mass spectrometry imaging platform provides similar ionization conditions as will be used in surgery.

Thus, according to this embodiment, a plurality of different locations of a sample are sampled using a device arranged and adapted to generate aerosol, smoke or vapour from the sample to obtain mass spectral data at each location. A sample classification model which was previously constructed, trained or improved according to a method of ion imaging as described herein is then used in order to classify the sample at each location.

Commercially available electrosurgical generators as used in operating theatres provide highly reproducible mass spectral patterns which are unique for different histological tissue types. The power supply setup used in conjunction with the imaging platform (as shown schematically illustrated in FIG. 72) may allow variation in the amplitude and/or frequency and/or waveform, while an oscilloscope may provide feedback ensuring correct working conditions. Depending on the application of the imaging platform, the experimental parameters can thus be changed in order to alter ionization conditions and to meet the requirements for recording reference mass spectra for intra-surgical tissue identification or bacterial classification purposes.

Rapid evaporative ionization mass spectrometry ionization mechanism is based on Joule-heating which is a thermal process wherein the heat created is proportional to the square of electric current and the impedance. As electric current density is also a function of cross sectional area, the contact surface area of the electrosurgical tip of the sampling probe 21 also has an impact on the heating process.

If an electric current is applied to a biological tissue then the intracellular temperature rises up to a point of vaporization where excess heat facilitates evaporation of particles and ions leading to the formation of surgical aerosol. The major ions created in this process are singly charged lipids being most abundant in the m/z 600-1000 mass range for eukaryotic tissue and additionally in the m/z 1100-1500 mass range in case of bacteria in form of e.g., lipid dimers or cardiolipins.

Depending on the thermal stability of the molecules, thermal degradation may occur as it was observed in the case of phosphatidyl-ethanolamine species which are partly ionized to both $[M-NH_4]^-$ and $[M-H]^-$, while other phospholipids species form $[M-H]^-$ ions. The density and frequency of the electric current can therefore have an important influence on the appearance of the mass spectrum.

Electrosurgical generators have an incorporated control loop providing constant power when cutting through tissue, even if the impedance is rapidly changing. This leads to gentle and reproducible cuts with minimized tissue heat exposure. Electrosurgical generators are not easily incorporated into an imaging set up due to a number of safety measures required when used in theatre, hence a simplified power supply was built. Since a p-p voltage amplitude-controlled RF power supply cannot follow the changing impedance of the sample, it was important to determine whether the simplified setup can provide spectra similar to those obtained when using proper electrosurgical equipment.

Optimization of the rapid evaporative ionization mass spectrometry imaging platform was carried out by finding the optimal frequency and voltage values to match the iKnife technology reference mass spectral pattern of porcine liver as shown in FIGS. 82A-B and FIGS. 83A-B. Concordance correlation coefficients ("CCC") between the rapid evaporative ionization mass spectrometry imaging and iKnife technology mass spectra were used as a quantitative measure to find the optimal spectral agreement.

In cutting mode, a factor influencing tissue heat exposure is cutting speed, which leads to high localized temperature for slow speeds and vice versa. Depending on the required ion current, the MS sampling time window needs to be sufficiently long, compromising either spatial resolution or cutting speeds. Therefore, prior to voltage and frequency optimization, a cutting speed should be chosen that satisfies requirements on ion yield and spatial resolution. Once a cutting speed is set, heat exposure can then be controlled by changing the voltage or frequency output of the power generator setup. The cutting speed may need further reiteration if the available range of voltages and frequencies is not sufficient for adequate heat production. An exemplary cutting speed of 1 mm/s was found to gently cut at high ion yields.

Figure 82A:
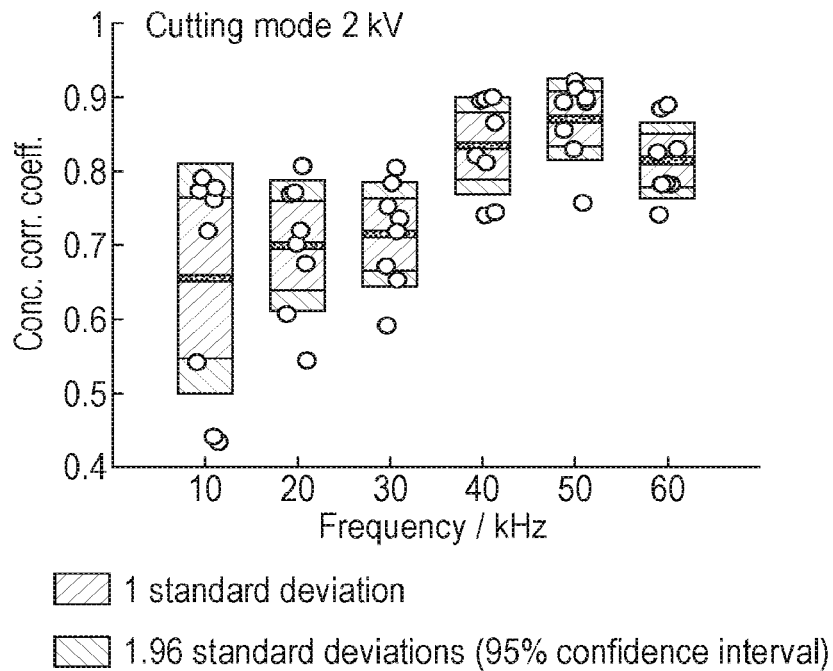
FIG. 82A shows concordance correlation coefficients (CCC) between rapid evaporative ionization mass spectrometry imaging in a cutting mode of operation and iKnife technology mass spectra in dependency on varying frequency at 2 kV for porcine liver and FIG. 82B shows concordance correlation coefficients (CCC) between rapid evaporative ionization mass spectrometry imaging in a cutting mode of operation and iKnife technology mass spectra in dependency on varying voltage at 40 kHz for porcine liver.

As shown in FIG. 82A, at a constant p-p voltage of 2 kV an increase in frequency leads to less thermal degradation and higher similarity to iKnife technology patterns. According to the oscilloscope readout, the power generator setup was not capable of maintaining a constant increase in power output above 50 kHz at a 2 kV amplitude, explaining the stable concordance correlation coefficient between about 40 kHz and about 60 kHz. At lower frequencies more in-depth heat dissipation was observed leading to wide burning valleys, carbonization and inconsistent mass spectral patterns with varying baseline noise levels. This was accompanied by strong soot particle production leading to contamination of the MS-inlet capillary, without contributing to the ion yield (see the total ion counts in FIG. 83A).

At higher frequencies (above about 40 kHz) visible soot particle production was negligible and no carbonization was observed. This led to mass spectral patterns very similar to those produced by electrosurgical equipment, as indicated by concordance correlation coefficients near 0.9. The highest and most consistent TIC was also found to be in that frequency window.

Figure 82B:
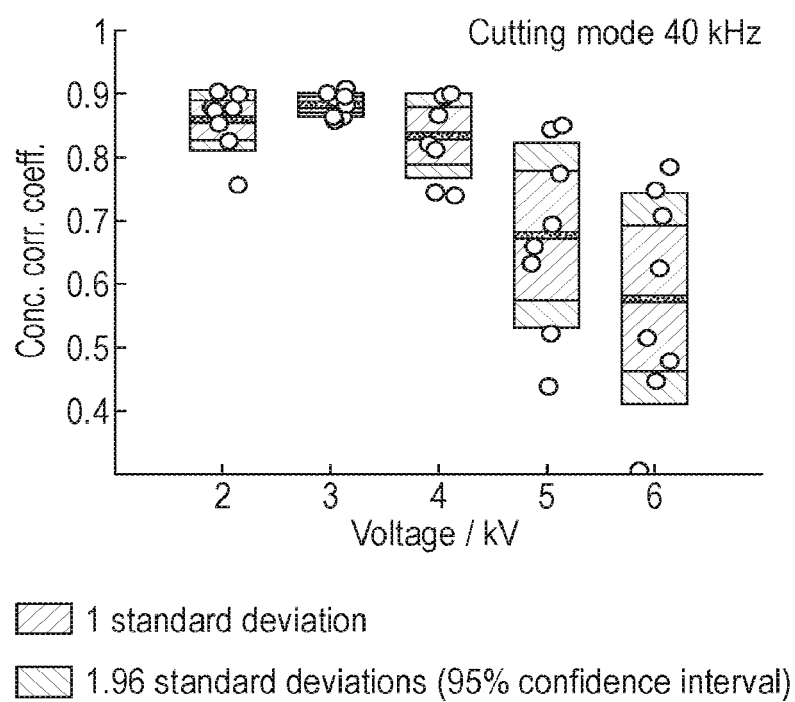
Figure 83A:
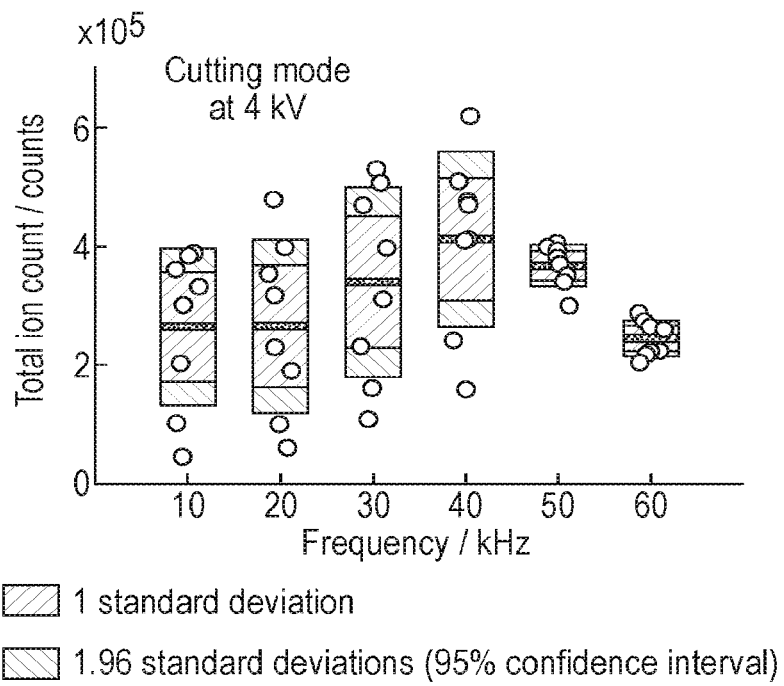
FIG. 83A shows total ion counts (TIC) at different frequencies in a cutting mode of operation and FIG. 83B shows total ion counts (TIC) at different voltages in a cutting mode of operation.
Figure 83B:
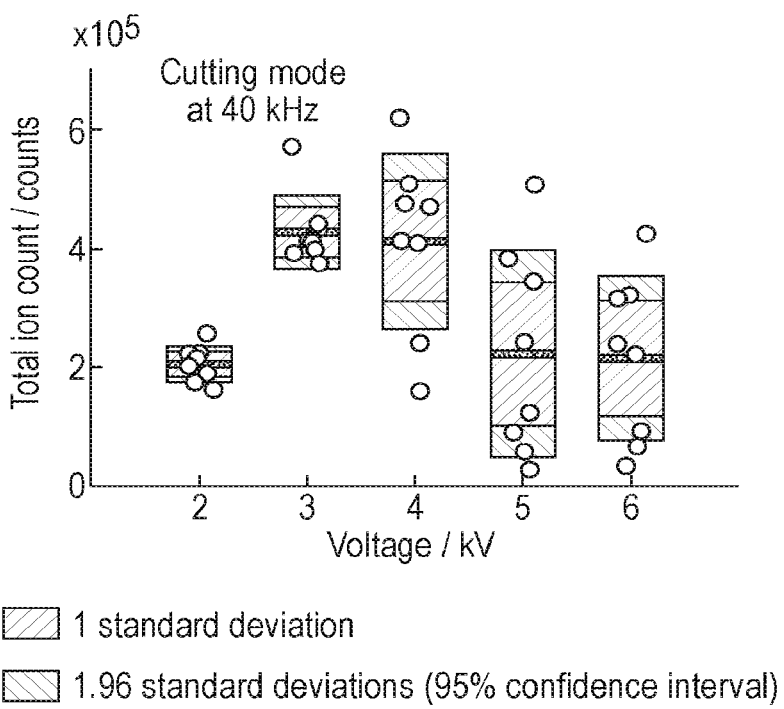
Figure 84A:
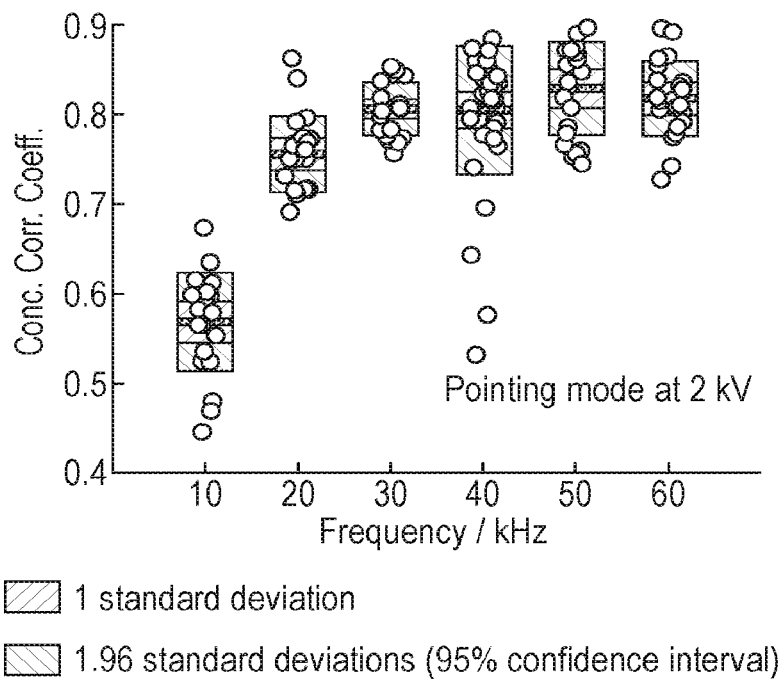
FIG. 84A shows concordance correlation coefficients between rapid evaporative ionization mass spectrometry imaging in a pointing mode of operation and iKnife technology mass spectra in dependency on frequency.
Figure 84B:
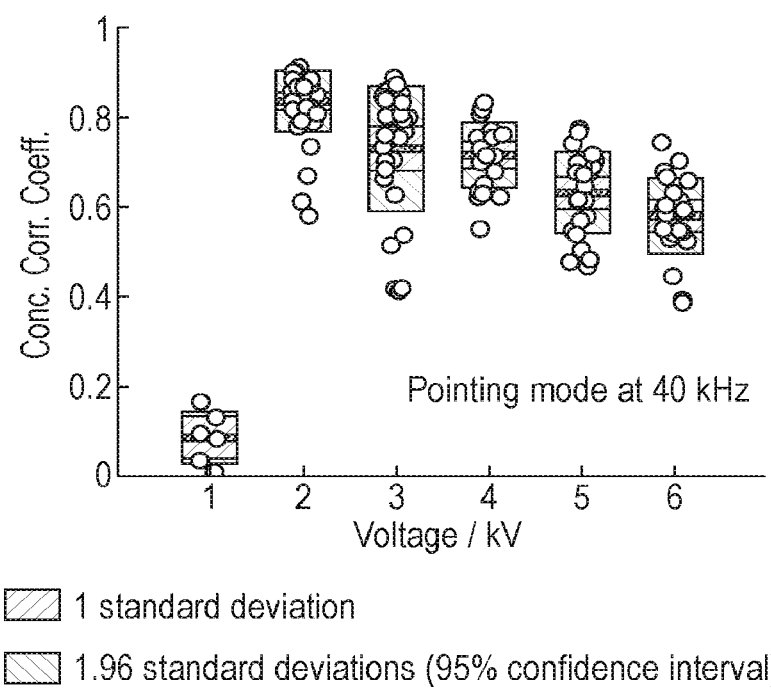
FIG. 84B shows concordance correlation coefficients (CCC) between rapid evaporative ionization mass spectrometry imaging in a pointing mode of operation and iKnife technology mass spectra in dependency on voltage.
Figure 84C:
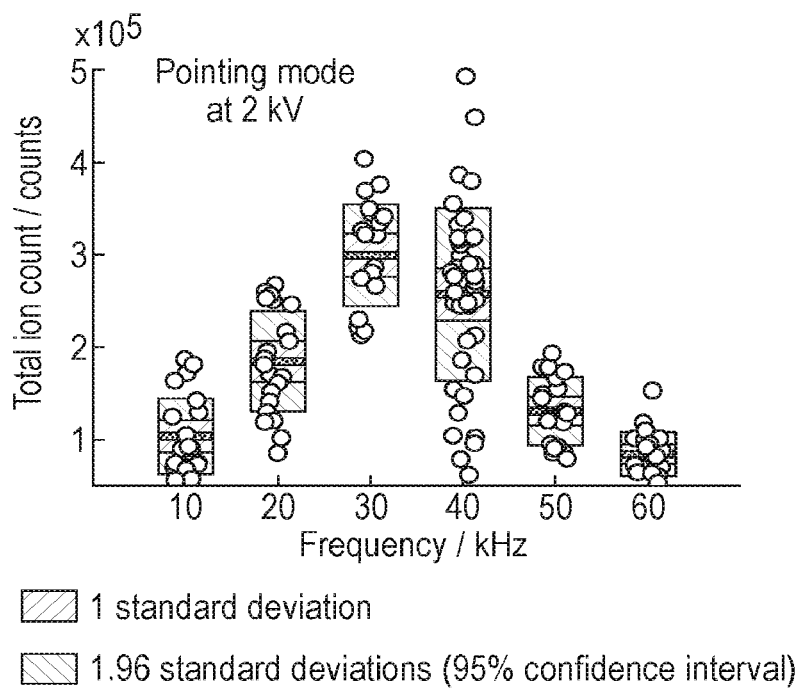
FIG. 84C shows total ion counts (TIC) at different frequencies in a pointing mode of operation and FIG. 84D shows total ion counts (TIC) at different voltages in a cutting mode of operation.
Figure 84D:
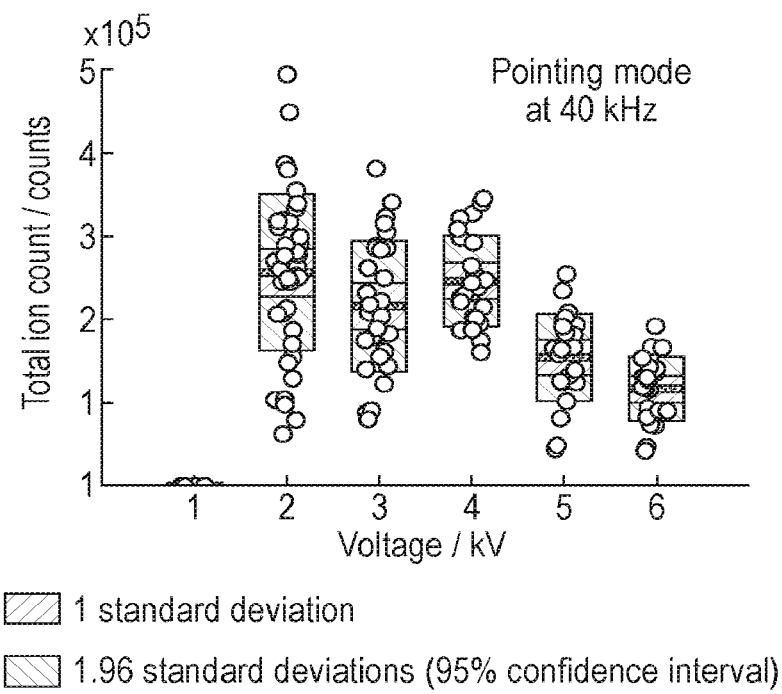

As shown in FIG. 82B, an increase in voltage at 40 kHz frequency resulted in similar phenomena as observed with decreasing frequency, such as carbonization and wide burning valleys, leading to high concordance correlation coefficients to be found at low voltages. However, once the voltage was set below about 2 kV, ion currents dramatically dropped (see the total ion counts in FIG. 83B). This led to an optimal parameter window between about 3-4 kV and about 40-50 kHz where concordance correlation coefficients are high and the total ion yield was also sufficient.

Similar behaviour was observed in a pointing mode of operation, as shown in the parameter optimization plots of FIGS. 84A-D which show the total ion counts and the concordance correlation coefficients between the rapid evaporative ionization mass spectrometry imaging and iKnife technology reference spectra at different operating frequencies and voltages. A difference between a pointing and a cutting mode of operation is the time the electrosurgical tip of the sampling probe 21 is in contact with the same part of tissue. In a cutting mode of operation, the tip is constantly moving and therefore continuously touches fresh tissue, whereas the tip remains at the same tissue spot for a defined amount of time in a pointing mode of operation. This leads to longer exposure of heat, thus voltage and frequency have to be chosen in a way that carbonization is kept at a minimum. At the same time, longer exposure also creates more ions, decreasing the need for higher voltages to gain a sufficiently high TIC. By decreasing the time the tip remained about 1 mm inside the sample to a value of about 0.1 s, the exposure could be successfully decreased so that burn crater diameter was about 500 μm while providing good TICs and concordance correlation coefficients at about 2 kV and about 40 kHz.

The impact of heat exposure on the mass spectral pattern is shown in FIGS. 85A-C. FIGS. 85A-C illustrate changes in mass spectral patterns of porcine liver obtained in cutting mode for high (FIG. 85A) and low (FIG. 85B) voltages compared to an iKnife technology reference spectrum (FIG. 85C). There is a prominent peak in all mass spectra at m/z=885.5 which is identified as a phosphatidyl-inositol species $[PI(38:4)-H]^-$.

The iKnife technology reference mass spectrum shown in FIG. 85C shows the highest TIC together with the most distinct intensity difference between the PI peak and all other phospholipid signals. The signal to noise ratio decreases with increasing voltage, which particularly impacts the spectral pattern in the mass range between about m/z 600 and 1000, used for classification. Although the intensity difference between the PI peak and all other peaks is larger for the 2 kV (FIG. 85B) compared to the 6 kV spectrum (FIG. 85A), the TIC of the 2 kV spectrum is lower, indicating a lower level of chemical noise.

Figure 86:
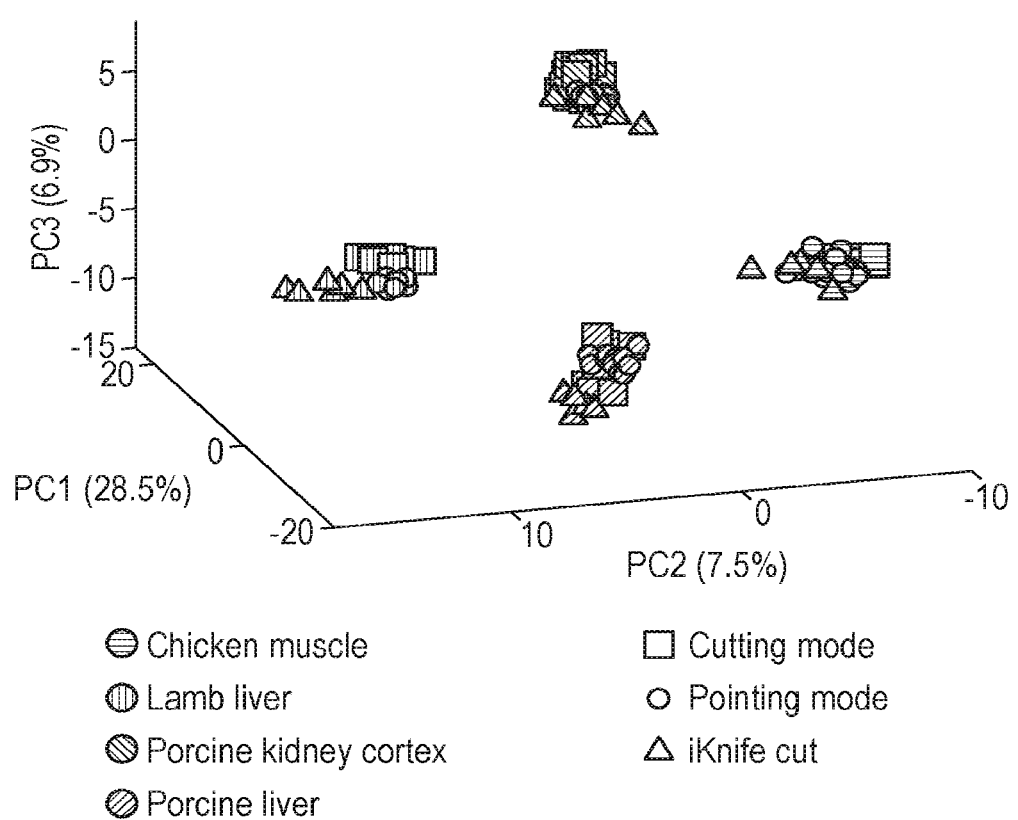
FIG. 86 shows a principal component analysis plot of various kinds of tissue types analysed with the same experimental rapid evaporative ionization mass spectrometry imaging parameters for cutting and pointing modes respectively.

Optimized cutting and pointing mode parameters were used to analyse various types of tissues from different animals, including porcine and lamb liver, porcine kidney cortex and chicken skeletal muscle. Additionally, all samples were analysed by proper electrosurgical equipment ('iKnife' technology setup) to ensure selected experimental rapid evaporative ionization mass spectrometry imaging parameters are suitable for multiple tissue types. Principal component analysis of the data showed that the overall variance is mostly associated with the tissue types, not the modes of analysis (see FIG. 86). This demonstrates that the experimental parameters are universally applicable to various tissue types in terms of matching the iKnife technology reference mass spectral patterns.

Imaging Liver with Metastatic Tumour

Figure 87:
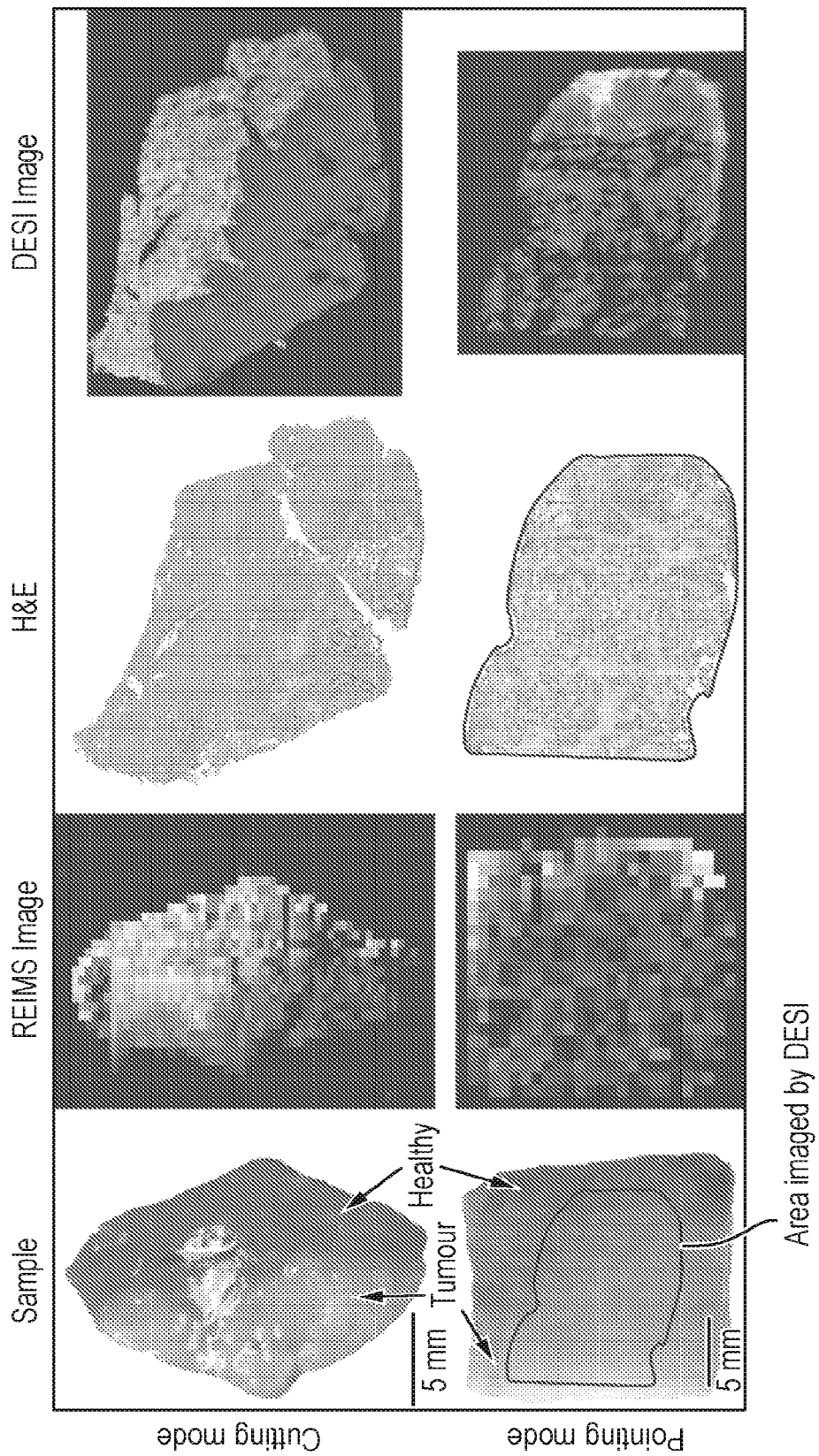
FIG. 87 shows a sample, H&E and mass spectrometric multivariate images of liver samples with metastatic tumour analysed by rapid evaporative ionization mass spectrometry and Desorption Electrospray Ionisation ("DESI") wherein it is apparent that both techniques clearly differentiate the tissue types.

The imaging capability of the novel rapid evaporative ionization mass spectrometry platform (i.e. ion imager) was studied using human liver tumour samples (as illustrated in FIG. 87). For demonstration of the versatility of the platform a cutting mode rapid evaporative ionization mass spectrometry image was obtained on a first instrument whilst a pointing mode image was obtained on a Time of Flight mass spectrometer. Spatially resolved mass spectrometric information was co-registered with H&E (haematoxylin and eosin) stained tissue images to locate mass spectra with the desired histological identity. Supervised multivariate analysis of the tissues revealed clear distinction between healthy and cancerous tissue for both rapid evaporative ionization mass spectrometry imaging and Desorption Electrospray Ionization ("DESI") imaging data.

The Desorption Electrospray Ionization ("DESI") images show a sharp border between the two tissue types as a result of the high spatial resolution and small pixel size of 100 µm. The upper half of the cutting mode rapid evaporative ionization mass spectrometry image contains pixels of mixed healthy and tumour pattern influences causing a blurred border. A possible explanation is due to the direction of the rapid evaporative ionization mass spectrometry cut that was performed which started at healthy tissue and continued towards the tumour region. This might have caused transport of tumour tissue pieces into the healthy area. Another reason may be inhomogeneous tissue below the surface of the seemingly cancerous area.

Assuming that the mass spectra are to be used as reference data for the iKnife technology, then only pixels with a high class-membership probability should be used for training the multivariate models (i.e. the sample classification model).

Figure 88:
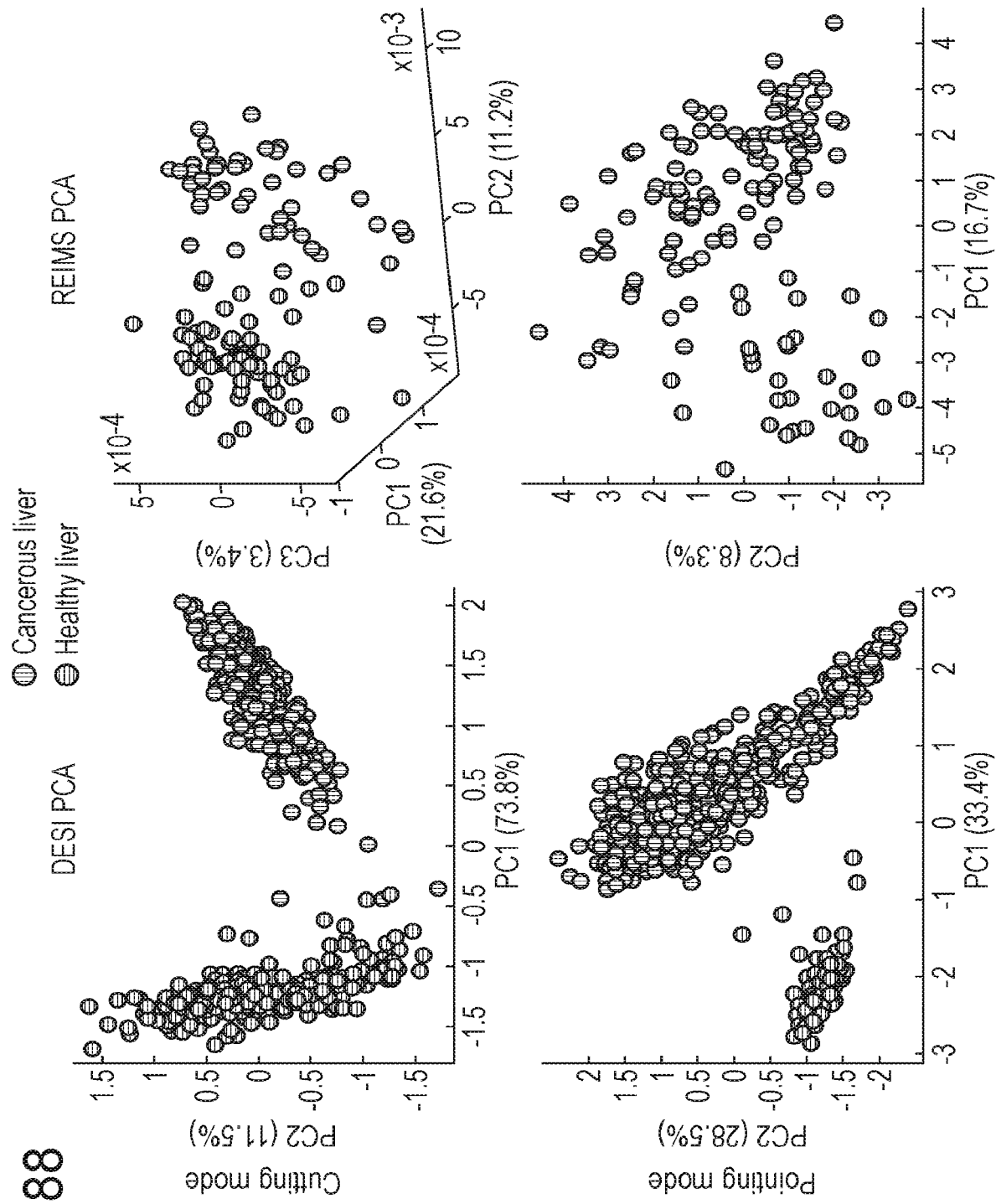
FIG. 88 shows principal component analysis plots of healthy and cancerous liver tissues for rapid evaporative ionization mass spectrometry imaging cutting and pointing modes as well as for Desorption Electrospray Ionisation ("DESI") data wherein PC is the principal component and percentage values are explained variance.

Unsupervised principal component analysis (PCA) demonstrates high intra-tissue-type spectral similarity together with spatially distinct clustering of healthy and cancerous data points in PCA space (see FIG. 88).

Desorption Electrospray Ionization ("DESI") imaging data acquired at high spatial resolution can also be used to locate histological fine structures and their corresponding mass spectra which can then be co-registered with the rapid evaporative ionization mass spectrometry data. A limiting factor for co-registration of Desorption Electrospray Ionization ("DESI") and rapid evaporative ionization mass spectrometry data is the spatial resolution currently achievable with the preferred rapid evaporative ionization mass spectrometry platform. While the cutting mode image was recorded at 500 µm pixel size, the pointing mode image features 750 µm sized pixels. In the case of this liver metastasis sample, the resolution is sufficient. However, in case of tissues with higher heterogeneity, higher spatial resolution images may be advantageous. The spatial resolution may be increased to decrease the diameter of the electrosurgical tip of the sampling probe 21 which would also be accompanied by lower spectral intensities. However, by connecting the sampling probe directly to the mass spectrometer inlet capillary (as is also done in the bipolar forceps approach described above) ion yield improves, thus overcoming the possible sensitivity issue. This also allows less penetration in z-direction, decreasing the probability of ionizing unanticipated tissue types.

Multivariate analysis of the liver metastasis samples shows a clear distinction of tissue types based on their molecular ion patterns. While rapid evaporative ionization mass spectrometry and Desorption Electrospray Ionization ("DESI") exhibit different ionization mechanisms resulting in mass spectrometric patterns that are not directly comparable to each other, univariate biochemical comparison of single ions provides a comparable measure for Desorption Electrospray Ionization ("DESI") and rapid evaporative ionization mass spectrometry co-registration. For certain compounds, the relative intensity difference between two tissue types is similar across all tissue types, ionization techniques and rapid evaporative ionization mass spectrometry analysis modes (cutting and pointing modes). This enables Desorption Electrospray Ionization ("DESI") to be used as a fold-change intensity-predictor for rapid evaporative ionization mass spectrometry based on up- and down-regulated compounds, which ultimately represents additional information for unknown tissue type identification. The higher spatial resolution of Desorption Electrospray Ionization ("DESI") allows the up- and down-regulated ions to be registered with certain histological features which may not be resolvable by rapid evaporative ionization mass spectrometry. This gives insight to the underlying histological composition of a tissue if certain changes in single ion intensities are observed in low resolution rapid evaporative ionization mass spectrometry.

Figure 89:
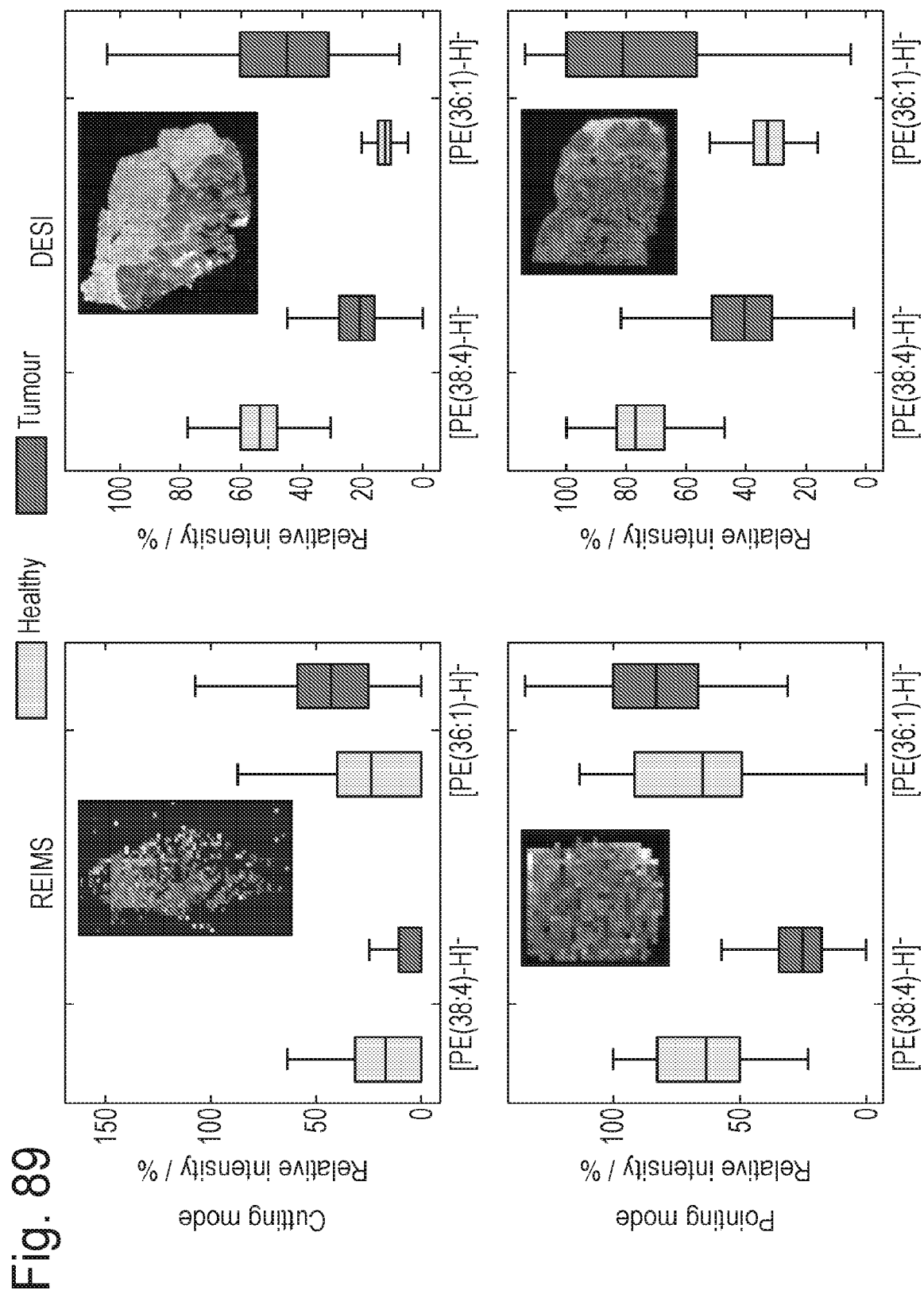
FIG. 89 shows an univariate intensity comparison of single phospholipid ion species wherein the depicted images of samples are ion-images of the respective ions and Desorption Electrospray Ionisation ("DESI") and rapid evaporative ionization mass spectrometry show similar relative intensity values for the same ions wherein PE is phosphatidyl-ethanolamine.

In the case of metastatic liver comparison, two different phosphatidyl-ethanolamine (PE) species were found to possess opposite relative intensities between healthy and metastatic tissue types as shown in FIG. 89. The represented images are ion images of the two PE ion species. PE(38:4) has a higher abundance in healthy tissue in all four cases, with the rapid evaporative ionization mass spectrometry cutting mode image showing barely any presence of this ion in tumour tissue. However, compared to the Desorption Electrospray Ionization ("DESI") images where this lipid is well abundant even in tumour tissue, the absence of intensity has to be associated with the lower sensitivity achieved by rapid evaporative ionization mass spectrometry cutting. Opposite behaviour is seen by the ion $[PE(36:1)-H]^-$ showing elevated intensities in tumour tissue.

Future research will be dedicated to the comparison of multiple samples to obtain cross-validated relative intensity levels for ions of interest. Once enough data is collected, Desorption Electrospray Ionization ("DESI") can serve as a biochemical blueprint, allowing tissue types to be histologically annotated with higher confidence when analysed by rapid evaporative ionization mass spectrometry.

The ion imager may include a monopolar device with a separate return electrode or a bipolar device. Other embodiments are also contemplated in which the ion imager may include a multi-phase or 3-phase device and may include, for example, three or more separate electrodes or probes.

Although the present invention has been described with reference to various embodiments, it will be understood by those skilled in the art that various changes in form and detail may be made without departing from the scope of the invention as set forth in the accompanying claims.

The invention claimed is:

1. A method of spectrometric analysis comprising:
obtaining one or more sample spectra for an aerosol, smoke or vapour sample;

pre-processing the one or more sample spectra, wherein pre-processing the one or more sample spectra comprises a deisotoping process, and wherein the deisotoping process comprises identifying one or more additional isotopic peaks in the one or more sample spectra and reducing or removing the one or more additional isotopic peaks in or from the one or more sample spectra; and analysing the one or more pre-processed sample spectra so as to classify the aerosol, smoke or vapour sample, wherein analysing the one or more sample spectra comprises multivariate and/or library-based analysis.

2. A method as claimed in claim 1, wherein the deisotoping process comprises an iterative process, optionally comprising iterative forward modelling, and/or wherein the deisotoping process comprises a probabilistic process, optionally a Bayesian inference process.

3. A method as claimed in claim 1, wherein the deisotoping process comprises a Monte Carlo method.

4. A method as claimed in claim 1, wherein the deisotoping process comprises one or more of: nested sampling; massive inference; and maximum entropy.

5. A method as claimed in claim 1, wherein the deisotoping process comprises deconvolving the one or more sample spectra with respect to theoretical mass and/or isotope and/or charge distributions.

6. A method as claimed in claim 5, wherein the theoretical mass and/or isotope and/or charge distributions are derived from known and/or typical and/or average properties of a class of aerosol, smoke or vapour sample.

7. A method as claimed in claim 1, wherein the deisotoping process comprises generating a set of trial hypothetical monoisotopic sample spectra.

8. A method as claimed in claim 7, wherein the set of trial hypothetical monoisotopic sample spectra is generated using one or more probability density functions for mass, intensity, charge state, and/or number of peaks, for a suspected class of sample to which the one or more sample spectra relate.

9. A method as claimed in claim 7, wherein the deisotoping process comprises generating a set of modelled sample spectra having isotopic peaks from the set of trial hypothetical monoisotopic sample spectra.

10. A method as claimed in claim 9, wherein the set of modelled sample spectra is generated using average isotopic distributions for the suspected class of sample to which the one or more sample spectra relate.

11. A method as claimed in claim 7, wherein the deisotoping process comprises deriving a likelihood for the one or more sample spectra given each trial hypothetical monoisotopic sample spectrum.

12. A method as claimed in claim 11, wherein the deisotoping process comprises deriving a likelihood for the one or more sample spectra given each trial hypothetical monoisotopic sample spectrum by comparing each modelled sample spectrum to a sample spectrum.

13. A method as claimed in claim 11, wherein the deisotoping process comprises iteratively re-generating a trial monoisotopic sample spectrum having the lowest likelihood until a maximum likelihood is reached for all the trial monoisotopic sample spectra.

14. A method as claimed in claim 1, wherein the deisotoping process comprises deriving a deisotoped spectrum.

15. A method as claimed in claim 13, wherein the deisotoping process comprises deriving a deisotoped spectrum from a final set of trial monoisotopic sample spectra.

16. A method as claimed in claim 1, wherein obtaining the one or more sample spectra comprises generating the aerosol, smoke or vapour sample using a sampling device.

17. A method as claimed in claim 16, wherein the sampling device comprises one or more ion sources selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electroflow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

18. A method of spectrometric analysis comprising:
obtaining one or more sample spectra for an aerosol, smoke or vapour sample, wherein obtaining the one or more sample spectra comprises causing the aerosol, smoke or vapour sample to impact upon a collision surface located within a vacuum chamber of a mass and/or ion mobility spectrometer so as to generate a plurality of analyte ions;

pre-processing the one or more sample spectra, wherein pre-processing the one or more sample spectra comprises a deisotoping process; and analysing the one or more pre-processed sample spectra so as to classify the aerosol, smoke or vapour sample, wherein analysing the one or more sample spectra comprises multivariate and/or library-based analysis.

19. A spectrometric analysis system comprising:
control circuitry arranged and adapted to:
obtain one or more sample spectra for an aerosol, smoke or vapour sample;
pre-process the one or more sample spectra, wherein pre-processing the one or more sample spectra comprises a deisotoping process, and wherein the deisotoping process comprises identifying one or more additional isotopic peaks in the one or more sample spectra and reducing or removing the one or more additional isotopic peaks in or from the one or more sample spectra; and
analyse the one or more pre-processed sample spectra so as to classify the aerosol, smoke or vapour sample, wherein analysing the one or more sample spectra comprises multivariate and/or library-based analysis.

* * * * *